US010465197B2

(12) United States Patent
McClain et al.

(10) Patent No.: US 10,465,197 B2
(45) Date of Patent: *Nov. 5, 2019

(54) INDUCIBLE EXPRESSION SYSTEM

(71) Applicant: AbSci, LLC, Portland, OR (US)

(72) Inventors: Sean McClain, Portland, OR (US); Mark Valasek, San Diego, CA (US)

(73) Assignee: AbiSci, LLC, Vancouver, WA (US)

( * ) Notice: Subject to any disclaimer, the term of this patent is extended or adjusted under 35 U.S.C. 154(b) by 52 days.

This patent is subject to a terminal disclaimer.

(21) Appl. No.: 14/952,535

(22) Filed: Nov. 25, 2015

(65) Prior Publication Data

US 2016/0152701 A1 Jun. 2, 2016

Related U.S. Application Data

(63) Continuation of application No. 14/419,653, filed as application No. PCT/US2013/053562 on Aug. 5, 2013.

(60) Provisional application No. 61/747,246, filed on Dec. 29, 2012, provisional application No. 61/679,751, filed on Aug. 5, 2012.

(51) Int. Cl.
| | | |
|---|---|---|
| *C12N 15/70* | (2006.01) | |
| *C07K 16/00* | (2006.01) | |
| *C12P 21/02* | (2006.01) | |
| *C07K 16/24* | (2006.01) | |
| *C07K 16/28* | (2006.01) | |

(52) U.S. Cl.
CPC ............ *C12N 15/70* (2013.01); *C07K 16/241* (2013.01); *C07K 16/2803* (2013.01); *C12P 21/02* (2013.01); *C07K 2317/14* (2013.01); *C07K 2317/20* (2013.01); *C07K 2317/21* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,803,210 | B2 | 10/2004 | Better |
| 6,872,563 | B1 | 3/2005 | Beckwith |
| 7,816,117 | B2 | 10/2010 | Beckwith |
| 8,178,338 | B2 | 5/2012 | Keasling |
| 9,238,817 | B2 | 1/2016 | Ruddock |
| 9,416,388 | B2 | 8/2016 | Ruddock |
| 2011/0117625 | A1* | 5/2011 | Lippow ............... C12N 9/22 435/196 |
| 2013/0244925 | A1* | 9/2013 | Nur ........................ A61K 38/06 514/1.1 |

FOREIGN PATENT DOCUMENTS

| | | | | |
|---|---|---|---|---|
| EP | 2386641 | A1 * | 11/2011 | ............ C12N 15/70 |
| WO | 2006133210 | A2 | 12/2006 | |

OTHER PUBLICATIONS

Lobstein, "SHuffle, a novel *Escherichia coli* protein expression strain capable of correctly folding disulfide bonded proteins in its cytoplasm", Microb Cell Fact May 8, 2012; 11: 56; doi: 10.1186/1475-2859-11-56.
Faulkner et al., "Functional plasticity of a peroxidase allows evolution of diverse disulfide-reducing pathways", Proc Natl Acad Sci U S A May 6, 2008; 105(18): 6735-6740, Epub May 2, 2008.
EMBL Protein Expression and Purification Facility, "Expression in *Escherichia coli*", Sep. 11, 2001, https://www.embl.de/pepcore/pepcore_services/protein_expression/ecoli/, retrieved Nov. 10, 2015.
Terpe, "Overview of bacterial expression systems for heterologous protein production: from molecular and biochemical fundamentals to commercial systems", Appl Microbial Biotechnol Sep. 2006; 72(2): 211-222; Epub Jun. 22, 2006; Review.
Sørensen and Mortensen, "Advanced genetic strategies for recombinant protein expression in *Escherichia coli*", J Biotechnol Jan. 26, 2005; 115(2): 113-128; Review.
Guzman et al., "Tight regulation, modulation, and high-level expression by vectors containing the arabinose PBAD promoter", J Bacteriol Jul. 1995; 177(14): 4121-4130.
Mayer, "A new set of useful cloning and expression vectors derived from pBlueScript", Gene Sep. 22, 1995; 163(1): 41-46.
Qiu et al., "Expression of active human tissue-type plasminogen activator in *Escherichia coli*", Appl Environ Microbiol Dec. 1998; 64(12): 4891-4896.
Lee and Keasling, "A propionate-inducible expression system for enteric bacteria", Appl Environ Microbiol Nov. 2005; 71(11): 6856-6862.
Levy et al., "Production of correctly folded Fab antibody fragment in the cytoplasm of *Escherichia coli* trxB gor mutants via the coexpression of molecular chaperones", Protein Expr Purif. Nov. 2001; 23(2): 338-347.
Stancombe et al., "Engineering botulinum neurotoxin domains for activation by toxin light chain", F

(56) References Cited

OTHER PUBLICATIONS

CIPO, Office Action in CN201380041522X; dated May 10, 2019.
CIPO, Office Action in CN201380041522X, English Translation; dated May 10, 2019.
Ollis et al., "Cytoplasmic membrane proton motive force energizes periplasmic interactions between ExbD and TonB", Mol Microbiol Aug. 2009; 73(3): 466-481; doi: 10A111/1365-2958.2009.06785.x; Epub Jul. 16, 2009.
Samuelson et al., "Recent developments in difficult protein expression: a guide to *E. coli* strains, promoters, and relevant host mutations", Methods Mol Biol 2011; 705: 195-209; Review.
USPTO, Non-Final Office Action in U.S. Appl. No. 14/909,707; dated Apr. 26, 2018.
USPTO, Final Office Action in U.S. Appl. No. 14/909,707; dated Nov. 8, 2018.
IP Australia, Examination Report in AU2013299910; dated Mar. 28, 2018.
Canadian IP Office, Examination Report in CA2880285; dated Jan. 15, 2019.
European Patent Office, Search Opinion in EP16201998; dated May 3, 2017.
Japan Patent Office, First Notification of Reasons for Refusal in JP 2015526598; dated Jun. 22, 2017.
Japan Patent Office, Second Notification of Reasons for Refusal in JP 2015526598; dated Jan. 30, 2018.

\* cited by examiner

INDUCIBLE EXPRESSION SYSTEM

REFERENCE TO RELATED APPLICATIONS

This application is a continuation of U.S. application Ser. No. 14/419,653, filed on Feb. 4, 2015, which is a national stage entry of International Application No. PCT/US2013/053562, filed on Aug. 5, 2013, which claims the benefit of U.S. Provisional Application No. 61/679,751, filed on Aug. 5, 2012, and U.S. Provisional Application No. 61/747,246, filed on Dec. 29, 2012, the entire disclosures of all of which are incorporated by reference herein.

REFERENCE TO THE SEQUENCE LISTING

This application includes a sequence listing submitted electronically, in a file entitled "AbSci-001PCTUS-ST25.txt", created on Feb. 4, 2015 and having a size of 137 kilobytes (KB), which is incorporated by reference herein.

FIELD OF THE INVENTION

The present invention is in the general technical fields of molecular biology and biotechnological manufacturing. More particularly, the present invention is in the technical field of recombinant protein expression.

BACKGROUND OF THE INVENTION

Production of biotechnological substances is a complex process, even more so when the desired product is a combination of molecules encoded by different genes, such as a multimeric protein formed from two or more different polypeptides. Successful coexpression of multiple gene products requires overcoming a number of challenges, which are compounded by the simultaneous expression of more than one gene product. Problems that must be overcome include creating compatible expression vectors when more than one type of vector is used; obtaining the correct stoichiometric ratio of products; producing gene products that are folded correctly and in the proper conformation with respect to binding partners; purifying the desired products away from cells and unwanted proteins, such as proteins that are folded incorrectly and/or are in an incorrect conformation; and minimizing the formation of inclusion bodies, as one aspect of maximizing the yield of the desired product(s). Many different approaches have been taken to address these challenges, but there is still a need for better coexpression methods.

Several inducible bacterial protein expression systems, including plasmids containing the lac and ara promoters, have been devised to express individual proteins. These systems have limited utility in the coexpression of difficult-to-express proteins as they fail to induce protein homogenously within the entire growth culture population in wild-type *E. coli* (Khlebnikov and Keasling, "Effect of lacY expression on homogeneity of induction from the $P_{tac}$ and $P_{trc}$ promoters by natural and synthetic inducers", Biotechnol Prog 2002 May-June; 18(3): 672-674). When expression of the transport proteins for inducers is dependent on the presence of inducer, as is the case for wild-type *E. coli* lac and ara systems, the cellular concentration of the inducer must reach a threshold level to initiate the production of transport proteins, but once that threshold has been reached, an uncontrolled positive feedback loop can occur, with the result being a high level of inducer in the cell and correspondingly high levels of expression from inducible promoters: the "all-or-none" phenomenon. Increasing the concentration of the inducer in the growth medium increases the proportion of cells in the population that are in high-expression mode. Although this type of system results in concentration-dependent induction of protein expression at the population scale, it is suboptimal for expression and production of proteins that require tight control of expression, including those that are toxic, have poor solubility, or require specific concentrations for other reasons.

Some efforts have been made to address the "all-or-none" induction phenomenon in single-promoter expression systems, by eliminating inducer-dependent transport of the inducer. One example is having a null mutation in the lactose permease gene (lacYam) and using an alternate inducer of the lac promoter such as IPTG (isopropyl-thio-(3-D-galactoside), which can get through the cell membrane to some degree in the absence of a transporter (Jensen et al., "The use of lac-type promoters in control analysis", Eur J Biochem 1993 Jan. 15; 211(1-2): 181-191). Another approach is the use of an arabinose-inducible promoter in a strain deficient in the arabinose transporter genes, but with a mutation in the lactose permease gene, lacY(A117C), that allows it to transport arabinose into the cell (Morgan-Kiss et al., "Long-term and homogeneous regulation of the *Escherichia coli* araBAD promoter by use of a lactose transporter of relaxed specificity", Proc Natl Acad Sci USA 2002 May 28; 99(11): 7373-7377).

The components of individual protein expression systems are often incompatible, precluding their use in coexpression systems, as they may be adversely affected by 'crosstalk' effects between different inducer-promoter systems, or require mutually exclusive genomic modifications, or be subject to general metabolic regulation. An attempt to address the 'crosstalk' problem between the lac and ara inducible promoter systems included directed evolution of the AraC transcriptional activator to improve its ability to induce the araBAD promoter in the presence of IPTG, an inducer of the lac promoter (Lee et al., "Directed evolution of AraC for improved compatibility of arabinose- and lactose-inducible promoters", Appl Environ Microbiol 2007 September; 73(18): 5711-5715; Epub 2007 Jul. 20). However, the compatibility between expression vectors based on ara and lac inducible promoters is still limited due to the requirement for mutually exclusive genomic modifications: a lacY point mutation (lacY(A117C)) for homogenous induction of the araBAD promoter by arabinose, and a null lacY gene for homogenous induction of the lac promoter by IPTG. General metabolic regulation—for example, carbon catabolite repression (CCR)—can also affect the compatibility of inducible promoters. CCR is characterized by the repression of genes needed for utilization of a carbon-containing compound when a more preferred compound is present, as seen in the preferential use of glucose before other sugars. In the case of the ara and prp inducible promoter systems, the presence of arabinose reduces the ability of propionate to induce expression from the prpBCDE promoter, an effect believed to involve CCR (Park et al., "The mechanism of sugar-mediated catabolite repression of the propionate catabolic genes in *Escherichia coli*", Gene 2012 Aug. 1; 504(1): 116-121, Epub 2012 May 3). There is clearly a need for an inducible coexpression system that overcomes these problems.

SUMMARY OF THE INVENTION

The present invention provides inducible coexpression systems capable of controlled-induction of each gene product component.

One embodiment of the invention is a host cell comprising two or more types of expression constructs, wherein the expression construct of each type comprises an inducible promoter and a polynucleotide sequence encoding a gene product, said polynucleotide sequence to be transcribed from the inducible promoter; wherein (1) at least one of said inducible promoters is responsive to an inducer that is not an inducer of another of said inducible promoters; and at least one of said gene products forms a multimer with another of said gene products; or (2) at least one of said gene products is selected from the group consisting of: (a) a polypeptide that lacks a signal peptide and that forms at least three disulfide bonds; (b) a polypeptide selected from the group consisting of arabinose- and xylose-utilization enzymes; and (c) a polypeptide selected from the group consisting of lignin-degrading peroxidases. Another embodiment of the invention is a host cell comprising two or more types of expression constructs, wherein the expression construct of each type comprises an inducible promoter and a polynucleotide sequence encoding a gene product, said polynucleotide sequence to be transcribed from the inducible promoter; wherein each inducible promoter is not a lactose-inducible promoter; and wherein at least one of said gene products is a polypeptide that forms at least two disulfide bonds, or forms at least two and fewer than seventeen disulfide bonds, or forms at least two and fewer than ten disulfide bonds, or forms a number of disulfide bonds selected from the group consisting of two, three, four, five, six, seven, eight, and nine. In some embodiments of the invention, this host cell is a prokaryotic cell, and in some instances, it is an *E. coli* cell. In other embodiments of the invention, the host cell is a eukaryotic cell, and in some instances it is a yeast cell, and in some further instances it is a *Saccharomyces cerevisiae* cell. In further embodiments, the expression constructs comprised by a host cell each comprise at least one inducible promoter, wherein the inducible promoter is an L-arabinose-inducible promoter or a propionate-inducible promoter, or is selected from the group consisting of: the araBAD promoter, the prpBCDE promoter, the rhaSR promoter, and the xlyA promoter, or wherein the inducible promoter is not a lactose-inducible promoter. In additional embodiments, at least one expression construct comprised by a host cell further comprises a polynucleotide sequence encoding a transcriptional regulator that binds to an inducible promoter; in some embodiments, the polynucleotide sequence encoding a transcriptional regulator and the inducible promoter to which said transcriptional regulator binds are in the same expression construct; and in further instances, the transcriptional regulator is selected from the group consisting of: AraC, PrpR, RhaR, and XylR; or in particular is AraC, or PrpR. In certain embodiments, at least one expression construct comprised by a host cell was produced by a method comprising a step of inserting a polynucleotide sequence into a plasmid selected from the group consisting of: pBAD18, pBAD18-Cm, pBAD18-Kan, pBAD24, pBAD28, pBAD30, pBAD33, pPRO18, pPRO18-Cm, pPRO18-Kan, pPRO24, pPRO30, and pPRO33; or particularly into pBAD24 or pPRO33. Other examples of the invention include a host cell comprising two or more types of expression constructs, wherein the expression construct of each type comprises an inducible promoter and a polynucleotide sequence encoding a gene product, wherein at least one gene product is a polypeptide, or is selected from the group consisting of: (a) an immunoglobulin heavy chain; (b) an immunoglobulin light chain; and (c) a fragment of any of (a)-(b), or is an immunoglobulin light chain, or is an immunoglobulin heavy chain; or is an infliximab heavy or light chain or a fragment thereof, or has at least 80% or 90% amino acid sequence identity with SEQ ID NO:30 or SEQ ID NO:31 across at least 50% or 80% of the length of SEQ ID NO:30 or SEQ ID NO:31, respectively, or has the amino acid sequence of SEQ ID NO:30 or SEQ ID NO:31.

In additional embodiments of the invention, the host cell comprises two or more types of expression constructs, wherein the expression construct of each type comprises an inducible promoter and a polynucleotide sequence encoding a gene product, said polynucleotide sequence to be transcribed from the inducible promoter; wherein at least one gene product is a polypeptide that lacks a signal peptide and that forms at least three disulfide bonds, or at least three and fewer than seventeen disulfide bonds, or at least eighteen and fewer than one hundred disulfide bonds, or at least three and fewer than ten disulfide bonds, or at least three and fewer than eight disulfide bonds; or forms a number of disulfide bonds selected from the group consisting of three, four, five, six, seven, eight, and nine; or is a polypeptide selected from the group consisting of: (a) an immunoglobulin heavy chain; (b) an immunoglobulin light chain; (c) manganese peroxidase; and (d) a fragment of any of (a)-(c); or is an infliximab heavy or light chain or a fragment thereof, or has at least 80% or 90% amino acid sequence identity with SEQ ID NO:30 or SEQ ID NO:31 across at least 50% or 80% of the length of SEQ ID NO:30 or SEQ ID NO:31, respectively, or has the amino acid sequence of SEQ ID NO:30 or SEQ ID NO:31; or has at least 80% or 90% amino acid sequence identity with SEQ ID NO:13, SEQ ID NO:15, or SEQ ID NO:23 across at least 50% or 80% of the length of SEQ ID NO:13, SEQ ID NO:15, or SEQ ID NO:23, respectively, or has the amino acid sequence of SEQ ID NO:13, SEQ ID NO: 15, or SEQ ID NO:23; or is a polypeptide selected from the group consisting of arabinose- and xylose-utilization enzymes such as xylose isomerase; or is a polypeptide selected from the group consisting of lignin-degrading peroxidases, such as manganese peroxidase or versatile peroxidase.

In further embodiments of the invention, a host cell is provided which comprises two types of expression constructs, and in certain instances, one type of expression construct is produced by a method comprising a step of inserting a polynucleotide sequence into a pBAD24 polynucleotide sequence, and the other type of expression construct is produced by a method comprising a step of inserting a polynucleotide sequence into a pPRO33 polynucleotide sequence.

Another instance of the invention is a host cell comprising two or more types of expression constructs, wherein the expression construct of each type comprises an inducible promoter, and wherein the host cell has an alteration of gene function of at least one gene encoding a transporter protein for an inducer of at least one said inducible promoter, and as another example, wherein the gene encoding the transporter protein is selected from the group consisting of araE, araF, araG, araH, rhaT, xylF, xylG, and xylH, or particularly is araE. As a further embodiment, a host cell is provided comprising two or more types of expression constructs, wherein the expression construct of each type comprises an inducible promoter, and wherein the host cell has a reduced level of gene function of at least one gene encoding a protein that metabolizes an inducer of at least one said inducible promoter, and as further examples, wherein the gene encoding a protein that metabolizes an inducer of at least one said inducible promoter is selected from the group consisting of araA, araB, araD, prpB, prpD, rhaA, rhaB, rhaD, xylA, and xylB. As an additional example, a host cell is provided comprising two or more types of expression constructs, wherein the expression construct of each type comprises an inducible promoter, and wherein the host cell has a reduced level of gene function of at least one gene encoding a protein involved in biosynthesis of an inducer of at least one said inducible promoter, which in further embodiments is selected from the group consisting of scpA/sbm, argK ygfD, scpB/ygfG, scpC/ygfH, rmlA, rmlB, rmlC, and rmlD.

The invention also provides a host cell comprising two or more types of expression constructs, wherein the expression construct of each type comprises an inducible promoter, and wherein the host cell has an altered gene function of a gene that affects the reduction/oxidation environment of the host cell cytoplasm, which in some examples is selected from the group consisting of gor and gshB; or wherein the host cell has a reduced level of gene function of a gene that encodes a reductase, which in some embodiments is trxB; or wherein the host cell comprises at least one expression construct encoding at least one disulfide bond isomerase protein, which in some embodiments is DsbC; or wherein the host cell comprises at least one polynucleotide encoding a form of DsbC lacking a signal peptide; or wherein the host cell comprises at least one polynucleotide encoding Erv1p.

In other aspects of the invention, a host cell is provided comprising two or more types of expression constructs, wherein the expression construct of each type comprises an inducible promoter, wherein the expression construct of each type comprises an inducible promoter that is not an inducible promoter of the expression construct of each other type, or wherein the expression construct of each type comprises an origin of replication that is different from the origin of replication of the expression construct of each other type.

As a particular example of the invention, an *E. coli* host cell is provided, comprising two types of expression constructs, wherein one type of expression construct is produced by a method comprising a step of inserting a polynucleotide sequence into a pBAD24 polynucleotide sequence, and the other type of expression construct is produced by a method comprising a step of inserting a polynucleotide sequence into a pPRO33 polynucleotide sequence; and the host cell further comprising two or more of the following: (a) a deletion of the araBAD genes; (b) an altered gene function of the araE and araFGH genes; (c) a lacY(A177C) gene; (d) a reduced gene function of the prpB and prpD genes; (e) a reduced gene function of the sbm/scpA-ygfD argK-ygfGH/scpBC genes, without altering expression of the ygfI gene; (f) a reduced gene function of the gor and trxB genes; (g) a reduced gene function of the AscG gene; (h) a polynucleotide encoding a form of DsbC lacking a signal peptide; and (i) a polynucleotide encoding Erv1p, ChuA, or a chaperone; and in certain examples, the host cell further comprises at least one expression construct comprising a polynucleotide sequence encoding a gene product, said polynucleotide sequence to be transcribed from an inducible promoter, and in some instances, the gene product is selected from the group consisting of: (a) an immunoglobulin heavy chain; (b) an immunoglobulin light chain; (c) manganese peroxidase; and (d) a fragment of any of (a)-(c); or is an infliximab heavy or light chain or a fragment thereof, or has at least 80% or 90% amino acid sequence identity with SEQ ID NO:30 or SEQ ID NO:31 across at least 50% or 80% of the length of SEQ ID NO:30 or SEQ ID NO:31, respectively, or has the amino acid sequence of SEQ ID NO:30 or SEQ ID NO:31; or has at least 80% or 90% amino acid sequence identity with SEQ ID NO:13, SEQ ID NO:15, or SEQ ID NO:23 across at least 50% or 80% of the length of SEQ ID NO:13, SEQ ID NO:15, or SEQ ID NO:23, respectively, or has the amino acid sequence of SEQ ID NO:13, SEQ ID NO:15, or SEQ ID NO:23; or is a polypeptide selected from the group consisting of arabinose- and xylose-utilization enzymes such as xylose isomerase; or is a polypeptide selected from the group consisting of lignin-degrading peroxidases, such as manganese peroxidase or versatile peroxidase.

Methods of producing products are also provided by the invention, such as by growing a culture of a host cell of the invention as described above; and adding an inducer of at least one inducible promoter to the culture; a gene product or a multimeric product produced by this method is also provided by the invention, and in some embodiments is an antibody, or in more particular instances, is an aglycosylated antibody, a chimeric antibody, or a human antibody.

Also provided by the systems and methods of the invention are kits comprising a host cell, the host cell comprising two or more types of expression constructs, wherein the expression construct of each type comprises an inducible promoter; and kits comprising a gene product or a multimeric product produced by growing a host cell of the invention and adding at least one inducer to the culture, where in some embodiments the multimeric product is an antibody, or in more particular instances, is an aglycosylated antibody, a chimeric antibody, or a human antibody.

Figure 5:
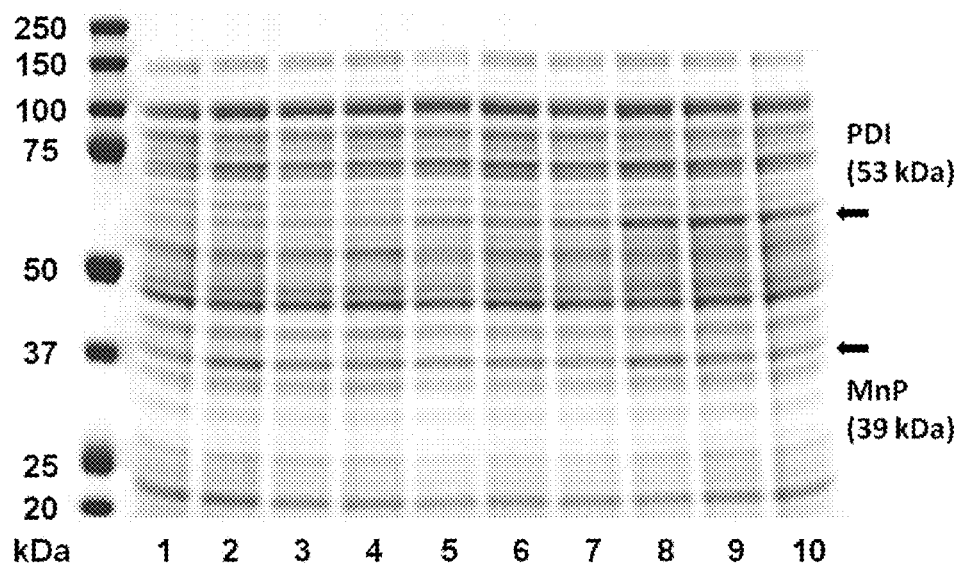

FIG. 5 shows the result of coexpression, in bacterial cells, of manganese peroxidase (MnP) and protein disulfide isomerase (PDI) in the presence of heme. SHuffle® Express cells, containing both the pPRO33-MnP-ChuA and pBAD24-PDI inducible expression vectors, were induced by growth in L-arabinose and propionate. Soluble protein extracts from uninduced and induced cells were separated by gel electrophoresis under reducing conditions on a 10% Bis-Glycine gel.

| Markers: | Bio-Rad Precision Plus Protein ™ Standard (pre-stained) | |
|---|---|---|
| Lane 1: | Not Induced (no hemin, no propionate, no arabinose) | |
| Lane 2: | 50 mM propionate | 0.002% arabinose |
| Lane 3: | 25 mM propionate | 0.002% arabinose |
| Lane 4: | 12.5 mM propionate | 0.002% arabinose |
| Lane 5: | 50 mM propionate | 0.01% arabinose |
| Lane 6: | 25 mM propionate | 0.01% arabinose |
| Lane 7: | 12.5 mM propionate | 0.01% arabinose |
| Lane 8: | 50 mM propionate | 0.05% arabinose |
| Lane 9: | 25 mM propionate | 0.05% arabinose |
| Lane 10: | 12.5 mM propionate | 0.05% arabinose |

The arrows indicate protein bands, MnP at 39 kDa and PDI at 53 kDa; these bands are present in the SHuffle® Express cells most strongly under certain of the inducing conditions, but are significantly reduced in the uninduced cells.

Figure 6:
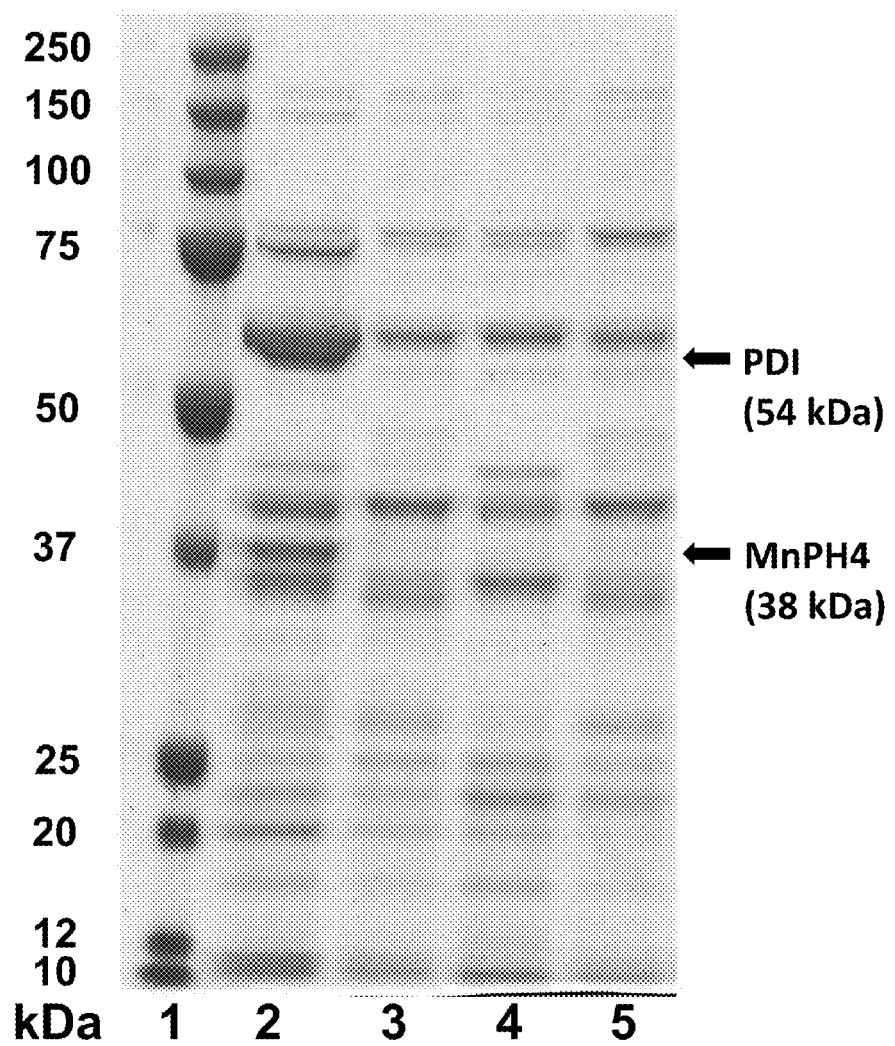

FIG. 6 shows the result of coexpression, in bacterial cells, of an alternate mature form of manganese peroxidase (MnP_FT) and protein disulfide isomerase (PDI) in the presence of heme. SHuffle® Express cells, containing both the pBAD24-MnP_FT-ChuA and pPRO33-PDI inducible expression vectors, were induced by growth in 0.1% L-arabinose and 50 mM propionate. Soluble protein extracts from uninduced and induced cells were separated by gel electrophoresis under reducing conditions on a 10% Bis-Glycine gel.

Lane 1: Molecular Weight Markers
   Bio-Rad Precision Plus Protein™ Standard (pre-stained)
Lane 2: Induced Coexpression (0.1% L-arabinose, 50 mM propionate)
Lane 3: Not Induced (no hemin, no L-arabinose, no propionate)
Lane 4: Control Induced (no protein-coding inserts)
Lane 5: Control Not Induced (no protein-coding inserts)

DETAILED DESCRIPTION OF THE INVENTION

The problem of incompatible coexpression system components is addressed by development of coordinated bacterial coexpression systems which utilize compatible homogenously inducible promoter systems located on separate expression constructs and, in some embodiments, activated by different inducers. The advantages of the present invention include, without limitation: 1) improved compatibility of components within the inducible coexpression system; 2) inducible expression of gene products that together form multimers, or other combinations of gene products (coexpression of two or more gene products); 3) improved control of gene product coexpression by independently titratible induction; 4) improved expression of gene product complexes and other products that are difficult to express such as multimeric products and products forming disulfide bonds; 5) streamlined optimization of gene product coexpression.

Coexpressed Gene Products.

The inducible coexpression systems of the invention are designed to coexpress two or more different gene products that contribute to a desired product. The desired product can be a multimer, formed from coexpressed gene products, or coexpression can be used to produce a combination of the desired product plus an additional product or products that assist in expression of the desired product.

A 'multimeric product' refers to a set of gene products that coassemble to carry out the function of the multimeric product, and does not refer to transitory associations between gene products and other molecules, such as modifying enzymes (kinases, peptidases, and the like), chaperones, transporters, etc. In certain embodiments of the invention, the multimeric products are heteromultimers. In many embodiments, the coexpressed gene products will be polypeptides that are subunits of multimeric proteins. However, it is also possible to use the inducible coexpression systems of the invention to coexpress multiple different non-coding RNA molecules, or a combination of polypeptide and non-coding RNA gene products. Non-coding RNA molecules, also called non-protein-coding RNA (npcRNA), non-messenger RNA (nmRNA), and functional RNA (fRNA), include many different types of RNA molecules such as microRNAs that are not messenger RNAs and thus are not templates for the formation of polypeptides through translation.

Many biologically important products are formed from combinations of different polypeptide chains. In addition to antibodies and antibody fragments, other multimeric products that can be produced by the inducible coexpression methods of the invention include G-coupled protein receptors and ligand-gated ion channels such as nicotinic acetylcholine receptors, $GABA_A$ receptors, glycine receptors, serotonin receptors, glutamate receptors, and ATP-gated receptors such as P2X receptors. The botulinum neurotoxin (often referred to as BoTN, BTX, or as one of its commercially available forms, BOTOX® (onabotulinumtoxinA)) is formed from a heavy chain and a light chain, linked by a disulfide bond (Simpson et al., "The role of the interchain disulfide bond in governing the pharmacological actions of botulinum toxin", J Pharmacol Exp Ther 2004 March; 308(3): 857-864, Epub 2003 Nov. 14). Another example of a product formed from different polypeptide chains is insulin, which in eukaryotes is first translated as a single polypeptide chain, folded, and then cleaved ultimately into two polypeptide chains held together by disulfide bonds. Efficient production of botulinum neurotoxin or of mature insulin in a single host cell are examples of uses of the inducible coexpression methods of the invention.

The methods of the invention are designed to produce gene products that have been correctly folded and/or assembled into functional products, and that have a desired number of disulfide bonds in the desired locations within such functional products (which can be determined by methods such as that of Example 11). The number of disulfide bonds for a gene product such as a polypeptide is the total number of intramolecular and intermolecular bonds formed by that gene product when it is present in a desired functional product. For example, a light chain of a human IgG antibody typically has three disulfide bonds (two intramolecular bonds and one intermolecular bond), and a heavy chain of a human IgG antibody typically has seven disulfide bonds (four intramolecular bonds and three intermolecular bonds). In some embodiments, desired gene products are coexpressed with other gene products, such as chaperones, that are beneficial to the production of the desired gene product. Chaperones are proteins that assist the non-covalent folding or unfolding, and/or the assembly or disassembly, of other gene products, but do not occur in the resulting monomeric or multimeric gene product structures when the structures are performing their normal biological functions (having completed the processes of folding and/or assembly). Chaperones can be expressed from an inducible promoter or a constitutive promoter within an expression construct, or can be expressed from the host cell chromosome; preferably, expression of chaperone protein(s) in the host cell is at a sufficiently high level to produce coexpressed gene products that are properly folded and/or assembled into the desired product. Examples of chaperones present in *E. coli* host cells are the folding factors DnaK/DnaJ/GrpE, DsbC/DsbG, GroEL/GroES, IbpA/IbpB, Skp, Tig (trigger factor), and FkpA, which have been used to prevent protein aggregation of cytoplasmic or periplasmic proteins. DnaK/DnaJ/GrpE, GroEL/GroES, and ClpB can function synergistically in assisting protein folding and therefore expression of these chaperones in combinations has been shown to be beneficial for protein expression (Makino et al., "Strain engineering for improved expression of recombinant proteins in bacteria", Microb Cell Fact 2011 May 14; 10: 32). When expressing eukaryotic proteins in prokaryotic host cells, a eukaryotic chaperone protein, such as protein disulfide isomerase (PDI) from the same or a related eukaryotic species, is coexpressed or inducibly coexpressed with the desired gene product in certain embodiments of the invention.

Inducible Promoters.

The following is a description of inducible promoters that can be used in expression constructs for coexpression of gene products, along with some of the genetic modifications that can be made to host cells that contain such expression constructs. Examples of these inducible promoters and related genes are, unless otherwise specified, from *Escherichia coli* (*E. coli*) strain MG1655 (American Type Culture Collection deposit ATCC 700926), which is a substrain of *E. coli* K-12 (American Type Culture Collection deposit ATCC 10798). Table 1 lists the genomic locations, in *E. coli* MG1655, of the nucleotide sequences for these examples of inducible promoters and related genes. Nucleotide and other genetic sequences, referenced by genomic location as in Table 1, are expressly incorporated by reference herein. Additional information about *E. coli* promoters, genes, and strains described herein can be found in many public sources, including the online EcoliWiki resource, located at ecoliwiki.net.

Arabinose Promoter.

(As used herein, 'arabinose' means L-arabinose.) Several *E. coli* operons involved in arabinose utilization are inducible by arabinose—araBAD, araC, araE, and araFGH—but the terms 'arabinose promoter' and 'ara promoter' are typically used to designate the araBAD promoter. Several additional terms have been used to indicate the *E. coli* araBAD promoter, such as $P_{ara}$, $P_{araB}$, $P_{araB}AD$, and $P_{BAD}$. The use herein of 'ara promoter' or any of the alternative terms given above, means the *E. coli* araBAD promoter. As can be seen from the use of another term, 'araC-araBAD promoter', the araBAD promoter is considered to be part of a bidirectional promoter, with the araBAD promoter controlling expression of the araBAD operon in one direction, and the araC promoter, in close proximity to and on the opposite strand from the araBAD promoter, controlling expression of the araC coding sequence in the other direction. The AraC protein is both a positive and a negative transcriptional regulator of the araBAD promoter. In the absence of arabinose, the AraC protein represses transcription from $P_{BAD}$, but in the presence of arabinose, the AraC protein, which alters its conformation upon binding arabinose, becomes a positive regulatory element that allows transcription from $P_{BAD}$. The araBAD operon encodes proteins that metabolize L-arabinose by converting it, through the intermediates L-ribulose and L-ribulose-phosphate, to D-xylulose-5-phosphate. For the purpose of maximizing induction of expression from an arabinose-inducible promoter, it is useful to eliminate or reduce the function of AraA, which catalyzes the conversion of L-arabinose to L-ribulose, and optionally to eliminate or reduce the function of at least one of AraB and AraD, as well. Eliminating or reducing the ability of host cells to decrease the effective concentration of arabinose in the cell, by eliminating or reducing the cell's ability to convert arabinose to other sugars, allows more arabinose to be available for induction of the arabinose-inducible promoter. The genes encoding the transporters which move arabinose into the host cell are araE, which encodes the low-affinity L-arabinose proton symporter, and the araFGH operon, which encodes the subunits of an ABC superfamily high-affinity L-arabinose transporter. Other proteins which can transport L-arabinose into the cell are certain mutants of the LacY lactose permease: the LacY(A177C) and the LacY(A177V) proteins, having a cysteine or a valine amino acid instead of alanine at position 177, respectively (Morgan-Kiss et al., "Long-term and homogeneous regulation of the *Escherichia coli* araBAD promoter by use of a lactose transporter of relaxed specificity", Proc Natl Acad Sci USA 2002 May 28; 99(11): 7373-7377). In order to achieve homogenous induction of an arabinose-inducible promoter, it is useful to make transport of arabinose into the cell independent of regulation by arabinose. This can be accomplished by eliminating or reducing the activity of the AraFGH transporter proteins and altering the expression of araE so that it is only transcribed from a constitutive promoter. Constitutive expression of araE can be accomplished by eliminating or reducing the function of the native araE gene, and introducing into the cell an expression construct which includes a coding sequence for the AraE protein expressed from a constitutive promoter. Alternatively, in a cell lacking AraFGH function, the promoter controlling expression of the host cell's chromosomal araE gene can be changed from an arabinose-inducible promoter to a constitutive promoter. In similar manner, as additional alternatives for homogenous induction of an arabinose-inducible promoter, a host cell that lacks AraE function can have any functional AraFGH coding sequence present in the cell expressed from a constitutive promoter. As another alternative, it is possible to express both the araE gene and the araFGH operon from constitutive promoters, by replacing the native araE and araFGH promoters with constitutive promoters in the host chromosome. It is also possible to eliminate or reduce the activity of both the AraE and the AraFGH arabinose transporters, and in that situation to use a mutation in the LacY lactose permease that allows this protein to transport arabinose. Since expression of the lacY gene is not normally regulated by arabinose, use of a LacY mutant such as LacY(A177C) or LacY(A177V), will not lead to the 'all or none' induction phenomenon when the arabinose-inducible promoter is induced by the presence of arabinose. Because the LacY(A177C) protein appears to be more effective in transporting arabinose into the cell, use of polynucleotides encoding the LacY(A177C) protein is preferred to the use of polynucleotides encoding the LacY (A177V) protein.

Propionate Promoter.

The 'propionate promoter' or 'prp promoter' is the promoter for the *E. coli* prpBCDE operon, and is also called $P_{prpB}$. Like the ara promoter, the prp promoter is part of a bidirectional promoter, controlling expression of the prpBCDE operon in one direction, and with the prpR promoter controlling expression of the prpR coding sequence in the other direction. The PrpR protein is the transcriptional regulator of the prp promoter, and activates transcription from the prp promoter when the PrpR protein binds 2-methylcitrate ('2-MC'). Propionate (also called propanoate) is the ion, $CH_3CH_2COO^-$, of propionic acid (or 'propanoic acid'), and is the smallest of the 'fatty' acids having the general formula $H(CH_2)_nCOOH$ that shares certain properties of this class of molecules: producing an oily layer when salted out of water and having a soapy potassium salt. Commercially available propionate is generally sold as a monovalent cation salt of propionic acid, such as sodium propionate ($CH_3CH_2COONa$), or as a divalent cation salt, such as calcium propionate ($Ca(CH_3CH_2COO)_2$). Propionate is membrane-permeable and is metabolized to 2-MC by conversion of propionate to propionyl-CoA by PrpE (propionyl-CoA synthetase), and then conversion of propionyl-CoA to 2-MC by PrpC (2-methylcitrate synthase). The other proteins encoded by the prpBCDE operon, PrpD (2-methylcitrate dehydratase) and PrpB (2-methylisocitrate lyase), are involved in further catabolism of 2-MC into smaller products such as pyruvate and succinate. In order to maximize induction of a propionate-inducible promoter by propionate added to the cell growth medium, it is therefore desirable to have a host cell with PrpC and PrpE activity, to convert propionate into 2-MC, but also having eliminated or reduced PrpD activity, and optionally eliminated or reduced PrpB activity as well, to prevent 2-MC from being metabolized. Another operon encoding proteins involved in 2-MC biosynthesis is the scpA-argK-scpBC operon, also called the sbm-ygfDGH operon. These genes encode proteins required for the conversion of succinate to propionyl-CoA, which can then be converted to 2-MC by PrpC. Elimination or reduction of the function of these proteins would remove a parallel pathway for the production of the 2-MC inducer, and thus might reduce background levels of expression of a propionate-inducible promoter, and increase sensitivity of the propionate-inducible promoter to exogenously supplied propionate. It has been found that a deletion of sbm-ygfD-ygfG-ygfH-ygfI, introduced into *E. coli* BL21(DE3) to create strain JSB (Lee and Keasling, "A propionate-inducible expression system for enteric bacteria", Appl Environ Microbiol 2005 November; 71(11): 6856-6862), was helpful in reducing background expression in the absence of exogenously supplied inducer, but this deletion also reduced overall expression from the prp promoter in strain JSB. It should be noted, however, that the deletion sbm-ygfD-ygfG-ygfH-ygfI also apparently affects ygfI, which encodes a putative LysR-family transcriptional regulator of unknown function. The genes sbm-ygfDGH are transcribed as one operon, and ygfI is transcribed from the opposite strand. The 3' ends of the ygfH and ygfI coding sequences overlap by a few base pairs, so a deletion that takes out all of the sbm-ygfDGH operon apparently takes out ygfI coding function as well. Eliminating or reducing the function of a subset of the sbm-ygfDGH gene products, such as YgfG (also called ScpB, methylmalonyl-CoA decarboxylase), or deleting the majority of the sbm-ygfDGH (or scpA-argK-scpBC) operon while leaving enough of the 3' end of the ygfH (or scpC) gene so that the expression of ygfI is not affected, could be sufficient to reduce background expression from a propionate-inducible promoter without reducing the maximal level of induced expression.

Rhamnose Promoter.

(As used herein, 'rhamnose' means L-rhamnose.) The 'rhamnose promoter' or 'rha promoter', or $P_{rhaSR}$, is the promoter for the *E. coli* rhaSR operon. Like the ara and prp promoters, the rha promoter is part of a bidirectional promoter, controlling expression of the rhaSR operon in one direction, and with the rhaBAD promoter controlling expression of the rhaBAD operon in the other direction. The rha promoter, however, has two transcriptional regulators involved in modulating expression: RhaR and RhaS. The RhaR protein activates expression of the rhaSR operon in the presence of rhamnose, while RhaS protein activates expression of the L-rhamnose catabolic and transport operons, rhaBAD and rhaT, respectively (Wickstrum et al., "The AraC/XylS family activator RhaS negatively autoregulates rhaSR expression by preventing cyclic AMP receptor protein activation", J Bacteriol 2010 January; 192(1): 225-232). Although the RhaS protein can also activate expression of the rhaSR operon, in effect RhaS negatively autoregulates this expression by interfering with the ability of the cyclic AMP receptor protein (CRP) to coactivate expression with RhaR to a much greater level. The rhaBAD operon encodes the rhamnose catabolic proteins RhaA (L-rhamnose isomerase), which converts L-rhamnose to L-rhamnulose; RhaB (rhamnulokinase), which phosphorylates L-rhamnulose to form L-rhamnulose-1-P; and RhaD (rhamnulose-1-phosphate aldolase), which converts L-rhamnulose-1-P to L-lactaldehyde and DHAP (dihydroxyacetone phosphate). To maximize the amount of rhamnose in the cell available for induction of expression from a rhamnose-inducible promoter, it is desirable to reduce the amount of rhamnose that is broken down by catalysis, by eliminating or reducing the function of RhaA, or optionally of RhaA and at least one of RhaB and RhaD. *E. coli* cells can also synthesize L-rhamnose from alpha-D-glucose-1-P through the activities of the proteins RmlA, RmlB, RmlC, and RmlD (also called RfbA, RfbB, RfbC, and RfbD, respectively) encoded by the rmlBDACX (or rfbBDACX) operon. To reduce background expression from a rhamnose-inducible promoter, and to enhance the sensitivity of induction of the rhamnose-inducible promoter by exogenously supplied rhamnose, it could be useful to eliminate or reduce the function of one or more of the RmlA, RmlB, RmlC, and RmlD proteins. L-rhamnose is transported into the cell by RhaT, the rhamnose permease or L-rhamnose:proton symporter. As noted above, the expression of RhaT is activated by the transcriptional regulator RhaS. To make expression of RhaT independent of induction by rhamnose (which induces expression of RhaS), the host cell can be altered so that all functional RhaT coding sequences in the cell are expressed from constitutive promoters. Additionally, the coding sequences for RhaS can be deleted or inactivated, so that no functional RhaS is produced. By eliminating or reducing the function of RhaS in the cell, the level of expression from the rhaSR promoter is increased due to the absence of negative autoregulation by RhaS, and the level of expression of the rhamnose catalytic operon rhaBAD is decreased, further increasing the ability of rhamnose to induce expression from the rha promoter.

Xylose Promoter.

(As used herein, 'xylose' means D-xylose.) The xylose promoter, or 'xyl promoter', or $P_{xylA}$, means the promoter for the *E. coli* xylAB operon. The xylose promoter region is similar in organization to other inducible promoters in that the xylAB operon and the xylFGHR operon are both expressed from adjacent xylose-inducible promoters in opposite directions on the *E. coli* chromosome (Song and Park, "Organization and regulation of the D-xylose operons in *Escherichia coli* K-12: XylR acts as a transcriptional activator", J Bacteriol. 1997 November; 179(22): 7025-7032). The transcriptional regulator of both the $P_{xylA}$ and $P_{xylF}$ promoters is XylR, which activates expression of these promoters in the presence of xylose. The xylR gene is expressed either as part of the xylFGHR operon or from its own weak promoter, which is not inducible by xylose, located between the xylH and xylR protein-coding sequences. D-xylose is catabolized by XylA (D-xylose isomerase), which converts D-xylose to D-xylulose, which is then phosphorylated by XylB (xylulokinase) to form D-xylulose-5-P. To maximize the amount of xylose in the cell available for induction of expression from a xylose-inducible promoter, it is desirable to reduce the amount of xylose that is broken down by catalysis, by eliminating or reducing the function of at least XylA, or optionally of both XylA and XylB. The xylFGHR operon encodes XylF, XylG, and XylH, the subunits of an ABC superfamily high-affinity D-xylose transporter. The xylE gene, which encodes the *E. coli* low-affinity xylose-proton symporter, represents a separate operon, the expression of which is also inducible by xylose. To make expression of a xylose transporter independent of induction by xylose, the host cell can be altered so that all functional xylose transporters are expressed from constitutive promoters. For example, the xylFGHR operon could be altered so that the xylFGH coding sequences are deleted, leaving XylR as the only active protein expressed from the xylose-inducible $P_{xylF}$ promoter, and with the xylE coding sequence expressed from a constitutive promoter rather than its native promoter. As another example, the xylR coding sequence is expressed from the $P_{xylA}$ or the $P_{xylF}$ promoter in an expression construct, while either the xylF-GHR operon is deleted and xylE is constitutively expressed, or alternatively an xylFGH operon (lacking the xylR coding sequence since that is present in an expression construct) is expressed from a constitutive promoter and the xylE coding sequence is deleted or altered so that it does not produce an active protein.

Lactose Promoter.

The term 'lactose promoter' refers to the lactose-inducible promoter for the lacZYA operon, a promoter which is also called lacZp1; this lactose promoter is located at ca. 365603-365568 (minus strand, with the RNA polymerase binding ('−35') site at ca. 365603-365598, the Pribnow box ('−10') at 365579-365573, and a transcription initiation site at 365567) in the genomic sequence of the *E. coli* K-12 substrain MG1655 (NCBI Reference Sequence NC_000913.2, 11 Jan. 2012). In some embodiments, inducible coexpression systems of the invention can comprise a lactose-inducible promoter such as the lacZYA promoter. In other embodiments, the inducible coexpression systems of the invention comprise one or more inducible promoters that are not lactose-inducible promoters.

TABLE 1

Genomic Locations of *E. coli* Inducible Promoters and Related Genes [1]

| Promoter or Gene | Genomic Location: | Comments: |
|---|---|---|
| araBAD promoter | [2] (ca. 70165) - 70074 (minus strand) | Smith and Schleif[3]: RNA pol [4] binding ('−35') 70110-70104, Pribnow box ('−10') 70092-70085 |
| araBAD operon | 70075 - 65855 (minus strand) | Smith and Schleif[3]: transcript start 70075, araB ATG 70048; NCBI: araB end of TAA 68348; araA ATG 68337, end of TAA 66835; araD ATG 66550, end of TAA 65855 |
| araC promoter | [2] (ca. 70166) - 70241 (plus strand) | Smith and Schleif[3]: RNA pol binding ('−35') 70210-7021, Pribnow box ('−10') 70230-70236 |
| araC gene | 70242-71265 (plus strand) | Miyada [5]: transcript start 70242, araC ATG 70387; NCBI: end of TAA 71265 |
| araE promoter | [2] (ca. 2980349) - 2980231 (minus strand) | Stoner and Schleif [6]: CRP binding 2980349-2980312, RNA pol binding ('−35') 2980269-2980264, Pribnow box ('−10') 2980244-2980239 |
| araE gene | 2980230 - 2978786 (minus strand) | Stoner and Schleif [6]: transcript start 2980230, ATG 2980204; NCBI: end of TGA 2978786 |
| araFGH promoter | [2] (ca. 1984423) - 1984264 (minus strand) | Hendrickson [7]: AraC binding ca. 1984423-ca. 1984414 and 1984326-1984317, CRP binding 1984315-1984297, RNA pol binding ('−35') 1984294-1984289, Pribnow box ('−10') 1984275-1984270 |
| araFGH operon | 1984263 - 1980578 (minus strand) | Hendrickson [7]: transcript start 1984263; NCBI: araF ATG 1984152, end of TAA 1983163; araG ATG 1983093, end of TGA 1981579; araH ATG 1981564, end of TGA 1980578 |
| lacY gene | 362403 - 361150 (minus strand) | Expressed as part of the lacZYA operon. NCBI: ATG 362403, end of TAA 361150 |
| prpBCDE promoter | [2]ca. 347790-ca. 347870 (plus strand) | Keasling [8]: RNA pol binding ('−24') 347844-347848, Pribnow box ('−12') 347855-347859 |
| prpBCDE operon | (ca. 347871) - 353816 (plus strand) | Keasling [8]: inferred transcript start ca. 347871, prpB ATG 347906; NCBI: prpB end of TAA 348796; prpC ATG 349236, end of TAA 350405; prpD ATG 350439, end of TAA 351890; prpE ATG 351930, end of TAG 353816 |
| prpR promoter | [2] ca. 347789 - ca. 347693 (minus strand) | Keasling [8]: CRP binding 347775-347753, RNA pol binding ('−35') 347728-347723, Pribnow box ('−10') 347707-347702 |

TABLE 1-continued

Genomic Locations of *E. coli* Inducible Promoters and Related Genes [1]

| Promoter or Gene | Genomic Location: | Comments: |
|---|---|---|
| prpR gene | (ca. 347692)-346081 (minus strand) | Keasling [8]: inferred transcript start ca. 347692, prpR ATG 347667; NCBI: end of TGA 346081 |
| scpA-argK-scpBC (or sbm-ygfDGH) operon | 3058872 - 3064302 (plus strand) | NCBI: scpA ATG 3058872, end of TAA 3061016; argK ATG 3061009, end of TAA 3062004; scpB ATG 3062015, end of TAA 3062800; scpC ATG 3062824, end of TAA 3064302 |
| rhaBAD promoter | [2] (ca. 4095605) - 4095496 (minus strand) | Wickstrum [9]: CRP binding 4095595-4095580, RNA pol binding ('−35') 4095530-4095525, Pribnow box ('−10') 4095506-4095501 |
| rhaBAD operon | 4095495 - 4091471 (minus strand) | Wickstrum [9]: transcript start 4095495, rhaB ATG 4095471; NCBI: rhaB end of TGA 4094002; rhaA ATG 4094005, end of TAA 4092746; rhaD ATG 4092295, end of TAA 4091471 |
| rhaSR promoter | [2] (ca. 4095606) - 4095733 (plus strand) | Wickstrum [9]: CRP binding 4095615-4095630, RNA pol binding ('−35') 4095699-4095704, Pribnow box ('−10') 4095722-4095727 |
| rhaSR operon | 4095734 - 4097517 (plus strand) | Wickstrum [9]: transcript start 4095734, rhaS ATG 4095759; NCBI: rhaS end of TAA 4096595; rhaR ATG 4096669, end of TAA 4097517 |
| rfbBDACX (or rmlBDACX) operon | 2111085 - 2106361 (minus strand) | NCBI: rfbB GTG 2111085, end of TAA 2110000; rfbD ATG 2110000, end of TAA 2109101; rfbA ATG 2109043, end of TAA 2108162; rfbC ATG 2108162, end of TGA 2107605; rfbX ATG 2107608, end of TGA 2106361 |
| rhaT promoter | [2] (ca. 4098690) - 4098590 (minus strand) | Via [10]: CRP binding 4098690-4098675, RNA pol binding ('−35') 4098621-4098616, Pribnow box ('−10') 4098601-4098596 |
| rhaT gene | 4098589-4097514 (minus strand) | Via [10]: transcript start 4098589, rhaT ATG 4098548; NCBI: rhaT end of TAA 4097514 |
| xylAB promoter | [2] (ca. 3728960) - 3728831 (minus strand) | Song and Park [11]: CRP binding 3728919-3728901, RNA pol binding ('−35') 3728865-3728860, Pribnow box ('−10') 3728841-3728836 |
| xylAB operon | 3728830-3725940 (minus strand) | Song and Park [11]: transcript start 3728830, xylA ATG 3728788; NCBI: xylA end of TAA 3727466; xylB ATG 3727394, end of TAA 3725940 |
| xylFGHR promoter | [2] (ca. 3728961) - 3729091 (plus strand) | Song and Park [11]: RNA pol binding ('−35') 3729058-3729063, Pribnow box ('−10') 3729080-3729085 |
| xylFGHR operon | 3729092 - 3734180 (plus strand) | Song and Park [11]: transcript start 3729092, xylF ATG 3729154; NCBI: xylF end of TAA 3730146, xylG ATG 3730224, end of TGA 3731765; xylH ATG 3731743, end of TGA 3732924; xylR ATG 3733002, end of TAG 3734180 |
| xylE promoter | [2]ca. 4240482 - ca. 4240320 (minus strand) | Davis and Henderson [12]: possible Pribnow box ('−10') 4240354 - 4240349, possible Pribnow box ('−10') 4240334-4240329 |
| xylE gene | (ca. 4240319) - 4238802 (minus strand) | Davis and Henderson [12]: inferred transcript start ca. 4240319, xylE ATG 4240277, end of TAA 4238802 |

Notes for Table 1:

[1] All genomic sequence locations refer to the genomic sequence of *E. coli* K-12 substrain MG1655, provided by the National Center for Biotechnology Information (NCBI) as NCBI Reference Sequence NC_000913.2, 11-JAN-2012.
[2] The location of the 5' (or 'upstream') end of the promoter region is approximated; for 'bidirectional' promoters, a nucleotide sequence location that is approximately equidistant between the transcription start sites is selected as the designated 5' 'end' for both of the individual promoters. In practice, the promoter portion of an expression construct can have somewhat less sequence at its 5' end than the promoter sequences as indicated in the table, or it can have a nucleotide sequence that includes additional sequence from the region 5' (or 'upstream') of the promoter sequences as indicated in the table, as long as it retains the ability to promote transcription of a downstream coding sequence in an inducible fashion.
[3] Smith and Schleif, "Nucleotide sequence of the L-arabinose regulatory region of *Escherichia coli* K12", J Biol Chem 1978 Oct 10; 253(19): 6931-6933.
[4] 'RNA pol' indicates RNA polymerase throughout the table.
[5] Miyada, et al., "DNA sequence of the araC regulatory gene from *Escherichia coli* B/r", Nucleic Acids Res 1980 Nov 25; 8(22): 5267-5274.
[6] Stoner and Schleif, "*E. coli* araE regulatory region araE codes for the low affinity L-arabinose uptake protein", GenBank Database Accession X00272.1, revision date 06-JUL-1989.
[7] Hendrickson et al., "Sequence elements in the *Escherichia coli* araFGH promoter", J Bacteriol 1992 Nov; 174(21): 6862-6871.
[8] U.S. Pat. No. 8,178,338 B2; May 15 2012; Keasling, Jay; FIG. 9.
[9] Wickstrum et al., "The AraC/XylS family activator RhaS negatively autoregulates rhaSR expression by preventing cyclic AMP receptor protein activation", J Bacteriol 2010 Jan; 192(1): 225-232.
[10] Via et al., "Transcriptional regulation of the *Escherichia coli* rhaT gene", Microbiology 1996 Jul; 142(Pt 7): 1833-1840.
[11] Song and Park, "Organization and regulation of the D-xylose operons in *Escherichia coli* K-12: XylR acts as a transcriptional activator", J Bacteriol. 1997 Nov; 179(22): 7025-7032.
[12] Davis and Henderson, "The cloning and DNA sequence of the gene xylE for xylose-proton symport in *Escherichia coli* K12", J Biol Chem 1987 Oct 15; 262(29): 13928-13932.

Expression Constructs.

Expression constructs are polynucleotides designed for the expression of one or more gene products of interest, and thus are not naturally occurring molecules. Expression constructs can be integrated into a host cell chromosome, or maintained within the host cell as polynucleotide molecules replicating independently of the host cell chromosome, such as plasmids or artificial chromosomes. An example of an expression construct is a polynucleotide resulting from the insertion of one or more polynucleotide sequences into a host cell chromosome, where the inserted polynucleotide sequences alter the expression of chromosomal coding sequences. An expression vector is a plasmid expression construct specifically used for the expression of one or more gene products. One or more expression constructs can be integrated into a host cell chromosome or be maintained on an extrachromosomal polynucleotide such as a plasmid or artificial chromosome. The following are descriptions of particular types of polynucleotide sequences that can be used in expression constructs for the coexpression of gene products.

Origins of Replication.

Expression constructs must comprise an origin of replication, also called a replicon, in order to be maintained within the host cell as independently replicating polynucleotides. Different replicons that use the same mechanism for replication cannot be maintained together in a single host cell through repeated cell divisions. As a result, plasmids can be categorized into incompatibility groups depending on the origin of replication that they contain, as shown in Table 2.

TABLE 2

Origins of Replication and Representative Plasmids for Use in Expression Constructs [1]

| Incompatibility Group: | Origin of Replication: | Copy Number: | Representative Plasmids (ATCC Deposit No.): |
|---|---|---|---|
| colE1, pMB1 | colE1 | 15-20 | colE1 (ATCC 27138) |
|  | pMB1 | 15-20 | pBR322 (ATCC 31344) |
|  | Modified pMB1 | 500-700 | pUC9 (ATCC 37252) |
| IncFII, pT181 | R1(ts) | 15-120 | pMOB45 (ATCC 37106) |
| F, P1, p15A, pSC101, R6K, RK2 [2] | p15A | 18-22 | pACYC177 (ATCC 37031); pACYC184 (ATCC 37033); pPRO33 (Addgene 17810) [3] |
|  | pSC101 | ~5 | pSC101 (ATCC 37032): pGBM1 (ATCC 87497) |
|  | RK2 | 4-7 [2] | RK2 (ATCC 37125) |
| CloDF13 [4] | CloDF13 | 20-40 [4] | pCDFDuet™-1 (EMD Millipore Catalog No. 71340-3) |
| ColA [4] | ColA | 20-40 [4] | pCOLADuet™-1 (EMD Millipore Catalog No. 71406-3) |
| RSF1030 [4] | RSF1030 (also called NTP1) | >100 [4] | pRSFDuet™-1 (EMD Millipore Catalog No. 71341-3) |

Notes for Table 2:
[1] Adapted from www.bio.davidson.edu/courses/Molbio/Protocols/ORIs.html, and Sambrook and Russell, "Molecular Cloning: A laboratory manual", 3$^{rd}$ Ed., Cold Spring Harbor Laboratory Press, 2001.
[2] Kües and Stahl, "Replication of plasmids in gram-negative bacteria", Microbiol Rev 1989 Dec; 53(4): 491-516.
[3] The pPRO33 plasmid (U.S. Pat. No. 8,178,338 B2; May 15 2012; Keasling, Jay) is available from Addgene (www.addgene.org) as Addgene plasmid 17810.
[4] openwetware.org/wiki/CH391L/S12/Origins_of_Replication; accessed 03 Aug 2013.

Origins of replication can be selected for use in expression constructs on the basis of incompatibility group, copy number, and/or host range, among other criteria. As described above, if two or more different expression constructs are to be used in the same host cell for the coexpression of multiple gene products, it is best if the different expression constructs contain origins of replication from different incompatibility groups: a pMB1 replicon in one expression construct and a p15A replicon in another, for example. The average number of copies of an expression construct in the cell, relative to the number of host chromosome molecules, is determined by the origin of replication contained in that expression construct. Copy number can range from a few copies per cell to several hundred (Table 2). In one embodiment of the invention, different expression constructs are used which comprise inducible promoters that are activated by the same inducer, but which have different origins of replication. By selecting origins of replication that maintain each different expression construct at a certain approximate copy number in the cell, it is possible to adjust the levels of overall production of a gene product expressed from one expression construct, relative to another gene product expressed from a different expression construct. As an example, to coexpress subunits A and B of a multimeric protein, an expression construct is created which comprises the colE1 replicon, the ara promoter, and a coding sequence for subunit A expressed from the ara promoter: 'colE1-$P_{ara}$-A'. Another expression construct is created comprising the p15A replicon, the ara promoter, and a coding sequence for subunit B: 'p15A-$P_{ara}$-B'. These two expression constructs can be maintained together in the same host cells, and expression of both subunits A and B is induced by the addition of one inducer, arabinose, to the growth medium. If the expression level of subunit A needed to be significantly increased relative to the expression level of subunit B, in order to bring the stoichiometric ratio of the expressed amounts of the two subunits closer to a desired ratio, for example, a new expression construct for subunit A could be created, having a modified pMB1 replicon as is found in the origin of replication of the pUC9 plasmid ('pUC9ori'): pUC9ori-$P_{ara}$-A. Expressing subunit A from a high-copy-number expression construct such as pUC9ori-$P_{ara}$-A should increase the amount of subunit A produced relative to expression of subunit B from p15A-$P_{ara}$-B. In a similar fashion, use of an origin of replication that maintains expression constructs at a lower copy number, such as pSC101, could reduce the overall level of a gene product expressed from that construct. Selection of an origin of replication can also determine which host cells can maintain an expression construct comprising that replicon. For example, expression constructs comprising the colE1 origin of replication have a relatively narrow range of available hosts, species within the Enterobacteriaceae family, while expression constructs comprising the RK2 replicon can be maintained in *E. coli, Pseudomonas aeruginosa, Pseudomonas putida, Azotobacter vinelandii*, and *Alcaligenes eutrophus*, and if an expression construct comprises the RK2 replicon and some regulator genes from the RK2 plasmid, it can be maintained in host cells as diverse as *Sinorhizobium meliloti, Agrobacterium tumefaciens, Caulobacter crescentus, Acinetobacter calcoaceticus*, and *Rhodobacter sphaeroides* (Kies and Stahl, "Replication of plasmids in gram-negative bacteria", Microbiol Rev 1989 December; 53(4): 491-516).

Similar considerations can be employed to create expression constructs for inducible coexpression in eukaryotic cells. For example, the 2-micron circle plasmid of *Saccharomyces cerevisiae* is compatible with plasmids from other yeast strains, such as pSR1 (ATCC Deposit Nos. 48233 and 66069; Araki et al., "Molecular and functional organization of yeast plasmid pSR1", J Mol Biol 1985 Mar. 20; 182(2): 191-203) and pKD1 (ATCC Deposit No. 37519; Chen et al., "Sequence organization of the circular plasmid pKD1 from the yeast *Kluyveromyces drosophilarum*", Nucleic Acids Res 1986 Jun. 11; 14(11): 4471-4481).

Selectable Markers.

Expression constructs usually comprise a selection gene, also termed a selectable marker, which encodes a protein necessary for the survival or growth of host cells in a selective culture medium. Host cells not containing the expression construct comprising the selection gene will not survive in the culture medium. Typical selection genes encode proteins that confer resistance to antibiotics or other toxins, or that complement auxotrophic deficiencies of the host cell. One example of a selection scheme utilizes a drug such as an antibiotic to arrest growth of a host cell. Those cells that contain an expression construct comprising the selectable marker produce a protein conferring drug resistance and survive the selection regimen. Some examples of antibiotics that are commonly used for the selection of selectable markers (and abbreviations indicating genes that provide antibiotic resistance phenotypes) are: ampicillin ($Amp^R$), chloramphenicol ($Cml^R$ or $Cm^R$), kanamycin ($Kan^R$), spectinomycin ($Spc^R$), streptomycin ($Str^R$), and tetracycline ($Tet^R$). Many of the representative plasmids in Table 1 comprise selectable markers, such as pBR322 ($Amp^R$, $Tet^R$); pMOB45 ($Cm^R$, $Tet^R$); pACYC177 ($Amp^R$, $Kan^R$); and pGBM1 ($Spc^R$, $Str^R$). The native promoter region for a selection gene is usually included, along with the coding sequence for its gene product, as part of a selectable marker portion of an expression construct. Alternatively, the coding sequence for the selection gene can be expressed from a constitutive promoter.

Inducible Promoter.

As described herein, there are several different inducible promoters that can be included in expression constructs as part of the inducible coexpression systems of the invention. Preferred inducible promoters share at least 80% polynucleotide sequence identity (more preferably, at least 90% identity, and most preferably, at least 95% identity) to at least 30 (more preferably, at least 40, and most preferably, at least 50) contiguous bases of a promoter polynucleotide sequence as defined in Table 1 by reference to the *E. coli* K-12 substrain MG1655 genomic sequence, where percent polynucleotide sequence identity is determined using the methods of Example 13. Under 'standard' inducing conditions (see Example 5), preferred inducible promoters have at least 75% (more preferably, at least 100%, and most preferably, at least 110%) of the strength of the corresponding 'wild-type' inducible promoter of *E. coli* K-12 substrain MG1655, as determined using the quantitative PCR method of De Mey et al. (Example 8). Within the expression construct, an inducible promoter is placed 5' to (or 'upstream of') the coding sequence for the gene product that is to be inducibly expressed, so that the presence of the inducible promoter will direct transcription of the gene product coding sequence in a 5' to 3' direction relative to the coding strand of the polynucleotide encoding the gene product.

Ribosome Binding Site.

For polypeptide gene products, the nucleotide sequence of the region between the transcription initiation site and the initiation codon of the coding sequence of the gene product that is to be inducibly expressed corresponds to the 5' untranslated region ('UTR') of the mRNA for the polypeptide gene product. Preferably, the region of the expression construct that corresponds to the 5' UTR comprises a polynucleotide sequence similar to the consensus ribosome binding site (RBS, also called the Shine-Dalgarno sequence) that is found in the species of the host cell. In prokaryotes (archaea and bacteria), the RBS consensus sequence is GGAGG or GGAGGU, and in bacteria such as *E. coli*, the RBS consensus sequence is AGGAGG or AGGAGGU. The RBS is typically separated from the initiation codon by 5 to 10 intervening nucleotides. In expression constructs, the RBS sequence is preferably at least 55% identical to the AGGAGGU consensus sequence, more preferably at least 70% identical, and most preferably at least 85% identical, and is separated from the initiation codon by 5 to 10 intervening nucleotides, more preferably by 6 to 9 intervening nucleotides, and most preferably by 6 or 7 intervening nucleotides. The ability of a given RBS to produce a desirable translation initiation rate can be calculated at the website salis.psu.edu/software/RBSLibraryCalculatorSearchMode, using the RBS Calculator; the same tool can be used to optimize a synthetic RBS for a translation rate across a 100,000+ fold range (Salis, "The ribosome binding site calculator", Methods Enzymol 2011; 498: 19-42).

Multiple Cloning Site.

A multiple cloning site (MCS), also called a polylinker, is a polynucleotide that contains multiple restriction sites in close proximity to or overlapping each other. The restriction sites in the MCS typically occur once within the MCS sequence, and preferably do not occur within the rest of the plasmid or other polynucleotide construct, allowing restriction enzymes to cut the plasmid or other polynucleotide construct only within the MCS. Examples of MCS sequences are those in the pBAD series of expression vectors, including pBAD18, pBAD18-Cm, pBAD18-Kan, pBAD24, pBAD28, pBAD30, and pBAD33 (Guzman et al., "Tight regulation, modulation, and high-level expression by vectors containing the arabinose PBAD promoter", J Bacteriol 1995 July; 177(14): 4121-4130); or those in the pPRO series of expression vectors derived from the pBAD vectors, such as pPRO18, pPRO18-Cm, pPRO18-Kan, pPRO24, pPRO30, and pPRO33 (U.S. Pat. No. 8,178,338 B2; May 15, 2012; Keasling, Jay). A multiple cloning site can be used in the creation of an expression construct: by placing a multiple cloning site 3' to (or downstream of) a promoter sequence, the MCS can be used to insert the coding sequence for a gene product to be coexpressed into the construct, in the proper location relative to the promoter so that transcription of the coding sequence will occur. Depending on which restriction enzymes are used to cut within the MCS, there may be some part of the MCS sequence remaining within the expression construct after the coding sequence or other polynucleotide sequence is inserted into the expression construct. Any remaining MCS sequence can be upstream or, or downstream of, or on both sides of the inserted sequence. A ribosome binding site can be placed upstream of the MCS, preferably immediately adjacent to or separated from the MCS by only a few nucleotides, in which case the RBS would be upstream of any coding sequence inserted into the MCS. Another alternative is to include a ribosome binding site within the MCS, in which case the choice of restriction enzymes used to cut within the MCS will determine whether the RBS is retained, and in what relation to, the inserted sequences. A further alternative is to include a RBS within the polynucleotide sequence that is to be inserted into the expression construct at the MCS, preferably in the proper relation to any coding sequences to stimulate initiation of translation from the transcribed messenger RNA.

Expression from Constitutive Promoters.

Expression constructs of the invention can also comprise coding sequences that are expressed from constitutive promoters. Unlike inducible promoters, constitutive promoters initiate continual gene product production under most growth conditions. One example of a constitutive promoter is that of the Tn3 bla gene, which encodes beta-lactamase and is responsible for the ampicillin-resistance (Amp$^R$) phenotype conferred on the host cell by many plasmids, including pBR322 (ATCC 31344), pACYC177 (ATCC 37031), and pBAD24 (ATCC 87399). Another constitutive promoter that can be used in expression constructs is the promoter for the E. coli lipoprotein gene, lpp, which is located at positions 1755731-1755406 (plus strand) in E. coli K-12 substrain MG1655 (Inouye and Inouye, "Up-promoter mutations in the lpp gene of Escherichia coli", Nucleic Acids Res 1985 May 10; 13(9): 3101-3110). A further example of a constitutive promoter that has been used for heterologous gene expression in E. coli is the trpLEDCBA promoter, located at positions 1321169-1321133 (minus strand) in E. coli K-12 substrain MG1655 (Windass et al., "The construction of a synthetic Escherichia coli trp promoter and its use in the expression of a synthetic interferon gene", Nucleic Acids Res 1982 Nov. 11; 10(21): 6639-6657). Constitutive promoters can be used in expression constructs for the expression of selectable markers, as described herein, and also for the constitutive expression of other gene products useful for the coexpression of the desired product. For example, transcriptional regulators of the inducible promoters, such as AraC, PrpR, RhaR, and XylR, if not expressed from a bidirectional inducible promoter, can alternatively be expressed from a constitutive promoter, on either the same expression construct as the inducible promoter they regulate, or a different expression construct. Similarly, gene products useful for the production or transport of the inducer, such as PrpEC, AraE, or Rha, or proteins that modify the reduction-oxidation environment of the cell, as a few examples, can be expressed from a constitutive promoter within an expression construct. Gene products useful for the production of coexpressed gene products, and the resulting desired product, also include chaperone proteins, cofactor transporters, etc.

Signal Peptides.

Polypeptide gene products coexpressed by the methods of the invention can contain signal peptides or lack them, depending on whether it is desirable for such gene products to be exported from the host cell cytoplasm into the periplasm, or to be retained in the cytoplasm, respectively. Signal peptides (also termed signal sequences, leader sequences, or leader peptides) are characterized structurally by a stretch of hydrophobic amino acids, approximately five to twenty amino acids long and often around ten to fifteen amino acids in length, that has a tendency to form a single alpha-helix. This hydrophobic stretch is often immediately preceded by a shorter stretch enriched in positively charged amino acids (particularly lysine). Signal peptides that are to be cleaved from the mature polypeptide typically end in a stretch of amino acids that is recognized and cleaved by signal peptidase. Signal peptides can be characterized functionally by the ability to direct transport of a polypeptide, either co-translationally or post-translationally, through the plasma membrane of prokaryotes (or the inner membrane of gram negative bacteria like E. coli), or into the endoplasmic reticulum of eukaryotic cells. The degree to which a signal peptide enables a polypeptide to be transported into the periplasmic space of a host cell like E. coli, for example, can be determined by separating periplasmic proteins from proteins retained in the cytoplasm, using a method such as that provided in Example 12.

Host Cells.

The inducible coexpression systems of the invention are designed to express multiple gene products; in certain embodiments of the invention, the gene products are coexpressed in a host cell. Examples of host cells are provided that allow for the efficient and cost-effective inducible coexpression of components of multimeric products. Host cells can include, in addition to isolated cells in culture, cells that are part of a multicellular organism, or cells grown within a different organism or system of organisms. In addition, the expression constructs of the inducible coexpression systems of the invention can be used in cell-free systems, such as those based on wheat germ extracts or on bacterial cell extracts, such as a continuous-exchange cell-free (CECF) protein synthesis system using E. coli extracts and an incubation apparatus such as the RTS ProteoMaster (Roche Diagnostics GmbH; Mannheim, Germany) (Jun et al., "Continuous-exchange cell-free protein synthesis using PCR-generated DNA and an RNase E-deficient extract", Biotechniques 2008 March; 44(3): 387-391).

Prokaryotic host cells. In some embodiments of the invention, expression constructs designed for coexpression of gene products are provided in host cells, preferably prokaryotic host cells. Prokaryotic host cells can include archaea (such as Haloferax volcanii, Sulfolobus solfataricus), Gram-positive bacteria (such as Bacillus subtilis, Bacillus licheniformis, Brevibacillus choshinensis, Lactobacillus brevis, Lactobacillus buchneri, Lactococcus lactis, and Streptomyces lividans), or Gram-negative bacteria, including Alphaproteobacteria (Agrobacterium tumefaciens, Caulobacter crescentus, Rhodobacter sphaeroides, and Sinorhizobium meliloti), Betaproteobacteria (Alcaligenes eutrophus), and Gammaproteobacteria (Acinetobacter calcoaceticus, Azotobacter vinelandii, Escherichia coli, Pseudomonas aeruginosa, and Pseudomonas putida). Preferred host cells include Gammaproteobacteria of the family Enterobacteriaceae, such as Enterobacter, Erwinia, Escherichia (including E. coli), Klebsiella, Proteus, Salmonella (including Salmonella typhimurium), Serratia (including Serratia marcescans), and Shigella.

Eukaryotic host cells. Many additional types of host cells can be used for the inducible coexpression systems of the invention, including eukaryotic cells such as yeast (Candida shehatae, Kluyveromyces lactis, Kluyveromyces fragilis, other Kluyveromyces species, Pichia pastoris, Saccharomyces cerevisiae, Saccharomyces pastorianus also known as Saccharomyces carlsbergensis, Schizosaccharomyces pombe, Dekkera/Brettanomyces species, and Yarrowia lipolytica); other fungi (Aspergillus nidulans, Aspergillus niger, Neurospora crassa, Penicillium, Tolypocladium, Trichoderma reesia); insect cell lines (Drosophila melanogaster Schneider 2 cells and Spodoptera frugiperda Sf9 cells); and mammalian cell lines including immortalized cell lines (Chinese hamster ovary (CHO) cells, HeLa cells, baby hamster kidney (BHK) cells, monkey kidney cells (COS), human embryonic kidney (HEK, 293, or HEK-293) cells, and human hepatocellular carcinoma cells (Hep G2)). The above host cells are available from the American Type Culture Collection.

Alterations to Host Cell Gene Functions.

Certain alterations can be made to the gene functions of host cells comprising inducible expression constructs, to promote efficient and homogeneous induction of the host cell population by an inducer. Preferably, the combination of expression constructs, host cell genotype, and induction conditions results in at least 75% (more preferably at least 85%, and most preferably, at least 95%) of the cells in the culture expressing gene product from each induced promoter, as measured by the method of Khlebnikov et al. described in Example 8. For host cells other than E. coli, these alterations can involve the function of genes that are structurally similar to an *E. coli* gene, or genes that carry out a function within the host cell similar to that of the *E. coli* gene. Alterations to host cell gene functions include eliminating or reducing gene function by deleting the gene protein-coding sequence in its entirety, or deleting a large enough portion of the gene, inserting sequence into the gene, or otherwise altering the gene sequence so that a reduced level of functional gene product is made from that gene. Alterations to host cell gene functions also include increasing gene function by, for example, altering the native promoter to create a stronger promoter that directs a higher level of transcription of the gene, or introducing a missense mutation into the protein-coding sequence that results in a more highly active gene product. Alterations to host cell gene functions include altering gene function in any way, including for example, altering a native inducible promoter to create a promoter that is constitutively activated. In addition to alterations in gene functions for the transport and metabolism of inducers, as described herein with relation to inducible promoters, and an altered expression of chaperone proteins, it is also possible to alter the carbon catabolite repression (CCR) regulatory system and/or the reduction-oxidation environment of the host cell.

Carbon Catabolite Repression (CCR).

The presence of an active CCR regulatory system within a host can affect the ability of an inducer to activate transcription from an inducible promoter. For example, when a host cell such as *E. coli* is grown in a medium containing glucose, genes needed for the utilization of other carbon sources, such as the araBAD and prpBCDE operons, are expressed at a low level if at all, even if the arabinose or propionate inducer is also present in the growth medium. There is also a hierarchy of utilization of carbon sources other than glucose: as in the case of the ara and prp inducible promoter systems, where the presence of arabinose reduces the ability of propionate to induce expression from the prpBCDE promoter (Park et al., "The mechanism of sugar-mediated catabolite repression of the propionate catabolic genes in *Escherichia coli*", Gene 2012 Aug. 1; 504(1): 116-121; Epub 2012 May 3). The CCR mechanism of the cell therefore makes it more difficult to use two or more carbon-source inducers in an inducible coexpression system, as the presence of the inducer that is the preferred carbon source will inhibit induction by less-preferred carbon sources. The Park et al. authors attempted to relieve the repression of the prp promoter by arabinose, by using either a mutant crp gene that produces an altered cAMP receptor protein that can function independently of cAMP, or a deletion of PTS (phosphotransferase system) genes involved in the regulation of CCR; both approaches were largely unsuccessful. However, the PTS-knockout strain used by the Park et al. authors is based on strain TP2811, which is a deletion of the *E. coli* ptsHI-crr operon (Hernandez-Montalvo et al., "Characterization of sugar mixtures utilization by an *Escherichia coli* mutant devoid of the phosphotransferase system", Appl Microbiol Biotechnol 2001 October; 57(1-2): 186-191). Deletion of the entire ptsHI-crr operon has been found to affect total cAMP synthesis more significantly than a deletion of just the crr gene (Levy et al., "Cyclic AMP synthesis in *Escherichia coli* strains bearing known deletions in the pts phosphotransferase operon", Gene 1990 Jan. 31; 86(1): 27-33). A different approach is to eliminate or reduce the function of ptsG gene in the host cell, which encodes glucose-specific EII A (EII $A^{glc}$), a key element for CCR in *E. coli* (Kim et al., "Simultaneous consumption of pentose and hexose sugars: an optimal microbial phenotype for efficient fermentation of lignocellulosic biomass", Appl Microbiol Biotechnol 2010 November; 88(5): 1077-1085, Epub 2010 Sep. 14). Another alteration in the genome of a host cell such as *E. coli*, which leads to increased transcription of the prp promoter, is to eliminate or reduce the gene function of the ascG gene, which encodes AscG. AscG is the repressor of the beta-D-glucoside-utilization operon ascFB under normal growth conditions, and also represses transcription of the prp promoter; disruption of the AscG coding sequence has been shown to increase transcription from the prp promoter (Ishida et al., "Participation of regulator AscG of the beta-glucoside utilization operon in regulation of the propionate catabolism operon", J Bacteriol 2009 October; 191(19): 6136-6144; Epub 2009 Jul. 24). A further alternative is to increase expression of the transcriptional regulator of promoters inducible by the less-preferred carbon-source inducer, by placing it either under the control of a strong constitutive promoter, or under the control of the more-preferred carbon-source inducer. For example, to increase the induction of genes needed for the utilization of the less-preferred carbon source xylose in the presence of the more-preferred arabinose, the coding sequence for XylR is placed into the *E. coli* araBAD operon (Groff et al., "Supplementation of intracellular XylR leads to coutilization of hemicellulose sugars", Appl Environ Microbiol 2012 April; 78(7): 2221-2229, Epub 2012 Jan. 27). Host cells comprising inducible coexpression constructs therefore preferably include an increased level of gene function for transcriptional regulators of promoters inducible by the less-preferred carbon-source inducer(s), and an eliminated or reduced gene function for genes involved in the CCR system, such as crr and/or ptsG and/or ascG.

Cellular Transport of Heme and Other Cofactors.

When using the inducible coexpression systems of the invention to produce enzymes that require cofactors for function, it is helpful to use a host cell capable of synthesizing the cofactor from available precursors, or taking it up from the environment. Common cofactors include ATP, coenzyme A, flavin adenine dinucleotide (FAD), $NAD^+$/NADH, and heme. Heme groups comprise an iron ion in the center of a large heterocyclic organic ring called a porphyrin. The most common type of heme group is heme B; other major types are heme A, heme C, and heme 0, which vary in the side chains of the porphyrin. Hemin is a chloride salt of heme B and can be added to bacterial growth medium as a source of heme. Other potential sources of heme include cytochromes, hemoglobin, and hemoglobin-containing substances such as blood. Laboratory strains of *E. coli* derived from *E. coli* K12 typically lack an outer-membrane heme receptor, and thus do not transport heme into the cell, failing to grow in media where heme is the only iron source. Pathogenic strains of *E. coli* such as O157:H7 and CFT073 contain an approximately 9-kb genomic segment that is not present in *E. coli* K12, and that contains two divergently transcribed operons encoding proteins involved in heme uptake and utilization: the chuAS operon, and the chuTWXYUhmuV operon. This genomic segment is found in *E. coli* CFT073 and includes the NCBI Reference Sequence NC_004431.1 (20 Jan. 2012) from position 4,084,974 to 4,093,975. Transformation with the chuA gene (for example, NCBI Gene ID No. 1037196), which encodes an outer-membrane hemin-specific receptor, was sufficient to confer on a K12-derived *E. coli* strain the ability to grow on hemin as an iron source (Torres and Payne, "Haem iron-transport system in enterohaemorrhagic *Escherichia coli* O157:H7", Mol Microbiol 1997 February; 23(4): 825-833). In addition to ChuA, some other heterologous heme receptors can allow *E. coli* K12-derived strains to take up heme: *Yersinia enterocolitica* HemR, *Serratia marcescens* HasR, and *Shigella dysenteria* ShuA; and from gram-negative bacteria: *Bordatella pertussis* and *B. bronchiseptica* BhuR, *Pseudomonas aeruginosa* PhuR, and *P. fluorescens* PfhR. The ChuS protein is also involved in the utilization of heme: it is a heme-degrading heme oxygenase. In an *E. coli* aroB strain, which is deficient in the synthesis of the iron-chelating molecule enterobactin, transformation with chuS was useful in reducing cellular toxicity caused by growth on hemin in the absence of enterobactin. Transcription of the chuAS and chuTWXYUhmuV operons, and several other operons that are involved in iron metabolism and present in *E. coli* K12 strains, is repressed by the *E. coli* Fur transcriptional regulator when Fur is associated with $Fe^{2+}$; transcription of these genes is thus activated when there is a drop in the intracellular concentration of iron ions.

Host cells such as *E. coli* K12-derived strains can be altered to enable them to take up heme by transforming them with all or part of the chuAS-chuTWXYUhmuV region containing at least chuA, or with the chuAS operon, optionally including additional genes from the chuTWXYUhmuV operon. In embodiments where the promoter directing chuA transcription is repressible by Fur, Fur repression can be eliminated or reduced by deleting the host cell gene encoding Fur, by growing host cells in the absence of free iron, by growing host cells in the presence of a chelator of free iron ions such as EDTA (ethylenediaminetetraacetic acid), or by transforming cells with polynucleotide constructs (such as plasmids maintained at high copy number) comprising multiple copies of the Fur binding site, to reduce the amount of $Fur-Fe^{2+}$ complex available for repression of iron-metabolism operons. In a preferred embodiment, an expression construct is introduced into the host cell, wherein the expression construct comprises a polynucleotide encoding ChuA, and optionally also encoding ChuS, under the transcriptional control of a constitutive promoter.

Host Cell Reduction-Oxidation Environment.

Many multimeric gene products, such as antibodies, contain disulfide bonds. The cytoplasm of *E. coli* and many other cells is normally maintained in a reduced state by the thioredoxin and the glutaredoxin/glutathione enzyme systems. This precludes the formation of disulfide bonds in the cytoplasm, and proteins that need disulfide bonds are exported into the periplasm where disulfide bond formation and isomerization is catalyzed by the Dsb system, comprising DsbABCD and DsbG. Increased expression of the cysteine oxidase DsbA, the disulfide isomerase DsbC, or combinations of the Dsb proteins, which are all normally transported into the periplasm, has been utilized in the expression of heterologous proteins that require disulfide bonds (Makino et al., "Strain engineering for improved expression of recombinant proteins in bacteria", Microb Cell Fact 2011 May 14; 10: 32). It is also possible to express cytoplasmic forms of these Dsb proteins, such as a cytoplasmic version of DsbC ('cDsbC'), that lacks a signal peptide and therefore is not transported into the periplasm. Cytoplasmic Dsb proteins such as cDsbC are useful for making the cytoplasm of the host cell more oxidizing and thus more conducive to the formation of disulfide bonds in heterologous proteins produced in the cytoplasm. The host cell cytoplasm can also be made more oxidizing by altering the thioredoxin and the glutaredoxin/glutathione enzyme systems directly: mutant strains defective in glutathione reductase (gor) or glutathione synthetase (gshB), together with thioredoxin reductase (trxB), render the cytoplasm oxidizing. These strains are unable to reduce ribonucleotides and therefore cannot grow in the absence of exogenous reductant, such as dithiothreitol (DTT).

Suppressor mutations (ahpC*) in the gene ahpC, which encodes the peroxiredoxin AhpC, convert it to a disulfide reductase that generates reduced glutathione, allowing the channeling of electrons onto the enzyme ribonucleotide reductase and enabling the cells defective in gor and trxB, or defective in gshB and trxB, to grow in the absence of DTT. A different class of mutated forms of AhpC can allow strains, defective in the activity of gamma-glutamylcysteine synthetase (gshA) and defective in trxB, to grow in the absence of DTT; these include AhpC V164G, AhpC S71F, AhpC E173/S71F, AhpC E171Ter, and AhpC dup162-169 (Faulkner et al., "Functional plasticity of a peroxidase allows evolution of diverse disulfide-reducing pathways", Proc Natl Acad Sci USA 2008 May 6; 105(18): 6735-6740, Epub 2008 May 2). In such strains with oxidizing cytoplasm, exposed protein cysteines become readily oxidized in a process that is catalyzed by thioredoxins, in a reversal of their physiological function, resulting in the formation of disulfide bonds.

Another alteration that can be made to host cells is to express the sulfhydryl oxidase Erv1p from the inner membrane space of yeast mitochondria in the host cell cytoplasm, which has been shown to increase the production of a variety of complex, disulfide-bonded proteins of eukaryotic origin in the cytoplasm of *E. coli*, even in the absence of mutations in gor or trxB (Nguyen et al., "Pre-expression of a sulfhydryl oxidase significantly increases the yields of eukaryotic disulfide bond containing proteins expressed in the cytoplasm of *E. coli*" Microb Cell Fact 2011 Jan. 7; 10: 1). Host cells comprising inducible coexpression constructs preferably also express cDsbC and/or Erv1p, are deficient in trxB gene function, are also deficient in the gene function of either gor, gshB, or gshA, and express an appropriate mutant form of AhpC so that the host cells can be grown in the absence of DTT.

Glycosylation of polypeptide gene products. Host cells can have alterations in their ability to glycosylate polypeptides. For example, eukaryotic host cells can have eliminated or reduced gene function in glycosyltransferase and/or oligo-saccharyltransferase genes, impairing the normal eukaryotic glycosylation of polypeptides to form glycoproteins. Prokaryotic host cells such as *E. coli*, which do not normally glycosylate polypeptides, can be altered to express a set of eukaryotic and prokaryotic genes that provide a glycosylation function (DeLisa et al., "Glycosylated protein expression in prokaryotes", WO2009089154A2, 2009 Jul. 16).

Available Host Cell Strains with Altered Gene Functions.

To create preferred strains of host cells to be used in the inducible coexpression systems and methods of the invention, it is useful to start with a strain that already comprises desired genetic alterations (Table 3).

TABLE 3

Host Cell Strains

| Strain: | Genotype: | Source: |
|---|---|---|
| E. coli TOP10 | F-mcrA Δ(mrr-hsdRMS-mcrBC) φ80lacZΔM15 ΔlacX74 recA1 araD139 Δ(ara-leu)7697 galU galK rpsL (Str$^R$) endA1 nupG λ- | Invitrogen Life Technologies Catalog nos. C4040-10, C4040-03, C4040-06, C4040-50, and C4040-52 |
| E. coli Origami™ 2 | Δ(ara-leu)7697 ΔlacX74 ΔphoA PvuII phoR araD139 ahpC galE galK rpsL F'[lac$^+$ lacI$^q$ pro] gor522::Tn10 trxB (Str$^R$, Tet$^R$) | Merck (EMD Millipore Chemicals) Catalog No. 71344 |
| E. coli SHuffle ® Express | fhuA2 [lon] ompT ahpC gal λatt::pNEB3-r1-cDsbC (Spec, lacI) ΔtrxB sulA11 R(mcr-73::miniTn10--Tet$^S$)2 [dcm] R(zgb-210::Tn10--Tet$^S$) endA1 Δgor Δ(mcrC-mrr)114::IS10 | New England Biolabs Catalog No. C3028H |

Methods of Altering Host Cell Gene Functions.

There are many methods known in the art for making alterations to host cell genes in order to eliminate, reduce, or change gene function. Methods of making targeted disruptions of genes in host cells such as E. coli and other prokaryotes have been described (Muyrers et al., "Rapid modification of bacterial artificial chromosomes by ET-recombination", Nucleic Acids Res 1999 Mar. 15; 27(6): 1555-1557; Datsenko and Wanner, "One-step inactivation of chromosomal genes in Escherichia coli K12 using PCR products", Proc Natl Acad Sci USA 2000 Jun. 6; 97(12): 6640-6645), and kits for using similar Red/ET recombination methods are commercially available (for example, the Quick & Easy E. coli Gene Deletion Kit from Gene Bridges GmbH, Heidelberg, Germany). In one embodiment of the invention, the function of one or more genes of host cells is eliminated or reduced by identifying a nucleotide sequence within the coding sequence of the gene to be disrupted, such as one of the E. coli K-12 substrain MG1655 coding sequences incorporated herein by reference to the genomic location of the sequence, and more specifically by selecting two adjacent stretches of 50 nucleotides each within that coding sequence. The Quick & Easy E. coli Gene Deletion Kit is then used according to the manufacturer's instructions to insert a polynucleotide construct containing a selectable marker between the selected adjacent stretches of coding sequence, eliminating or reducing the normal function of the gene. Red/ET recombination methods can also be used to replace a promoter sequence with that of a different promoter, such as a constitutive promoter, or an artificial promoter that is predicted to promote a certain level of transcription (De Mey et al., "Promoter knock-in: a novel rational method for the fine tuning of genes", BMC Biotechnol 2010 Mar. 24; 10: 26). The function of host cell genes can also be eliminated or reduced by RNA silencing methods (Man et al., "Artificial trans-encoded small non-coding RNAs specifically silence the selected gene expression in bacteria", Nucleic Acids Res 2011 April; 39(8): e50, Epub 2011 Feb. 3). Further, known mutations that alter host cell gene function can be introduced into host cells through traditional genetic methods.

Inducible Coexpression Systems of the Invention

Figure 1:
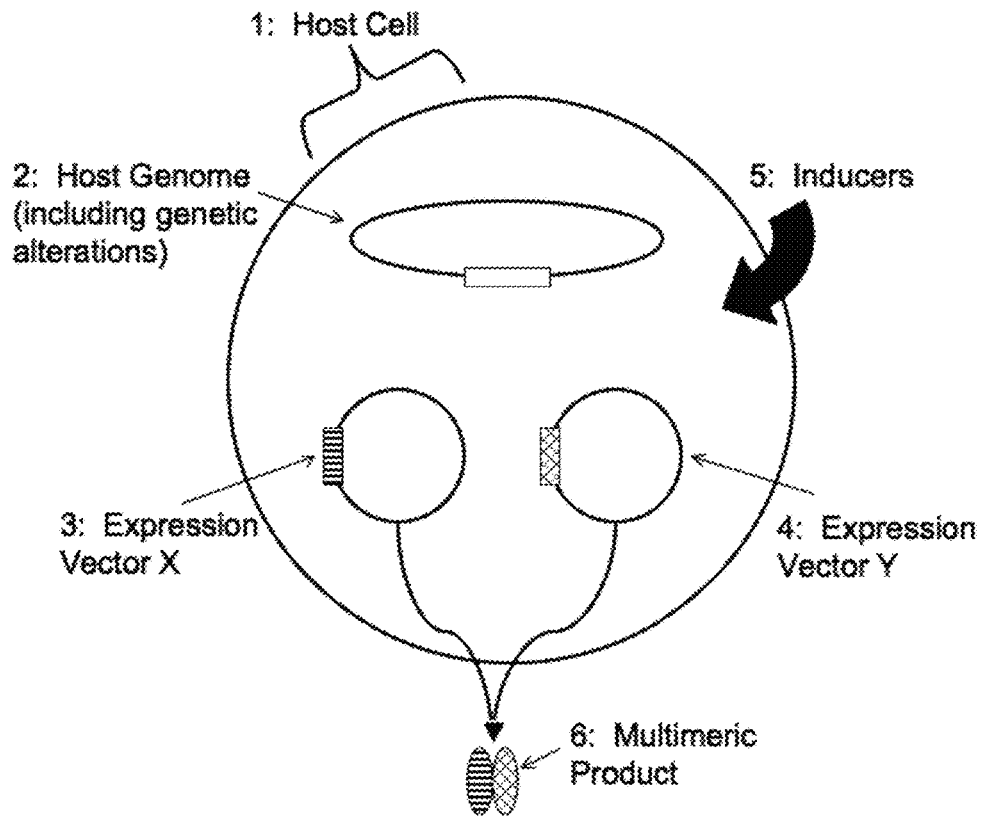
FIG. 1 is a schematic illustration of the inducible coexpression system, which includes a host cell (1) comprising two different inducible expression vectors (3) and (4), which express different gene products upon application of inducers (5), forming a multimeric product (6).

Inducible coexpression systems of the invention involve host cells comprising two or more expression constructs, where the expression constructs comprise inducible promoters directing the expression of gene products, and the host cells have altered gene functions that allow for homogeneous inducible expression of the gene products. FIG. 1 shows a schematic representation of an inducible coexpression system of the invention, with the following components: (1) host cell, (2) host genome (including genetic alterations), (3) an expression vector 'X' comprising an inducible promoter directing expression of a gene product, (4) a different expression vector 'Y' comprising an inducible promoter directing expression of another gene product, (5) chemical inducers of expression, and (6) the multimeric coexpression product.

Figure 2:
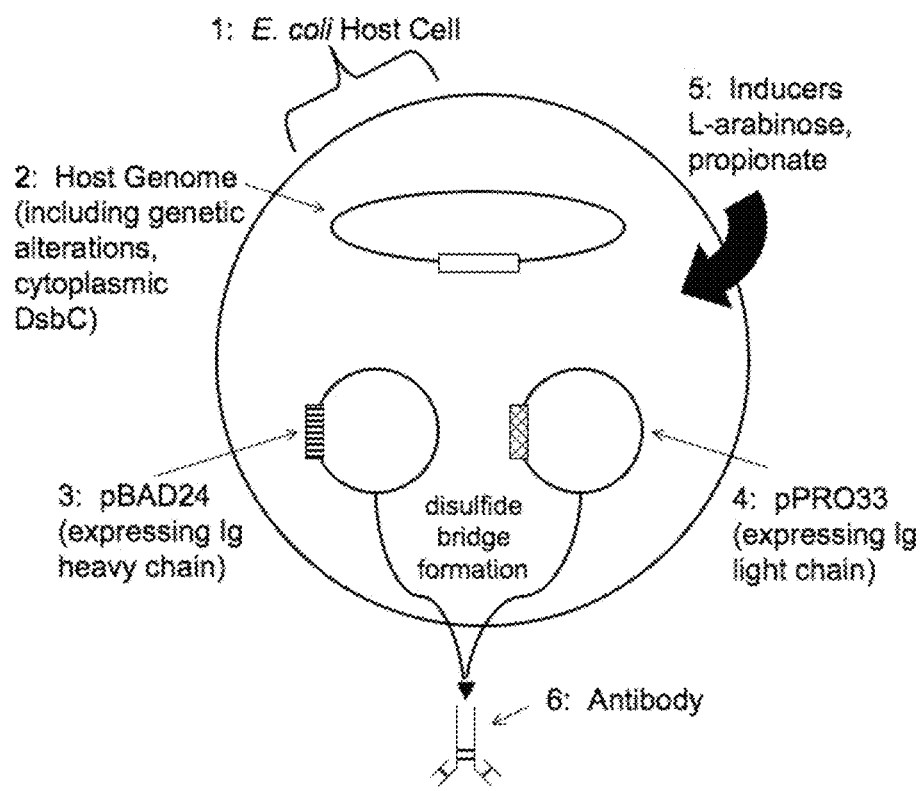
FIG. 2 is a schematic illustration of a particular use of the inducible coexpression system, in which the *E. coli* host cell genome (2) encodes a cytoplasmic form of the disulfide isomerase DsbC which lacks a signal peptide; the expression vector pBAD24 (3) provides L-arabinose-inducible expression of an immunoglobulin heavy chain, and the expression vector pPRO33 (4) provides propionate-inducible expression of an immunoglobulin light chain; forming upon induction (5) the multimeric antibody product (6).

FIG. 2 shows a schematic representation of a particular example of an inducible coexpression system of the invention, utilizing the araBAD promoter on a pBAD24 expression vector in combination with a propionate-inducible promoter (prpBCDE promoter) on a pPRO33 expression vector (U.S. Pat. No. 8,178,338 B2; May 15, 2012; Keasling, Jay), in an E. coli host cell housing the appropriate genomic alterations which allow for homogenously inducible expression. In this manner, tight control and optimization of expression of each component of a multimeric product can be achieved for use in a number of coexpression applications. In this embodiment, the host cell (1) is the Gram-negative bacterium Escherichia coli, commonly used in the art for protein expression. The host genome (2) is the genome of the host cell organism with mutations or other alterations that facilitate homogenously inducible protein coexpression, including expression of a cytoplasmic form of the disulfide isomerase DsbC which lacks a signal peptide. In one embodiment, the genomic alterations include both an araBAD operon knockout mutation, and either expression of araE and araFGH from constitutive promoters, or a point mutation in the lacY gene (A117C) in an araEFGH-deficient background, to facilitate homogenous induction of plasmid-based ara promoters with exogenously applied L-arabinose, and also an inactivated proprionate metabolism gene, prpD, to facilitate homogenous induction of plasmid-based propionate promoters with exogenously applied propionate, which is converted to 2-methylcitrate in vivo. Other genomic alterations that are useful for the inducible coexpression system, and may be introduced into the host cell, include without limitation: targeted inactivation of the scpA-argK-scpBC operon, to reduce background expression from the prpBCDE promoter; expression of the transcriptional regulator (prpR) for the less-preferred carbon-source (propionate) from an L-arabinose-inducible promoter such as the araBAD promoter, and/or an eliminated or reduced gene function for genes involved in the CCR system, such as crr and/or ptsG, to avoid suppression by the CCR system of induction by propionate in the presence of L-arabinose; reductions in the level of gene function for glutathione reductase (gor) or glutathione synthetase (gshB), together with thioredoxin reductase (trxB), and/or expression of yeast mitochondrial sulfhydryl oxidase Erv1p in the host cell cytoplasm, to provide a less strongly reducing environment in the host cell cytoplasm and promote disulfide bond formation; increased levels of expression, such as from a strong constitutive promoter, of chaperone proteins such as DnaK/DnaJ/GrpE, DsbC/DsbG, GroEL/GroES, IbpA/IbpB, Skp, Tig (trigger factor), and/or FkpA; and other mutations to reduce endogenous protease activity (such as that of the Lon and OmpT proteases) and recombinase activities.

As shown in FIG. 2, two compatible expression vectors (3, 4) are maintained in the host cell to allow for simultaneous expression (coexpression) of two different gene products. In this embodiment, one expression vector ('L-arabinose-induced expression vector') contains an L-arabinose-induced promoter, and is similar or identical to pBAD or related plasmids in which an araBAD promoter drives expression of an inserted expression sequence cloned into the multiple cloning site (MCS). The L-arabinose-induced expression vector also contains a coding sequence for an antibiotic-resistance gene (such as the Tn3 bla gene, which encodes beta-lactamase and confers resistance to ampicillin) to facilitate selection of host cells (bacterial colonies) which contain an intact expression vector. An origin of replication (ORI) is required for propagation of the plasmid within bacterial host cells. The L-arabinose induced expression plasmid also contains a polynucleotide sequence encoding araC, a transcriptional regulator that allows for L-arabinose induction of the araBAD promotor and through transcriptional repression reduces 'leaky' background expression in the non-induced state. The other expression vector ('propionate-induced expression vector') is similar or identical to pPRO or related plasmids, in which a propionate-induced promoter drives expression of an inserted expression sequence cloned into the multiple cloning site (MCS). The plasmid also contains a coding sequence for an antibiotic-resistance gene (such as the cat gene, encoding chloramphenicol acetyltransferase, which confers resistance to chloramphenicol) to facilitate selection of host cells which contain an intact expression vector. An origin of replication (ORI) is required for propagation of the plasmid within bacterial host cells. In addition, the propionate-induced expression vector contains a polynucleotide sequence encoding prpR, a transcriptional regulator that allows for propionate (2-methylcitrate) induction of the prpBCDE promotor and reduces 'leaky' background expression in the non-induced state. To facilitate separate titration of induction, plasmid compatibility, and copropagation of the expression vectors, it is useful for the expression vectors to contain promoters responsive to different inducers, compatible origins of replication, and different antibiotic-resistance markers. In one embodiment of the invention, a pBAD24 or related expression vector (pMB1 or 'pBR322' ORI, Amp$^R$) containing an L-arabinose-inducible araBAD promoter is combined in a host cell with a pPRO33 or related expression vector (p15A ORI, Cm$^R$) containing a propionate-inducible prpBCDE promoter. The expression vectors are co-propagated and maintained using growth medium supplemented with ampicillin and chloramphenicol. In one embodiment, one expression vector comprises a polynucleotide sequence encoding the heavy chain of a full-length antibody, and the other expression vector comprises a polynucleotide sequence encoding the light chain of a full-length antibody, each coding sequence cloned in-frame into the MCS of the respective expression vector. For production of certain gene products such as antibodies, coding sequence optimization for the host organism (including adjustment for codon bias and GC-content, among other considerations) will determine the coding sequences to be inserted into the expression constructs of the coexpression system.

Referring again to FIG. 2, coexpression of gene products is induced by inexpensive exogenously applied chemical metabolites, L-arabinose and propionate (5). The level of induction of expression of each gene product is independently titrated with its own chemical inducer, thereby facilitating optimization of protein coexpression. This is useful for expression of protein complexes and proteins that require a binding partner for stabilization, and may facilitate expression of otherwise difficult to express proteins, such as those with poor solubility or cellular toxicity. In this example, upon induction, antibody heavy and short chains are each separately expressed, then the proteins join and form interchain disulfide bridges (within the cytoplasm of the bacterial host) which allows the formation and stabilization of full-length antibody comprised of the heavy and light chains. Proteins can be directed to various compartments of the host organism. For example, in E. coli the protein can be expressed in the cytoplasm, cell membrane, periplasm, or secreted into the medium. After an appropriate incubation time, cells and media are collected, and the total protein extracted, which includes the coexpressed gene products (6). After extraction, the desired product can be purified using a number of methods well known in the art depending on the nature of the gene products produced in the coexpression system (for example liquid chromatography). In the example shown in FIG. 2, the multimeric product (full-length antibody) is extracted and purified using chromatographic methods. Purified intact antibody is visualized on a non-denaturing gel using standard techniques, including protein-binding dyes or immunohistochemistry. The full-length antibody product can then be used for a number of research, diagnostic, or other applications.

Products Made by the Methods of the Invention

There is broad versatility in utilizing the inducible coexpression systems of the present invention in numerous coexpression applications, and in the properties of the products.

Glycosylation.

Gene products coexpressed by the methods of the invention may be glycosylated or unglycosylated. In one embodiment of the invention, the coexpressed gene products are polypeptides. Glycosylated polypeptides are polypeptides that comprise a covalently attached glycosyl group, and include polypeptides comprising all the glycosyl groups normally attached to particular residues of that polypeptide (fully glycosylated polypeptides), partially glycosylated polypeptides, polypeptides with glycosylation at one or more residues where glycosylation does not normally occur (altered glycosylation), and polypeptides glycosylated with at least one glycosyl group that differs in structure from the glycosyl group normally attached to one or more specified residues (modified glycosylation). An example of modified glycosylation is the production of "defucosylated" or "fucose-deficient" polypeptides, polypeptides lacking fucosyl moieties in the glycosyl groups attached to them, by expression of polypeptides in host cells lacking the ability to fucosylate polypeptides. Unglycosylated polypeptides are polypeptides that do not comprise a covalently bound glycosyl group. An unglycosylated polypeptide can be the result of deglycosylation of a polypeptide, or of production of an aglycosylated polypeptide. Deglycosylated polypeptides can be obtained by enzymatically deglycosylating glycosylated polypeptides, whereas aglycosylated polypeptides can be produced by expressing polypeptides in host cells that do not have the capability to glycosylate polypeptides, such as prokaryotic cells or cells in which the function of at least one glycosylation enzyme has been eliminated or reduced. In a particular embodiment, the coexpressed polypeptides are aglycosylated, and in a more specific embodiment, the aglycosylated polypeptides are coexpressed in prokaryotic cells such as *E. coli*.

Other Modifications of Gene Products.

Gene products coexpressed by the methods of the invention may be covalently linked to other types of molecules. Examples of molecules that may be covalently linked to coexpressed gene products, without limiting the scope of the invention, include polypeptides (such as receptors, ligands, cytokines, growth factors, polypeptide hormones, DNA-binding domains, protein interaction domains such as PDZ domains, kinase domains, antibodies, and fragments of any such polypeptides); water-soluble polymers (such as polyethylene glycol (PEG), carboxymethylcellulose, dextran, polyvinyl alcohol, polyoxyethylated polyols (such as glycerol), polyethylene glycol propionaldehyde, and similar compounds, derivatives, or mixtures thereof); and cytotoxic agents (such as chemotherapeutic agents, growth-inhibitory agents, toxins (such as enzymatically active toxins of bacterial, fungal, plant, or animal origin, or fragments thereof), and radioactive isotopes).

In addition, gene products to be coexpressed by the methods of the invention can be designed to include molecular moieties that aid in the purification and/or detection of the gene products. Many such moieties are known in the art; as one example, a polypeptide gene product can be designed to include a polyhistidine 'tag' sequence—a run of six or more histidines, preferably six to ten histidine residues, and most preferably six histidines—at its N- or C-terminus. The presence of a polyhistidine sequence on the end of a polypeptide allows it to be bound by cobalt- or nickel-based affinity media, and separated from other polypeptides. The polyhistidine tag sequence can be removed by exopeptidases. As another example, fluorescent protein sequences can be expressed as part of a polypeptide gene product, with the amino acid sequence for the fluorescent protein preferably added at the N- or C-terminal end of the amino acid sequence of the polypeptide gene product. The resulting fusion protein fluoresces when exposed to light of certain wavelengths, allowing the presence of the fusion protein to be detected visually. A well-known fluorescent protein is the green fluorescent protein of *Aequorea victoria*, and many other fluorescent proteins are commercially available, along with nucleotide sequences encoding them.

Antibodies.

In one embodiment of the invention, the coexpressed gene products are antibodies. The term 'antibody' is used in the broadest sense and specifically includes 'native' antibodies, fully-human antibodies, humanized antibodies, chimeric antibodies, multispecific antibodies (such as bispecific antibodies), monoclonal antibodies, polyclonal antibodies, antibody fragments, and other polypeptides derived from antibodies that are capable of binding antigen. Unless indicated otherwise herein, the numbering of the residues in an immunoglobulin heavy chain ('EU numbering') is that of the EU index (the residue numbering of the human IgG1 EU antibody) as in Kabat et al., *Sequences of Proteins of Immunological Interest*, Fifth Edition, 1991, National Institute of Health, Bethesda, Md.

'Native' antibodies are usually heterotetrameric glycoproteins of about 150,000 daltons, composed of two identical light (L) chains and two identical heavy (H) chains. Each light chain is linked to a heavy chain by one covalent disulfide bond, while the number of inter-chain disulfide linkages varies among the heavy chains of different immunoglobulin isotypes. Each heavy and light chain also has regularly spaced intrachain disulfide bridges. Each heavy chain has at its N-terminal end a variable domain ($V_H$) followed by a number of constant domains. Each light chain has a variable domain at it N-terminal end ($V_L$) and a constant domain at its C-terminal end; the constant domain of the light chain is aligned with the first constant domain of the heavy chain, and the light-chain variable domain is aligned with the variable domain of the heavy chain. The term 'variable' refers to the fact that certain portions of the variable domains differ extensively in sequence among antibodies and are used in the binding and specificity of each particular antibody for an antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, connected by three HVRs, and with the HVRs from the other chain, contribute to the formation of the antigen-binding site of antibodies.

The term 'Fc region' refers to a C-terminal region of an immunoglobulin heavy chain, and includes native Fc regions and variant Fc regions. Although the boundaries of the Fc region of an immunoglobulin heavy chain might vary, the human IgG heavy-chain Fc region can be defined to stretch from an amino acid residue at position Cys226, or from Pro230, to the carboxyl-terminus thereof. Alternatively, the Fc region can be defined to extend from the N-terminal residue (Ala231) of the conserved $C_H2$ immunoglobulin domain to the C-terminus, and may include multiple conserved domains such as $C_H2$, $C_H3$, and $C_H4$. The C-terminal lysine (residue 447 according to the EU numbering system) of the native Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. The Fc region of an antibody is crucial for recruitment of immunological cells and antibody dependent cytotoxicity (ADCC). In particular, the nature of the ADCC response elicited by antibodies depends on the interaction of the Fc region with receptors (FcRs) located on the surface of many cell types. Humans contain at least five different classes of Fc receptors. The binding of an antibody to FcRs determines its ability to recruit other immunological cells and the type of cell recruited. Hence, the ability to engineer antibodies with altered Fc regions that can recruit only certain kinds of cells can be critically important for therapy (US Patent Application 20090136936 A1, May 28, 2009, Georgiou, George). Native antibodies produced by mammalian cells typically comprise a branched, biantennary oligosaccharide that is generally attached by an N-linkage to Asn297 of the CH2 domain of the Fc region. In certain embodiments, antibodies produced by the methods of the invention are not glycosylated or are aglycosylated, for example, due to a substitution at residue 297 of the Fc region, or to expression in a host cell that does not have the capability to glycosylate polypeptides. Due to altered ADCC responses, unglycosylated antibodies may stimulate a lower level of inflammatory responses such as neuroinflammation. Also, since an antibody having an aglycosylated Fc region has very low binding affinity for Fc receptors, such antibodies would not bind to the large number of immune cells that bear these receptors. This is a significant advantage since it reduces non-specific binding, and also increases the half-life of the antibody in vivo, making this attribute very beneficial in therapeutics.

The terms 'full-length antibody', 'intact antibody', and 'whole antibody' are used interchangeably to refer to an antibody in its substantially intact 'native' form, not antibody fragments as defined below. The terms particularly refer to an antibody with heavy chains that each comprise a variable domain and an Fc region. 'Antibody fragments' comprise a portion of an intact antibody, preferably comprising the antigen-binding region thereof. Examples of antibody fragments include Fab, Fab', F(ab')$_2$, Fc, Fd, and Fv fragments; diabodies; linear antibodies; single-chain antibody molecules such as scFv; and multispecific antibodies formed from antibody fragments.

A 'human antibody' is one that possesses an amino-acid sequence corresponding to that of an antibody produced by a human. A 'chimeric' antibody is one in which a portion of the heavy and/or light chain is identical to, or shares a certain degree of amino acid sequence identity with, corresponding sequences in antibodies derived from a particular species or belonging to a particular antibody class or subclass, while the remainder of the chain(s) is identical to, or shares a certain degree of amino acid sequence identity with, corresponding sequences in antibodies derived from another species or belonging to another antibody class or subclass, as well as fragments of such antibodies. A 'humanized' antibody is a chimeric antibody that contains minimal amino acid residues derived from non-human immunoglobulin molecules. In one embodiment, a humanized antibody is a human immunoglobulin (recipient antibody) in which HVR residues of the recipient antibody are replaced by residues from an immunoglobulin HVR of a non-human species (donor antibody) such as mouse, rat, rabbit, or non-human primate. In some instances, FR residues of the human recipient antibody are replaced by corresponding non-human residues. Furthermore, humanized antibodies may comprise residues that are not found in the recipient antibody or in the donor antibody. The term 'monoclonal antibody' refers to an antibody obtained from a population of substantially homogeneous antibodies, in that the individual antibodies comprising the population are identical except for possible mutations, such as naturally occurring mutations, that may be present in minor amounts. Thus, the modifier 'monoclonal' indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against the same single determinant on an antigen. In addition to their specificity, monoclonal antibody preparations are advantageous in that they are typically uncontaminated by other immunoglobulins.

The 'binding affinity' of a molecule such as an antibody generally refers to the strength of the sum total of non-covalent interactions between a single binding site of a molecule and its binding partner (such as an antibody and the antigen it binds). Unless indicated otherwise, 'binding affinity' refers to intrinsic binding affinity that reflects a 1:1 interaction between members of a binding pair (such as antibody and antigen). The affinity of a molecule X for its partner Y can generally be represented by the dissociation constant (Kd). Low-affinity antibodies (higher Kd) generally bind antigen slowly and tend to dissociate readily, whereas high-affinity antibodies (lower Kd) generally bind antigen faster and tend to remain bound longer. A variety of ways to measure binding affinity are known in the art, any of which can be used for purposes of the present invention. Specific illustrative methods for measuring binding affinity are described in Example 10. Antibodies and antibody fragments produced by and/or used in methods of the invention preferably have binding affinities of less than 100 nM, more preferably have binding affinities of less than 10 nM, and most preferably have binding affinities of less than 2 nM, as measured by a surface-plasmon resonance assay as described in Example 10.

Antibodies (Secondary) that Recognize Aglycosylated Antibodies.

Production of antibodies in *E. coli*-based or other prokaryotic expression systems without glycosylation enzymes will generally yield aglycosylated antibodies, which can be used as primary antibodies. In addition to using the inducible coexpression systems of the invention to produce aglycosylated primary antibodies, the inducible coexpression systems of the invention can also be used to efficiently produce secondary antibodies that specifically recognize aglycosylated primary antibodies. One aspect of the present invention is a secondary antibody system capable of detecting an unglycosylated or aglycosylated primary antibody for research, analytic, diagnostic, or therapeutic purposes. As one example, a secondary antibody system is provided with the following components: epitope, primary antibody, secondary antibody, and detection system. The epitope is a portion of an antigen (usually a protein) which is the antigenic determinant that produces an immunological response when introduced into a live animal or is otherwise recognizable by an antibody. In practice, the epitope of interest may be present within a mixture or a tissue. In one embodiment, the epitope is a protein expressed in carcinoma cells in human tissue. The primary antibody is an antibody fragment, a single full-length antibody (monoclonal), or a mixture of different full-length antibodies (polyclonal), which recognizes and binds to the epitope, and preferably binds specifically to the epitope. A full-length antibody in this example comprises two heavy polypeptide chains and two light polypeptide chains joined by disulfide bridges. Each of the chains comprises a constant region (Fc) and a variable region (Fv). There are two antigen binding sites in the full-length antibody. In one embodiment of the present invention, the primary antibody is a full-length aglycosylated antibody (such as that produced in an *E. coli*-based expression system) which recognizes and binds an epitope of interest. The secondary antibody is an antibody fragment, a single full-length antibody (monoclonal), or a mixture of different full-length antibodies (polyclonal), which recognizes and binds to the aglycosylated primary antibody, and preferably binds specifically to the aglycosylated primary antibody. In one embodiment of the present invention, the secondary antibody is a full-length antibody which recognizes and binds the aglycosylated Fc portion of a full-length primary antibody. In this case, the antibody binding sites are selected and/or engineered to specifically recognize the Fc portion of the aglycosylated primary antibody, with or without the C-terminal lysine residue. In other embodiments, the secondary antibody could be engineered to recognize additional regions (epitopes) of the aglycosylated primary antibody, or additional engineered epitopes including but not limited to polypeptide sequences covalently attached to the primary antibody. The secondary antibody can be directed at single or multiple sites (epitopes) present on full-length aglycosylated antibodies molecules (including various immunoglobulin classes such as IgG, IgA, etc.) or antibody fragments such as Fc or Fab. Therefore, some secondary antibodies generated in this way would have broad specificity for any aglycosylated full-length antibody. The primary and secondary antibodies of the present invention can also include those produced by traditional methods (polyclonal antibody production using immunized rabbits or monoclonal antibody production using mouse hybridomas) and recombinant DNA technology such as phage display methods for identifying antigen-binding polypeptides.

Detection systems generally comprise an agent that is linked to or which binds the secondary antibody, enabling detection, visualization, and/or quantification of the secondary antibody. Various detection systems are well known in the art including but not limited to fluorescent dyes, enzymes, radioactive isotopes, or heavy metals. These may or may not involve direct physical linkage of additional polypeptides to the secondary antibody. Applications of this secondary antibody system include but are not limited to immunohistochemistry, Western blotting, and enzyme-linked immunosorbent assay (ELISA). For example, in one embodiment for use in immunohistochemistry, the epitope of interest would be present on a thin section of tissue, then an aglycosylated primary antibody would be applied to the tissue and allowed to bind the epitope. The unbound primary antibody would be removed, and then a secondary antibody capable of specifically binding the aglycosylated primary antibody is applied to the tissue and allowed to bind to the primary antibody. The unbound secondary antibody would be removed, and then detection system reagents applied. For example, if the secondary antibody were linked to an enzyme, then colorigenic enzymatic substrates would be applied to the tissue and allowed to react. Direct microscopic or fluoroscopic visualization of the reactive enzymatic substrates could then be performed. Other detection methods are well known in the art. The advantages of a system using secondary antibodies that recognize aglycosylated antibodies include, without limitation, the following: 1) increased specificity in immunohistochemistry because the secondary antibody is designed to bind the aglycosylated Fc portion of the primary antibody which is not otherwise present in eukaryotic tissues; 2) decreased background staining because of increased specificity for the primary antibody; 3) decreased cost of secondary antibody system production because the primary and/or secondary antibodies can be generated in prokaryotes such as *E. coli*; and 4) avoiding unnecessary utilization of mammals, including mice and rabbits, because the entire process of antibody development can be performed in prokaryotes such as *E. coli*.

Enzymes Used in Industrial Applications.

Many industrial processes utilize enzymes that can be produced by the methods of the invention. These processes include treatment of wastewater and other bioremediation and/or detoxification processes; bleaching of materials in the paper and textile industries; and degradation of biomass into material that can be fermented efficiently into biofuels. In many instances it would be desirable to produce enzymes for these applications in microbial host cells or preferably in bacterial host cells, but the active enzyme is difficult to express in large quantities due to problems with enzyme folding and/or a requirement for a cofactor. In the following embodiments of the invention, the inducible coexpression methods of the invention are used to produce enzymes with industrial applications.

Arabinose- and Xylose-Utilization Enzymes.

D-xylose is the most abundant pentose in plant biomass, found in polysaccharides, hemicellulose, and pectin, with L-arabinose being the second most abundant pentose. For the development and production of biofuels and other bioproducts, it is useful to convert D-xylose and L-arabinose into hexoses including glucose and fructose, as hexoses are more efficiently fermented into biofuels such as ethanol. As described above, the *E. coli* araBAD operon encodes proteins that metabolize L-arabinose as follows: L-arabinose by L-arabinose isomerase (AraA, EC 5.3.1.4) to L-ribulose; L-ribulose by L-ribulokinase (AraB, EC 2.7.1.16) to L-ribulose-phosphate; L-ribulose-phosphate by L-ribulose-5-phosphate 4-epimerase (AraD, EC 5.1.3.4) to D-xylulose-5-phosphate (also called D-xylulose-5-P), which is part of the pentose phosphate pathway to the formation of fructose and glucose. Another enzymatic pathway (an "oxo-reductive pathway") that converts L-arabinose to xylitol, which can then be converted to D-xylulose-5-P, is as follows: L-arabinose by L-arabinose/D-xylose reductase (EC 1.1.1.21) to L-arabinitol; L-arabinitol by L-arabinitol dehydrogenase (EC 1.1.1.12) to L-xylulose; and L-xylulose by L-xylulose reductase (EC 1.1.1.10) to xylitol. The *E. coli* xylAB operon encodes one enzymatic pathway (the "isomerase pathway") for utilizing D-xylose, as follows: D-xylose by D-xylose isomerase (XylA, EC 5.3.1.5) to D-xylulose; D-xylulose by xylulokinase (XylB, EC 2.7.1.17) to D-xylulose-5-P. Another enzymatic pathway (an "oxo-reductive pathway") for converting D-xylose to D-xylulose-5-P is: D-xylose by D-xylose reductase (EC 1.1.1.21) to xylitol; xylitol by xylitol dehydrogenase (EC 1.1.1.9) to D-xylulose; D-xylulose by xylulokinase (XylB, EC 2.7.1.17) to D-xylulose-5-P. Because of the varying cofactors needed in the oxo-reductive pathways, such as NADPH, NAD$^-$, and ATP, and the degree to which these cofactors are available for usage, an imbalance can result in an overproduction of xylitol byproduct. D-xylulose-5-P plus erythrose 4-phosphate can be converted by transketolase (EC 2.2.1.1) to glyceraldehyde 3-phosphate plus fructose 6-phosphate.

The inducible coexpression methods of the invention can be used to produce arabinose- and xylose-utilization enzymes, which are defined as being the enzymes listed by EC number in the preceding paragraph. The EC (or 'Enzyme Commission') number for each enzyme is established by the International Union of Biochemistry and Molecular Biology (IUBMB). Further information about these enzymes and specific examples of them can readily be obtained through the UniProt protein database (www.uniprot.org/uniprot) and the BRENDA database, (www.brenda-enzymes.org/index); the BRENDA and UniProt database entries for the arabinose- and xylose-utilization enzymes are incorporated by reference herein. In some embodiments, an arabinose- or xylose-utilization enzyme is coexpressed with a chaperone protein; in further embodiments of the invention, an arabinose- or xylose-utilization enzyme is coexpressed with a transporter for a cofactor. In certain embodiments, L-arabinose isomerase (AraA, EC 5.3.1.4) or L-arabinose reductase (EC 1.1.1.21) is produced by the methods of the invention; in these embodiments, an arabinose-inducible promoter is not utilized in any expression construct because the inducer, L-arabinose, would be converted to L-ribulose or L-arabinitol, respectively. For production of arabinose-utilization enzymes other than L-arabinose isomerase (AraA, EC 5.3.1.4) or L-arabinose reductase (EC 1.1.1.21), an arabinose-inducible promoter can be utilized if the host cell is deficient in EC 5.3.1.4 and/or EC 1.1.1.21, such as an araA mutant, and cannot catabolize L-arabinose. Similarly, in embodiments where D-xylose isomerase (XylA, EC 5.3.1.5) or D-xylose reductase (EC 1.1.1.21) is produced by the methods of the invention, a xylose-inducible promoter is not utilized in any expression construct because the inducer, D-xylose, would be converted to D-xylulose or xylitol, respectively. For production of xylose-utilization enzymes other than D-xylose isomerase (XylA, EC 5.3.1.5) or D-xylose reductase (EC 1.1.1.21), a xylose-inducible promoter can be utilized if the host cell is deficient in EC 5.3.1.5 and/or EC 1.1.1.21, such as a xylA mutant, and cannot catabolize D-xylose.

Xylose isomerase (XylA, EC 5.3.1.5) is an enzyme found in microorganisms, anaerobic fungi, and plants, which catalyzes the interconversion of an aldo sugar (D-xylose) to a keto sugar (D-xylulose). It can also isomerize D-ribose to D-ribulose and D-glucose to D-fructose. This enzyme belongs to the family of isomerases, specifically those intramolecular oxidoreductases interconverting aldoses and ketoses. The systematic name of this enzyme class is D-xylose aldose-ketose-isomerase. Other names in common use include D-xylose isomerase, D-xylose ketoisomerase, D-xylose ketol-isomerase, and glucose isomerase. The enzyme is used industrially to convert glucose to fructose in the manufacture of high-fructose corn syrup, and as described above can be used in the conversion of pentoses to hexoses for biofuel production. Xylose isomerase is a homotetramer and requires two divalent cations—$Mg^{2+}$, $Mn^{2+}$, and/or $Co^{2+}$—for maximal activity. Xylose isomerase activity can be measured using an NADH-linked arabitol dehydrogenase assay (Smith et al., "D-Xylose (D-glucose) isomerase from *Arthrobacter* strain N.R.R.L. B3728. Purification and properties", Biochem J 1991 Jul. 1; 277 (Pt 1): 255-261), in which one unit of xylose isomerase activity is the amount of enzyme that converts 1 micromol of D-xylose into D-xylulose in one minute. In at least some species, xylose isomerase requires magnesium (or manganese in the case of plants) for its activity, while cobalt may be necessary to stabilize the tetrameric structure of the enzyme. Each xylose isomerase subunit contains an alpha/beta-barrel fold similar to that of other divalent metal-dependent TIM (triosephosphate isomerase) barrel enzymes, and the C-terminal smaller part forms an extended helical fold implicated in multimerization. Conserved residues in all known xylose isomerases are a histidine in the N-terminal section of the enzyme, shown to be involved in the catalytic mechanism of the enzyme, and two glutamate residues, a histidine, and four aspartate residues that form the two metal-binding sites, each of which binds an ion of magnesium, cobalt, or manganese (Katz et al., "Locating active-site hydrogen atoms in D-xylose isomerase: time-of-flight neutron diffraction", Proc Natl Acad Sci USA 2006 May 30; 103(22): 8342-8347; Epub 2006 May 17).

In some embodiments of the invention, inducible coexpression is used to express a xylose isomerase protein; in certain embodiments, the xylose isomerase ("XI") is selected from the group consisting of: *Arthrobacter* sp. strain NRRL B3728 XI (UniProt P12070); *Bacteroides stercoris* XI (UniProt B0NPH3); *Bifidobacterium longum* XI (UniProt Q8G3Q1); *Burkholderia cenocepacia* XI (UniProt Q1BG90); *Ciona intestinalis* XI (UniProt F6WBF5); *Clostridium phytofermentans* XI (UniProt A9KN98); *Orpinomyces* sp. ukk1 XI (UniProt B7SLY1); *Piromyces* sp. E2 XI (UniProt Q9P8C9); *Streptomyces lividans* XI (UniProt Q9RFM4); *Streptomyces lividans* TK24 XI (UniProt D6ESI7); *Thermoanaerobacter ethanolicus* JW 200 XI (UniProt D2DK62); *Thermoanaerobacter yonseii* XI (UniProt Q9KGU2); *Thermotoga neapolitana* XI (UniProt P45687); *Thermus thermophilus* XI (UniProt P26997); and *Vibrio* sp. strain XY-214 XI (UniProt C7G532). In particular embodiments, a xylose isomerase is inducibly coexpressed with a divalent ion transporter such as CorA (UniProt P0ABI4): using an inducible promoter to control the timing and extent of the transport of ions can be helpful in reducing toxicity to host cells from metal ions such as $Co^{2+}$. In additional embodiments, mutations are introduced into xylose isomerase proteins that affect the interaction between pairs of XI monomers; for example, the introduction of cysteine residues so that disulfide bonds between a pair of monomers can be formed (see Varsani et al., "*Arthrobacter* D-xylose isomerase: protein-engineered subunit interfaces", Biochem J 1993 Apr. 15; 291 (Pt 2): 575-583). In this example, because cysteine residues are introduced in reciprocal but not identical locations within the monomers, two different types of altered monomers are produced, and the inducible coexpression systems of the invention are used to titrate the relative expression of the two types of monomers to achieve the desired stoichiometric ratio.

Lignin-Degrading Peroxidases.

Peroxidases are a subgroup of oxidoreductases and are used to catalyze a variety of industrial processes. Oxidoreductases can break down lignin or act as reductases in the degradation of cellulose and hemi-cellulose, allowing the enzymes used in the processing of plant biomass to more easily access the saccharide residues during the production of biofuels such as ethanol. Oxidoreductases can be oxidases or dehydrogenases.

Oxidases use molecular oxygen as an electron acceptor, while dehydrogenases oxidize a substrate by transferring an H group to an acceptor, such as $NAD/NADP^+$ or a flavin-dependent enzyme. Peroxidases catalyze the reduction of a peroxide, such as hydrogen peroxide ($H_2O_2$). Other types of oxidoreductases include oxygenases, hydroxylases, and reductases. In addition to oxygen, flavin adenine dinucleotide (FAD), and the nicotinamide adenine dinucleotides NAD and NADP, potential cofactors of oxidoreductases include cytochromes and hemes, disulfide, and iron-sulfur proteins.

Lignin-degrading peroxidases can oxidize a variety of aromatic compounds including high-redox-potential compounds such as lignin, industrial dyes, pesticides, etc. Four types of lignin-modifying enzymes have been identified and characterized: lignin peroxidase (LiP, EC 1.11.1.14), manganese peroxidase (MnP, EC 1.11.1.13), versatile peroxidase (VP, EC 1.11.1.16), and laccase (EC 1.10.3.2). LiP, MnP, and VP are heme proteins with four or five disulfide bonds and two binding sites for structural Ca2+ ions, and are high-redox-potential peroxidases, which can directly oxidize high-redox-potential substrates and/or $Mn^{2+}$. The peroxidase activity of MnP can be measured using the 2,6-dimethoxyphenol (2,6-DMP) oxidation assay described in Example 4, Section E, below; LiP activity can be measured by the oxidation of veratryl alcohol to veratryl aldehyde in the presence of $H_2O_2$ (Orth et al., "Overproduction of lignin-degrading enzymes by an isolate of *Phanerochaete chrysosporium*", Appl Environ Microbiol 1991 September; 57(9): 2591-2596). Laccases are not associated with heme, but are associated with copper ions (usually 4 copper ions per laccase protein), and are low-redox-potential oxidoreductases, which can only oxidize high-redox-potential substrates in the presence of redox mediators. The activity of laccases can be measured using the ABTS (2,2'-azinobis-(3-ethylbenzothiazoline-6-sulphonic acid)) oxidation assay as described in Zhao et al., "Characterisation of a novel white laccase from the deuteromycete fungus *Myrothecium verrucaria* NF-05 and its decolourisation of dyes", PLoS One 2012; 7(6): e38817; Epub 2012 Jun. 8; one unit of activity is defined as the production of 1 micromol of product per minute.

The inducible coexpression methods of the invention can be used to produce lignin-degrading peroxidases, which are defined as being the enzymes listed by EC number in the preceding paragraph; the BRENDA and UniProt database entries for the lignin-degrading peroxidases are incorporated by reference herein. In some embodiments, a lignin-degrading peroxidase is coexpressed with a chaperone protein; in further embodiments of the invention, a lignin-degrading peroxidase is coexpressed with a transporter for a cofactor such as heme.

LiP can be expressed using the inducible coexpression systems of the invention; in certain embodiments, the LiP is selected from the group consisting of: *Phanerochaete chrysosporium* (*Sporotrichum pruinosum*) LiP isoenzymes "Ligninase A" (UniProt P31837), "Ligninase B" (UniProt P31838), "Ligninase H2" (UniProt P11542), "Ligninase H8" (UniProt P06181), "Ligninase LG2" (UniProt P49012), "Ligninase LG3" (UniProt P21764), "Ligninase LG5" (UniProt P11543), and "Ligninase LG6" (UniProt P50622); *Phlebia radiata* "Ligninase-3" (UniProt P20010); *Trametes versicolor* (*Coriolus versicolor*) LiP isozymes "Ligninase C" (UniProt P20013), LP7 (UniProt Q99057), and LP12 (UniProt Q7LHY3); and *Trametopsis cervina* LiP (UniProt Q3C1R8) and (UniProt Q60FD2).

In some embodiments of the invention, inducible coexpression is used to express MnP; in certain embodiments, the MnP is selected from the group consisting of: *Agaricus bisporus* MnP (UniProt Q5TJC2); *Agrocybe praecox* MnP (UniProt G4WG41); *Ganoderma lucidum* MnP (UniProt C0IMT8); *Lenzites gibbosa* MnP (UniProt C3V8Q9); *Phanerochaete chrysosporium* MnP isozymes MNP1 (UniProt Q02567); H3 (UniProt P78733); and H4 (UniProt P19136); *Phlebia radiata* MnP isozymes MnP2 (UniProt Q70LM3) and MnP3 (UniProt Q96TS6); *Phlebia* sp. b19 MnP (UniProt B2BF37); *Phlebia* sp. MG60 MnP isozymes MnP1, MnP2, MnP3 (UniProt B1B554, B1B555, and B1B556, respectively); *Pleurotus ostreatus* MnP3 (UniProt B9VR21); *Pleurotus pulmonarius* MnP5 (UniProt Q2VT17); *Spongipellis* sp. FERM P-18171 MnP (UniProt Q2HWK0); and *Trametes versicolor* (*Coriolus versicolor*) MnP isozymes (UniProt Q99058, Q6B6M9, Q6B6NO, Q6B6N1, and Q6B6N2). Coexpression of MnP with protein disulfide isomerase in the presence of heme is described in Example 4.

Laccase can be expressed using the inducible coexpression systems of the invention; in certain embodiments, the laccase is selected from the group consisting of: *Botryotinia fuckeliana* (*Botrytis cinerea*) laccase isozymes (UniProt Q12570, Q96UM2, and Q96WM9); *Cerrena* sp. WR1 laccase isozymes (UniProt E7BLQ8, E7BLQ9, and E7BLR0); *Cerrena unicolor* (*Daedalea unicolor*) Laccase (UniProt B8YQ97); *Ganoderma lucidum* laccase isozymes (UniProt Q6RYA2, B5G547, B5G549, B5G550, B5G551, and B5G552); *Melanocarpus albomyces* Laccase (UniProt Q70KY3); *Pleurotus ostreatus* laccase isozymes (UniProt Q12729, Q12739, Q6RYA4, Q6RYA4, and G3FGX5); *Pycnoporus cinnabarinus* laccase isozymes (UniProt O59896, Q9UVQ2, D2CSG0, D2CSG1, D2CSG4, D2CSG6, and D2CSG7); *Pycnoporus coccineus* laccase isozymes (UniProt D2CSF2, D2CSF5, D2CSF6, D2CSM7, and D7F484); *Trametes hirsuta* (*Coriolus hirsutus*) Laccase (UniProt Q02497); *Trametes maxima* (*Cerrena maxima*) Laccase (UniProt D0VWU3); *Trametes versicolor* (*Coriolus versicolor*) laccase isozymes (UniProt Q12717, Q12718, and Q12719); and *Trametes villosa* laccase isozymes (UniProt Q99044, Q99046, Q99049, Q99055, and Q99056).

While the three main lignin-modifying enzymes of white rot fungi are LiP, MnP, and laccase, another type of peroxidase, versatile peroxidase (VP), is found in several species from the genera *Pleurotus* and *Bjerkandera*. VP is of interest due to its catalytic versatility: it can oxidise LiP substrates, veratryl alcohol, methoxybenzenes, and non-phenolic lignin model compounds, as well as the MnP substrate $Mn^{2+}$. The versatile activity of VP can be assayed using the MnP 2,6-DMP assay, or the LiP veratryl alcohol assay, or the laccase ABTS assay (see above). In some embodiments of the invention, inducible coexpression is used to express VP; in certain embodiments, the VP is selected from the group consisting of: *Bjerkandera adusta* VP (UniProt A5JTV4); *Pleurotus eryngii* VP isozymes (UniProt O94753, Q9UR19, and Q9UVP6); and *Pleurotus pulmonarius* VP (UniProt I6TLM2).

Example 1

Inducible Coexpression of IgG1 Heavy and Light Chains to Produce Full-Length Antibodies in Bacterial Cells A. Construction of Expression Vectors The inducible coexpression system was used to produce full-length antibodies, specifically mouse anti-human CD19 IgG1 antibodies, in bacterial cells. The coding sequence for the mouse anti-human CD19 IgG1 heavy chain ('IgG1 heavy chain', 'IgG1HC', 'heavy chain', or 'HC') is provided as SEQ ID NO:1 and is the same as that of GenBank Accession No. AJ555622.1, and specifically bases 13 through 1407 of the GenBank AJ555622.1 nucleotide sequence. The corresponding full-length mouse anti-human CD19 IgG1 heavy chain amino acid sequence is provided as SEQ ID NO:2 (and is the same as GenBank Accession No. CAD88275.1). The coding sequence for the mouse anti-human CD19 IgG1 light chain ('IgG1 light chain', 'IgG1LC', 'light chain', or 'LC') is provided as SEQ ID NO:3 and is the same as that of GenBank Accession No. AJ555479.1, and specifically bases 23 through 742 of the GenBank AJ555479.1 nucleotide sequence. The corresponding full-length mouse anti-human CD19 IgG1 light chain amino acid sequence is provided as SEQ ID NO:4 (and is the same as GenBank Accession No. CAD88204.1).

Synthesis of polynucleotides encoding the IgG1 heavy and light chains, and optimization for expression in *E. coli*, was performed by GenScript (Piscataway, N.J.). GenScript's OptimumGene™ Gene Design system uses an algorithm, the OptimumGene™ algorithm, which takes into consideration a variety of factors involved in different stages of protein expression, such as codon usage bias, GC content, CpG dinucleotide content, predicted mRNA structure, and various cis-elements in transcription and translation. The optimized sequences for the IgG1 heavy and light chains are provided as SEQ ID NO:5 and SEQ ID NO:6, respectively; these optimized sequences include some additional nucleotides upstream and downstream of the coding sequence; the coding sequences are bases 25 through 1419 of SEQ ID NO:5, and bases 25 through 747 of SEQ ID NO:6. The optimized coding sequence in SEQ ID NO:10 for the IgG1 light chain encodes an additional amino acid, an alanine residue, at position 2 of the encoded amino acid sequence, relative to the IgG1 light chain amino acid sequence of SEQ ID NO:4. The optimized heavy and light chain sequences both contain TAA stop codons, and a preferred *E. coli* ribosome-binding sequence (AGGAGG), located at −14 to −9 bases upstream of the initiation codon. In addition, the IgG1 heavy chain optimized sequence (SEQ ID NO:5) contains an NcoI restriction site comprising the ATG initiation codon, and a HindIII restriction site immediately downstream of the TAA stop codon, while the IgG1 light chain optimized sequence (SEQ ID NO:6) contains an NheI restriction site immediately upstream of the ribosome-binding sequence, and also a HindIII restriction immediately downstream of the TAA stop codon.

The optimized coding sequences for the IgG1 heavy and light chains were obtained from GenScript as polynucleotide inserts cloned into pUC57. The pBAD24 vector was obtained from the American Type Culture Collection (ATCC) as ATCC 87399, and has the nucleotide sequence shown in GenBank Database Accession No. X81837.1 (25 Oct. 1995); the pPRO33 vector was obtained from the University of California (Berkeley, Calif.), and has the nucleotide sequence shown in SEQ ID NO:7. The nucleotide sequence of pPRO33 was compiled from the sequences of the pBAD18 vector (GenBank Accession No. X81838.1), the E. coli genomic sequence of the prpR-$P_{prpB}$ region, and the pBAD33 vector, as described in Guzman et al., "Tight regulation, modulation, and high-level expression by vectors containing the arabinose PBAD promoter", J Bacteriol 1995 July; 177(14): 4121-4130, and in U.S. Pat. No. 8,178,338 B2; May 15, 2012; Keasling, Jay. To clone the IgG1 heavy chain into the pBAD24 vector, and the IgG1 light chain into the pPRO33 vector, the pUC57-HC and pUC57-LC constructs were first transformed into E. coli BL21 cells (New England Biolabs (or 'NEB'), Ipswich, Mass.) using the heat-shock method. Plasmid DNA for each of these vectors was then obtained by a miniprep method. Unless otherwise noted, growth of E. coli cells in liquid culture was at 37° C. with rotary shaking at 250 RPM. E. coli cell strains containing plasmids (BL21 containing pUC57-HC, BL21 containing pUC57-LC, and DH5alpha containing pBAD24) were each grown in 8 mL LB+ampicillin ('AMP') medium, and E. coli DH10B cells (Life Technologies, Grand Island, N.Y.) containing pPRO33 were grown in 5 mL LB+chloramphenicol ('CAM') medium, for 14 hours or overnight, then cells were pelleted, lysed, and the plasmid DNA separated using a QIAprep® spin column (QIAGEN, Germantown, Md.) according to the manufacturer's protocol. For increased yields, the QIAprep® spin column protocol was performed with 100% ethanol added to the PE buffer, and the supernatant was sent through the column twice instead of once.

To clone the IgG1 heavy chain into pBAD24, the purified pUC57-HC and pBAD24 plasmids were digested with NcoI and HindIII restriction enzymes (NEB), then the IgG1HC NcoI-HindIII fragment and the NcoI-HindIII-cut pBAD24 plasmid were separated from other polynucleotide fragments by gel electrophoresis, excised from the gel, and purified using the illustra GFX Gel Band Purification Kit (GE Healthcare Life Sciences, Piscataway, N.J.) according to the manufacturer's instructions. The IgG1HC NcoI-HindIII fragment was then ligated (overnight at 16° C.) to the NcoI-HindIII-cut pBAD24 plasmid to form the pBAD24-HC expression construct. Because the NcoI restriction site in the IgG1HC NcoI-HindIII fragment comprises the ATG initiation codon of the IgG1HC coding sequence, when the IgG1HC NcoI-HindIII fragment is inserted into the NcoI-HindIII-cut pBAD24 vector, the IgG1HC coding sequence is placed downstream of a preferred E. coli ribosome-binding sequence AGGAGG present in the pBAD24 vector (see FIG. 1 of Guzman et al., "Tight regulation, modulation, and high-level expression by vectors containing the arabinose PBAD promoter", J Bacteriol 1995 July; 177(14): 4121-4130). In the resulting pBAD24-HC expression construct, the ribosome-binding sequence is located at −14 to −9 bases upstream of the IgG1HC initiation codon.

To clone the IgG1 light chain into pPRO33, the purified pUC57-LC and pPRO33 plasmids were digested with NheI and HindIII restriction enzymes (NEB). Because the pPRO33 plasmid has two HindIII restriction sites, there were two fragments to be gel-purified from the pPRO33 NheI-HindIII digest: a 4.4 kb fragment and a 1.5 kb fragment. After gel-purification of all the desired fragments, using an illustra GFX Gel Band Purification Kit (see above), the purified 4.4 kb pPRO33 fragment was treated with alkaline phosphatase (also called calf intestinal phosphatase or CIP) (NEB), according to the manufacturer's instructions. The CIP-treated 4.4 kb pPRO33 fragment was purified from the phosphatase reaction mixture using an illustra GFX Purification Kit (see above), and was then ligated to the 1.5 kb pPRO33 fragment (at 16° C. for 10.5 hours). The resulting NheI-HindIII-cut pPRO33 plasmid was ligated to the IgG1LC NheI-HindIII fragment (overnight at 16° C.) to form the pPRO33-LC expression construct. Because the NheI restriction site in the IgG1LC NheI-HindIII fragment is immediately upstream of the ribosome-binding sequence AGGAGG in the optimized light chain sequence (SEQ ID NO:6), when the IgG1LC NheI-HindIII fragment is inserted into the NheI-HindIII-cut pPRO33 vector, the IgG1LC sequence retains its preferred E. coli ribosome-binding sequence.

B. Inducible Coexpression of IgG1 Heavy and Light Chains in Bacterial Cells

The pBAD24-HC expression construct and the pPRO33-LC expression construct were co-transformed into E. coli BL21 and into E. coli SHuffle® Express cells (NEB) using the heat-shock method. Transformed BL21 (pBAD24-HC/pPRO33-LC) and SHuffle® Express (pBAD24-HC/pPRO33-LC) cells were grown at 37° C. overnight in 5 mL LB broth with 30 micrograms/mL CAM and 100 micrograms/mL AMP. Because the SHuffle® Express cells seem to grow more slowly than the BL21 cells, 2% (100 microliters) of the overnight culture of SHuffle® Express (pBAD24-HC/pPRO33-LC), and 1% (50 microliters) of the overnight culture of BL21 (pBAD24-HC/pPRO33-LC), were used to inoculate 5 mL of M9 minimal media with casamino acids and 0.2% glycerol, plus 30 micrograms/mL CAM and 100 micrograms/mL AMP. These cultures were grown until the $OD_{600}$ was approximately 0.5: 3.1 hours for the SHuffle® Express (pBAD24-HC/pPRO33-LC) cells and 2.5 hours for the BL21 (pBAD24-HC/pPRO33-LC) cells. Prior to induction, control samples were taken from each culture that would be grown without induction. The remaining SHuffle® Express (pBAD24-HC/pPRO33-LC) and BL21 (pBAD24-HC/pPRO33-LC) cell cultures were then induced by adding 0.2% arabinose and 50 mM propionate, and growing them in parallel with the non-induced control samples for 6 hours. At the end of that time, all cell cultures were centrifuged to pellet the cells, and placed in a −80° C. freezer. The cell pellets were thawed on ice, and the cells were lysed using a Qproteome Bacterial Lysis Kit (QIAGEN), according to the manufacturer's instructions, with the exceptions that a Complete Mini Protease Inhibitor Cocktail Tablet (Roche, Indianapolis, Ind.) was added to 10 mL native lysis buffer before adding the lysozyme and nuclease, and that the samples were centrifuged at 25° C. instead of at 4° C.

The soluble protein extracts from the induced cells and uninduced controls were separated by SDS gel electrophoresis under reducing conditions on a NuPAGE® 4-12%

Figure 3:
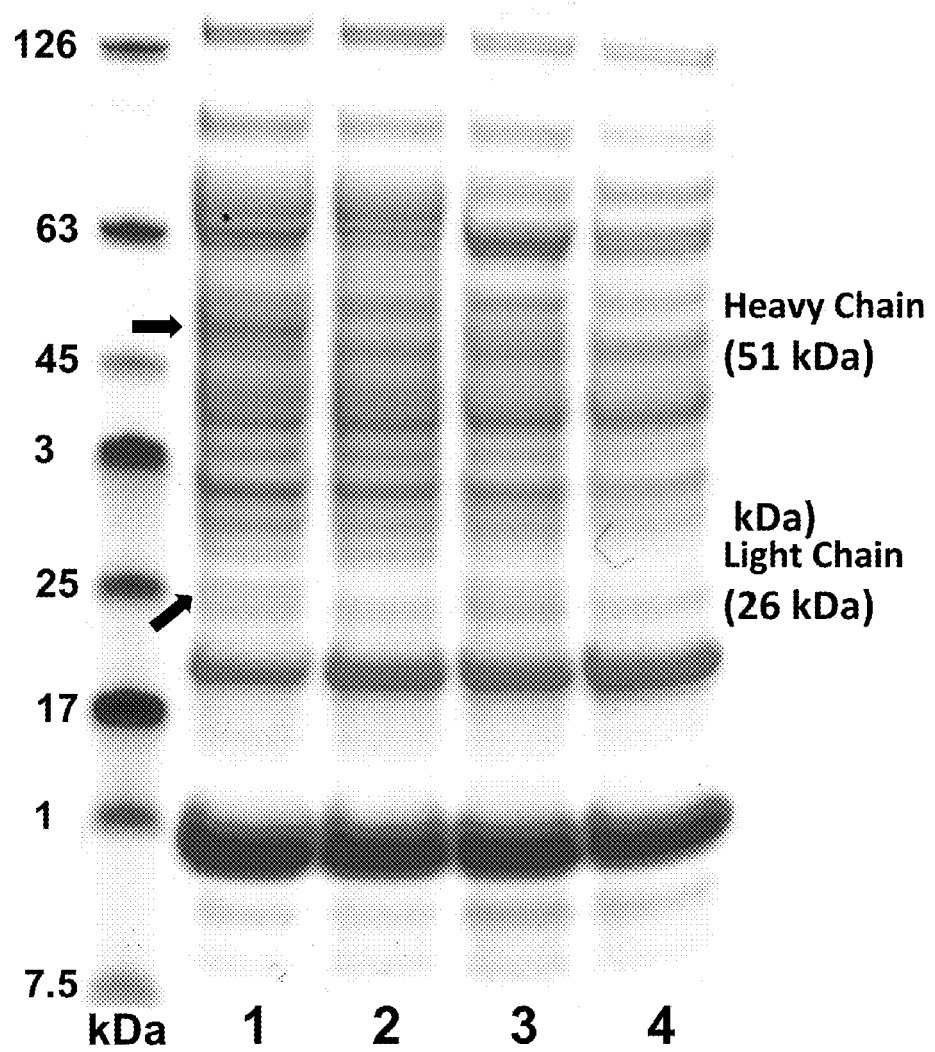
FIG. 3 shows the result of coexpression of immunoglobulin heavy and light chains in bacterial cells. SHuffle® Express and BL21 cells containing both the pBAD24-HC and pPRO33-LC inducible expression vectors were induced by growth in L-arabinose and propionate. Soluble protein extracts from induced cells and uninduced controls were separated by SDS gel electrophoresis under reducing conditions on a 4-12% Bis-Tris gel. Lane 1: Induced SHuffle® Express. Lane 2: Uninduced SHuffle® Express. Lane 3: Induced BL21. Lane 4: Uninduced BL21. Arrows indicate a protein band (IgG1 heavy chain) at 51 kDa and another protein band (IgG1 light chain) at 26 kDa; these bands are present in the induced cells but not in the uninduced cells.
Figure 4:
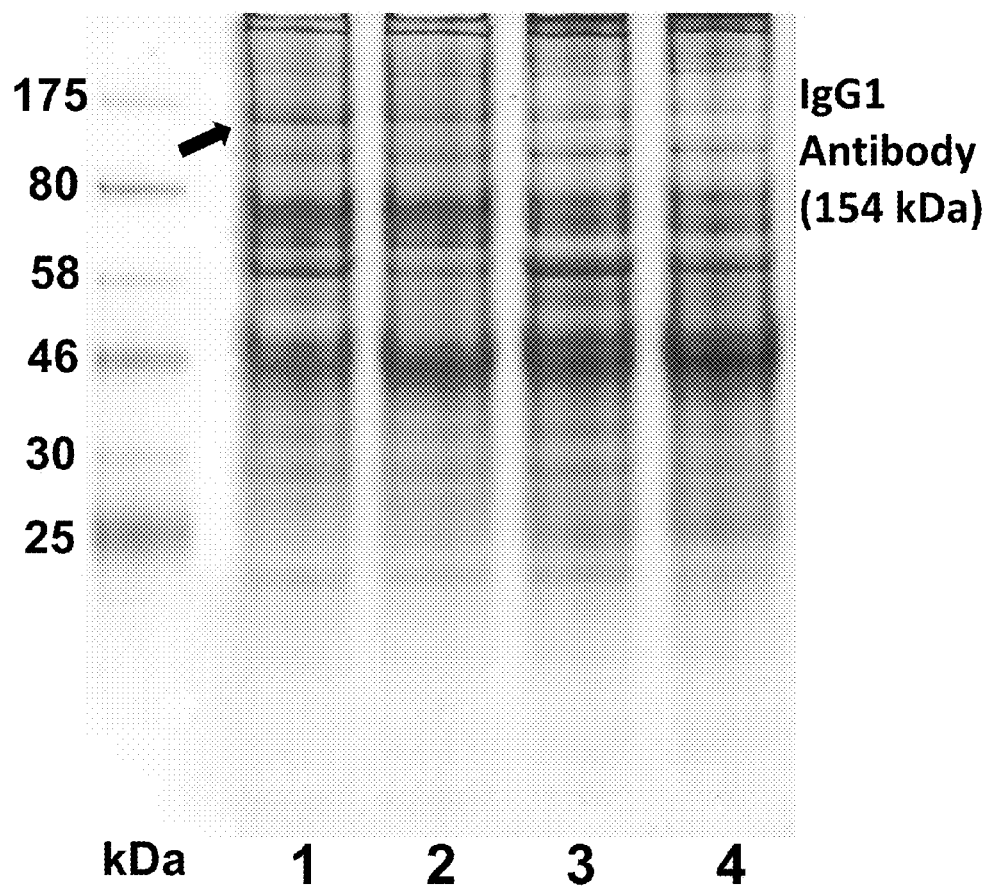
FIG. 4 shows the result of coexpression of immunoglobulin heavy and light chains in bacterial cells. The same soluble protein extracts from induced and uninduced SHuffle® Express and BL21 cells containing both the pBAD24-HC and pPRO33-LC inducible expression vectors, as described for FIG. 3, were separated by gel electrophoresis under native (non-reducing) conditions on a 10-20% Tris-Glycine gel. Lane 1: Induced SHuffle® Express. Lane 2: Uninduced SHuffle® Express. Lane 3: Induced BL21. Lane 4: Uninduced BL21. Arrow indicates a protein band (IgG1 antibody comprising heavy and light chains) at 154 kDa; this band is present in the induced SHuffle® Express cells, but is significantly reduced or absent in the induced BL21 cells and in the uninduced cells.

Bis-Tris gel (Life Technologies, Grand Island, N.Y.). The gel was stained using RAPIDstain™ (G-Biosciences, St. Louis, Mo.). As shown in FIG. 3, a protein band (heavy chain) is seen migrating at 51 kDa and another protein band (light chain) at 26 kDa; these bands are present in the induced cells but not in the uninduced cells. The same soluble protein extracts from induced and uninduced SHuffle® Express and BL21 cells containing both the pBAD24-HC and pPRO33-LC inducible expression vectors were separated by gel electrophoresis under native (non-reducing) conditions on a Novex® 10-20% Tris-Glycine gel (Life Technologies). The gel was stained using RAPIDstain™ (G-Biosciences). As shown in FIG. 4, a protein band (IgG1 antibody comprising heavy and light chains) migrates at 154 kDa; this band is present in the induced SHuffle® Express cells, but is significantly reduced or absent in the induced BL21 cells and in the uninduced cells.

Example 2

Characterization of Expression Constructs and IgG1 Full-Length Antibodies Produced in Bacterial Cells
A. Characterization of Expression Vectors
The sequence of the pBAD24-HC and pPRO33-LC expression constructs is confirmed using the primers shown in the following table to initiate dideoxy chain-termination sequencing reactions, along with other primers designed as needed. The nucleotide sequence of the prpBCDE promoter and the region of the pPRO24 vector upstream of the MCS, as shown in FIG. 1C of U.S. Pat. No. 8,178,338 B2, is used to design at least one forward oligonucleotide primer to sequence coding sequences cloned into the MCS of pPRO expression vectors.

nitrocellulose membrane is then washed to remove unbound antibody, and incubated with a secondary antibody, goat anti-mouse IgG conjugated to alkaline phosphatase, for one hour at room temperature. The nitrocellulose membrane is then washed to remove unbound secondary antibody, incubated with a solution containing nitroblue tetrazolium (NBT) and 5-bromo-4-chloro-indolyl-phosphate (BCIP) to stain the protein band(s), and then washed to remove excess staining solution.

Example 3

Introduction of Genomic Alterations into Host Cells to Facilitate Coexpression
As described above, certain changes in host cell gene expression can improve the coexpression of the desired gene product(s). The following deletions and alterations were made in the E. coli SHuffle® Express host cell genome by Gene Bridges GmbH (Heidelberg, Germany) using a recombineering method, described as deletion by counterselection, that seamlessly removes genomic sequences. A deletion of the host cell araBAD operon was made to reduce arabinose catabolism by the host cell, so that more of the arabinose inducer will be available for induction of a coexpressed gene product from an expression construct comprising the araBAD promoter. This deletion removes 4269 basepairs of the araBAD operon, corresponding to position 70,135 through 65,867 (minus strand) of the E. coli genome (positions within genomic nucleotide sequences are all given as in Table 1), so that most of the native araBAD promoter through all but a few codons of the AraD coding region are removed. The nucleotide sequence (minus strand) around the deletion junction (position 70,136|position 65,866) is:

TABLE 4

Oligonucleotide primers

| Primer | SEQ ID NO: | Sequence | Comments |
|---|---|---|---|
| IgG1HC Fc forward | 8 | 5'- TTC ACC ATG GAA GTT TCA TCG GTC TTT ATT TTC CCG -3' | Matches bases 780-807 of SEQ ID NO: 5, adds a NcoI site at 5' end |
| IgG1HC Fc reverse | 9 | 5'- AGC CAA GCT TTT ATT TAC CCG GCG AGT GGG AC -3' | Match in reverse orientation to bases 1398-1429 of SEQ ID NO: 6 |
| pBAD24/33 forward | 10 | 5'- CTG TTT CTC CAT ACC CGT T - 3' | Located between the pBAD promoter and the MCS in all pBAD vectors |
| pBAD24/33 reverse #1 | 11 | 5'- CTC ATC CGC CAA AAC AG -3' | Just downstream of MCS in pBAD and pPRO vectors, separated from MCS HindIII site by 2 bases (GG) |
| pBAD24/33 reverse #2 | 12 | 5'- GGC TGA AAA TCT TCT CT - 3' | Downstream of reverse primer #1 in pBAD and pPRO vectors and overlaps with it, last two bases are first two of #1 |

B. Detection of Mouse IgG1 Full-Length Antibodies on a Western Blot
Protein gels used to separate soluble protein extracts by electrophoresis (NuPAGE® 4-12% Bis-Tris gels or Novex® 10-20% Tris-Glycine gels), as described in Example 1, are placed into a XCell II™ Blot Module (Life Technologies, Grand Island, N.Y.). Current is applied to the gel in accordance with the manufacturer's instructions, resulting in the transfer of proteins from the gel to a nitrocellulose membrane. The nitrocellulose membrane is then incubated with a primary antibody, anti-mouse IgG, at 4° C. overnight. The TTAT TACG. Another deletion was made within the sbm-ygfDGH (also called scpA-argK-scpBC) operon, eliminating the function of genes involved in the biosynthesis of 2-methylcitrate, to increase sensitivity of the host cell's propionate-inducible promoter to exogenously supplied propionate. The sbm-ygfDGH deletion removes 5542 basepairs (position 3,058,754 through 3,064,295 of the E. coli genome), taking out the sbm-ygfDGH promoter and all of the operon except for the last codon of the ygfH coding sequence, while leaving the adjacent ygfI coding sequence and stop codon intact. The nucleotide sequence (plus strand)

around the deletion junction (position 3,058,753|position 3,064,296) is: ACAA|GGGT. In addition to these deletions made in the *E. coli* SHuffle® Express host cell genome, Gene Bridges GmbH introduced a point mutation in the genomic rpsL gene coding sequence, which extends on the minus strand from position 3,472,574 through 3,472,200, changing the A at position 3,472,447 to a G, altering the codon for Lys43 to a codon for Arg, which results in a streptomycin-resistant phenotype when the mutant rpsL-Arg43 gene is expressed. Another alteration to the host cell genome, allowing for more tightly controlled inducible expression as described above, is to make the araE promoter constitutive rather than responsive to arabinose. Most of the native araE promoter, including CRP-cAMP and AraC binding sites, was removed by deleting 97 basepairs (position 2,980,335 through 2,980,239 (minus strand)) and replacing that sequence with the 35-basepair sequence of the constitutive J23104 promoter, with the resulting junction site sequences: TGAA|TTGA←J23104 promoter→TAGC|T-TCA. An *E. coli* host cell, such as an *E. coli* SHuffle® Express host cell, with any of these genomic alterations, or any combination of them, can be employed in the inducible coexpression of gene products.

Example 4

Inducible Coexpression of Manganese Peroxidase and Protein Disulfide Isomerase in the Presence of Heme A. Construction of Expression Vectors Manganese peroxidase ('MnP'; also called manganese-dependant peroxidase) is an enzyme that enables some types of fungi to degrade lignin to carbon dioxide, and to mediate oxidation of a wide variety of organic pollutants. One example of manganese peroxidase is the H4 isozyme (referred to herein as 'MnP-H4') of the white rot fungus *Phanerochaete chrysosporium* (UniProtKB/Swiss-Prot Accession No. P19136). In its functional form, MnP-H4 is associated with a manganese ion ($Mn^{2+}$), an iron-containing heme molecule, and two calcium ions ($Ca^{2+}$); MnP-H4 also has five disulfide bonds (Sundaramoorthy et al., "The crystal structure of manganese peroxidase from *Phanerochaete chrysosporium* at 2.06-Å resolution", J Biol Chem 1994 Dec. 30; 269(52): 32759-32767). Thermal inactivation of the MnP-H4 enzyme involves a loss of the interactions between MnP-H4 and the calcium ions. Creating an additional disulfide bond in MnP-H4 by altering the amino acid sequence of MnP-H4 to substitute cysteine for another amino acid at two positions near the distal calcium interaction site, such as an MnP-H4 A48C/A63C variant, makes the resulting MnP-H4 A48C/A63C enzyme more resistant to thermal inactivation (Reading and Aust, "Engineering a disulfide bond in recombinant manganese peroxidase results in increased thermostability", Biotechnol Prog 2000 May-June; 16(3): 326-333). To express MnP-H4 in a way that promotes formation of the disulfide bonds, an expression construct was created encoding an MnP-H4 enzyme lacking the signal peptide, so that the protein remains in the oxidizing cytoplasmic environment of the host cell (*E. coli* SHuffle® Express).

The amino acid sequence of MnP-H4 without a signal peptide is shown as SEQ ID NO:13; this form of the MnP-H4 protein has an initial methionine residue attached to the predicted mature amino acid sequence, starting at A14 of the full-length amino acid sequence, as described in Pease et al., "Manganese-dependent peroxidase from *Phanerochaete chrysosporium*. Primary structure deduced from cDNA sequence", J Biol Chem 1989 Aug. 15; 264(23): 13531-13535. In other references, such as Sundaramoorthy et al., "The crystal structure of manganese peroxidase from *Phanerochaete chrysosporium* at 2.06-Å resolution", J Biol Chem 1994 Dec. 30; 269(52): 32759-32767, the mature MnP-H4 amino acid sequence is indicated as starting at A25 of the full-length amino acid sequence. Proteins comprising amino acids 13 though 370 of SEQ ID NO:13 (which corresponds to the shorter mature amino acid sequence) are also produced by the methods of the invention, and in certain embodiments have an initial methionine residue attached to amino acids 13 though 370 of SEQ ID NO: 13, and thus have the amino acid sequence shown as SEQ ID NO:23. The nucleotide sequence that has been optimized for the expression of the SEQ ID NO:13 form of MnP-H4 in *E. coli* is shown as SEQ ID NO:14; expression constructs comprising SEQ ID NO:14 were used in the methods of the invention to express MnP-H4. Nucleotides 37 through 1110 of SEQ ID NO:14 encode the shorter MnP-H4 mature amino acid sequence (starting at A25 of the full-length amino acid sequence); polynucleotides comprising nucleotides 37 through 1110 of SEQ ID NO: 14 are used in some embodiments of the invention for production of MnP-H4 protein, and in certain embodiments comprise an ATG codon for an initial methionine residue attached to the 5' end of the nucleotide sequence of 37 through 1110 of SEQ ID NO:14.

A similar expression construct is created for expression of an MnP-H4 protein corresponding to the A48C/A63C MnP-H4 protein and lacking a signal peptide (amino acid sequence shown as SEQ ID NO:15; optimized coding sequence shown as SEQ ID NO: 16). Due to the additional twelve amino acids in SEQ ID NO:15 as compared to the shorter mature MnP-H4 amino acid sequence, the alanine-to-cysteine alterations are indicated as A60C/A75C in SEQ ID NO:15. Additional examples of expression constructs that are used in the methods of the invention encode a protein comprising SEQ ID NO:15, or amino acids 13 though 370 of SEQ ID NO: 15, or an initial methionine residue attached to amino acids 13 though 370 of SEQ ID:15. In certain embodiments, expression constructs that are used in the methods of the invention comprise SEQ ID NO:16, or nucleotides 37 through 1110 of SEQ ID:16, or an ATG codon for an initial methionine residue attached to the 5' end of the nucleotide sequence of 37 through 1110 of SEQ ID:16. Another variation of the MnP-H4 amino acid sequence occurs at position 105 of the full-length amino acid sequence, where a serine is changed to an asparagine. The methods of the invention are used to produce MnP-H4 proteins with this variation (serine changed to asparagine at position 93 of SEQ ID NO:13 or SEQ ID NO:15), with expression constructs comprising nucleotide sequences having a G at position 278 of SEQ ID NO:14 or SEQ ID NO: 16 changed to an A, altering the AGC codon for serine to an AAC codon for asparagine.

In addition to promoting the formation of disulfide bonds in MnP-H4, to produce fully active MnP-H4 enzyme, the enzyme is optimally expressed in the presence of heme. To allow the *E. coli* host cell to take up heme-containing molecules such as hemin from the medium, a nucleotide sequence encoding the *E. coli* O157:H7 ChuA outer-membrane hemin-specific receptor is also included in the MnP-H4 expression construct. The ChuA polypeptide has the same N-terminal amino acid sequence, including the signal peptide, as the native *E. coli* O157:H7 str. EC4113 ChuA protein (SEQ ID NO:17), so that it will be inserted into the outer membrane of the *E. coli* host cell. The optimized coding sequence for the ChuA polypeptide (SEQ ID NO:17) is shown at positions 68 through 2047 of SEQ ID NO:19.

The ChuA amino acid sequence shown in SEQ ID NO:17, from *E. coli* O157:H7 str. EC4113, differs from that of the ChuA amino acid sequence from *E. coli* CFT073 (NCBI Gene ID No. 1037196) by having a valine (EC4113) instead of an isoleucine (CFT073) at position 106 of SEQ ID NO:17. A V106I change in the ChuA amino acid sequence can be encoded by a change in the GTG Val codon to an ATT or ATC Ile codon at positions 383-385 of SEQ ID NO:19. Other variations in the amino acid sequence of ChuA proteins used in the expression of heme-associated proteins include, for example, a change from glutamic acid to glycine at position 259 of SEQ ID NO:17 (encoded by a change in the GAG Glu codon to a GGT or GGC Gly codon at positions 842-844 of SEQ ID NO: 19), or a change from glutamic acid to asparagine at position 262 of SEQ ID NO: 17 (encoded by a change in the GAG Glu codon to a GAT or GAC Asp codon at positions 851-853 of SEQ ID NO: 19).

Optimization for expression in *E. coli* and synthesis of polynucleotides corresponding to SEQ ID NOs 18, 19, and 22 was performed by DNA2.0 (Menlo Park, Calif.). SEQ ID NO:18 encodes the MnP-H4 protein, and is designed to be inserted immediately downstream of a promoter, such as an inducible promoter. The SEQ ID NO: 18 nucleotide sequence starts at its 5' end with a GCTAGC NheI restriction site, and has an AGGAGG ribosome binding site at nucleotides 7 through 12 of SEQ ID NO:18, followed by the optimized MnP-H4 coding sequence at nucleotides 21 through 1130 of SEQ ID NO: 18. Downstream of the MnP-H4 stop codon is the B0015 double terminator, from position 1142 through 1270 of SEQ ID NO:18, followed by a TCTAGA XbaI restriction site. The nucleotide sequence of the B0015 double terminator was obtained from the partsregistry.org website. SEQ ID NO:19 encodes ChuA, and includes a constitutive promoter, so this expression construct for ChuA could be placed in any expression vector or within the host cell genome; because the ChuA coding sequence has been placed under the control of the J23104 constitutive promoter, its transcription is no longer subject to repression by Fur. In this embodiment, SEQ ID NO:19 starts at its 5' end with a TCTAGA XbaI restriction site, and is designed to be placed within an expression vector 3' to the sequences of SEQ ID NO:18. Nucleotides 7 through 41 of SEQ ID NO:19 are the J23104 constitutive promoter and nucleotides 50 through 61 of SEQ ID NO:19 are the B0034 ribosome binding site, both placed upstream of the ChuA coding sequence at nucleotides 68 through 2047 of SEQ ID NO:19; the nucleotide sequences of J23104 and B0034 were obtained from the partsregistry.org website. SEQ ID NO:19 ends with a GTCGAC SalI restriction site. The XbaI sites in SEQ ID NO:18 and SEQ ID NO:19 allow these nucleotide sequences to be ligated together at a XbaI site; the nucleotide sequence of the resulting MnP-H4 ChuA expression construct is shown in SEQ ID NO:20. The NheI and SalI sites in SEQ ID NOs 18 and 19, respectively, and in SEQ ID NO:20, allow the MnP-H4 ChuA expression construct to be inserted into an expression vector such as pPRO33 using the NheI and SalI restriction sites in its multiple cloning site.

To facilitate production of correctly folded MnP-H4 enzyme, MnP-H4 was coexpressed with the chaperone protein disulfide isomerase ('PDI') from *Humicola insolens*, a thermophilic, cellulolytic, and saprophytic soil hyphomycete (soft-rot fungus). The amino acid sequence of PDI that was coexpressed is shown as SEQ ID NO:21; it lacks the signal peptide of the native protein so that it remains in the host cell cytoplasm as the MnP-H4 polypeptides are produced. The nucleotide sequence encoding PDI was also optimized for expression in *E. coli*; the expression construct for PDI is shown as SEQ ID NO:22. SEQ ID NO:22 contains a GCTAGC NheI restriction site at its 5' end, an AGGAGG ribosome binding site at nucleotides 7 through 12, the PDI coding sequence at nucleotides 21 through 1478, and a GTCGAC SalI restriction site at its 3' end. The nucleotide sequence of SEQ ID NO:22 was designed to be inserted immediately downstream of a promoter, such as an inducible promoter. The NheI and SalI restriction sites in SEQ ID NO:22 were used to insert it into the multiple cloning site of the pBAD24 expression vector.

The synthesized expression constructs comprising SEQ ID NO:20 and SEQ ID NO:22, and the pPRO33 and pBAD24 vectors, were cut with NheI and SalI restriction enzymes, and the synthesized expression construct fragments were ligated into the vectors to create pPRO33-MnP-ChuA and pBAD24-PDI, as described immediately above and in Example 1. *E. coli* SHuffle® Express cells (New England Biolabs (or 'NEB'), Ipswich, Mass.) were co-transformed with the resulting expression vectors (pPRO33-MnP-ChuA and pBAD24-PDI) using the heat-shock method.

B. Inducible Coexpression of Manganese Peroxidase and Protein Disulfide Isomerase in Bacterial Cells Host cells co-transformed with the pPRO33-MnP-ChuA and pBAD24-PDI expression vectors (SHuffle® Express (pPRO33-MnP-ChuA/pBAD24-PDI) cells) were used to inoculate four shake tubes each containing 5 ml LB broth plus 34 micrograms/mL CAM and 100 micrograms/mL AMP. After incubation (at 30° C. with rotary shaking at 250 RPM) for 16 hours, the cells were spun at 4000 rpm for 10 minutes at 4° C., the LB broth decanted off, and the cells were resuspended in 4×400 microliters of M9 minimal media with casamino acids and 0.2% glycerol, plus 34 micrograms/mL CAM and 100 micrograms/mL AMP ('M9-CA-gly+CAM+AMP'). Then 75 microliters of the combined volume of 1.6 ml of resuspended cells was added to each of ten shake tubes containing 5 ml M9-CA-gly+CAM+AMP, and the $OD_{600}$ of the resulting culture was determined to be 0.6. Hemin (Sigma-Aldrich, St. Louis, Mo.) was added to a final concentration of 8 micromolar in all tubes except tube 1, the uninduced control. The L-arabinose and propionate inducers were added to tubes 2-10 in the following concentrations:

| Tube 1: | Not Induced (no hemin, no propionate, no arabinose) | |
|---|---|---|
| Tube 2: | 50 mM propionate | 0.002% arabinose |
| Tube 3: | 25 mM propionate | 0.002% arabinose |
| Tube 4: | 12.5 mM propionate | 0.002% arabinose |
| Tube 5: | 50 mM propionate | 0.01% arabinose |
| Tube 6: | 25 mM propionate | 0.01% arabinose |
| Tube 7: | 12.5 mM propionate | 0.01% arabinose |
| Tube 8: | 50 mM propionate | 0.05% arabinose |
| Tube 9: | 25 mM propionate | 0.05% arabinose |
| Tube 10: | 12.5 mM propionate | 0.05% arabinose |

The cells were induced at 25° C. for 12 hours with rotary shaking, then spun down and placed in a −80° C. freezer. The cell pellets were thawed on ice, and the cells were lysed using a Qproteome Bacterial Lysis Kit (QIAGEN), according to the manufacturer's instructions; Protease Inhibitor Cocktail was not added, and the samples were centrifuged at 4° C. The soluble protein extracts from the induced cells and uninduced control were separated by SDS gel electrophoresis under reducing conditions on a 10% Bis-Tris gel (Life Technologies, Grand Island, N.Y.). The gel was stained using RAPIDstain™ (G-Biosciences). As shown in FIG. 5, lysate from induced cells contained proteins corresponding to PDI (53 kDa) and MnP-H4 (39 kDa), indicating that these proteins were expressed as soluble proteins in the bacterial cells. The greatest amount of soluble MnP-H4 was produced by induction with 50 mM propionate and 0.002% arabinose (lane 2).

C. Inducible Coexpression of an Alternate Mature Form of Manganese Peroxidase Along with Protein Disulfide Isomerase, and Measurement of MnP-H4 Activity Expression vectors were prepared to express a more fully truncated version of MnP-H4, referred to as MnP-H4_FT, which corresponds to the mature version of MnP-H4 protein as described in Sundaramoorthy et al., 1994 (cited above). The MnP-H4_FT amino acid sequence thus has an initial methionine residue attached to amino acids 13 though 370 of SEQ ID NO:13, and is provided as SEQ ID NO:23. In this experiment, the MnP-H4_FT coding sequence optimized for expression in *E. coli* (derived from the optimized MnP-H4 coding sequence described above), and the ChuA coding sequence, were expressed in the pBAD24 vector, and the PDI coding sequence (similarly optimized for expression in *E. coli* as described above) was expressed in the pPRO33 vector. The pBAD24-MnP_FT-ChuA expression construct was prepared by PCR-amplifying the MnP-H4 coding sequence and terminator from a template comprising the nucleotide sequence of SEQ ID NO: 18, using the forward and reverse primers of SEQ ID NOs 24 and 25, respectively. Use of the SEQ ID NO:24 forward primer places a NcoI restriction site and an ATG codon immediately upstream of the coding sequence for amino acids 13 though 370 of SEQ ID NO:13, and thus creates a coding sequence for the MnP-H4_FT amino acid sequence of SEQ ID NO:23. The ChuA expression construct sequences were PCR-amplified from a template comprising the nucleotide sequence of SEQ ID NO: 19, using the forward and reverse primers of SEQ ID NOs 26 and 27, respectively. The MnP-H4_FT and ChuA PCR products were cut with NcoI and SalI, and with SalI and HindIII, respectively, and were gel-purified and ligated together into the pBAD24 vector, which had been cut with NcoI and HindIII, CIP-treated, and gel-purified. The ligated pBAD24-MnP_FT-ChuA products comprise the MnP-H4_FT coding sequence expressed from the pBAD promoter, followed by the B0015 double terminator, the J23104 constitutive promoter, the B0034 ribosome binding site, and the ChuA protein-coding sequence. This pBAD24-MnP_FT-ChuA expression construct has the nucleotide sequence provided in SEQ ID NO:28.

The pPRO33-PDI expression construct was made by cutting the pPRO33 vector and the PDI expression construct, optimized for expression in *E. coli* as described above and comprising the nucleotide sequence of SEQ ID NO:22, with NheI and SalI, treating the cut pPRO33 vector with CIP, gel-purifying the fragments, and ligating them together. The resulting pPRO33-PDI expression construct has the nucleotide sequence provided in SEQ ID NO:29. The pBAD24-MnP_FT-ChuA and pPRO33-PDI expression constructs were used to cotransform *E. coli* SHuffle® Express cells (NEB) at 37 degrees C. overnight, to form SHuffle® Express (pBAD24-MnP_FT-ChuA/pPRO33-PDI) cells.

SHuffle® Express(pBAD24-MnP_FT-ChuA/pPRO33-PDI) and control SHuffle® Express(pBAD24/pPRO33) cells were used to inoculate 5 milliliters of LB media+CAM (34 micrograms/milliliter)+AMP (100 micrograms/milliliter) and grown overnight at 30 degrees C. with shaking at 250 rpm. Cells were spun down at 4000 rpm for 10 minutes at 4 degrees C., and resuspended, first in 400 microliters of M9 minimal (CA_noGlycerol: with casamino acids as a carbon source, but no glycerol)+CAM+AMP media, and then 75 microliters of that was added to 5 milliliters of M9 (CA_noGlycerol) minimal media+CAM+AMP. After the culture, grown at 30 degrees C. with shaking at 250 rpm, reached an OD600 of 0.6, ten aliquots of SHuffle® Express (pBAD24-MnP_FT-ChuA/pPRO33-PDI) cells were taken and induced in varying concentrations of hemin and of the arabinose and propionate inducers. Sample 1, the control, received no hemin and no inducers; the other nine samples had hemin added to a final concentration of 8 micromolar; arabinose concentrations of 0.025%, 0.05%, or 0.1%; and propionate concentrations 12.5 mM, 25 mM, or 50 mM. The control SHuffle® Express(pBAD24/pPRO33) cells (no inserts) were also included in the induction process, with an 'induced' sample and an uninduced control sample. The cells were induced for 12 hours at 25 degrees C. with shaking at 250 rpm, then were spun down and stored at −80 degrees C. To visualize the proteins produced by the induced coexpression, the frozen cell pellets were thawed and lysed using a Qproteome Bacterial Lysis Kit (QIAGEN) according to the instructions, but with 35 microliters of lysis buffer used for each 1 microliter of bacterial culture. Soluble protein extracts from the SHuffle® Express(pBAD24-MnP_FTChuA/pPRO33-PDI) induced cells and the uninduced control were separated by SDS gel electrophoresis under reducing conditions on a 10% Bis-Tris gel; samples were heated at 70 degrees C. for 10 minutes prior to loading on the gel. After staining the gel with RAPIDstain™ (gel not shown), there were visible bands corresponding to MnP-H4_FT and PDI in all the induced samples but not in the uninduced control, and the apparent density of bands on the gel indicated that the combination of 0.1% arabinose and 50 mM propionate produced the most MnP-H4_FT protein, and that higher arabinose concentrations generally produced more MnP-H4_FT, while lower arabinose concentrations generally produced more PDI, possibly due to catabolite repression of the propionate promoter by arabinose.

To determine the activity levels of the MnP-H4_FT produced by the inducible coexpression, 0.5 milliliters of the soluble cell lysis fraction, derived from the coexpression of MnP-H4_FT protein at 0.1% arabinose and 50 mM propionate, was dialyzed against 10 millimolar sodium acetate, 5 millimolar $CaCl_2$, ph 4.5, using a 0.5-milliliter 20,000-MWCO (molecular weight cutoff) Slide-A-Lyzer™ (Thermo Fisher Scientific Inc., Waltham Mass.). The sample was dialyzed at 4 degrees C. for 2 hours, the buffer changed for fresh buffer, and dialysis continued at 4 degrees C. overnight. There was protein precipitation at the end of the dialysis, but the MnP-H4 FT protein was still soluble and active, as shown by gel electrophoresis, and by a colorimetric enzymatic activity assay. The dialyzed protein sample containing MnP-H4_FT, along with the soluble protein fractions obtained from the SHuffle® Express(pBAD24-MnP_FT-ChuA/pPRO33-PDI) uninduced control cell, and from the no-insert SHuffle® Express(pBAD24/pPRO33) induced and uninduced control cells, were separated by SDS gel electrophoresis under reducing conditions on a 10% Bis-Tris gel; samples were heated at 70 degrees C. for 10 minutes prior to loading on the gel. After staining the gel with RAPIDstain™, as shown in FIG. 6, bands corresponding to PDI (54 kDa) and MnP-H4_FT (38 kDa) are clearly visible in the dialyzed protein sample produced by coexpression in 0.1% arabinose and 50 mM propionate (FIG. 6, Lane 2), and not visible in any of the control samples (Lane 3—SHuffle® Express(pBAD24-MnP_FT-ChuA/pPRO33-PDI) uninduced control; Lane 4—no-insert induced control; Lane 5—no-insert uninduced control). The enzymatic activity of the MnP-H4_FT protein produced by the inducible coexpression was assayed using the colorimetric manganese peroxidase assay described in Example 4 section E below, and the coexpressed MnP-H4_FT protein was shown to have comparable manganese peroxidase activity to that of a positive control MnP sample.

D. Production and Purification of Manganese Peroxidase

Host cells that have been co-transformed with MnP-ChuA and PDI expression vectors are streaked onto LB plates containing chloramphenicol and ampicillin. Single colonies are picked and each is used to inoculate a shake tube containing 15 ml LB+CAM+AMP broth. After incubation (at 30-37° C. with rotary shaking at 250 RPM) for an adequate length of time to generate stationary phase cultures, 5 ml from each tube with successful growth is used to inoculate an Erlenmeyer shake flask containing 100 ml LB+CAM+AMP broth. After further incubation (at 30-37° C. with rotary shaking at 250 RPM) sufficient to generate stationary phase cultures, a sample from each shake flask is checked for adequate cell density. An appropriate volume from a shake flask is introduced into a sterilized and pH-calibrated bioreactor and grown at 30-37° C. with agitation; after a period of growth, the cells are grown in medium containing hemin or another source of heme, until the cells reach an $OD_{600}$ of approximately 0.5. The cells are then induced by adding arabinose and propionate; for example, 0.02% arabinose and 50 mM propionate, or as determined by the titration methods of Example 7, and growth at 25-30° C. with agitation is continued. After incubation the cells are recovered from the growth medium, lysed, and the lysis supernatant (soluble protein extract) is collected. The MnP-H4 protein is purified from the soluble protein extract using methods such as fast protein liquid chromatography (FPLC) with a size-exclusion column or an ion-exchange column.

E. Assay for Manganese Peroxidase Activity

The amount of manganese peroxidase activity in a sample, and thus the concentration of active manganese peroxidase, can be determined by testing it for the ability to oxidize 2,6-dimethoxyphenol (2,6-DMP) to coerulignone in the presence of manganese and hydrogen peroxide. The following assay is for a 10-microliter sample; alternate amounts for a 1-microliter sample are given in parentheses. The following is added to a spectrophotometer cuvette before sample addition: 0.590 ml $dH_2O$ (0.599 ml $dH_2O$); 0.1 ml malonate disodium salt monohydrate (MDSH) solution (5 g MDSH in 60 ml $dH_2O$, pH 4.5); and 0.1 ml $MnSO_4.H_2O$ solution (0.06 g $MnSO_4.H_2O$ in 90 ml $dH_2O$). Immediately before measuring, 0.1 ml 2,6-DMP solution (0.014 g 2,6-dimethoxyphenol in 90 ml $dH_2O$) and the 10 microliter (1 microliter) sample is added to the cuvette. The cuvette is placed in the spectrophotometer and zeroed at 469 nm, and 0.1 ml fresh $H_2O_2$ (3.4 microliters 30% $H_2O_2$ in 30 ml $dH_2O$) is then added to the cuvette. The cuvette contents are mixed by pipetting up and down three times. One minute after addition of $H_2O_2$, the OD at 469 nm is measured. If the OD is greater than 0.2, the sample size is decreased to 1 microliter, or the sample to be measured is diluted; if the OD is less than 0.005, the sample size is increased to 0.1 ml and the $dH_2O$ volume is decreased to 0.500 ml, with all other volumes remaining the same; the assay is then repeated.

The measured absorbance is used to calculate the enzyme concentration (EC) in Units/L according to the following equation:

$$EC[U/L] = \frac{(Absorbance)(Assay\ volume\ [ml])(10^6\ \mu mol/mol)(1\ cm)}{(\varepsilon_{1\ cm}) * (Sample\ volume\ [ml])}$$

where $\varepsilon_{cm}$=49600 absorbance/M·cm·min and path length=1 cm. The enzyme concentration as calculated above is converted to mg/L according to the following equation: EC [mg/L]=enzyme concentration [U/L]/enzyme specific activity [U/mg], where a standard enzyme specific activity for MnP is 160 U/mg. The enzyme specific activity is calculated for any MnP sample by independently measuring the concentration of protein in the sample in mg/L, for example by spectrophotometric analysis at 280 nm. When the enzyme concentration (EC) is determined using the above 2,6-DMP oxidation assay, the specific activity in U/mg is calculated as: EC [U/L]/concentration [mg/L]=specific activity [U/mg].

Example 5

Inducible Coexpression of Infliximab

Infliximab is a chimeric monoclonal antibody that binds to TNF-alpha, an inflammatory cytokine, and is used in the treatment of conditions that involve TNF-alpha such as autoimmune diseases (Crohn's disease, rheumatoid arthritis, psoriasis, etc.). Infliximab is formed from a heavy chain (amino acid sequence shown as SEQ ID NO:30) and a light chain (amino acid sequence shown as SEQ ID NO:31); each of these chains has a variable domain sequence derived from mouse anti-TNF-alpha antibodies, and a human constant domain. Codon optimization for expression in E. coli and synthesis of polynucleotides encoding SEQ ID NOs 30 and 31 was performed by DNA2.0 (Menlo Park, Calif.). The expression construct formed by ligating the optimized coding sequence for the infliximab heavy chain into the multiple cloning site (MCS) of the pBAD24 expression vector is pBAD24-Infliximab_HC, which has the nucleotide sequence shown as SEQ ID NO:32. The expression construct formed by ligating the optimized coding sequence for the infliximab light chain into the MCS of the pPRO33 expression vector is pPRO33-Infliximab_LC, which has the nucleotide sequence shown as SEQ ID NO:33. The pBAD24-Infliximab_HC and pPRO33-Infliximab_LC expression constructs are used to transform E. coli SHuffle® Express cells (NEB) at 37 degrees C. overnight, creating SHuffle® Express(pBAD24-Infliximab_HC/pPRO33-Infliximab_LC) cells. These cells are grown generally as described in Examples 1 and 4, including the addition of selective compounds such as ampicillin and/or chloramphenicol as needed, with the exception that iron is preferably but optionally added to the LB growth medium, for example in the form of $FeSO_4.7H_2O$ at a concentration of 3.0 miligrams per liter. Cells are spun down and resuspended in M9 medium, preferably but optionally with acetate (for example, 0.27% sodium acetate ($C_2H_3O_2Na$)) added as the carbon source along with casamino acids (which provide essential amino acids, along with being a carbon source), and also preferably but optionally with iron supplementation of the media as described above, and grown until the optical density (OD600) of the culture reaches 0.8. (See Paliy and Gunasekera, "Growth of E. coli BL21 in minimal media with different gluconeogenic carbon sources and salt contents", Appl Microbiol Biotechnol 2007 January; 73(5): 1169-1172; Epub 2006 Aug. 30; Erratum in: Appl Microbiol Biotechnol 2006 December; 73(4): 968). At that point cells are induced by addition of arabinose (initially at concentrations including 0.1%) and propionate (initially at concentrations including 50 mM). Adjustment of the concentrations of arabinose and propionate can be made as described in EXAMPLE 7, and the infliximab antibodies produced are purified and characterized as described in EXAMPLE 9 through EXAMPLE 11.

Example 6

Inducible Coexpression of Proteins in Yeast Cells

Expression constructs for the inducible coexpression in yeast host cells of MnP-H4_FT with PDI, and of the mouse anti-human CD19 IgG1 antibody heavy and light chains, were created by the following method carried out by GenWay Biotech Inc. (San Diego Calif.). The pJ1231-03C and pJ1234-03C vectors (DNA2.0, Menlo Park, Calif.) were used as the backbone part of the yeast expression constructs, as they contain elements necessary for plasmid maintenance in either *E. coli* (pUC origin of replication) or *Saccharomyces cerevisiae* (2-micron circle origin of replication, along with selectable markers useful in either host: KanR (*E. coli*) and Leu2 (yeast) in pJ1231-03C; AmpR (*E. coli*) and Ura3 (yeast) in pJ1234-03C. The nucleotide sequences of the pJ1231-03C and pJ1234-03C vectors are shown as SEQ ID NOs 34 and 35, respectively. The pJ1231-03C and pJ1234-03C vectors were treated with BfuA1 restriction endonuclease (NEB, Catalog No. R0701S); fragments of the vectors that were not retained after BfuA1 digestion comprise an expression promoter, the DasherGFP coding sequence, and the CYC1 terminator sequence. PCR was performed on four expression constructs containing coding sequences for the polypeptides to be expressed, to create sequences that were then ligated into the BfuA1-cut pJ1231-03C and pJ1234-03C vectors. All PCR reactions were performed using Platinum® Pfx DNA Polymerase (Life Technologies, Grand Island, N.Y., Catalog No. 11708021), and the QIAEX II DNA purification kit (QIAGEN, Catalog No. 20051) was used for purification of PCR-product and vector fragments, according to the manufacturers' instructions.

The pBAD24-MnP_FT-ChuA expression construct (SEQ ID NO:28), containing the AraC coding sequence, the pBAD arabinose-inducible promoter, and the MnP-H4_FT and ChuA coding sequences, is used as the template in two separate PCR reactions in order to add a 6×His tag at the C-terminal ends of the MnP-H4_FT coding sequence and the ChuA coding sequence, and BsaI restriction sites for cloning into the vectors. (Preferably, but optionally, the ChuA coding sequence is not altered to add a His tag at its C-terminal end; this can be accomplished by using a primer similar in sequence to that of SEQ ID NO:39, but without bases 21 through 38 of SEQ ID NO:39.) The primers used in these two PCR reactions are (1) the BsaI-AraC-MnP-H4_FT primer (SEQ ID NO:36) and the MnP-H4_FT-6× His-reverse primer (SEQ ID NO:37), and (2) the MnP-H4_FT-6×His-forward primer (SEQ ID NO:38) and the ChuA-6×His-BsaI primer (SEQ ID NO:39). A further PCR reaction is then performed on the two purified PCR products, using the BsaI-AraC-MnP-H4_FT and ChuA-6×His-BsaI primers, to create a single product (AraC-MnP-H4_FT-ChuA, SEQ ID NO:40) that is purified, cut with BsaI (NEB, Catalog No. R0535S), and ligated into the BfuA1-cut pJ1231-03C vector using T4 DNA ligase (Life Technologies, Catalog No. 15224025) to create the pJ1231-AraC-MnP-H4_FT-ChuA expression construct. (Preferably, the BsaI-cut AraC-MnP-H4_FT-ChuA fragment is also ligated into the BfuA1-cut pJ1234-03C vector, to create the pJ1234-AraC-MnP-H4_FT-ChuA expression construct.)

The pPRO33-PDI expression construct (SEQ ID NO:29), containing the PrpR coding sequence, the pPRO propionate-inducible promoter, and the PDI coding sequence, was used as the template in a PCR reaction, which added a 5×His tag at the C-terminal end of the PDI coding sequence, and BsaI restriction sites for cloning into the vectors. (Preferably, but optionally, the PDI coding sequence is not altered to add a His tag at its C-terminal end; this can be accomplished by using a primer similar in sequence to that of SEQ ID NO:42, but without bases 21 through 35 of SEQ ID NO:42.) The primers used in this PCR reaction were the BsaI-PrpR-PDI primer (SEQ ID NO:41) and the PDI-5×His-BsaI primer (SEQ ID NO:42), creating a PCR product (PrpR-PDI, SEQ ID NO:43) that was purified, cut with BsaI, and ligated into the BfuA1-cut pJ1231-03C vector using T4 DNA ligase to create the pJ1231-PrpR-PDI expression construct. (Preferably, the BsaI-cut PrpR-PDI fragment is also ligated into the BfuA1-cut pJ1234-03C vector to create the pJ1234-PrpR-PDI expression construct.)

The expression constructs encoding the mouse anti-human CD19 IgG1 heavy chain and the mouse anti-human CD19 IgG1 light chain—pBAD24-HC and pPRO33-LC, respectively—were used as the templates in two separate PCR reactions each in order to remove the signal sequence from each coding sequence and to add BsaI restriction sites for cloning into the vectors. For pBAD24-HC, the primers used in these two PCR reactions were (1) the BsaI-AraC-HC-forward primer (SEQ ID NO:44) and the HC-reverse primer (SEQ ID NO:45), and (2) the HC-forward primer (SEQ ID NO:46) and the HC-BsaI-reverse primer (SEQ ID NO:47). For pPRO33-LC, the primers used in these two PCR reactions were (1) the BsaI-PrpR-LC-forward primer (SEQ ID NO:48) and the LC-reverse primer (SEQ ID NO:49), and (2) the LC-forward primer (SEQ ID NO:50) and the LC-BsaI-reverse primer (SEQ ID NO:51). Use of the BsaI-AraC-HC-forward primer (SEQ ID NO:44) and the BsaI-PrpR-LC-forward primer (SEQ ID NO:48) in these reactions results in HC and LC coding sequences lacking the signal sequence, referred to as HC_NS (no signal) and LC_NS: the modified HC_NS coding sequence results in an HC_NS polypeptide having an initial methionine residue followed by amino acids 20 through 464 of SEQ ID NO:2; the modified LC_NS coding sequence results in an LC_NS polypeptide having an initial methionine residue followed by an alanine residue and then amino acids 21 through 239 of SEQ ID NO:4. A further PCR reaction was then performed on each set of two purified PCR products, using the BsaI-AraC-HC-forward and HC-BsaI-reverse primers, and the BsaI-PrpR-LC-forward and LC-BsaI-reverse primers, respectively, to create two individual products (AraC-HC_NS, SEQ ID NO:52, and PrpR-LC_NS, SEQ ID NO:53) that were each purified, cut with BsaI, and ligated into the BfuA1-cut pJ1231-03C vector (PrpR-LC_NS) or the BfuA1-cut pJ1234-03C vector (AraC-HC_NS) using T4 DNA ligase, to create the pJ1231-PrpR-LC NS and pJ1234-AraC-HC_NS expression constructs.

The ligase mixtures were transformed into *E. coli* DH5alpha cells and plated on LB agar plates with sufficient amounts of kanamycin or ampicillin to maintain the plasmids in the DH5alpha cells. Preparation of plasmid DNA was performed according to standard methods. (Optionally but preferably, the prepared plasmid DNA is used in sequencing reactions to confirm the sequences of the plasmid inserts.)

Competent INVSc-1 *S. cerevisiae* cells were prepared using the S.c. EasyComp™ Transformation Kit (Life Technologies, Catalog No. K5050-01) according to the manufacturer's instructions. The INVSc-1 *S. cerevisiae* strain has the following genotype (MATa his3Δ1 leu2 trp1-289 ura3-52/MATα his3Δ1 leu2 trp1-289 ura3-52) and phenotype:

His⁻, Leu⁻, Trp⁻, Ura⁻. Briefly, a single colony from the INVSc-1 strain was inoculated in 10 milliliters of YPD medium (contains, per liter: 10 g yeast extract, 20 g peptone, 20 g glucose) and grown overnight at 30 degrees C. in a shaking incubator at 250 rpm. Next day, the overnight culture was diluted in 10 milliliters fresh YPD medium to an OD600 of 0.3 and grown until OD600 reached 0.8. The cells were collected by centrifugation at 1500 rpm for 5 minutes at room temperature. After that, the cells were resuspended in 10 milliliters of Solution 1 (wash solution) and collected by centrifugation at 1500 rpm for 5 minutes at room temperature. Supernatant was discarded and cells were resuspended in 1 milliliter of Solution 2 (resuspension solution), divided in 50-microliter aliquots and stored at −80 degrees C. To transform the competent yeast cells with the expression constructs, 50 microliters of INVSc-1 competent cells were mixed with 1.2 micrograms of each expression vector or control vector and 500 microliters of Solution 3 (transformation solution). Then cells were mixed vigorously and incubated in a 30 degrees C. water bath for 1 hour and vortexed for 10 seconds every 15 minutes. 100- and 400-microliter aliquots of transformation mixtures were seeded on SC minimal agar plates in the absence of appropriate selective reagent. SC minimal medium contains, per liter: 6.7 g yeast nitrogen base, 20 g glucose, 0.05 g aspartic acid, 0.05 g histidine, 0.05 g isoleucine, 0.05 g methionine, 0.05 g phenylalanine, 0.05 g proline, 0.05 g serine, 0.05 g tyrosine, 0.05 g valine, 0.1 g adenine, 0.1 g arginine, 0.1 g cysteine, 0.1 g leucine (omitted in -Leu selective media), 0.1 g lysine, 0.1 g threonine, 0.1 g tryptophan, and 0.1 g uracil (omitted in -Ura selective media). INVSc-1 cells transformed with pJ1231-PrpR-PDI, with pJ1231-PrpR-LC_NS, and with the pJ1231-03C control vector were selected on plates without leucine at 30 degrees C. for 48-72 hours. INVSc-1 cells transformed with pJ1234-AraC-HC_NS and with the pJ1234-03C control vector were grown under the same conditions on SC minimal agar plates without uracil. (Preferably, INVSc-1 cells transformed with pJ1231-AraC-MnP-H4_FT-ChuA, with pJ1234-AraC-MnP-H4_FT-ChuA, and with pJ1234-PrpR-PDI are also grown under the same conditions on SC minimal agar plates without uracil.) INVSc-1 cells co-transformed simultaneously with pJ1234-AraC-HC_NS and pJ1231-PrpR-LC_NS were selected under the same conditions on SC minimal agar plates without leucine or uracil. (Preferably, INVSc-1 cells co-transformed simultaneously with pJ1231-AraC-MnP-H4_FT-ChuA and pJ1234-PrpR-PDI, or with pJ1234-AraC-MnP-H4_FT-ChuA and pJ1231-PrpR-PDI, are selected under the same conditions on SC minimal agar plates without leucine or uracil.)

Cells from all colonies from each transformation were scraped and resuspended in 4 milliliters of liquid minimal SC medium in absences of appropriate selective reagent and carbon source. $OD_{600}$ in each culture was measured and normalized to 0.4 optical units. Protein expression was induced by addition of 2% sterile filtered arabinose (Sigma-Aldrich, St. Louis, Mo., Catalog No. A3256-25G) to cultures transformed with pJ1234-AraC-HC_NS. In cells transformed with pJ1231-PrpR-PDI and with pJ1231-PrpR-LC_NS, protein expression was induced by addition of 2% sterile filtered propionate (Sigma-Aldrich, Catalog No. P188-100G). And co-expression of pJ1234-AraC-HC_NS and pJ1231-PrpR-LC_NS in corresponding culture was induced by addition of 1% arabinose and 1% propionate. (Preferably, the induction medium for protein expression by cells transformed with pJ1231-AraC-MnP-H4_FT-ChuA, and for cells co-transformed with pJ1231-AraC-MnP-H4_FT-ChuA and pJ1234-PrpR-PDI, or with pJ1234-AraC-MnP-H4_FT-ChuA and pJ1231-PrpR-PDI, also contains hemin (Sigma-Aldrich, Catalog Nos. H9039 or 51280) added to a final concentration of 8 micromolar.) The time course for protein expression was 24 hours, at 30 degrees C. in a shaking incubator at 250 rpm. Cells from 0.5 milliliters of each pre-induced cultures were collected by centrifugation, washed with 1 milliliter of deionized water and stored at −80 degrees C. Samples from post-induced cultures were prepared in the same way. Total protein extracts were prepared from pre- and post-induced cultures, resolved in 4-20% SDS-PAGE, and transferred to a PDVF membrane. Expression level of target proteins was analyzed by Western blotting using anti-6×His tag and anti-Human IgG antibodies.

Example 7

Titration of Coexpression by Varying Inducer Concentration

To optimize production of a multimeric product using the inducible coexpression systems of the invention, it is possible to independently adjust or titrate the concentrations of the inducers. Host cells containing L-arabinose-inducible and propionate-inducible expression constructs are grown to the desired density (such as an $OD_{600}$ of approximately 0.5) in M9 minimal medium containing the appropriate antibiotics, then cells are aliquoted into small volumes of M9 minimal medium, optionally prepared with no carbon source such as glycerol, and with the appropriate antibiotics and varying concentrations of each inducer. The concentration of L-arabinose necessary to induce expression is typically less than 2%. In a titration experiment, the tested concentrations of L-arabinose can range from 2% to 1.5%, 1%, 0.5%, 0.2%, 0.1%, 0.05%, 0.04%, 0.03%, 0.02%, 0.01%, 0.005%, 0.002%, and 0.001%. The concentrations of L-rhamnose or D-xylose necessary to induce expression of L-rhamnose-inducible or D-xylose-inducible promoters are tested similarly, with the tested concentrations ranging from 5% to 0.01%. For each concentration 'x' of L-arabinose (or L-rhamnose or D-xylose) that is tested, the concentration of a different inducer such as propionate, added to each of the tubes containing concentration 'x' of the first inducer, is varied in each series of samples, which in the case of propionate range from 1 M to 750 mM, 500 mM, 250 mM, 100 mM, 75 mM, 50 mM, 25 mM, 10 mM, 5 mM, and 1 mM. Alternatively, titration experiments can start at a 'standard' combination of inducer concentrations, which is 0.002% of any of L-arabinose, L-rhamnose, or D-xylose, and/or 50 mM propionate, and test new combinations of inducer concentrations that vary from that of the 'standard' combination. Similar titration experiments can be performed with any combination of inducers used in an inducible coexpression system of the invention, including but not limited to L-arabinose, propionate, L-rhamnose, and D-xylose. After growth in the presence of inducers for 6 hours, the cells are pelleted, the desired product is extracted from the cells, and the yield of product per mass value of cells is determined by a quantitative immunological assay such as ELISA, or by purification of the product and quantification by UV absorbance at 280 nm.

It is also possible to titrate inducer concentrations using a high-throughput assay, in which the proteins to be expressed are engineered to include a fluorescent protein moiety, such as that provided by the mKate2 red fluorescent protein (Evrogen, Moscow, Russia), or the enhanced green fluorescent proteins from *Aequorea victoria* and *Bacillus cereus*.

Another approach to determining the amount and activity of gene products produced by different concentrations of inducers in a high-throughput titration experiment, is to use a sensor capable of measuring biomolecular binding interactions, such as a sensor that detects surface plasmon resonance, or a sensor that employs bio-layer interferometry (BLI) (for example, an Octet® QK system from forteBIO, Menlo Park, Calif.).

Example 8

Measurement of the Strength of Promoters and the Homogeneity of Inducible Expression The strength of a promoter is measured as the amount of transcription of a gene product initiated at that promoter, relative to a suitable control. For constitutive promoters directing expression of a gene product in an expression construct, a suitable control could use the same expression construct, except that the 'wild-type' version of the promoter, or a promoter from a 'housekeeping' gene, is used in place of the promoter to be tested. For inducible promoters, expression of the gene product from the promoter can be compared under inducing and non-inducing conditions.

A. Measuring Promoter Strength Using Quantitative PCR to Determine Levels of RNA Transcribed from the Promoter The method of De Mey et al. ("Promoter knock-in: a novel rational method for the fine tuning of genes", BMC Biotechnol 2010 Mar. 24; 10: 26) is used to determine the relative strength of promoters in host cells that can be grown in culture. Host cells containing an expression construct with the promoter to be tested, and control host cells containing a control expression construct, are grown in culture in triplicate. One-ml samples are collected at $OD_{600}=1.0$ for mRNA and protein collection. Total RNA extraction is done using an RNeasy mini kit (QIAGEN, The Netherlands). The purity of RNA is verified on a FA-agarose gel as recommended by QIAGEN and the RNA concentration is determined by measuring the absorbance at 260 nm. Two micrograms of RNA is used to synthesize cDNA using a random primer and RevertAid H Minus M-MulV reverse transcriptase (Fermentas, Glen Burnie, Md.). The strength of the promoter is determined by RT-qPCR carried out in an iCycler IQ® (Bio-Rad, Eke, Belgium) using forward and reverse primers designed to amplify the cDNA corresponding to the transcript produced from the promoter. (For this purpose, the De Mey et al. authors used the Fw-ppc-qPCR and Rv-ppc-qPCR primers, and the primers Fw-rpoB-qPCR and Rv-rpoB-qPCR from the control housekeeping gene rpoB.) SYBR GreenER qPCR supermix (Life Technologies, Grand Island, N.Y.) is used to perform a brief UDG (uracil DNA glycosylase) incubation (50° C. for 2 min) immediately followed by PCR amplification (95° C. for 8.5 min; 40 cycles of 95° C. for 15 s and 60° C. for 1 min) and melting curve analysis (95° C. for 1 min, 55° C. for 1 min and 80 cycles of 55° C.+0.5° C./cycles for 10 s) to identify the presence of primer dimers and analyze the specificity of the reaction. This UDG incubation step before PCR cycling destroys any contaminating dU-containing products from previous reactions. UDG is then inactivated by the high temperatures during normal PCR cycling, thereby allowing the amplification of genuine target sequences. Each sample is performed in triplicate. The relative expression ratios are calculated using the "Delta-delta ct method" of PE Applied Biosystems (PerkinElmer, Forster City, Calif.).

B. Measuring Inducible Promoter Strength and Homogeneity of Induction Using a Fluorescent Reporter Gene These experiments are performed using the methods of Khlebnikov et al. ("Regulatable arabinose-inducible gene expression system with consistent control in all cells of a culture", J Bacteriol 2000 December; 182(24): 7029-7034). Experiments measuring the induction of an inducible promoter are performed in C medium supplemented with 3.4% glycerol as a carbon source (Helmstetter, "DNA synthesis during the division cycle of rapidly growing *Escherichia coli* B/r", J Mol Biol 1968 Feb. 14; 31(3): 507-518). *E. coli* strains containing expression constructs comprising at least one inducible promoter controlling expression of a fluorescent reporter gene are grown at 37° C. under antibiotic selection to an optical density at 600 nm (OD600) of 0.6 to 0.8. Cells are collected by centrifugation (15,000×g), washed in C medium without a carbon source, resuspended in fresh C medium containing antibiotics, glycerol, and/or inducer (for the induction of gene expression) to an OD600 of 0.1 to 0.2, and incubated for 6 h. Samples are taken routinely during the growth period for analysis. Culture fluorescence is measured on a Versafluor Fluorometer (Bio-Rad Inc., Hercules, Calif.) with 360/40-nm-wavelength excitation and 520/10-nm-wavelength emission filters. The strength of expression from an inducible promoter upon induction can be expressed as the ratio of the maximum population-averaged fluorescence (fluorescence/OD ratio) of the induced cells relative to that of control (such as uninduced) cells. To determine the homogeneity of induction within the cell population, flow cytometry is performed on a Beckman-Coulter EPICS XL flow cytometer (Beckman Instruments Inc., Palo Alto, Calif.) equipped with an argon laser (emission at a wavelength of 488 nm and 15 mW) and a 525-nm-wavelength band pass filter. Prior to the analysis, sampled cells are washed with phosphate-buffered saline that had been filtered (filter pore size, 0.22 micrometers), diluted to an OD600 of 0.05, and placed on ice. For each sample, 30,000 events are collected at a rate between 500 and 1,000 events/s. The percentage of induced (fluorescent) cells in each sample can be calculated from the flow cytometry data.

Example 9

Purification of Antibodies

Antibodies produced by the inducible coexpression systems of the invention are purified by centrifuging samples of lysed host cells at 10,000×g for 10 minutes to remove any cells and debris. The supernatant is filtered through a 0.45 micrometer filter. A 1-ml Recombinant Protein G—Sepharose® 4B column (Life Technologies, Grand Island, N.Y.) is set up to achieve flow rates of 1 ml/min, and is used with the following buffers: binding buffer: 0.02 M sodium phosphate, pH 7.0; elution buffer: 0.1 M glycine-HCl, pH 2.7; and neutralization buffer: 1 M Tris-HCl, pH 9.0. The column is equilibrated with 5 column volumes (5 ml) of binding buffer, and then the sample is applied to the column. The column is washed with 5-10 column volumes of the binding buffer to remove impurities and unbound material, continuing until no protein is detected in the eluent (determined by UV absorbance at 280 nm). The column is then eluted with 5 column volumes of elution buffer, and the column is immediately re-equilibrated with 5-10 column volumes of binding buffer.

Example 10

Measurement of Antibody Binding Affinity

The antibody binding affinity, expressed as "Kd" or "Kd value", is measured by a radiolabeled antigen-binding assay (RIA) performed with the Fab version of an antibody of interest and its antigen as described by the following assay. Production of the Fab version of a full-length antibody is well known in the art. Solution-binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, for example, Chen et al., "Selection and analysis of an optimized anti-VEGF antibody: crystal structure of an affinity-matured Fab in complex with antigen", J Mol Biol 1999 Nov. 5; 293(4): 865-881). To establish conditions for the assay, microtiter plates (DYNEX Technologies, Inc., Chantilly, Va.) are coated overnight with 5 micrograms/ml of a capturing anti-Fab antibody (Cappel Labs, West Chester, Pa.) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620; Thermo Scientific, Rochester, N.Y.), 100 pM or 26 pM [$^{125}$I]-antigen are mixed with serial dilutions of a Fab of interest (e.g., consistent with assessment of the anti-VEGF antibody, Fab-12, in Presta et al., "Humanization of an anti-vascular endothelial growth factor monoclonal antibody for the therapy of solid tumors and other disorders", Cancer Res 1997 Oct. 15; 57(20): 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% TWEEN-20™ surfactant in PBS. When the plates have dried, 150 microliters/well of scintillant (MICROSCINT-20™; PerkinElmer, Waltham, Mass.) is added, and the plates are counted on a TOPCOUNT™ gamma counter (PerkinElmer) for ten minutes. Concentrations of each Fab that give less than or equal to 20% of maximal binding are chosen for use in competitive-binding assays.

Alternatively, the Kd or Kd value is measured by using surface-plasmon resonance assays using a BIACORE®-2000 or a BIACORE®-3000 instrument (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micrograms/ml (~0.2 micromolar) before injection at a flow rate of 5 microliters/minute to achieve approximately 10 RU of coupled protein. Following the injection of antigen, 1 M ethanolamine is injected to block unreacted groups. For kinetics measurements, two-fold serial dilutions of Fab (0.78 nM to 500 nM) are injected in PBS with 0.05% TWEEN 20™ surfactant (PBST) at 25° C. at a flow rate of approximately 25 microliters/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio $k_{off}/k_{on}$. If the on-rate exceeds $10^6$ $M^{-1}s^{-1}$ by the surface-plasmon resonance assay above, then the on-rate can be determined by using a fluorescent quenching technique that measures the increase or decrease in fluorescence-emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

Example 11

Characterizing the Disulfide Bonds Present in Coexpression Products

The number and location of disulfide bonds in coexpressed protein products can be determined by digestion of the protein with a protease, such as trypsin, under non-reducing conditions, and subjecting the resulting peptide fragments to mass spectrometry (MS) combining sequential electron transfer dissociation (ETD) and collision-induced dissociation (CID) MS steps (MS2, MS3) (Nili et al., "Defining the disulfide bonds of insulin-like growth factor-binding protein-5 by tandem mass spectrometry with electron transfer dissociation and collision-induced dissociation", J Biol Chem 2012 Jan. 6; 287(2): 1510-1519; Epub 2011 Nov. 22).

Digestion of Coexpressed Protein.

To prevent disulfide bond rearrangements, any free cysteine residues are first blocked by alkylation: the coexpressed protein is incubated protected from light with the alkylating agent iodoacetamide (5 mM) with shaking for 30 minutes at 20° C. in buffer with 4 M urea, and then is separated by non-reducing SDS-PAGE using precast gels. Alternatively, the coexpressed protein is incubated in the gel after electrophoresis with iodoacetamide, or without as a control. Protein bands are stained, de-stained with double-deionized water, excised, and incubated twice in 500 microliters of 50 mM ammonium bicarbonate, 50% (v/v) acetonitrile while shaking for 30 minutes at 20° C. Protein samples are dehydrated in 100% acetonitrile for 2 minutes, dried by vacuum centrifugation, and rehydrated with 10 mg/ml of trypsin or chymotrypsin in buffer containing 50 mM ammonium bicarbonate and 5 mM calcium chloride for 15 minutes on ice. Excess buffer is removed and replaced with 50 microliters of the same buffer without enzyme, followed by incubation for 16 hours at 37° C. or 20° C., for trypsin and chymotrypsin, respectively, with shaking. Digestions are stopped by addition of 3 microliters of 88% formic acid, and after brief vortexing, the supernatant is removed and stored at −20° C. until analysis.

Localization of Disulfide Bonds by Mass Spectrometry.

Peptides are injected onto a 1 mm×8 mm trap column (Michrom BioResources, Inc., Auburn, Calif.) at 20 microliters/minute in a mobile phase containing 0.1% formic acid. The trap cartridge is then placed in-line with a 0.5 mm×250 mm column containing 5 mm Zorbax SB-C18 stationary phase (Agilent Technologies, Santa Clara, Calif.), and peptides separated by a 2-30% acetonitrile gradient over 90 minutes at 10 microliters/minute with a 1100 series capillary HPLC (Agilent Technologies). Peptides are analyzed using a LTQ Velos linear ion trap with an ETD source (Thermo Scientific, San Jose, Calif.). Electrospray ionization is performed using a Captive Spray source (Michrom Bioresources, Inc.). Survey MS scans are followed by seven data-dependant scans consisting of CID and ETD MS2 scans on the most intense ion in the survey scan, followed by five MS3 CID scans on the first- to fifth-most intense ions in the ETD MS2 scan. CID scans use normalized collision energy of 35, and ETD scans use a 100 ms activation time with supplemental activation enabled. Minimum signals to initiate MS2 CID and ETD scans are 10,000, minimum signals for initiation of MS3 CID scans are 1000, and isolation widths for all MS2 and MS3 scans are 3.0 m/z. The dynamic exclusion feature of the software is enabled with a repeat count of 1, exclusion list size of 100, and exclusion duration of 30 s. Inclusion lists to target specific cross-linked species for collection of ETD MS2 scans are used. Separate data files for MS2 and MS3 scans are created by Bioworks 3.3 (Thermo Scientific) using ZSA charge state analysis. Matching of MS2 and MS3 scans to peptide sequences is performed by Sequest (V27, Rev 12, Thermo Scientific). The analysis is performed without enzyme specificity, a parent ion mass tolerance of 2.5, fragment mass tolerance of 1.0, and a variable mass of +16 for oxidized methionine residues. Results are then analyzed using the program Scaffold (V3_00_08, Proteome Software, Portland, Oreg.) with minimum peptide and protein probabilities of 95 and 99% being used. Peptides from MS3 results are sorted by scan number, and cysteine containing peptides are identified from groups of MS3 scans produced from the five most intense ions observed in ETD MS2 scans. The identities of cysteine peptides participating in disulfide-linked species are further confirmed by manual examination of the parent ion masses observed in the survey scan and the ETD MS2 scan.

Example 12

Isolation of Coexpression Products from Bacterial Cell Periplasm, from Spheroplasts, and from Whole Cells The inducible coexpression system of the invention can be used to express gene products that accumulate in different compartments of the cell, such as the cytoplasm or periplasm. Host cells such as *E. coli* or *S. cerevisiae* have an outer cell membrane or cell wall, and can form spheroplasts when the outer membrane or wall is removed. Coexpressed proteins made in such hosts can be purified specifically from the periplasm, or from spheroplasts, or from whole cells, using the following method (Schoenfeld, "Convenient, rapid enrichment of periplasmic and spheroplasmic protein fractions using the new PeriPreps™ Periplasting Kit", Epicentre Forum 1998 5(1): 5; see www.epibio.com/newsletter/f5_1/f5_1pp.asp). This method, using the PeriPreps™ Periplasting Kit (Epicentre® Biotechnologies, Madison Wis.; protocol available at www.epibio.com/pdftechlit/107pl0612.pdf), is designed for *E. coli* and other gram negative bacteria, but the general approach can be modified for other host cells such as *S. cerevisiae*.

1. The bacterial host cell culture is grown to late log phase only, as older cell cultures in stationary phase commonly demonstrate some resistance to lysozyme treatment. If the expression of recombinant protein is excessive, cells may prematurely lyse; therefore, cell cultures are not grown in rich medium or at higher growth temperatures that might induce excessive protein synthesis. Protein expression is then induced; the cells should be in log phase or early stationary phase.

2. The cell culture is pelleted by centrifugation at a minimum of 1,000×g for 10 minutes at room temperature. Note: the cells must be fresh, not frozen. The wet weight of the cell pellet is determined in order to calculate the amount of reagents required for this protocol.

3. The cells are thoroughly resuspended in a minimum of 2 ml of PeriPreps Periplasting Buffer (200 mM Tris-HCl pH 7.5, 20% sucrose, 1 mM EDTA, and 30 U/microliter Ready-Lyse Lysozyme) for each gram of cells, either by vortex mixing or by pipeting until the cell suspension is homogeneous. Note: excessive agitation may cause premature lysing of the spheroplasts resulting in contamination of the periplasmic fraction with cytoplasmic proteins.

4. Incubate for five minutes at room temperature. Ready-Lyse Lysozyme is optimally active at room temperature. Lysis at lower temperatures (0° C.–4° C.) requires additional incubation time; at such temperatures incubation times are extended 2- to 4-fold.

5. Add 3 ml of purified water at 4° C. for each gram of original cell pellet weight (Step 2) and mix by inversion.

6. Incubate for 10 minutes on ice.

7. The lysed cells are pelleted by centrifugation at a minimum of 4,000×g for 15 minutes at room temperature.

8. The supernatant containing the periplasmic fraction is transferred to a clean tube.

9. To degrade contaminating nucleic acids, OmniCleave Endonuclease is optionally added to PeriPreps Lysis Buffer. Inclusion of a nuclease will generally improve the yield of protein and the ease of handling of the lysates, but addition of a nuclease is undesirable in some cases: for example, the use of a nuclease should be avoided if residual nuclease activity or transient exposure to the magnesium cofactor will interfere with subsequent assays or uses of the purified protein. The addition of EDTA to the lysate to inactivate OmniCleave Endonuclease, likewise, may interfere with subsequent assay or use of the purified protein. If nuclease is to be added, 2 microliters of OmniCleave Endonuclease and 10 microliters of 1.0 M $MgCl_2$ are diluted up to 1 ml with PeriPreps Lysis Buffer (10 mM Tris-HCl pH 7.5, 50 mM KCl, 1 mM EDTA, and 0.1% deoxycholate) for each milliliter of Lysis Buffer needed in Step 10.

10. The pellet is resuspended in 5 ml of PeriPreps Lysis Buffer for each gram of original cell pellet weight.

11. The pellet is incubated at room temperature for 10 minutes (if included, OmniCleave Endonuclease activity will cause a significant decrease in viscosity; the incubation is continued until the cellular suspension has the consistency of water).

12. The cellular debris is pelleted by centrifugation at a minimum of 4,000×g for 15 minutes at 4° C.

13. The supernatant containing the spheroplast fraction is transferred to a clean tube.

14. If OmniCleave Endonuclease was added to the PeriPreps Lysis Buffer, 20 microliters of 500 mM EDTA is added for each milliliter of the resultant spheroplastic fraction, to chelate the magnesium (the final concentration of EDTA in the lysate is 10 mM). Following hydrolysis of nucleic acids with OmniCleave Endonuclease, lysates may contain substantial amounts of mono- or oligonucleotides. The presence of these degradation products may affect further processing of the lysate: for example, nucleotides may decrease the binding capacity of anion exchange resins by interacting with the resin.

The above protocol can be used to prepare total cellular protein with the following modifications. The cells pelleted in Step 2 can be fresh or frozen; at Step 4, the cells are incubated for 15 minutes; Steps 5 through 8 are omitted; at Step 10, 3 ml of PeriPreps Lysis Buffer is added for each gram of original cell pellet weight.

After preparation of periplasmic, or spheroplastic, or whole-cell protein samples, the samples can be analyzed by any of a number of protein characterization and/or quantification methods. In one example, the successful fractionation of periplasmic and spheroplastic proteins is confirmed by analyzing an aliquot of both the periplasmic and spheroplastic fractions by SDS-PAGE (two microliters of each fraction is generally sufficient for visualization by staining with Coomassie Brilliant Blue). The presence of unique proteins or the enrichment of specific proteins in a given fraction indicates successful fractionation. For example, if the host cell contains a high-copy number plasmid with the ampicillin resistance marker, then the presence of (3-lactamase (31.5 kDa) mainly in the periplasmic fraction indicates successful fractionation. Other E. coli proteins found in the periplasmic space include alkaline phosphatase (50 kDa) and elongation factor Tu (43 kDa). The amount of protein found in a given fraction can be quantified using any of a number of methods (such as SDS-PAGE and densitometry analysis of stained or labeled protein bands, scintillation counting of radiolabeled proteins, enzyme-linked immunosorbent assay (ELISA), or scintillation proximity assay, among other methods.) Comparing the amounts of a protein found in the periplasmic fraction as compared to the spheroplastic fraction indicates the degree to which the protein has been exported from the cytoplasm into the periplasm.

Example 13

Determination of Polynucleotide or Amino Acid Sequence Similarity

Percent polynucleotide sequence or amino acid sequence identity is defined as the number of aligned symbols, i.e. nucleotides or amino acids, that are identical in both aligned sequences, divided by the total number of symbols in the alignment of the two sequences, including gaps. The degree of similarity (percent identity) between two sequences may be determined by aligning the sequences using the global alignment method of Needleman and Wunsch (J. Mol. Biol. 48:443, 1970), as implemented by the National Center for Biotechnology Information (NCBI) in the Needleman-Wunsch Global Sequence Alignment Tool, available through the website blast.ncbi.nlm.nih.gov/Blast.cgi. In one embodiment, the Needleman and Wunsch alignment parameters are set to the default values (Match/Mismatch Scores of 2 and −3, respectively, and Gap Costs for Existence and Extension of 5 and 2, respectively). Other programs used by those skilled in the art of sequence comparison may also be used to align sequences, such as, for example, the basic local alignment search tool or BLAST® program (Altschul et al., "Basic local alignment search tool", J Mol Biol 1990 Oct. 5; 215(3): 403-410), as implemented by NCBI, using the default parameter settings described at the blast.ncbi.nlm.nih.gov/Blast.cgi website. The BLAST algorithm has multiple optional parameters including two that may be used as follows: (A) inclusion of a filter to mask segments of the query sequence that have low compositional complexity or segments consisting of short-periodicity internal repeats, which is preferably not utilized or set to 'off', and (B) a statistical significance threshold for reporting matches against database sequences, called the 'Expect' or E-score (the expected probability of matches being found merely by chance; if the statistical significance ascribed to a match is greater than this E-score threshold, the match will not be reported). If this 'Expect' or E-score value is adjusted from the default value (10), preferred threshold values are 0.5, or in order of increasing preference, 0.25, 0.1, 0.05, 0.01, 0.001, 0.0001, 0.00001, and 0.000001.

In practicing the present invention, many conventional techniques in molecular biology, microbiology, and recombinant DNA technology are optionally used. Such conventional techniques relate to vectors, host cells, and recombinant methods. These techniques are well known and are explained in, for example, Berger and Kimmel, Guide to Molecular Cloning Techniques, Methods in Enzymology volume 152 Academic Press, Mc, San Diego, Calif.; Sambrook et al., Molecular Cloning—A Laboratory Manual (3rd Ed.), Vol. 1-3, Cold Spring Harbor Laboratory, Cold Spring Harbor, N.Y., 2000; and Current Protocols in Molecular Biology, F. M. Ausubel et al., eds., Current Protocols, a joint venture between Greene Publishing Associates, Inc. and John Wiley & Sons, Inc., (supplemented through 2006). Other useful references, for example for cell isolation and culture and for subsequent nucleic acid or protein isolation, include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York); and Atlas and Parks (Eds.) The Handbook of Microbiological Media (1993) CRC Press, Boca Raton, Fla. Methods of making nucleic acids (for example, by in vitro amplification, purification from cells, or chemical synthesis), methods for manipulating nucleic acids (for example, by site-directed mutagenesis, restriction enzyme digestion, ligation, etc.), and various vectors, cell lines, and the like useful in manipulating and making nucleic acids are described in the above references. In addition, essentially any polynucleotide (including labeled or biotinylated polynucleotides) can be custom or standard ordered from any of a variety of commercial sources.

The present invention has been described in terms of particular embodiments found or proposed to comprise certain modes for the practice of the invention. It will be appreciated by those of ordinary skill in the art that, in light of the present disclosure, numerous modifications and changes can be made in the particular embodiments exemplified without departing from the intended scope of the invention.

All cited references, including patent publications, are incorporated herein by reference in their entirety. Nucleotide and other genetic sequences, referred to by published genomic location or other description, are also expressly incorporated herein by reference.

| SEQUENCES PRESENTED IN THE SEQUENCE LISTING | | | | |
|---|---|---|---|---|
| SEQ ID NO: | Length: | Type: | Organism: | Description; 'Other Information' |
| 1 | 1526 | DNA | Mus musculus | Coding sequence for the mouse anti-human CD19 IgG1 heavy chain |
| 2 | 464 | PRT | Mus musculus | Full-length mouse anti-human CD19 IgG1 heavy chain amino acid sequence |

SEQUENCES PRESENTED IN THE SEQUENCE LISTING

| SEQ ID NO: | Length: | Type: | Organism: | Description; 'Other Information' |
|---|---|---|---|---|
| 3 | 958 | DNA | *Mus musculus* | Coding sequence for the mouse anti-human CD19 IgG1 light chain |
| 4 | 239 | PRT | *Mus musculus* | Full-length mouse anti-human CD19 IgG1 light chain amino acid sequence |
| 5 | 1429 | DNA | Artificial Sequence | Optimized coding sequence for the mouse anti-human CD19 IgG1 heavy chain |
| 6 | 757 | DNA | Artificial Sequence | Optimized coding sequence for the mouse anti-human CD19 IgG1 light chain |
| 7 | 5874 | DNA | Artificial Sequence | pPRO33 vector |
| 8 | 36 | DNA | Artificial Sequence | IgG1HC Fc forward primer |
| 9 | 32 | DNA | Artificial Sequence | IgG1HC Fc reverse primer |
| 10 | 19 | DNA | Artificial Sequence | pBAD24/33 forward primer |
| 11 | 17 | DNA | Artificial Sequence | pBAD24/33 reverse primer #1 |
| 12 | 17 | DNA | Artificial Sequence | pBAD24/33 reverse primer #2 |
| 13 | 370 | PRT | Artificial Sequence | *P. chrysosporium* MnP-H4 amino acid sequence, without signal peptide |
| 14 | 1113 | DNA | Artificial Sequence | Optimized coding sequence for *P. chrysosporium* MnP-H4, without signal peptide |
| 15 | 370 | PRT | Artificial Sequence | *P. chrysosporium* MnP-H4 A60C/A75C amino acid sequence, without signal peptide |
| 16 | 1113 | DNA | Artificial Sequence | Optimized coding sequence for *P. chrysosporium* MnP-H4 A60C/A75C, without signal peptide |
| 17 | 660 | PRT | *E. coli* O157:H7 | *E. coli* O157:H7 str. EC4113 ChuA amino acid sequence |
| 18 | 1276 | DNA | Artificial Sequence | MnP-H4 expression construct |
| 19 | 2056 | DNA | Artificial Sequence | ChuA expression construct |
| 20 | 3326 | DNA | Artificial Sequence | MnP-H4 ChuA expression construct |
| 21 | 486 | PRT | Artificial Sequence | *Humicola insolens* PDI amino acid sequence, without signal peptide |
| 22 | 1487 | DNA | Artificial Sequence | PDI expression construct |
| 23 | 359 | PRT | Artificial Sequence | *P. chrysosporium* MnP-H4 amino acid sequence, mature and "fully truncated" |
| 24 | 25 | DNA | Artificial Sequence | MnP-H4_FT NcoI forward primer |
| 25 | 27 | DNA | Artificial Sequence | MnP-H4_FT SalI reverse primer |
| 26 | 24 | DNA | Artificial Sequence | ChuA SalI forward primer |
| 27 | 31 | DNA | Artificial Sequence | ChuA HindIII reverse primer |
| 28 | 7768 | DNA | Artificial Sequence | pBAD24-MnP_FT-ChuA expression construct |
| 29 | 7316 | DNA | Artificial Sequence | pPRO33-PDI expression construct |
| 30 | 451 | PRT | Artificial Sequence | Infliximab chimeric (murine variable doman, human constant domain) heavy chain |
| 31 | 215 | PRT | Artificial Sequence | Infliximab chimeric (murine variable doman, human constant domain) light chain |
| 32 | 5875 | DNA | Artificial Sequence | pBAD24-Infliximab_HC expression construct |
| 33 | 6503 | DNA | Artificial Sequence | pPRO33-Infliximab_LC expression construct |
| 34 | 6545 | DNA | Artificial Sequence | pJ1231-03C plasmid |
| 35 | 6009 | DNA | Artificial Sequence | pJ1234-03C plasmid |
| 36 | 42 | DNA | Artificial Sequence | BsaI-AraC-MnP-H4_FT primer |
| 37 | 63 | DNA | Artificial Sequence | MnP-H4_FT-6xHis-reverse primer |
| 38 | 38 | DNA | Artificial Sequence | MnP-H4_FT-6xHis-forward primer |
| 39 | 66 | DNA | Artificial Sequence | ChuA-6xHis-BsaI primer |
| 40 | 4569 | DNA | Artificial Sequence | AraC-MnP-H4_FT-ChuA PCR product |
| 41 | 42 | DNA | Artificial Sequence | BsaI-PrpR-PDI primer |
| 42 | 55 | DNA | Artificial Sequence | PDI-5xHis-BsaI primer |
| 43 | 3326 | DNA | Artificial Sequence | PrpR-PDI PCR product |
| 44 | 44 | DNA | Artificial Sequence | BsaI-AraC-HC-forward primer |
| 45 | 46 | DNA | Artificial Sequence | HC-reverse primer |
| 46 | 46 | DNA | Artificial Sequence | HC-forward primer |
| 47 | 45 | DNA | Artificial Sequence | HC-BsaI-reverse primer |
| 48 | 43 | DNA | Artificial Sequence | BsaI-PrpR-LC-forward primer |
| 49 | 50 | DNA | Artificial Sequence | LC-reverse primer |
| 50 | 50 | DNA | Artificial Sequence | LC-forward primer |
| 51 | 43 | DNA | Artificial Sequence | LC-BsaI-reverse primer |
| 52 | 2615 | DNA | Artificial Sequence | AraC-HC_NS PCR product |
| 53 | 2584 | DNA | Artificial Sequence | PrpR-LC_NS PCR product |

What is claimed is:

1. A composition comprising a host cell and at least one inducer;

wherein the host cell comprises at least one extrachromosomal expression construct comprising at least one first *Escherichia coli* sugar-inducible promoter and at least one polynucleotide sequence encoding a polypeptide, wherein at least one said polynucleotide sequence is to be transcribed from said first inducible promoter, wherein the polypeptide lacks a signal peptide; and wherein the host cell comprises at least one extrachromosomal expression construct comprising at least one second inducible promoter, selected from the group consisting of an *Escherichia coli* sugar-inducible promoter and a propionate-inducible promoter, that is inducible by at least one inducer that is different than that of said first inducible promoter; and wherein none of said inducible promoters is a lactose-inducible promoter; and wherein the host cell has an altered gene function of at least one gene that affects the reduction/oxidation environment of the host cell cytoplasm; and wherein the host cell has a reduced level of gene function of at least one gene encoding a protein that metabolizes an inducer of at least one said inducible promoter; and wherein each inducer is selected from the group consisting of a sugar and propionate.

2. The composition of claim 1 wherein at least one inducible promoter is selected from the group consisting of an L-arabinose-inducible promoter, a propionate-inducible promoter, a rhamnose-inducible promoter, and a xylose-inducible promoter.

3. The composition of claim 2 wherein at least one inducible promoter is an L-arabinose-inducible promoter.

4. The composition of claim 2 wherein at least one inducible promoter is selected from the group consisting of: the araBAD promoter, the prpBCDE promoter, the rhaSR promoter, and the xlyA promoter.

5. The composition of claim 1 wherein the polypeptide lacking a signal peptide comprises a polypeptide sequence selected from the group consisting of: (a) a polypeptide chain of mature insulin; (b) a botulinum neurotoxin heavy chain; (c) a botulinum neurotoxin light chain; (d) a chaperone; (e) an immunoglobulin heavy chain; (f) an immunoglobulin light chain; (g) a manganese peroxidase; (h) an arabinose-utilization enzyme; (i) a xylose-utilization enzyme; (j) a lignin-degrading peroxidase; and (k) a fragment of any of (e)-(g).

6. The composition of claim 1 wherein the at least one gene that affects the reduction/oxidation environment of the host cell cytoplasm is selected from the group consisting of gor, gshA, gshB, and trxB.

7. The composition of claim 1 wherein at least one gene encoding a protein that metabolizes an inducer of at least one said inducible promoter is selected from the group consisting of araA, araB, araD, prpB, prpD, rhaA, rhaB, rhaD, xylA, and xylB.

8. The composition of claim 1 wherein at least one inducer is L-arabinose.

9. The composition of claim 8 wherein at least one inducer is L-arabinose added to the composition per host cell density ($OD_{600}$) of 0.5 at a concentration of less than 0.01%.

10. The composition of claim 9 wherein at least one inducer is L-arabinose added to the composition per host cell density ($OD_{600}$) of 0.5 at a concentration of 0.002%.

11. The composition of claim 1 wherein the host cell comprises at least one expression construct encoding at least one disulfide bond isomerase protein.

12. The composition of claim 1 wherein the host cell comprises at least one polynucleotide encoding a form of DsbC lacking a signal peptide.

13. The composition of claim 1 wherein the host cell comprises at least one polynucleotide encoding Erv1p.

14. The composition of claim 1 wherein the host cell has an alteration of gene function of at least one gene encoding a transporter protein for an inducer of at least one said inducible promoter.

15. The composition of claim 14 wherein at least one gene encoding a transporter protein is selected from the group consisting of araE, araF, araG, araH, rhaT, xylF, xylG, and xylH.

16. The composition of claim 1 wherein the host cell is a prokaryotic cell.

17. The composition of claim 16 wherein the host cell is *E. coli*.

18. The composition of claim 1 wherein at least one inducer is selected from the group consisting of L-arabinose, L-rhamnose, D-xylose, and propionate.

19. The composition of claim 18 wherein at least one inducer is present in the composition at a concentration per host cell density ($OD_{600}$) of 0.5, and is selected from the group consisting of: L-arabinose at a concentration of less than 0.1%; L-rhamnose at a concentration between 5% and 0.002%; D-xylose at a concentration between 5% and 0.002%; and propionate at a concentration between 1 M and 1 mM.

20. The composition of claim 19 wherein at least one inducer is L-arabinose present in the composition per host cell density ($OD_{600}$) of 0.5 at a concentration of less than 0.05%.

21. The composition of claim 1 wherein said expression construct comprising at least one first inducible promoter, and said expression construct comprising at least one second inducible promoter, are maintained on the same extrachromosomal polynucleotide.

* * * * *

SEQUENCE LISTING

<160> NUMBER OF SEQ ID NOS: 53

<210> SEQ ID NO 1
<211> LENGTH: 1526
<212> TYPE: DNA
<213> ORGANISM: Mus musculus

<400> SEQUENCE: 1

| | | | | | |
|---|---|---|---|---|---|
| ctgactctaa | ccatggaatg | gagttggata | tttctctttc | tcctgtcagg | aactgcaggt | 60 |
| gtccactctg | aggtccagct | gcagcagtct | ggacctgagc | tgataaagcc | tggggcttca | 120 |
| gtgaagatgt | cctgcaaggc | ttctggatac | acattcacta | gctatgttat | gcactgggtg | 180 |
| aagcagaagc | ctgggcaggg | ccttgagtgg | attggatata | ttaatcctta | caatgatggt | 240 |
| actaagtaca | atgagaagtt | caaaggcaag | gccacactga | cttcagacaa | atcctccagc | 300 |
| acagcctaca | tggagctcag | cagcctgacc | tctgaggact | ctgcggtcta | ttactgtgca | 360 |
| agagggactt | attactacgg | tagtagggta | tttgactact | ggggccaagg | caccactctc | 420 |
| acagtctcct | cagccaaaac | gacaccccca | tctgtctatc | cactggcccc | tggatctgct | 480 |
| gcccaaacta | actccatggt | gaccctggga | tgcctggtca | agggctattt | ccctgagcca | 540 |
| gtgacagtga | cctggaactc | tggatccctg | tccagcggtg | tgcacacctt | cccagctgtc | 600 |
| ctgcagtctg | acctctacac | tctgagcagc | tcagtgactg | tcccctccag | cacctggccc | 660 |
| agcgagaccg | tcacctgcaa | cgttgcccac | ccggccagca | gcaccaaggt | ggacaagaaa | 720 |
| attgtgccca | gggattgtgg | ttgtaagcct | tgcatatgta | cagtcccaga | agtatcatct | 780 |
| gtcttcatct | tccccccaaa | gcccaaggat | gtgctcacca | ttactctgac | tcctaaggtc | 840 |
| acgtgtgttg | tggtagacat | cagcaaggat | gatcccgagg | tccagttcag | ctggtttgta | 900 |
| gatgatgtgg | aggtgcacac | agctcagacg | caaccccggg | aggagcagtt | caacagcact | 960 |
| ttccgctcag | tcagtgaact | tcccatcatg | caccaggact | ggctcaatgg | caaggagttc | 1020 |
| aaatgcaggg | tcaacagtgc | agctttccct | gcccccatcg | agaaaaccat | ctccaaaacc | 1080 |
| aaaggcagac | cgaaggctcc | acaggtgtac | accattccac | ctcccaagga | gcagatggcc | 1140 |
| aaggataaag | tcagtctgac | ctgcatgata | acagacttct | tccctgaaga | cattactgtg | 1200 |
| gagtggcagt | ggaatgggca | gccagcggag | aactacaaga | acactcagcc | catcatggac | 1260 |
| acagatggct | cttacttcgt | ctacagcaag | ctcaatgtgc | agaagagcaa | ctgggaggca | 1320 |
| ggaaatactt | tcacctgctc | tgtgttacat | gagggcctgc | acaaccacca | tactgagaag | 1380 |
| agcctctccc | actctcctgg | taaatgatcc | cagtgtcctt | ggagccctct | ggtcctacag | 1440 |
| gactctgaca | cctacctcca | cccctccctg | tataaataaa | gcacccagca | ctgccttggg | 1500 |
| accctgcaat | aaaaaaaaaa | aaaaaa | | | | 1526 |

<210> SEQ ID NO 2
<211> LENGTH: 464
<212> TYPE: PRT
<213> ORGANISM: Mus musculus

<400> SEQUENCE: 2

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Ile Lys
            20                  25                  30

Pro Gly Ala Ser Val Lys Met Ser Cys Lys Ala Ser Gly Tyr Thr Phe
        35                  40                  45

```
Thr Ser Tyr Val Met His Trp Val Lys Gln Lys Pro Gly Gln Gly Leu
     50                  55                  60

Glu Trp Ile Gly Tyr Ile Asn Pro Tyr Asn Asp Gly Thr Lys Tyr Asn
 65                  70                  75                  80

Glu Lys Phe Lys Gly Lys Ala Thr Leu Thr Ser Asp Lys Ser Ser Ser
                 85                  90                  95

Thr Ala Tyr Met Glu Leu Ser Ser Leu Thr Ser Glu Asp Ser Ala Val
            100                 105                 110

Tyr Tyr Cys Ala Arg Gly Thr Tyr Tyr Gly Ser Arg Val Phe Asp
            115                 120                 125

Tyr Trp Gly Gln Gly Thr Thr Leu Thr Val Ser Ser Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val
            195                 200                 205

Thr Val Pro Ser Ser Thr Trp Pro Ser Glu Thr Val Thr Cys Asn Val
210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
                260                 265                 270

Thr Pro Lys Val Thr Cys Val Val Asp Ile Ser Lys Asp Asp Pro
            275                 280                 285

Glu Val Gln Phe Ser Trp Phe Val Asp Val Glu Val His Thr Ala
            290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
                340                 345                 350

Ile Ser Lys Thr Lys Gly Arg Pro Lys Ala Pro Gln Val Tyr Thr Ile
                355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
            435                 440                 445

Leu His Asn His His Thr Glu Lys Ser Leu Ser His Ser Pro Gly Lys
450                 455                 460
```

<210> SEQ ID NO 3
<211> LENGTH: 958
<212> TYPE: DNA
<213> ORGANISM: Mus musculus

<400> SEQUENCE: 3

```
cttttttgtat caagttctca gaatgaggtg cctagctgag ttcctggggc tgcttgtgct    60
ctggatccct ggagccattg gggatattgt gatgactcag gctgcaccct ctatacctgt   120
cactcctgga gagtcagtat ccatctcctg caggtctagt aagagtctcc tgaatagtaa   180
tggcaacact tacttgtatt ggttcctgca gaggccaggc cagtctcctc agctcctgat   240
atatcggatg tccaaccttg cctcaggagt cccagacagg ttcagtggca gtgggtcagg   300
aactgctttc acactgagaa tcagtagagt ggaggctgag gatgtgggtg tttattactg   360
tatgcaacat ctagaaatatc cgttcacgtt cggtgctggg accaagctgg agctgaaacg   420
ggctgatgct gcaccaactg tatccatctt cccaccatcc agtgagcagt taacatctgg   480
aggtgcctca gtcgtgtgct tcttgaacaa cttctacccc aaagacatca atgtcaagtg   540
gaagattgat ggcagtgaac gacaaaatgg cgtcctgaac agttggactg atcaggacag   600
caaagacagc acctacagca tgagcagcac cctcacgttg accaaggacg agtatgaacg   660
acataacagc tatacctgtg aggccactca caagacatca acttcaccca ttgtcaagag   720
cttcaacagg aatgagtgtt agagacaaag gtcctgagac gccaccacca gctcccagc   780
tccatcctat cttcccttct aaggtcttgg aggcttcccc acaagcgacc taccactgtt   840
gcggtgctcc aaacctcctc cccacctcct tctcctcctc ctcccctttcc ttggcttta    900
tcatgctaat atttgcagaa aatattcaat aaagtgagtc tttgcacttg aaaaaaaa    958
```

<210> SEQ ID NO 4
<211> LENGTH: 239
<212> TYPE: PRT
<213> ORGANISM: Mus musculus

<400> SEQUENCE: 4

```
Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Ile Pro
            20                  25                  30

Val Thr Pro Gly Glu Ser Val Ser Ile Ser Cys Arg Ser Ser Lys Ser
        35                  40                  45

Leu Leu Asn Ser Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Phe Thr Phe Gly Ala Gly Thr Lys
        115                 120                 125

Leu Glu Leu Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175
```

Gly Ser Glu Arg Gln Asn Gly Val Leu Asn Ser Trp Thr Asp Gln Asp
        180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 5
<211> LENGTH: 1429
<212> TYPE: DNA
<213> ORGANISM: Artificial Sequence
<220> FEATURE:
<223> OTHER INFORMATION: Optimized coding sequence for the mouse anti-
      human CD19 IgG1 heavy chain

<400> SEQUENCE: 5

```
ttgggctagc aggaggaatt caccatggaa tggtcgtgga tttttctgtt tctgctgtcg     60
ggtacggcgg gcgttcatag cgaagttcaa ctgcaacaaa gcggtccgga actgattaaa    120
ccgggcgcga gcgtgaagat gtcttgcaaa gccagtggtt acacctttac gtcttatgtg    180
atgcattggg ttaaacagaa gccgggccaa ggtctggaat ggattggcta catcaacccg    240
tacaacgatg taccaagta caacgaaaag ttcaagggca agcaaccct gacgagtgac    300 aaaagctcta gtacggctta tatggaactg tcctcactga cctcagaaga ttcggcagtg    360
tattactgcg ctcgtggcac gtattactat ggttcccgcg ttttgatta ctggggccag    420 ggtaccacgc tgaccgtttc gagcgcgaaa accacgccgc cgagcgtcta tccgctggca    480
ccgggttcgg cagcacagac gaatagcatg gtgaccctgg gctgtctggt taaaggttac    540
tttccggaac cggtgaccgt tacgtggaac agcggctctc tgtctagtgg tgtccatacg    600 ttcccggcg tgctgcagtc tgatctgtat accctgtcct catcggtcac ggtgccgagc    660
tctacctggc cgagtgaaac cgtcacgtgc aacgtggcac acccggcaag ttccaccaaa    720
gttgataaaa agattgtccc gcgtgactgc ggctgtaaac cgtgcatctg tccgtgccg    780 gaagtttcat cggtctttat ttttcccgccg aagccgaaag atgtcctgac catcacgctg    840
accccgaagg tgacctgtgt ggttgtcgac atttctaaag atgacccgga agttcagttt    900
agttggttcg tcgatgacgt tgaagtccat acggcgcaga cccaaccgcg tgaagaacag    960
tttaatagca ccttccgcag tgtgtccgaa ctgccgatca tgcaccaaga ctggctgaat    1020
ggcaaggaat taaatgccg tgttaactcg gcagctttcc cggccccgat tgaaaagacg    1080
atcagcaaga ccaaaggtcg cccgaaagca ccgcaggtgt ataccattcc gccgccgaaa    1140
gaacaaatgg ctaaggataa agttagcctg acgtgtatga ttaccgattt ctttccggaa    1200
gacatcaccg tggaatggca gtggaacggc aaccggccg aaaactataa aaatacgcag    1260
ccgatcatgg ataccgacgg ttcctacttt gtgtattcaa gctgaacgt tcaaaaatcc    1320 aattgggaag ccgtaacac gttcacctgt tcagttctgc acgaaggtct gcacaatcac    1380
catacggaaa agtcgctgtc ccactcgccg ggtaaataaa agcttggct               1429
```

<210> SEQ ID NO 6
<211> LENGTH: 757
<212> TYPE: DNA
<213> ORGANISM: Artificial Sequence
<220> FEATURE:
<223> OTHER INFORMATION: Optimized coding sequence for the mouse anti-human CD19 IgG1 light chain

<400> SEQUENCE: 6

```
ttgggctagc aggaggaatt caccatggct cgttgtctgg cggaatttct gggtctgctg      60
gttctgtgga tcccgggcgc gattggcgat attgttatga cgcaagcggc tccgtctatt     120
ccggttaccc cgggtgaaag cgtctctatc agttgccgca gctctaaatc gctgctgaac     180
agcaatggta acacctatct gtactggttt ctgcagcgtc cgggtcagag cccgcaactg     240
ctgatttatc gcatgtctaa tctggcaagt ggtgtcccgg atcgttttc cggttcaggt      300
tcgggtacgg cattcaccct gcgtatctcc cgcgttgaag ccgaagacgt cggcgtgtat     360
tactgcatgc agcatctgga atacccgttt acgttcggtg caggcaccaa actggaactg     420
aaacgcgctg atgcagcacc gaccgtgagc attttcccgc cgagttccga caactgacc      480
tccggcggtg catcagtggt tgttttctg aacaacttct acccgaaaga tatcaacgtg      540
aaatggaaaa tcgacggttc ggaacgtcag aatggcgttc tgaacagctg gacggatcaa     600
gacagtaaag attccaccta ctcaatgtca tcgaccctga cgctgaccaa agacgaatat     660
gaacgccata actcttacac gtgcgaagct acccacaaaa cgagcacctc tccgatcgtt     720
aaaagttta tcgtaacga atgttaaaag cttggct                                757
```

<210> SEQ ID NO 7
<211> LENGTH: 5874
<212> TYPE: DNA
<213> ORGANISM: Artificial Sequence
<220> FEATURE:
<223> OTHER INFORMATION: pPRO33 vector

<400> SEQUENCE: 7

```
atcgattcag cttttcagcc gccgccagaa cgtcgtccgg ctgatgccta ataattcgc       60
cgctgctgtt ttatcgccat taaatttctc cagtgcctgt tgtggtgtca gtaagcgtgg     120
agcgggagtt ttcgccgact cgcgcgccag ttccggcagt agcagttgca taaactgcgg     180
cgttaaatcc ggcgtcggtt ccacacttaa aaacagcgcc agtcgttcca tcatattgcg     240
cagttcacga atattgcctg ccagtcgta gtgcagcagc acagtttcac ttgcctgtaa      300
ccctggcgt aatgcagcag aaatggggc ggagagcgcc gccagagaca ctttcaaaaa       360
gctttccgcc agcggaagaa tatccgccac ccgctcgcgc agtggtggca attgcagacg     420
caaatactc agccgataaa acagatcacg gcgaaacgt ccttgctgca tatcttcttc       480
cagattgcag tgagtggcgc taatgacccg tacatctacc ggaacaggct gatgcccgcc     540
gacgcgggtg acctcttttt cttccagcac ccgcagcagc cgggtctgca aggtagcgg      600
catttcgcca atctcatcca gaaacagcgt accgccgtgg caatttcga acagcccggc      660
gcgacctccg cgtcgcgagc cggtaaacgc cccttcctca tagccaaaca gttctgcttc     720
cagcagcgat tcggcaatcg ccccgcagtt gacggcaaca aacggatgcg acttttttgcc    780
ctgtcgcgca tcgtggcggg caaaatattc ccgatgaatc gcctgggccg ccagctcttt     840
gcccgtcccc gtttcccct caatcaacac cgccgcactg agcgggcat acagcaaaat       900
agtctgccgt acttgttcca tctgtggtga ttgaccgagc atatcgccca gcacgtaacg     960
agtacgcagg gcgttgcggg tggcatcgtg agtgttatgg cgtaacgaca tgcgcgtcat    1020
atccagcgca tcgctgaacg cctggcgcac ggtggcggcg gaatagataa aaattccggt    1080
cattccggct tcttctgcca aatcggtaat cagccctgcg ccgaccaccg cttcggtgcc    1140
gttagctttt agctcgttaa tctgcccgcg tgcgtcttcc tcggtaatgt agctacgttg    1200
```

```
gtcgaggcgc aaattaaagg ttttttgaaa cgccaccagc gctggaatgg tttcctgata    1260
ggtgacaacg ccgatagaag aggtgagttt tccggctttt gccagtgcct gtaacacatc    1320
gtagccgctc ggtttaatca aaataactgg cactgacagg cggcttttca ggtacgcgcc    1380
gttagagcca gccgcgatga tggcgtcaca gcgttcgttt gccagtttct tgcggatgta    1440
ggtcactgct ttttcaaagc caagctgaat aggggtaatg ttcgccaggt gatcaaactc    1500
gaggctgata tcgcgaaaca gctcgaacag gcgcgttaca gataccgtcc agataaccgg    1560
tttgtcgtca ttaagccgtg gtggatgtgc catagcgcac cgcaaagtta agaaaccgaa    1620
tattgggttt agtcttgttt cataattgtt gcaatgaaac gcggtgaaac attgcctgaa    1680
acgttaactg aaacgcatat ttgcggatta gttcatgact ttatctctaa caaattgaaa    1740
ttaaacattt aattttatta aggcaattgt ggcacacccc ttgctttgtc tttatcaacg    1800
caaataacaa gttgataaca agctagcgaa ttcgagctcg gtacccgggg atcctctaga    1860
gtcgacctgc aggcatgcaa gcttggctgt tttggcggat gagagaagat tttcagcctg    1920
atacagatta aatcagaacg cagaagcggt ctgataaaac agaatttgcc tggcggcagt    1980
agcgcggtgg tcccacctga ccccatgccg aactcagaag tgaaacgccg tagcgccgat    2040
ggtagtgtgg ggtctcccca tgcgagagta gggaactgcc aggcatcaaa taaaacgaaa    2100
ggctcagtcg aaagactggg cctttcgttt tatctgttgt ttgtcggtga acgctctcct    2160
gagtaggaca atccgccgg gagcggattt gaacgttgcg aagcaacggc ccggagggtg    2220
gcgggcagga cgcccgccat aaactgccag gcatcaaatt aagcagaagg ccatcctgac    2280
ggatggcctt tttgcgtttc tacaaactct tttgtttatt tttctaaata cattcaaata    2340
tgtatccgct catgagacaa taaccctgat aaatgcttca ataatattga aaaaggaaga    2400
gtatgagtat tcaacatttc cgtgtcgccc ttattccctt ttttgcggca ttttgccttc    2460 ctgttttgc tcacccagaa acgctggtga agtaaaaga tgctgaagat cagttggggc    2520
aaactattaa ctggcgaact acttactcta gcttcccggc aacaattaat agactggatg    2580
gaggcggata agttgcagg accacttctg cgctcggccc ttccggctgg ctggtttatt    2640
gctgataaat ctggagccgg tgagcgtggg tctcgcggta tcattgcagc actggggcca    2700
gatggtaagc cctcccgtat cgtagttatc tacacgacgg ggagtcaggc aactatggat    2760
gaacgaaata gacagatcgc tgagataggt gcctcactga ttaagcattg gtaactgtca    2820
gaccaagttt actcatatat actttagatt gatttacgcg ccctgtagcg cgcattaag    2880 cgcggcgggt gtggtggtta cgcgcagcgt gaccgctaca cttgccagcg ccctagcgcc    2940
cgctcctttc gctttcttcc cttcctttct cgccacgttc gccggctttc cccgtcaagc    3000
tctaaatcgg gggctccctt tagggttccg atttagtgct ttacggcacc tcgaccccaa    3060
aaaacttgat ttgggtgatg gttcacgtag tgggccatcg ccctgataga cggttttttcg    3120 ccctttgacg ttggagtcca cgttctttaa tagtggactc ttgttccaaa cttgaacaac    3180
actcaaccct atctcgggct attcttttga tttataaggg attttgccga tttcggccta    3240
ttggttaaaa aatgagctga tttaacaaaa attttaacgcg aattttaaca aaatattaac    3300
gtttacaatt taaaaggatc taggtgaaga tccttttttga taatctcatg accaaaatcc    3360
cttaacgtga gttttcgttc cactgagcgt cagaccccgt agaaaagatc aaaggatctt    3420
cttgagatcc ttttttttctg cgcgtaatct gctgcttgca acaaaaaaaa ccaccgctac    3480
cagcggtggt ttgtttgccg gatcaagagc taccaactct ttttccgaag gtaactggct    3540
```

```
tcagcagagc gcagatacca aatactgtcc ttctagtgta gccgtagtta ggccaccact    3600
tcaagaactc tgtagcaccg cctacatacc tcgctctgct aatcctgtta ccagtcaggc    3660
atttgagaag cacacggtca cactgcttcc ggtagtcaat aaaccggtaa accagcaata    3720
gacataagcg gctatttaac gaccctgccc tgaaccgacg accgggtcga atttgctttc    3780
gaatttctgc cattcatccg cttattatca cttattcagg cgtagcacca ggcgtttaag    3840
ggcaccaata actgccttaa aaaaattacg ccccgccctg ccactcatcg cagtactgtt    3900
gtaattcatt aagcattctg ccgacatgga agccatcaca gacggcatga tgaacctgaa    3960
tcgccagcgg catcagcacc ttgtcgcctt gcgtataata tttgcccatg gtgaaaacgg    4020
gggcgaagaa gttgtccata ttggccacgt ttaaatcaaa actggtgaaa ctcacccagg    4080
gattggctga gacgaaaaac atattctcaa taaacccttt agggaaatag gccaggtttt    4140
caccgtaaca cgccacatct tgcgaatata tgtgtagaaa ctgccggaaa tcgtcgtggt    4200
attcactcca gagcgatgaa aacgtttcag tttgctcatg gaaaacggtg taacaagggt    4260
gaacactatc ccatatcacc agctcaccgt ctttcattgc catacggaat tccggatgag    4320
cattcatcag gcgggcaaga atgtgaataa aggccggata aaacttgtgc ttatttttct    4380
ttacggtctt taaaaaggcc gtaatatcca gctgaacggt ctggttatag gtacattgag    4440
caactgactg aaatgcctca aaatgttctt tacgatgcca ttgggatata tcaacggtgg    4500
tatatccagt gatttttttc tccattttag cttccttagc tcctgaaaat ctcgataact    4560
caaaaaatac gcccggtagt gatcttattt cattatggtg aaagttggaa cctcttacgt    4620
gccgatcaac gtctcatttt cgccaaaagt tgggccaggg cttcccggta tcaacaggga    4680
caccaggatt tatttattct gcgaagtgat cttccgtcac aggtatttat tcggcgcaaa    4740
gtgcgtcggg tgatgctgcc aacttactga tttagtgtat gatggtgttt ttgaggtgct    4800
ccagtggctt ctgtttctat cagctgtccc tcctgttcag ctactgacgg ggtggtgcgt    4860
aacggcaaaa gcaccgccgg acatcagcgc tagcggagtg tatactggct tactatgttg    4920
gcactgatga gggtgtcagt gaagtgcttc atgtggcagg agaaaaaagg ctgcaccggt    4980
gcgtcagcag aatatgtgat acaggatata ttccgcttcc tcgctcactg actcgctacg    5040
ctcggtcgtt cgactgcggc gagcggaaat ggcttacgaa cggggcggag atttcctgga    5100
agatgccagg aagatactta acagggaagt gagagggccg cggcaaagcc gttttttccat    5160
aggctccgcc cccctgacaa gcatcacgaa atctgacgct caaatcagtg gtggcgaaac    5220
ccgacaggac tataaagata ccaggcgttt ccccctggcg ctccctcgt gcgctctcct    5280
gttcctgcct ttcggtttac cggtgtcatt ccgctgttat ggccgcgttt gtctcattcc    5340
acgcctgaca ctcagttccg ggtaggcagt tcgctccaag ctggactgta tgcacgaacc    5400
ccccgttcag tccgaccgct gcgccttatc cggtaactat cgtcttgagt ccaacccgga    5460
aagacatgca aaagcaccac tggcagcagc cactggtaat tgatttagag gagttagtct    5520
tgaagtcatg cgccggttaa ggctaaactg aaaggacaag ttttggtgac tgcgctcctc    5580
caagccagtt acctcggttc aaagagttgg tagctcagag aaccttcgaa aaaccgccct    5640
gcaaggcggt ttttcgtttt tcagagcaag agattacgcg cagaccaaaa cgatctcaag    5700
aagatcatct tattaatcag ataaaatatt tgctcatgag cccgaagtgg cgagcccgat    5760
cttccccatc ggtgatgtcg gcgatatagg cgccagcaac cgcacctgtg gcgccggtga    5820
tgccggccac gatgcgtccg gcgtagagga tctgctcatg tttgacagct tatc          5874
```

```
<210> SEQ ID NO 8
<211> LENGTH: 36
<212> TYPE: DNA
<213> ORGANISM: Artificial Sequence
<220> FEATURE:
<223> OTHER INFORMATION: IgG1HC Fc forward primer

<400> SEQUENCE: 8
ttcaccatgg aagtttcatc ggtctttatt ttcccg                               36

<210> SEQ ID NO 9
<211> LENGTH: 32
<212> TYPE: DNA
<213> ORGANISM: Artificial Sequence
<220> FEATURE:
<223> OTHER INFORMATION: IgG1HC Fc reverse primer

<400> SEQUENCE: 9
agccaagctt ttatttaccc ggcgagtggg ac                                   32

<210> SEQ ID NO 10
<211> LENGTH: 19
<212> TYPE: DNA
<213> ORGANISM: Artificial Sequence
<220> FEATURE:
<223> OTHER INFORMATION: pBAD24/33 forward primer

<400> SEQUENCE: 10
ctgtttctcc atacccgtt                                                  19

<210> SEQ ID NO 11
<211> LENGTH: 17
<212> TYPE: DNA
<213> ORGANISM: Artificial Sequence
<220> FEATURE:
<223> OTHER INFORMATION: pBAD24/33 reverse primer #1

<400> SEQUENCE: 11
ctcatccgcc aaaacag                                                    17

<210> SEQ ID NO 12
<211> LENGTH: 17
<212> TYPE: DNA
<213> ORGANISM: Artificial Sequence
<220> FEATURE:
<223> OTHER INFORMATION: pBAD24/33 reverse primer #2

<400> SEQUENCE: 12
ggctgaaaat cttctct                                                    17

<210> SEQ ID NO 13
<211> LENGTH: 370
<212> TYPE: PRT
<213> ORGANISM: Artificial Sequence
<220> FEATURE:
<223> OTHER INFORMATION: P. chrysosporium MnP-H4 amino acid sequence,
      without signal peptide

<400> SEQUENCE: 13
```

Met Ala Ile Thr Arg Ala Ala Pro Thr Ala Glu Ser Ala Val Cys Pro
1               5                   10                  15

Asp Gly Thr Arg Val Thr Asn Ala Ala Cys Cys Ala Phe Ile Pro Leu
            20                  25                  30

Ala Gln Asp Leu Gln Glu Thr Leu Phe Gln Gly Asp Cys Gly Glu Asp
        35                  40                  45

```
Ala His Glu Val Ile Arg Leu Thr Phe His Asp Ala Ile Ala Ile Ser
 50                  55                  60
Gln Ser Leu Gly Pro Gln Ala Gly Gly Ala Asp Gly Ser Met Leu
 65                  70                  75                  80
His Phe Pro Thr Ile Glu Pro Asn Phe Ser Ala Asn Ser Gly Ile Asp
                 85                  90                  95
Asp Ser Val Asn Asn Leu Leu Pro Phe Met Gln Lys His Asp Thr Ile
                100                 105                 110
Ser Ala Ala Asp Leu Val Gln Phe Ala Gly Ala Val Ala Leu Ser Asn
                115                 120                 125
Cys Pro Gly Ala Pro Arg Leu Glu Phe Met Ala Gly Arg Pro Asn Thr
130                 135                 140
Thr Ile Pro Ala Val Glu Gly Leu Ile Pro Glu Pro Gln Asp Ser Val
145                 150                 155                 160
Thr Lys Ile Leu Gln Arg Phe Glu Asp Ala Gly Asn Phe Ser Pro Phe
                165                 170                 175
Glu Val Val Ser Leu Leu Ala Ser His Thr Val Ala Arg Ala Asp Lys
                180                 185                 190
Val Asp Glu Thr Ile Asp Ala Ala Pro Phe Asp Ser Thr Pro Phe Thr
                195                 200                 205
Phe Asp Thr Gln Val Phe Leu Glu Val Leu Leu Lys Gly Thr Gly Phe
210                 215                 220
Pro Gly Ser Asn Asn Asn Thr Gly Glu Val Met Ser Pro Leu Pro Leu
225                 230                 235                 240
Gly Ser Gly Ser Asp Thr Gly Glu Met Arg Leu Gln Ser Asp Phe Ala
                245                 250                 255
Leu Ala Arg Asp Glu Arg Thr Ala Cys Phe Trp Gln Ser Phe Val Asn
                260                 265                 270
Glu Gln Glu Phe Met Ala Ala Ser Phe Lys Ala Ala Met Ala Lys Leu
                275                 280                 285
Ala Ile Leu Gly His Ser Arg Ser Ser Leu Ile Asp Cys Ser Asp Val
                290                 295                 300
Val Pro Val Pro Lys Pro Ala Val Asn Lys Pro Ala Thr Phe Pro Ala
305                 310                 315                 320
Thr Lys Gly Pro Lys Asp Leu Asp Thr Leu Thr Cys Lys Ala Leu Lys
                325                 330                 335
Phe Pro Thr Leu Thr Ser Asp Pro Gly Ala Thr Glu Thr Leu Ile Pro
                340                 345                 350
His Cys Ser Asn Gly Gly Met Ser Cys Pro Gly Val Gln Phe Asp Gly
                355                 360                 365
Pro Ala
    370
```

<210> SEQ ID NO 14
<211> LENGTH: 1113
<212> TYPE: DNA
<213> ORGANISM: Artificial Sequence
<220> FEATURE:
<223> OTHER INFORMATION: Optimized coding sequence for P. chrysosporium
      MnP-H4, without signal peptide

<400> SEQUENCE: 14
atggcaatca cgagagcagc accaaccgca gaatccgcag tatgtccaga cggtaccaga    60
gtgacgaatg cagcgtgttg cgcgttcatt ccgctggcgc aggatctgca ggaaaccctg   120
ttccaaggcg attgcggcga ggacgcgcac gaggtcattc gcctgacctt tcacgatgcc   180

```
attgcaatca gccagtcttt gggtccgcaa gcgggtggtg gcgcggacgg cagcatgttg      240
cactttccga ccatcgagcc gaatttctcg gccaatagcg gtattgacga tagcgttaac      300
aacctgttgc cgtttatgca aaagcatgac accatcagcg ctgcggacct ggttcagttc      360
gcaggcgccg tggcgctgag caactgtcct ggtgcgccac gtctggagtt catggcgggt      420
cgcccgaata ccacgatccc ggcagttgaa ggtctgattc cggagccgca ggacagcgtc      480
accaaaattc tgcagcgttt cgaggatgcc ggtaacttta gcccgttcga ggtcgtgagc      540
ctgttggcga gccatacggt ggcgcgtgct gacaaagttg atgaaaccat cgacgccgct      600
ccgttcgaca gcaccccgtt tacgtttgat acccaggttt tcctggaagt tctgttgaaa      660
ggcaccggct ttccgggttc aataacaac accggtgaag tcatgtctcc gctgcctctg      720
ggctcgggta gcgatactgg tgagatgcgc ctgcaaagcg actttgctct ggcccgtgat      780
gagcgtaccg cgtgcttctg gcagtccttc gtcaacgaac aagagtttat ggcggccagc      840
tttaaggctg cgatggcaaa actggcaatt ctgggccata gccgttccag cctgatcgat      900
tgcagcgacg tggttccggt gccgaagcct gcggtcaata agccggcgac cttcccggcg      960
accaaaggcc cgaaggacct ggatactctg acgtgtaaag cgctgaagtt tccgacgctg     1020
acgtctgatc cgggtgccac ggagactctg atcccgcact gcagcaatgg tggcatgagc     1080
tgcccgggtg tgcaattcga cggtccggcg taa                                  1113
```

<210> SEQ ID NO 15
<211> LENGTH: 370
<212> TYPE: PRT
<213> ORGANISM: Artificial Sequence
<220> FEATURE:
<223> OTHER INFORMATION: P. chrysosporium MnP-H4 A60C/A75C amino acid
      sequence, without signal peptide

<400> SEQUENCE: 15

```
Met Ala Ile Thr Arg Ala Ala Pro Thr Ala Glu Ser Ala Val Cys Pro
1               5                   10                  15

Asp Gly Thr Arg Val Thr Asn Ala Ala Cys Cys Ala Phe Ile Pro Leu
            20                  25                  30

Ala Gln Asp Leu Gln Glu Thr Leu Phe Gln Gly Asp Cys Gly Glu Asp
        35                  40                  45

Ala His Glu Val Ile Arg Leu Thr Phe His Asp Cys Ile Ala Ile Ser
    50                  55                  60

Gln Ser Leu Gly Pro Gln Ala Gly Gly Gly Cys Asp Gly Ser Met Leu
65                  70                  75                  80

His Phe Pro Thr Ile Glu Pro Asn Phe Ser Ala Asn Ser Gly Ile Asp
                85                  90                  95

Asp Ser Val Asn Asn Leu Leu Pro Phe Met Gln Lys His Asp Thr Ile
            100                 105                 110

Ser Ala Ala Asp Leu Val Gln Phe Ala Gly Ala Val Ala Leu Ser Asn
        115                 120                 125

Cys Pro Gly Ala Pro Arg Leu Glu Phe Met Ala Gly Arg Pro Asn Thr
    130                 135                 140

Thr Ile Pro Ala Val Glu Gly Leu Ile Pro Glu Pro Gln Asp Ser Val
145                 150                 155                 160

Thr Lys Ile Leu Gln Arg Phe Glu Asp Ala Gly Asn Phe Ser Pro Phe
                165                 170                 175

Glu Val Val Ser Leu Leu Ala Ser His Thr Val Ala Arg Ala Asp Lys
            180                 185                 190
```

```
Val Asp Glu Thr Ile Asp Ala Ala Pro Phe Asp Ser Thr Pro Phe Thr
    195                 200                 205
Phe Asp Thr Gln Val Phe Leu Glu Val Leu Leu Lys Gly Thr Gly Phe
    210                 215                 220
Pro Gly Ser Asn Asn Thr Gly Glu Val Met Ser Pro Leu Pro Leu
225                 230                 235                 240
Gly Ser Gly Ser Asp Thr Gly Glu Met Arg Leu Gln Ser Asp Phe Ala
                245                 250                 255
Leu Ala Arg Asp Glu Arg Thr Ala Cys Phe Trp Gln Ser Phe Val Asn
                260                 265                 270
Glu Gln Glu Phe Met Ala Ala Ser Phe Lys Ala Ala Met Ala Lys Leu
            275                 280                 285
Ala Ile Leu Gly His Ser Arg Ser Ser Leu Ile Asp Cys Ser Asp Val
        290                 295                 300
Val Pro Val Pro Lys Pro Ala Val Asn Lys Pro Ala Thr Phe Pro Ala
305                 310                 315                 320
Thr Lys Gly Pro Lys Asp Leu Asp Thr Leu Thr Cys Lys Ala Leu Lys
                325                 330                 335
Phe Pro Thr Leu Thr Ser Asp Pro Gly Ala Thr Glu Thr Leu Ile Pro
            340                 345                 350
His Cys Ser Asn Gly Met Ser Cys Pro Gly Val Gln Phe Asp Gly
        355                 360                 365
Pro Ala
    370

<210> SEQ ID NO 16
<211> LENGTH: 1113
<212> TYPE: DNA
<213> ORGANISM: Artificial Sequence
<220> FEATURE:
<223> OTHER INFORMATION: Optimized coding sequence for P. chrysosporium
    MnP-H4 A60C/A75C, without signal peptide

<400> SEQUENCE: 16
atggcaatca cgagagcagc accaaccgca gaatccgcag tatgtccaga cggtaccaga      60
gtgacgaatg cagcgtgttg cgcgttcatt ccgctggcgc aggatctgca ggaaaccctg     120
ttccaaggcg attgcggcga ggacgcgcac gaggtcattc gcctgacctt tcacgattgc    180
attgcaatca gccagtcttt gggtccgcaa gcgggtggtg gctgcgacgg cagcatgttg    240
cactttccga ccatcgagcc gaatttctcg gccaatagcg gtattgacga tagcgttaac    300
aacctgttgc gtttatgca aaagcatgac accatcagcg ctgcggacct ggttcagttc    360
gcaggcgccg tggcgctgag caactgtcct ggtgcgccac gtctggagtt catggcgggt    420
cgcccgaata ccacgatccc ggcagttgaa ggtctgattc cggagccgca ggacagcgtc    480
accaaaattc tgcagcgttt cgaggatgcc ggtaacttta gccgttcga ggtcgtgagc    540 ctgttggcga gccatacggt ggcgcgtgct gacaaagttg atgaaaccat cgacgccgct    600
ccgttcgaca gcaccccgtt tacgtttgat acccaggttt tcctggaagt tctgttgaaa    660
ggcaccggct ttccgggttc caataacaac accggtgaag tcatgtctcc gctgcctctg    720
ggctcgggta gcgatactgg tgagatgcgc ctgcaaagcg actttgctct ggcccgtgat    780
gagcgtaccg cgtgcttctg gcagtccttc gtcaacgaac aagagtttat ggcggccagc    840
tttaaggctg cgatggcaaa actggcaatt ctgggccata gccgtccag cctgatcgat    900 tgcagcgacg tggttccggt gccgaagcct gcggtcaata agccggcgac cttcccggcg    960
```

```
accaaaggcc cgaaggacct ggatactctg acgtgtaaag cgctgaagtt tccgacgctg   1020
acgtctgatc cgggtgccac ggagactctg atcccgcact gcagcaatgg tggcatgagc   1080
tgcccgggtg tgcaattcga cggtccggcg taa                               1113
```

<210> SEQ ID NO 17
<211> LENGTH: 660
<212> TYPE: PRT
<213> ORGANISM: E. coli O157:H7

<400> SEQUENCE: 17

```
Met Ser Arg Pro Gln Phe Thr Ser Leu Arg Leu Ser Leu Leu Ala Leu
1               5                   10                  15

Ala Val Ser Ala Thr Leu Pro Thr Phe Ala Phe Ala Thr Glu Thr Met
                20                  25                  30

Thr Val Thr Ala Thr Gly Asn Ala Arg Ser Ser Phe Glu Ala Pro Met
            35                  40                  45

Met Val Ser Val Ile Asp Thr Ser Ala Pro Glu Asn Gln Thr Ala Thr
    50                  55                  60

Ser Ala Thr Asp Leu Leu Arg His Val Pro Gly Ile Thr Leu Asp Gly
65                  70                  75                  80

Thr Gly Arg Thr Asn Gly Gln Asp Val Asn Met Arg Gly Tyr Asp His
                85                  90                  95

Arg Gly Val Leu Val Leu Val Asp Gly Val Arg Gln Gly Thr Asp Thr
            100                 105                 110

Gly His Leu Asn Gly Thr Phe Leu Asp Pro Ala Leu Ile Lys Arg Val
        115                 120                 125

Glu Ile Val Arg Gly Pro Ser Ala Leu Leu Tyr Gly Ser Gly Ala Leu
    130                 135                 140

Gly Gly Val Ile Ser Tyr Asp Thr Val Asp Ala Lys Asp Leu Leu Gln
145                 150                 155                 160

Glu Gly Gln Ser Ser Gly Phe Arg Val Phe Gly Thr Gly Gly Thr Gly
                165                 170                 175

Asp His Ser Leu Gly Leu Gly Ala Ser Ala Phe Gly Arg Thr Glu Asn
            180                 185                 190

Leu Asp Gly Ile Val Ala Trp Ser Arg Asp Arg Gly Asp Leu Arg
        195                 200                 205

Gln Ser Asn Gly Glu Thr Ala Pro Asn Asp Glu Ser Ile Asn Asn Met
    210                 215                 220

Leu Ala Lys Gly Thr Trp Gln Ile Asp Ser Ala Gln Ser Leu Ser Gly
225                 230                 235                 240

Leu Val Arg Tyr Tyr Asn Asn Asp Ala Arg Glu Pro Lys Asn Pro Gln
                245                 250                 255

Thr Val Glu Ala Ser Glu Ser Ser Asn Pro Met Val Asp Arg Ser Thr
            260                 265                 270

Ile Gln Arg Asp Ala Gln Leu Ser Tyr Lys Leu Ala Pro Gln Gly Asn
        275                 280                 285

Asp Trp Leu Asn Ala Asp Ala Lys Ile Tyr Trp Ser Glu Val Arg Ile
    290                 295                 300

Asn Ala Gln Asn Thr Gly Ser Ser Gly Glu Tyr Arg Glu Gln Ile Thr
305                 310                 315                 320

Lys Gly Ala Arg Leu Glu Asn Arg Ser Thr Leu Phe Ala Asp Ser Phe
                325                 330                 335

Ala Ser His Leu Leu Thr Tyr Gly Gly Glu Tyr Tyr Arg Gln Glu Gln
```

```
                340             345             350
His Pro Gly Gly Ala Thr Thr Gly Phe Pro Gln Ala Lys Ile Asp Phe
            355                 360                 365

Ser Ser Gly Trp Leu Gln Asp Glu Ile Thr Leu Arg Asp Leu Pro Ile
370                 375                 380

Thr Leu Leu Gly Gly Thr Arg Tyr Asp Ser Tyr Arg Gly Ser Ser Asp
385                 390                 395                 400

Gly Tyr Lys Asp Val Asp Ala Asp Lys Trp Ser Ser Arg Ala Gly Met
            405                 410                 415

Thr Ile Asn Pro Thr Asn Trp Leu Met Leu Phe Gly Ser Tyr Ala Gln
            420                 425                 430

Ala Phe Arg Ala Pro Thr Met Gly Glu Met Tyr Asn Asp Ser Lys His
            435                 440                 445

Phe Ser Ile Gly Arg Phe Tyr Thr Asn Tyr Trp Val Pro Asn Pro Asn
450                 455                 460

Leu Arg Pro Glu Thr Asn Glu Thr Gln Glu Tyr Gly Phe Gly Leu Arg
465                 470                 475                 480

Phe Asp Asp Leu Met Leu Ser Asn Asp Ala Leu Glu Phe Lys Ala Ser
                485                 490                 495

Tyr Phe Asp Thr Lys Ala Lys Asp Tyr Ile Ser Thr Thr Val Asp Phe
            500                 505                 510

Ala Ala Ala Thr Thr Met Ser Tyr Asn Val Pro Asn Ala Lys Ile Trp
            515                 520                 525

Gly Trp Asp Val Met Thr Lys Tyr Thr Thr Asp Leu Phe Ser Leu Asp
            530                 535                 540

Val Ala Tyr Asn Arg Thr Arg Gly Lys Asp Thr Asp Thr Gly Glu Tyr
545                 550                 555                 560

Ile Ser Ser Ile Asn Pro Asp Thr Val Thr Ser Thr Leu Asn Ile Pro
                565                 570                 575

Ile Ala His Ser Gly Phe Ser Val Gly Trp Val Gly Thr Phe Ala Asp
                580                 585                 590

Arg Ser Thr His Ile Ser Ser Tyr Ser Lys Gln Pro Gly Tyr Gly
            595                 600                 605

Val Asn Asp Phe Tyr Val Ser Tyr Gln Gly Gln Gln Ala Leu Lys Gly
            610                 615                 620

Met Thr Thr Thr Leu Val Leu Gly Asn Ala Phe Asp Lys Glu Tyr Trp
625                 630                 635                 640

Ser Pro Gln Gly Ile Pro Gln Asp Gly Arg Asn Gly Lys Ile Phe Val
                645                 650                 655

Ser Tyr Gln Trp
            660

<210> SEQ ID NO 18
<211> LENGTH: 1276
<212> TYPE: DNA
<213> ORGANISM: Artificial Sequence
<220> FEATURE:
<223> OTHER INFORMATION: MnP-H4 expression construct

<400> SEQUENCE: 18
gctagcagga ggaattcacc atggcaatca cgagagcagc accaaccgca gaatccgcag      60
tatgtccaga cggtaccaga gtgacgaatg cagcgtgttg cgcgttcatt ccgctggcgc     120
aggatctgca ggaaaccctg ttccaaggcg attgcggcga ggacgcgcac gaggtcattc     180
gcctgacctt tcacgatgcc attgcaatca gccagtcttt gggtccgcaa gcgggtggtg     240
```

```
gcgcggacgg cagcatgttg cactttccga ccatcgagcc gaatttctcg gccaatagcg      300
gtattgacga tagcgttaac aacctgttgc cgtttatgca aaagcatgac accatcagcg      360
ctgcggacct ggttcagttc gcaggcgccg tggcgctgag caactgtcct ggtgcgccac      420
gtctggagtt catggcgggt cgcccgaata ccacgatccc ggcagttgaa ggtctgattc      480
cggagccgca ggacagcgtc accaaaattc tgcagcgttt cgaggatgcc ggtaacttta      540
gcccgttcga ggtcgtgagc ctgttggcga gccatacggt ggcgcgtgct gacaaagttg      600
atgaaaccat cgacgccgct ccgttcgaca gcaccccgtt tacgtttgat acccaggttt      660
tcctggaagt tctgttgaaa ggcaccggct ttccgggttc caataacaac accggtgaag      720
tcatgtctcc gctgcctctg ggctcgggta gcgatactgg tgagatgcgc ctgcaaagcg      780
actttgctct ggcccgtgat gagcgtaccg cgtgcttctg gcagtccttc gtcaacgaac      840
aagagtttat ggcggccagc tttaaggctg cgatggcaaa actggcaatt ctgggccata      900
gccgttccag cctgatcgat tgcagcgacg tggttccggt gccgaagcct gcggtcaata      960
agccggcgac cttcccggcg accaaaggcc cgaaggacct ggatactctg acgtgtaaag     1020
cgctgaagtt tccgacgctg acgtctgatc cgggtgccac ggagactctg atcccgcact     1080
gcagcaatgg tggcatgagc tgcccggggtg tgcaattcga cggtccggcg taatactaga     1140
gccaggcatc aaataaaacg aaaggctcag tcgaaagact gggcctttcg ttttatctgt     1200
tgtttgtcgg tgaacgctct ctactagagt cacactggct caccttcggg tgggcctttc     1260
tgcgtttata tctaga                                                     1276

<210> SEQ ID NO 19
<211> LENGTH: 2056
<212> TYPE: DNA
<213> ORGANISM: Artificial Sequence
<220> FEATURE:
<223> OTHER INFORMATION: ChuA expression construct

<400> SEQUENCE: 19
tctagattga cagctagctc agtcctaggt attgtgctag ctactagaga aagaggagaa       60
atactagatg tcccgccctc aattcacctc gctccgtttg tctttgctcg cactcgccgt      120
atccgcaacg ctgccgacct ttgccttcgc taccgaaacc atgaccgtta ccgcgaccgg      180
caacgcacgc agctcgttcg aggcgccgat gatggtgagc gtgatcgata cctctgctcc      240
ggagaaccag acggcgacga gcgctaccga tctgctgcgc cacgtgccgg gtattacgct      300
ggacggtacc ggtcgcacga acggtcaaga cgtgaacatg cgcggctacg accatcgcgg      360
tgtgctggtc ctggtcgatg gtgtgcgtca gggtacggat accggtcact tgaatggtac      420
ctttctggat ccggcgctga ttaagcgtgt cgaaatcgtg cgtggccgt cggcactgct      480 gtatggtagc ggtgcgctgg gcggtgtgat cagctacgat accgtcgatg cgaaagacct      540
gttgcaagag ggtcaaagct ccggtttccg cgttttttggt actggtggta ccggtgacca      600
tagcctgggc ctgggcgcga gcgcgtttgg tcgcacggaa aacctggatg gcatcgttgc      660
gtggagcagc cgtgatcgtg gtgacttgcg ccagtctaat ggcgaaacgg cccctaacga      720
tgaaagcatt aacaacatgc tggccaaggg tacgtggcag atcgatagcg cgcagagcct      780
gagcggcctg gtccgttact acaacaacga cgcgcgtgag ccgaaaaacc gcagacggt      840 cgaggcgagc gagagcagca cccgatggt ggaccgtagc accattcaac gtgatgccca      900
actgagctat aagctggcac cgcaaggtaa tgactggctg aatgcggatg cgaaaatcta      960
```

```
ctggagcgaa gttcgcatca atgcacagaa tacgggtagc tctggcgagt accgtgaaca    1020
gattaccaaa ggtgcacgtc tggagaatcg ttctacgctg tttgctgaca gcttcgcttc    1080
gcatctgctg acgtatggtg gcgagtatta tcgtcaggaa caacacccag gtggtgcgac    1140
cacgggtttc ccgcaggcga agatcgattt tagcagcggc tggctgcaag atgagatcac    1200
cttgcgtgac ttgccgatta ccctgctggg tggtacgcgt tatgacagct accgtggcag    1260
cagcgacggt tacaaagacg tcgatgcaga taaatggagc tcccgtgccg gcatgaccat    1320
taatccgacc aattggctga tgctgttcgg cagctatgcg caagcgttcc gtgccccaac    1380
catgggtgag atgtacaatg acagcaagca tttcagcatt ggtcgcttct acacgaatta    1440
ctgggtgccg aacccgaatc tgcgtccgga gactaatgaa acccaggagt atggttttgg    1500
cctgcgcttt gatgatctga tgctgagcaa cgacgccctg gaattcaagg cgagctactt    1560
tgacactaaa gccaaagact acattagcac tacgcgttga tttttgcggctg ctaccaccat    1620 gtcctataat gttccaaacg caaagatttg gggctgggac gtcatgacca agtacaccac    1680
cgacctgttt agcttggatg ttgcatacaa tcgcacccgt ggcaaagaca ccgataccgg    1740
cgaatacatc agcagcatca atccggacac cgttacgtcc accctgaaca tcccgattgc    1800
gcacagcggt ttcagcgttg gttgggttgg tacgtttgcg gatcgctcca cccacatctc    1860
gtcgtcttat agcaagcaac cgggctacgg cgtgaatgat ttctatgtga gctatcaggg    1920
ccagcaagcc ctgaaaggta tgacgactac cctggttctg ggcaacgcat cgacaaaga    1980 gtattggagc ccgcagggca ttccgcagga cggtcgtaac ggcaagattt cgtttccta    2040 ccaatggtaa gtcgac                                                    2056

<210> SEQ ID NO 20
<211> LENGTH: 3326
<212> TYPE: DNA
<213> ORGANISM: Artificial Sequence
<220> FEATURE:
<223> OTHER INFORMATION: MnP-H4 ChuA expression construct

<400> SEQUENCE: 20
gctagcagga ggaattcacc atggcaatca cgagagcagc accaaccgca gaatccgcag      60
tatgtccaga cggtaccaga gtgacgaatg cagcgtgttg cgcgttcatt ccgctggcgc     120
aggatctgca ggaaaccctg ttccaagcg attgcggcga ggacgcgcac gaggtcattc     180
gcctgacctt tcacgatgcc attgcaatca gccagtcttt gggtccgcaa gcgggtggtg     240
gcgcggacgg cagcatgttg cactttccga ccatcgagcc gaatttctcg gccaatagcg     300
gtattgacga tagcgttaac aacctgttgc cgtttatgca aaagcatgac accatcagcg     360
ctgcggacct ggttcagttc gcaggcgccg tggcgctgag caactgtcct ggtgcgccac     420
gtctggagtt catggcgggt cgcccgaata ccacgatccc ggcagttgaa ggtctgattc     480
cggagccgca ggacagcgtc accaaaattc tgcagcgttt cgaggatgcc ggtaacttta     540
gcccgttcga ggtcgtgagc ctgttggcga gccatacggt ggcgcgtgct gacaaagttg     600
atgaaaccat cgacgccgct ccgttcgaca gcaccccgtt tacgtttgat acccaggttt     660
tcctggaagt tctgttgaaa ggcaccggct tccgggttc caataacaac accggtgaag     720
tcatgtctcc gctgcctctg ggctcgggta gcgatactgg tgagatgcgc ctgcaaagcg     780
actttgctct ggcccgtgat gagcgtaccg cgtgcttctg gcagtccttc gtcaacgaac     840
aagagtttat ggcggccagc tttaaggctg cgatggcaaa actggcaatt ctgggccata     900
gccgttccag cctgatcgat tgcagcgacg tggttccggt gccgaagcct gcggtcaata     960
```

```
agccggcgac cttccggcg accaaaggcc cgaaggacct ggatactctg acgtgtaaag    1020
cgctgaagtt tccgacgctg acgtctgatc cgggtgccac ggagactctg atcccgcact    1080
gcagcaatgg tggcatgagc tgcccgggtg tgcaattcga cggtccggcg taatactaga    1140
gccaggcatc aaataaaacg aaaggctcag tcgaaagact gggcctttcg ttttatctgt    1200
tgtttgtcgg tgaacgctct ctactagagt cacactggct caccttcggg tgggcctttc    1260 tgcgttttata tctagattga cagctagctc agtcctaggt attgtgctag ctactagaga    1320
aagaggagaa atactagatg tcccgccctc aattcacctc gctccgtttg tctttgctcg    1380
cactcgccgt atccgcaacg ctgccgacct ttgccttcgc taccgaaacc atgaccgtta    1440
ccgcgaccgg caacgcacgc agctcgttcg aggcgccgat gatggtgagc gtgatcgata    1500
cctctgctcc ggagaaccag acggcgacga gcgctaccga tctgctgcgc acgtgccgg    1560 gtattacgct ggacggtacc ggtcgcacga acggtcaaga cgtgaacatg cgcggctacg    1620
accatcgcgg tgtgctggtc ctggtcgatg gtgtgcgtca gggtacggat accggtcact    1680
tgaatggtac ctttctggat ccggcgctga ttaagcgtgt cgaaatcgtg cgtggcccgt    1740
cggcactgct gtatggtagc ggtgcgctgg gcggtgtgat cagctacgat accgtcgatg    1800
cgaaagacct gttgcaagag ggtcaaagct ccggtttccg cgttttggt actggtggta    1860 ccggtgacca tagcctgggc ctgggcgcga gcgcgtttgg tcgcacggaa aacctggatg    1920
gcatcgttgc gtggagcagc cgtgatcgtg gtgacttgcg ccagtctaat ggcgaaacgg    1980
cccctaacga tgaaagcatt aacaacatgc tggccaaggg tacgtggcag atcgatagcg    2040
cgcagagcct gagcggcctg gtccgttact acaacaacga cgcgcgtgag ccgaaaaacc    2100
cgcagacggt cgaggcgagc gagagcagca acccgatggt ggaccgtagc accattcaac    2160
gtgatgccca actgagctat aagctggcac cgcaaggtaa tgactggctg aatgcggatg    2220
cgaaaatcta ctggagcgaa gttcgcatca atgcacagaa tacgggtagc ctggcgagt    2280 accgtgaaca gattaccaaa ggtgcacgtc tggagaatcg ttctacgctg tttgctgaca    2340
gcttcgcttc gcatctgctg acgtatggtg gcgagtatta tcgtcaggaa caacacccag    2400
gtggtgcgac cacgggtttc ccgcaggcga agatcgattt tagcagcggc tggctgcaag    2460
atgagatcac cttgcgtgac ttgccgatta ccctgctggg tggtacgcgt tatgacagct    2520
accgtggcag cagcgacggt tacaaagacg tcgatgcaga taaatggagc tcccgtgccg    2580
gcatgaccat taatccgacc aattggctga tgctgttcgg cagctatgcg caagcgttcc    2640
gtgccccaac catgggtgag atgtacaatg acagcaagca tttcagcatt ggtcgcttct    2700
acacgaatta ctgggtgccg aacccgaatc tgcgtccgga gactaatgaa acccaggagt    2760
atggttttgg cctgcgcttt gatgatctga tgctgagcaa cgacgccctg gaattcaagg    2820
cgagctactt tgacactaaa gccaaagact acattagcac tacggttgat tttgcggctg    2880
ctaccaccat gtcctataat gttccaaacg caaagatttg gggctgggac gtcatgacca    2940
agtacaccac cgacctgttt agcttggatg ttgcatacaa tcgcacccgt ggcaaagaca    3000
ccgataccgg cgaatacatc agcagcatca atcggacac cgttacgtcc accctgaaca    3060
tcccgattgc gcacagcgt ttcagcgttg gttgggttgg tacgtttgcg gatcgctcca    3120
cccacatctc gtcgtcttat agcaagcaac cgggctacgg cgtgaatgat ttctatgtga    3180
gctatcaggg ccagcaagcc ctgaaaggta tgacgactac cctggttctg ggcaacgcat    3240
tcgacaaaga gtattggagc ccgcagggca ttccgcagga cggtcgtaac ggcaagattt    3300
```
tcgtttccta ccaatggtaa gtcgac                                    3326

<210> SEQ ID NO 21
<211> LENGTH: 486
<212> TYPE: PRT
<213> ORGANISM: Artificial Sequence
<220> FEATURE:
<223> OTHER INFORMATION: Humicola insolens PDI amino acid sequence,
      without signal peptide

<400> SEQUENCE: 21

Met Ser Asp Val Val Gln Leu Lys Lys Asp Thr Phe Asp Asp Phe Ile
1               5                   10                  15

Lys Thr Asn Asp Leu Val Leu Ala Glu Phe Phe Ala Pro Trp Cys Gly
            20                  25                  30

His Cys Lys Ala Leu Ala Pro Glu Tyr Glu Glu Ala Ala Thr Thr Leu
        35                  40                  45

Lys Glu Lys Asn Ile Lys Leu Ala Lys Val Asp Cys Thr Glu Glu Thr
    50                  55                  60

Asp Leu Cys Gln Gln His Gly Val Glu Gly Tyr Pro Thr Leu Lys Val
65                  70                  75                  80

Phe Arg Gly Leu Asp Asn Val Ser Pro Tyr Lys Gly Gln Arg Lys Ala
                85                  90                  95

Ala Ala Ile Thr Ser Tyr Met Ile Lys Gln Ser Leu Pro Ala Val Ser
            100                 105                 110

Glu Val Thr Lys Asp Asn Leu Glu Glu Phe Lys Lys Ala Asp Lys Ala
        115                 120                 125

Val Leu Val Ala Tyr Val Asp Ala Ser Asp Lys Ala Ser Ser Glu Val
    130                 135                 140

Phe Thr Gln Val Ala Glu Lys Leu Arg Asp Asn Tyr Pro Phe Gly Ser
145                 150                 155                 160

Ser Ser Asp Ala Ala Leu Ala Glu Ala Glu Gly Val Lys Ala Pro Ala
                165                 170                 175

Ile Val Leu Tyr Lys Asp Phe Asp Glu Gly Lys Ala Val Phe Ser Glu
            180                 185                 190

Lys Phe Glu Val Glu Ala Ile Glu Lys Phe Ala Lys Thr Gly Ala Thr
        195                 200                 205

Pro Leu Ile Gly Glu Ile Gly Pro Glu Thr Tyr Ser Asp Tyr Met Ser
    210                 215                 220

Ala Gly Ile Pro Leu Ala Tyr Ile Phe Ala Glu Thr Ala Glu Glu Arg
225                 230                 235                 240

Lys Glu Leu Ser Asp Lys Leu Lys Pro Ile Ala Glu Ala Gln Arg Gly
                245                 250                 255

Val Ile Asn Phe Gly Thr Ile Asp Ala Lys Ala Phe Gly Ala His Ala
            260                 265                 270

Gly Asn Leu Asn Leu Lys Thr Asp Lys Phe Pro Ala Phe Ala Ile Gln
        275                 280                 285

Glu Val Ala Lys Asn Gln Lys Phe Pro Phe Asp Gln Glu Lys Glu Ile
    290                 295                 300

Thr Phe Glu Ala Ile Lys Ala Phe Val Asp Asp Phe Val Ala Gly Lys
305                 310                 315                 320

Ile Glu Pro Ser Ile Lys Ser Glu Pro Ile Pro Glu Lys Gln Glu Gly
                325                 330                 335

Pro Val Thr Val Val Ala Lys Asn Tyr Asn Glu Ile Val Leu Asp
            340                 345                 350

```
Asp Thr Lys Asp Val Leu Ile Glu Phe Tyr Ala Pro Trp Cys Gly His
            355                 360                 365
Cys Lys Ala Leu Ala Pro Lys Tyr Glu Glu Leu Gly Ala Leu Tyr Ala
        370                 375                 380
Lys Ser Glu Phe Lys Asp Arg Val Val Ile Ala Lys Val Asp Ala Thr
385                 390                 395                 400
Ala Asn Asp Val Pro Asp Glu Ile Gln Gly Phe Pro Thr Ile Lys Leu
                405                 410                 415
Tyr Pro Ala Gly Ala Lys Gly Gln Pro Val Thr Tyr Ser Gly Ser Arg
            420                 425                 430
Thr Val Glu Asp Leu Ile Lys Phe Ile Ala Glu Asn Gly Lys Tyr Lys
        435                 440                 445
Ala Ala Ile Ser Glu Asp Ala Glu Thr Ser Ser Ala Thr Glu Thr
    450                 455                 460
Thr Thr Glu Thr Ala Thr Lys Ser Glu Glu Ala Ala Lys Glu Thr Ala
465                 470                 475                 480
Thr Glu His Asp Glu Leu
            485
```

<210> SEQ ID NO 22
<211> LENGTH: 1487
<212> TYPE: DNA
<213> ORGANISM: Artificial Sequence
<220> FEATURE:
<223> OTHER INFORMATION: PDI expression construct

<400> SEQUENCE: 22

```
gctagcagga ggaattcacc atgtctgatg ttgtacaact gaagaaagat acgttcgatg      60
actttatcaa aactaatgac ttggtgctgg cagagttttt cgccccgtgg tgtggccact     120
gcaaagctct ggctccggag tacgaagagg ccgcgaccac cctgaaagaa aagaacatca     180
aactggcgaa agtggactgt acggaagaaa ccgacctgtg tcagcagcac ggcgtggaag     240
gttacccgac cctgaaggtg tttcgtggcc tggacaatgt tagcccgtac aaaggtcaac     300
gtaaggccgc agcgatcacc agctacatga tcaagcagtc gctgcctgca gtctctgagg     360
tgaccaaaga taatctggaa gagttcaaaa aggcagataa ggcggtgctg gttgcctatg     420
ttgatgcaag cgacaaggcg agcagcgagg tctttaccca ggtcgcggag aaattgcgcg     480
ataactaccc gttcggcagc agctccgatg cagctttggc cgaggcgaaa ggtgtcaagg     540
ctccggcgat cgttctgtac aaagatttcg acgagggtaa agcggtgttc agcgaaaagt     600
ttgaggtgga agcaattgaa aagttcgcaa aaccggtgc cacgcctttg attggcgaaa     660
tcggtccgga aacctattct gactatatga gcgccggtat cccgctggcc tacattttcg     720
cagaaacggc agaagagcgc aaagaactga gcgacaagtt gaagccaatt gcagaggcac     780
agcgtggcgt catcaacttt ggtaccattg acgcgaaagc atttggtgcg catgccggta     840
acctgaatct gaaacggac aaatttccgg cgtttgcgat tcaagaggtg gcgaagaacc     900
aaaagttcc gttcgatcaa gaaaaagaga ttaccttcga ggcgatcaaa gcgttcgttg     960
acgactttgt tgccggtaaa atcgagccga cattaagag cgagccgatc ccggagaagc    1020
aggaaggccc ggtgaccgtc gtcgtcgcga agaattacaa cgagattgtt ctggatgaca    1080
cgaaagacgt cctgattgag ttctatgcgc cgtggtgcgg tcattgcaaa gcgctggccc    1140
cgaaatatga agagctgggt gcgctgtacg cgaagagcga gtttaaggac cgtgtggtta    1200
tcgcgaaagt agatgcgacc gccaatgacg ttcctgacga gatccaaggc ttcccgacca    1260
```

```
ttaaactgta tccggctggt gctaaaggcc agccagttac ctatagcggt agccgcacgg   1320
ttgaggatct gattaagttc attgccgaga acggcaagta caaggcggca atcagcgagg   1380
atgcagaaga acgagctcc gcaaccgaaa ccacgacgga aaccgctact aagtccgaag    1440
aggcggcgaa agaaaccgcg acggagcacg atgagctgta agtcgac                 1487
```

<210> SEQ ID NO 23
<211> LENGTH: 359
<212> TYPE: PRT
<213> ORGANISM: Artificial Sequence
<220> FEATURE:
<223> OTHER INFORMATION: P. chrysosporium MnP-H4 amino acid sequence, mature and "fully truncated"

<400> SEQUENCE: 23

```
Met Ala Val Cys Pro Asp Gly Thr Arg Val Thr Asn Ala Ala Cys Cys
1               5                   10                  15

Ala Phe Ile Pro Leu Ala Gln Asp Leu Gln Glu Thr Leu Phe Gln Gly
                20                  25                  30

Asp Cys Gly Glu Asp Ala His Glu Val Ile Arg Leu Thr Phe His Asp
            35                  40                  45

Ala Ile Ala Ile Ser Gln Ser Leu Gly Pro Gln Ala Gly Gly Gly Ala
        50                  55                  60

Asp Gly Ser Met Leu His Phe Pro Thr Ile Glu Pro Asn Phe Ser Ala
65                  70                  75                  80

Asn Ser Gly Ile Asp Asp Ser Val Asn Asn Leu Leu Pro Phe Met Gln
                85                  90                  95

Lys His Asp Thr Ile Ser Ala Ala Asp Leu Val Gln Phe Ala Gly Ala
                100                 105                 110

Val Ala Leu Ser Asn Cys Pro Gly Ala Pro Arg Leu Glu Phe Met Ala
            115                 120                 125

Gly Arg Pro Asn Thr Thr Ile Pro Ala Val Glu Gly Leu Ile Pro Glu
        130                 135                 140

Pro Gln Asp Ser Val Thr Lys Ile Leu Gln Arg Phe Glu Asp Ala Gly
145                 150                 155                 160

Asn Phe Ser Pro Phe Glu Val Val Ser Leu Leu Ala Ser His Thr Val
                165                 170                 175

Ala Arg Ala Asp Lys Val Asp Glu Thr Ile Asp Ala Ala Pro Phe Asp
            180                 185                 190

Ser Thr Pro Phe Thr Phe Asp Thr Gln Val Phe Leu Glu Val Leu Leu
        195                 200                 205

Lys Gly Thr Gly Phe Pro Gly Ser Asn Asn Asn Thr Gly Glu Val Met
    210                 215                 220

Ser Pro Leu Pro Leu Gly Ser Gly Ser Asp Thr Gly Glu Met Arg Leu
225                 230                 235                 240

Gln Ser Asp Phe Ala Leu Ala Arg Asp Glu Arg Thr Ala Cys Phe Trp
                245                 250                 255

Gln Ser Phe Val Asn Glu Gln Glu Phe Met Ala Ala Ser Phe Lys Ala
            260                 265                 270

Ala Met Ala Lys Leu Ala Ile Leu Gly His Ser Arg Ser Ser Leu Ile
        275                 280                 285

Asp Cys Ser Asp Val Val Pro Val Pro Lys Pro Ala Val Asn Lys Pro
    290                 295                 300

Ala Thr Phe Pro Ala Thr Lys Gly Pro Lys Asp Leu Asp Thr Leu Thr
305                 310                 315                 320
```

Cys Lys Ala Leu Lys Phe Pro Thr Leu Thr Ser Asp Pro Gly Ala Thr
            325                 330                 335

Glu Thr Leu Ile Pro His Cys Ser Asn Gly Gly Met Ser Cys Pro Gly
        340                 345                 350

Val Gln Phe Asp Gly Pro Ala
        355

<210> SEQ ID NO 24
<211> LENGTH: 25
<212> TYPE: DNA
<213> ORGANISM: Artificial Sequence
<220> FEATURE:
<223> OTHER INFORMATION: MnP-H4_FT NcoI forward primer

<400> SEQUENCE: 24
cgatgaccat ggcagtatgt ccaga                                  25

<210> SEQ ID NO 25
<211> LENGTH: 27
<212> TYPE: DNA
<213> ORGANISM: Artificial Sequence
<220> FEATURE:
<223> OTHER INFORMATION: MnP-H4_FT SalI reverse primer

<400> SEQUENCE: 25
ccgtctgtcg actataaacg cagaaag                                27

<210> SEQ ID NO 26
<211> LENGTH: 24
<212> TYPE: DNA
<213> ORGANISM: Artificial Sequence
<220> FEATURE:
<223> OTHER INFORMATION: ChuA SalI forward primer

<400> SEQUENCE: 26
tgcagagtcg acttgacagc tagc                                   24

<210> SEQ ID NO 27
<211> LENGTH: 31
<212> TYPE: DNA
<213> ORGANISM: Artificial Sequence
<220> FEATURE:
<223> OTHER INFORMATION: ChuA HindIII reverse primer

<400> SEQUENCE: 27
cgtctaaagc ttttaccatt ggtaggaaac g                           31

<210> SEQ ID NO 28
<211> LENGTH: 7768
<212> TYPE: DNA
<213> ORGANISM: Artificial Sequence
<220> FEATURE:
<223> OTHER INFORMATION: pBAD24-MnP_FT-ChuA expression construct

<400> SEQUENCE: 28
atcgatgcat aatgtgcctg tcaaatggac gaagcaggga ttctgcaaac cctatgctac    60
tccgtcaagc cgtcaattgt ctgattcgtt accaattatg acaacttgac ggctacatca   120 ttcactttt cttcacaacc ggcacggaac tcgctcgggc tggccccggt gcattttta    180 aatacccgcg agaaatagag ttgatcgtca aaaccaacat tgcgaccgac ggtggcgata   240
ggcatccggg tggtgctcaa aagcagcttc gcctggctga tacgttggtc ctcgcgccag   300
cttaagacgc taatccctaa ctgctggcgg aaaagatgtg acagacgcga cggcgacaag   360

```
caaacatgct gtgcgacgct ggcgatatca aaattgctgt ctgccaggtg atcgctgatg    420
tactgacaag cctcgcgtac ccgattatcc atcggtggat ggagcgactc gttaatcgct    480
tccatgcgcc gcagtaacaa ttgctcaagc agatttatcg ccagcagctc cgaatagcgc    540
ccttccccct tgcccggcgtt aatgatttgc ccaaacaggt cgctgaaatg cggctggtgc    600
gcttcatccg ggcgaaagaa ccccgtattg gcaaatattg acggccagtt aagccattca    660
tgccagtagg cgcgcggacg aaagtaaacc cactggtgat accattcgcg agcctccgga    720
tgacgaccgt agtgatgaat ctctcctggc gggaacagca aaatatcacc cggtcggcaa    780
acaaattctc gtccctgatt tttcaccacc ccctgaccgc gaatggtgag attgagaata    840
taacctttca ttcccagcgg tcggtcgata aaaaaatcga gataaccgtt ggcctcaatc    900
ggcgttaaac ccgccaccag atgggcatta acgagtatc ccggcagcag gggatcattt    960
tgcgcttcag ccatactttt catactcccg ccattcagag aagaaaccaa ttgtccatat   1020
tgcatcagac attgccgtca ctgcgtcttt tactggctct ctcgctaac caaaccggta   1080 accccgctta ttaaaagcat tctgtaacaa agcgggacca aagccatgac aaaaacgcgt   1140
aacaaaagtg tctataatca cggcagaaaa gtccacattg attatttgca cggcgtcaca   1200
ctttgctatg ccatagcatt tttatccata agattagcgg atcctacctg acgctttta   1260 tcgcaactct ctactgtttc tccatacccg ttttttgggg ctagcaggag gaattcacca   1320
tggcagtatg tccagacggt accagagtga cgaatgcagc gtgttgcgcg ttcattccgc   1380
tggcgcagga tctgcaggaa accctgttcc aaggcgattg cggcgaggac gcgcacgagg   1440
tcattcgcct gacctttcac gatgccattg caatcagcca gtctttgggt ccgcaagcgg   1500
gtggtggcgc ggacggcagc atgttgcact tccgaccat cgagccgaat ttctcggcca   1560
atagcggtat tgacgatagc gttaacaacc tgttgccgtt tatgcaaaag catgacacca   1620
tcagcgctgc ggacctggtt cagttcgcag cgccgtggc gctgagcaac tgtcctggtg   1680
cgccacgtct ggagttcatg gcgggtcgcc cgaataccac gatcccggca gttgaaggtc   1740
tgattccgga gccgcaggac agcgtcacca aaattctgca gcgtttcgag gatgccggta   1800
actttagccc gttcgaggtc gtgagcctgt tggcgagcca tacggtggcg cgtgctgaca   1860
aagttgatga aaccatcgac gccgctccgt tcgacagcac cccgtttacg tttgataccc   1920
aggttttcct ggaagttctg ttgaaaggca ccggcttttcc gggttccaat aacaacaccg   1980
gtgaagtcat gtctccgctg cctctgggct cgggtagcga tactggtgag atgcgcctgc   2040
aaagcgactt tgctctggcc cgtgatgagc gtaccgcgtg cttctggcag tccttcgtca   2100
acgaacaaga gtttatggcg ccagcttta aggctgcgat ggcaaaactg gcaattctgg   2160
gccatagccg ttccagcctg atcgattgca gcgacgtggt tccggtgccg aagcctgcgg   2220
tcaataagcc ggcgaccttc ccggcgacca aaggcccgaa ggacctggat actctgacgt   2280
gtaaagcgct gaagtttccg acgctgacgt ctgatccggg tgccacggag actctgatcc   2340
cgcactgcag caatggtggc atgagctgcc cgggtgtgca attcgacggt ccggcgtaat   2400
actagagcca ggcatcaaat aaaacgaaag gctcagtcga agactgggc ctttcgtttt   2460 atctgttgtt tgtcggtgaa cgctctctac tagagtcaca ctggctcacc ttcgggtggg   2520
cctttctgcg tttatagtcg acttgacagc tagctcagtc ctaggtattg tgctagctac   2580
tagagaaaga ggagaaatac tagatgtccc gccctcaatt cacctcgctc cgtttgtctt   2640
tgctcgcact cgccgtatcc gcaacgctgc cgacctttgc cttcgctacc gaaaccatga   2700
ccgttaccgc gaccggcaac gcacgcagct cgttcgaggc gccgatgatg gtgagcgtga   2760
```

-continued

```
tcgatacctc tgctccggag aaccagacgg cgacgagcgc taccgatctg ctgcgccacg    2820
tgccgggtat tacgctggac ggtaccggtc gcacgaacgg tcaagacgtg aacatgcgcg    2880
gctacgacca tcgcggtgtg ctggtcctgg tcgatggtgt gcgtcagggt acggataccg    2940
gtcacttgaa tggtaccttt ctggatccgg cgctgattaa gcgtgtcgaa atcgtgcgtg    3000
gcccgtcggc actgctgtat ggtagcggtg cgctgggcgg tgtgatcagc tacgataccg    3060
tcgatgcgaa agacctgttg caagagggtc aaagctccgg tttccgcgtt tttggtactg    3120
gtggtaccgg tgaccatagc ctgggcctgg gcgcgagcgc gtttggtcgc acggaaaacc    3180
tggatggcat cgttgcgtgg agcagccgtg atcgtggtga cttgcgccag tctaatggcg    3240
aaacggcccc taacgatgaa agcattaaca acatgctggc caagggtacg tggcagatcg    3300
atagcgcgca gagcctgagc ggcctggtcc gttactacaa caacgacgcg cgtgagccga    3360
aaaacccgca gacggtcgag gcgagcgaga gcagcaaccc gatggtggac cgtagcacca    3420
ttcaacgtga tgcccaactg agctataagc tggcaccgca aggtaatgac tggctgaatg    3480
cggatgcgaa aatctactgg agcgaagttc gcatcaatgc acagaatacg ggtagctctg    3540
gcgagtaccg tgaacagatt accaaaggtg cacgtctgga gaatcgttct acgctgtttg    3600
ctgacagctt cgcttcgcat ctgctgacgt atggtggcga gtattatcgt caggaacaac    3660
acccaggtgg tgcgaccacg ggtttcccgc aggcgaagat cgattttagc agcggctggc    3720
tgcaagatga gatcaccttg cgtgacttgc cgattaccct gctgggtggt acgcgttatg    3780
acagctaccg tggcagcagc gacggttaca aagacgtcga tgcagataaa tggagctccc    3840
gtgccggcat gaccattaat ccgaccaatt ggctgatgct gttcggcagc tatgcgcaag    3900
cgttccgtgc cccaaccatg ggtgagatgt acaatgacag caagcatttc agcattggtc    3960
gcttctacac gaattactgg gtgccgaacc cgaatctgcg tccggagact aatgaaaccc    4020
aggagtatgg ttttggcctg cgcttttgatg atctgatgct gagcaacgac gccctggaat    4080
tcaaggcgag ctactttgac actaaagcca aagactacat tagcactacg gttgattttg    4140
cggctgctac caccatgtcc tataatgttc caaacgcaaa gatttggggc tgggacgtca    4200
tgaccaagta caccaccgac ctgtttagct tggatgttgc atacaatcgc acccgtggca    4260
aagacaccga taccggcgaa tacatcagca catcaatcc ggacaccgtt acgtccaccc    4320
tgaacatccc gattgcgcac agcggtttca gcgttggttg ggttggtacg tttgcggatc    4380
gctccaccca catctcgtcg tcttatagca agcaaccggg ctacggcgtg aatgatttct    4440
atgtgagcta tcagggccag caagccctga aggtatgac gactaccctg gttctgggca    4500
acgcattcga caaagagtat tggagcccgc agggcattcc gcaggacggt cgtaacggca    4560
agattttcgt ttcctaccaa tggtaaaagc ttggctgttt tggcggatga gagaagatt    4620
tcagcctgat acagattaaa tcagaacgca gaagcggtct gataaaacag aatttgcctg    4680
gcggcagtag cgcggtggtc ccacctgacc ccatgcgaa ctcagaagtg aaacgccgta    4740
gcgccgatgg tagtgtgggg tctccccatg cgagagtagg gaactgccag gcatcaaata    4800
aaacgaaagg ctcagtcgaa agactgggcc tttcgtttta tctgttgttt gtcggtgaac    4860
gctctcctga gtaggacaaa tccgccggga gcggatttga acgttgcgaa gcaacggccc    4920
ggagggtggc gggcaggacg cccgccataa actgccaggc atcaaattaa gcagaaggcc    4980
atcctgacga atggccttt tgcgtttcta caaactcttt tgtttatttt tctaaataca    5040
ttcaaatatg tatccgctca tgagacaata accctgataa atgcttcaat aatattgaaa    5100
```

```
aaggaagagt atgagtattc aacatttccg tgtcgccctt attcccttt  ttgcggcatt    5160
ttgccttcct gttttgctc acccagaaac gctggtgaaa gtaaagatg ctgaagatca     5220
gttgggtgca cgagtgggtt acatcgaact ggatctcaac agcggtaaga tccttgagag   5280
ttttcgcccc gaagaacgtt ttccaatgat gagcactttt aaagttctgc tatgtggcgc   5340
ggtattatcc cgtgttgacg ccgggcaaga gcaactcggt cgccgcatac actattctca   5400
gaatgacttg gttgagtact caccagtcac agaaaagcat cttacggatg gcatgacagt   5460
aagagaatta tgcagtgctg ccataaccat gagtgataac actgcggcca acttacttct   5520
gacaacgatc ggaggaccga aggagctaac cgcttttttg cacaacatgg gggatcatgt   5580
aactcgcctt gatcgttggg aaccggagct gaatgaagcc ataccaaacg acgagcgtga   5640
caccacgatg cctgtagcaa tggcaacaac gttgcgcaaa ctattaactg gcgaactact   5700
tactctagct tcccggcaac aattaataga ctggatggag gcggataaag ttgcaggacc   5760
acttctgcgc tcggcccttc cggctggctg gtttattgct gataaatctg gagccggtga   5820
gcgtgggtct cgcggtatca ttgcagcact ggggccagat ggtaagccct cccgtatcgt   5880
agttatctac acgacgggga gtcaggcaac tatggatgaa cgaaatagac agatcgctga   5940
gataggtgcc tcactgatta agcattggta actgtcagac caagtttact catatatact   6000
ttagattgat ttacgcgccc tgtagcggcg cattaagcgc ggcgggtgtg gtggttacgc   6060
gcagcgtgac cgctacactt gccagcgccc tagcgcccgc tcctttcgct ttcttccctt   6120
cctttctcgc cacgttcgcc ggctttcccc gtcaagctct aaatcggggg ctccctttag   6180
ggttccgatt tagtgcttta cggcacctcg accccaaaaa acttgatttg ggtgatggtt   6240
cacgtagtgg gccatcgccc tgatagacgg ttttcgccc tttgacgttg gagtccacgt    6300
tctttaatag tggactcttg ttccaaactt gaacaacact caaccctatc tcgggctatt   6360
cttttgattt ataagggatt ttgccgattt cggcctattg gttaaaaaat gagctgattt   6420
aacaaaaatt taacgcgaat tttaacaaaa tattaacgtt acaatttaa aaggatctag    6480
gtgaagatcc ttttgataa tctcatgacc aaaatccctt aacgtgagtt ttcgttccac   6540
tgagcgtcag accccgtaga aaagatcaaa ggatcttctt gagatccttt ttttctgcgc   6600
gtaatctgct gcttgcaaac aaaaaaacca ccgctaccag cggtggtttg tttgccggat   6660
caagagctac caactctttt tccgaaggta actggcttca gcagagcgca gataccaaat   6720
actgtccttc tagtgtagcc gtagttaggc caccacttca agaactctgt agcaccgcct   6780
acatacctcg ctctgctaat cctgttacca gtggctgctg ccagtggcga taagtcgtgt   6840
cttaccgggt tggactcaag acgatagtta ccggataagg cgcagcggtc gggctgaacg   6900
gggggttcgt gcacacagcc cagcttggag cgaacgacct acaccgaact gagatacccta  6960
cagcgtgagc tatgagaaag cgccacgctt cccgaaggga gaaaggcgga caggtatccg   7020
gtaagcggca gggtcggaac aggagagcgc acgagggagc ttccagggg aaacgcctgg    7080
tatctttata gtcctgtcgg gtttcgccac ctctgacttg agcgtcgatt tttgtgatgc   7140
tcgtcagggg gcggagcct atggaaaaac gccagcaacg cggcctttt acggttcctg     7200
gccttttgct ggccttttgc tcacatgttc tttcctgcgt tatcccctga ttctgtggat   7260
aaccgtatta ccgcctttga gtgagctgat accgctcgcc gcagccgaac gaccgagcgc   7320
agcgagtcag tgagcgagga agcggaagag cgcctgatgc ggtattttct ccttacgcat   7380
ctgtgcggta tttcacaccg catagggtca ggctgcgcc ccgacacccg ccaacacccg    7440
ctgacgcgcc ctgacgggct tgtctgctcc cggcatccgc ttacagacaa gctgtgaccg   7500
```

```
tctccgggag ctgcatgtgt cagaggtttt caccgtcatc accgaaacgc gcgaggcagc    7560
aaggagatgg cgcccaacag tcccccggcc acggggcctg ccaccatacc cacgccgaaa    7620
caagcgctca tgagcccgaa gtggcgagcc cgatcttccc catcggtgat gtcggcgata    7680
taggcgccag caaccgcacc tgtggcgccg gtgatgccgg ccacgatgcg tccggcgtag    7740
aggatctgct catgtttgac agcttatc                                       7768
```

<210> SEQ ID NO 29
<211> LENGTH: 7316
<212> TYPE: DNA
<213> ORGANISM: Artificial Sequence
<220> FEATURE:
<223> OTHER INFORMATION: pPRO33-PDI expression construct

<400> SEQUENCE: 29

```
atcgattcag cttttcagcc gccgccagaa cgtcgtccgg ctgatgccta ataattcgc      60 cgctgctgtt ttatcgccat taaatttctc cagtgcctgt tgtggtgtca gtaagcgtgg    120
agcgggagtt ttcgccgact cgcgcgccag ttccggcagt agcagttgca taaactgcgg    180
cgttaaatcc ggcgtcggtt ccacacttaa aaacagcgcc agtcgttcca tcatattgcg    240
cagttcacga atattgcctg ccagtcgta gtgcagcagc acagtttcac ttgcctgtaa    300
cccctggcgt aatgcagcag aaaatggggc ggagagcgcc gccagagaca ctttcaaaaa    360
gctttccgcc agcggaagaa tatccgccac ccgctcgcgc agtggtggca attgcagacg    420
caaaatactc agccgataaa acagatcacg gcgaaaacgt ccttgctgca tatcttcttc    480
cagattgcag tgagtggcgc taatgacccg tacatctacc ggaacaggct gatgcccgcc    540
gacgcgggtg acctcttttt cttccagcac ccgcagcagc cgggtctgca aaggtagcgg    600
catttcgcca atctcatcca gaaacagcgt accgccgtgg gcaatttcga acagcccggc    660
gcgacctccg cgtcgcgagc cggtaaacgc cccttcctca tagccaaaca gttctgcttc    720
cagcagcgat tcggcaatcg ccccgcagtt gacggcaaca aacggatgcg acttttttgcc    780 ctgtcgcgca tcgtgcgggc aaaatattc ccgatgaatc gcctgggccg ccagctcttt    840
gcccgtcccc gtttccccct caatcaacac cgccgcactg gagcgggcat acagcaaaat    900
agtctgccgt acttgttcca tctgtggtga ttgaccgagc atatcgccca gcacgtaacg    960
agtacgcagg gcgttgcggg tggcatcgtg agtgttatgg cgtaacgaca tgcgcgtcat   1020
atccagcgca tcgctgaacg cctggcgcac ggtggcggcg aatagataa aaattccggt    1080 cattccggct tcttctgcca aatcggtaat cagccctgcg ccgaccaccg cttcggtgcc   1140
gttagctttt agctcgttaa tctgcccgcg tgcgtcttcc tcggtaatgt agctacgttg   1200
gtcgaggcgc aaattaaagg ttttttgaaa cgccaccagc gctggaatgg ttcctgata    1260 ggtgacaacg ccgatagaag aggtgagttt tccggctttt gccagtgcct gtaacacatc   1320
gtagccgctc ggtttaatca aaataactgg cactgacagg cggcttttca ggtacgcgcc   1380
gttagagcca gccgcgatga tggcgtcaca gcgttcgttt gccagtttct tgcggatgta   1440
ggtcactgct ttttcaaagc caagctgaat aggggtaatg ttcgccaggt gatcaaactc   1500
gaggctgata tcgcgaaaca gctcgaacag gcgcgttaca gataccgtcc agataaccgg   1560
tttgtcgtca ttaagccgtg gtggatgtgc catagcgcac cgcaaagtta agaaaccgaa   1620
tattgggttt agtcttgttt cataattgtt gcaatgaaac gcggtgaaac attgcctgaa   1680
acgttaactg aaacgcatat ttgcggatta gttcatgact ttatctctaa caaattgaaa   1740
```

```
ttaaacattt aatttttatta aggcaattgt ggcacacccc ttgctttgtc tttatcaacg    1800
caaataacaa gttgataaca agctagcagg aggaattcac catgtctgat gttgtacaac    1860
tgaagaaaga tacgttcgat gactttatca aaactaatga cttggtgctg gcagagtttt    1920
tcgccccgtg gtgtggccac tgcaaagctc tggctccgga gtacgaagag gccgcgacca    1980
ccctgaaaga aaagaacatc aaactggcga aagtggactg tacggaagaa accgacctgt    2040
gtcagcagca cggcgtggaa ggttacccga ccctgaaggt gtttcgtggc ctggacaatg    2100
ttagcccgta caaaggtcaa cgtaaggccg cagcgatcac cagctacatg atcaagcagt    2160
cgctgcctgc agtctctgag gtgaccaaag ataatctgga agagttcaaa aaggcagata    2220
aggcggtgct ggttgcctat gttgatgcaa gcgacaaggc gagcagcgag gtctttaccc    2280
aggtcgcgga gaaattgcgc gataactacc cgttcggcag cagctccgat gcagctttgg    2340
ccgaggcgga aggtgtcaag gctccggcga tcgttctgta caaagatttc gacgagggta    2400
aagcggtgtt cagcgaaaag tttgaggtgg aagcaattga aaagttcgca aaaaccggtg    2460
ccacgccttt gattggcgaa atcggtccgg aaacctattc tgactatatg agcgccggta    2520
tcccgctggc ctacatttc gcagaaacgg cagaagagcg caaagaactg agcgacaagt    2580
tgaagccaat tgcagaggca cagcgtggcg tcatcaactt tggtaccatt gacgcgaaag    2640
catttggtgc gcatgccggt aacctgaatc tgaaaacgga caaatttccg gcgtttgcga    2700
ttcaagaggt ggcgaagaac caaaagtttc cgttcgatca agaaaaagag attaccttcg    2760
aggcgatcaa agcgttcgtt gacgactttg ttgccggtaa aatcgagccg agcattaaga    2820
gcgagccgat cccggagaag caggaaggcc cggtgaccgt cgtcgtcgcg aagaattaca    2880
acgagattgt tctggatgac acgaaagacg tcctgattga gttctatgcg ccgtggtgcg    2940
gtcattgcaa agcgctggcc ccgaaatatg aagagctggg tgcgctgtac gcgaagagcg    3000
agtttaagga ccgtgtggtt atcgcgaaag tagatgcgac cgccaatgac gttcctgacg    3060
agatccaagg cttcccgacc attaaactgt atccggctgg tgctaaaggc cagccagtta    3120
cctatagcgg tagccgcacg gttgaggatc tgattaagtt cattgccgag aacggcaagt    3180
acaaggcggc aatcagcgag gatgcagaag aaacgagctc cgcaaccgaa accacgacgg    3240
aaaccgctac taagtccgaa gaggcggcga agaaaccgc gacggagcac gatgagctgt    3300
aagtcgacct gcaggcatgc aagcttggct gttttggcgg atgagagaag attttcagcc    3360
tgatacagat taaatcagaa cgcagaagcg gtctgataaa acagaatttg cctggcggca    3420
gtagcgcggt ggtcccacct gaccccatgc cgaactcaga agtgaaacgc cgtagcgccg    3480
atggtagtgt ggggtctccc catgcgagag tagggaactg ccaggcatca aataaaacga    3540
aaggctcagt cgaaagactg ggcctttcgt tttatctgtt gtttgtcggt gaacgctctc    3600
ctgagtagga caaatccgcc gggagcggat ttgaacgttg cgaagcaacg gcccggaggg    3660
tggcgggcag gacgcccgcc ataaactgcc aggcatcaaa ttaagcagaa ggccatcctg    3720
acggatggcc ttttgcgtt tctacaaact ctttgtttta tttttctaaa tacattcaaa    3780
tatgtatccg ctcatgagac aataaccctg ataaatgctt caataatatt gaaaaggaa    3840 gagtatgagt attcaacatt tccgtgtcgc ccttattccc ttttttgcgg cattttgcct    3900
tcctgttttt gctcacccag aaacgctggt gaaagtaaaa gatgctgaag atcagttggg    3960
gcaaactatt aactggcgaa ctacttactc tagcttcccg gcaacaatta atagactgga    4020
tggaggcgga taaagttgca ggaccacttc tgcgctcggc ccttccggct ggctggttta    4080
ttgctgataa atctggagcc ggtgagcgtg ggtctcgcgg tatcattgca gcactggggc    4140
```

```
cagatggtaa gccctcccgt atcgtagtta tctacacgac ggggagtcag gcaactatgg    4200
atgaacgaaa tagacagatc gctgagatag gtgcctcact gattaagcat tggtaactgt    4260
cagaccaagt ttactcatat atactttaga ttgatttacg cgccctgtag cggcgcatta    4320
agcgcggcgg gtgtggtggt tacgcgcagc gtgaccgcta cacttgccag cgccctagcg    4380
cccgctcctt tcgctttctt cccttccttt ctcgccacgt tcgccggctt tccccgtcaa    4440
gctctaaatc gggggctccc tttagggttc cgatttagtg ctttacggca cctcgacccc    4500
aaaaaacttg atttgggtga tggttcacgt agtgggccat cgccctgata cgggttttt    4560 cgcccttttga cgttggagtc cacgttcttt aatagtggac tcttgttcca aacttgaaca    4620
acactcaacc ctatctcggg ctattctttt gatttataag gattttgcc gatttcggcc    4680 tattggttaa aaaatgagct gatttaacaa aaatttaacg cgaattttaa caaaatatta    4740
acgtttacaa tttaaaagga tctaggtgaa gatcctttt gataatctca tgaccaaaat    4800
cccttaacgt gagttttcgt tccactgagc gtcagacccc gtagaaaaga tcaaaggatc    4860
ttcttgagat cctttttttc tgcgcgtaat ctgctgcttg caaacaaaaa aaccaccgct    4920
accagcggtg gtttgtttgc cggatcaaga gctaccaact cttttccga aggtaactgg    4980 cttcagcaga gcgcagatac caaatactgt ccttctagtg tagccgtagt taggccacca    5040
cttcaagaac tctgtagcac cgcctacata cctcgctctg ctaatcctgt taccagtcag    5100
gcatttgaga agcacacggt cacactgctt ccggtagtca ataaaccggt aaaccagcaa    5160
tagacataag cggctattta cgaccctgc cctgaaccga cgaccgggtc gaatttgctt    5220
tcgaatttct gccattcatc cgcttattat cacttattca ggcgtagcac caggcgttta    5280
agggcaccaa taactgcctt aaaaaaatta cgccccgccc tgccactcat cgcagtactg    5340
ttgtaattca ttaagcattc tgccgacatg gaagccatca cagacggcat gatgaacctg    5400
aatcgccagc ggcatcagca ccttgtcgcc ttgcgtataa tatttgccca tggtgaaaac    5460
gggggcgaag aagttgtcca tattggccac gtttaaatca aaactggtga actcaccca    5520 gggattggct gagacgaaaa acatattctc aataaaccct ttagggaaat aggccaggtt    5580
ttcaccgtaa cacgccacat cttgcgaata tatgtgtaga actgccgga atcgtcgtg    5640 gtattcactc cagagcgatg aaaacgtttc agtttgctca tggaaaacgg tgtaacaagg    5700
gtgaacacta tcccatatca ccagctcacc gtctttcatt gccatacgga attccggatg    5760
agcattcatc aggcgggcaa gaatgtgaat aaaggccgga taaaacttgt gcttattttt    5820
ctttacggtc tttaaaaagg ccgtaatatc cagctgaacg gtctggttat aggtacattg    5880
agcaactgac tgaaatgcct caaaatgttc tttacgatgc cattgggata tatcaacggt    5940
ggtatatcca gtgatttttt tctccatttt agcttcctta gctcctgaaa atctcgataa    6000
ctcaaaaaat acgcccggta gtgatcttat ttcattatgg tgaaagttgg aacctcttac    6060
gtgccgatca acgtctcatt ttcgccaaaa gttggcccag gcttccccgg tatcaacagg    6120
gacaccagga tttatttatt ctgcgaagtg atcttccgtc acaggtattt attcggcgca    6180
aagtgcgtcg ggtgatgctg ccaacttact gatttagtgt atgatggtgt ttttgaggtg    6240
ctccagtggc ttctgtttct atcagctgtc cctcctgttc agctactgac ggggtggtgc    6300
gtaacggcaa aagcaccgcc ggacatcagc gctagcggag tgtatactgg cttactatgt    6360
tggcactgat gagggtgtca gtgaagtgct tcatgtggca ggagaaaaaa ggctgcaccg    6420
gtgcgtcagc agaatatgtg atacaggata tattccgctt cctcgctcac tgactcgcta    6480
```

-continued

```
cgctcggtcg ttcgactgcg gcgagcggaa atggcttacg aacggggcgg agatttcctg    6540
gaagatgcca ggaagatact taacagggaa gtgagagggc cgcggcaaag ccgttttttcc   6600 ataggctccg ccccctgac aagcatcacg aaatctgacg ctcaaatcag tggtggcgaa    6660
acccgacagg actataaaga taccaggcgt ttccccctgg cggctccctc gtgcgctctc    6720
ctgttcctgc ctttcggttt accggtgtca ttccgctgtt atggccgcgt ttgtctcatt    6780
ccacgcctga cactcagttc cgggtaggca gttcgctcca agctggactg tatgcacgaa    6840 cccccgttc agtccgaccg ctgcgcctta tccggtaact atcgtcttga gtccaacccg    6900
gaaagacatg caaaagcacc actggcagca gccactggta attgatttag aggagttagt    6960
cttgaagtca tgcgccggtt aaggctaaac tgaaaggaca agttttggtg actgcgctcc    7020
tccaagccag ttacctcggt tcaaagagtt ggtagctcag agaaccttcg aaaaaccgcc    7080
ctgcaaggcg gttttttcgt tttcagagca agagattacg cgcagaccaa aacgatctca    7140
agaagatcat cttattaatc agataaaata tttgctcatg agcccgaagt ggcgagcccg    7200
atcttcccca tcggtgatgt cggcgatata ggcgccagca accgcacctg tggcgccggt    7260
gatgccggcc acgatgcgtc cggcgtagag gatctgctca tgtttgacag cttatc        7316
```

<210> SEQ ID NO 30
<211> LENGTH: 451
<212> TYPE: PRT
<213> ORGANISM: Artificial Sequence
<220> FEATURE:
<223> OTHER INFORMATION: Infliximab chimeric (murine variable doman, human constant domain) heavy chain

<400> SEQUENCE: 30

```
Met Glu Val Lys Leu Glu Glu Ser Gly Gly Gly Leu Val Gln Pro Gly
1               5                   10                  15

Gly Ser Met Lys Leu Ser Cys Val Ala Ser Gly Phe Ile Phe Ser Asn
            20                  25                  30

His Trp Met Asn Trp Val Arg Gln Ser Pro Glu Lys Gly Leu Glu Trp
        35                  40                  45

Val Ala Glu Ile Arg Ser Lys Ser Ile Asn Ser Ala Thr His Tyr Ala
    50                  55                  60

Glu Ser Val Lys Gly Arg Phe Thr Ile Ser Arg Asp Asp Ser Lys Ser
65                  70                  75                  80

Ala Val Tyr Leu Gln Met Thr Asp Leu Arg Thr Glu Asp Thr Gly Val
                85                  90                  95

Tyr Tyr Cys Ser Arg Asn Tyr Tyr Gly Ser Thr Tyr Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

-continued

```
            210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 31
<211> LENGTH: 215
<212> TYPE: PRT
<213> ORGANISM: Artificial Sequence
<220> FEATURE:
<223> OTHER INFORMATION: Infliximab chimeric (murine variable doman,
      human constant domain) light chain

<400> SEQUENCE: 31

Met Asp Ile Leu Leu Thr Gln Ser Pro Ala Ile Leu Ser Val Ser Pro
1               5                   10                  15

Gly Glu Arg Val Ser Phe Ser Cys Arg Ala Ser Gln Phe Val Gly Ser
                20                  25                  30

Ser Ile His Trp Tyr Gln Gln Arg Thr Asn Gly Ser Pro Arg Leu Leu
            35                  40                  45

Ile Lys Tyr Ala Ser Glu Ser Met Ser Gly Ile Pro Ser Arg Phe Ser
        50                  55                  60

Gly Ser Gly Ser Gly Thr Asp Phe Thr Leu Ser Ile Asn Thr Val Glu
65                  70                  75                  80

Ser Glu Asp Ile Ala Asp Tyr Tyr Cys Gln Gln Ser His Ser Trp Pro
                85                  90                  95

Phe Thr Phe Gly Ser Gly Thr Asn Leu Glu Val Lys Arg Thr Val Ala
            100                 105                 110
```

```
Ala Pro Ser Val Phe Ile Phe Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 32
<211> LENGTH: 5875
<212> TYPE: DNA
<213> ORGANISM: Artificial Sequence
<220> FEATURE:
<223> OTHER INFORMATION: pBAD24-Infliximab_HC expression construct

<400> SEQUENCE: 32
atcgatgcat aatgtgcctg tcaaatggac gaagcaggga ttctgcaaac cctatgctac      60
tccgtcaagc cgtcaattgt ctgattcgtt accaattatg acaacttgac ggctacatca     120
ttcactttt cttcacaacc ggcacggaac tcgctcgggc tggccccggt gcatttttta     180
aatacccgcg agaaatagag ttgatcgtca aaaccaacat tgcgaccgac ggtggcgata     240
ggcatccggg tggtgctcaa aagcagcttc gcctggctga tacgttggtc ctcgcgccag     300
cttaagacgc taatccctaa ctgctggcgg aaaagatgtg acagacgcga cggcgacaag     360
caaacatgct gtgcgacgct ggcgatatca aaattgctgt ctgccaggtg atcgctgatg     420
tactgacaag cctcgcgtac ccgattatcc atcggtggat ggagcgactc gttaatcgct     480
tccatgcgcc gcagtaacaa ttgctcaagc agatttatcg ccagcagctc cgaatagcgc     540
ccttcccctt gcccggcgtt aatgatttgc ccaaacaggt cgctgaaatg cggctggtgc     600
gcttcatccg ggcgaaagaa ccccgtattg gcaaatattg acggccagtt aagccattca     660
tgccagtagg cgcgcggacg aaagtaaacc cactggtgat accattcgcg agcctccgga     720
tgacgaccgt agtgatgaat ctctcctggc gggaacagca aatatcaccc ggtcggcaa      780
acaaattctc gtccctgatt tttcaccacc cctgaccgc gaatggtgag attgagaata     840
taacctttca ttcccagcgg tcggtcgata aaaaaatcga dataaccgtt ggcctcaatc     900
ggcgttaaac ccgccaccag atgggcatta acgagtatc cggcagcag gggatcattt     960
tgcgcttcag ccatactttt catactcccg ccattcagag aagaaaccaa ttgtccatat    1020
tgcatcagac attgccgtca ctgcgtcttt tactggctct ctcgctaac caaaccggta    1080
accccgctta ttaaaagcat tctgtaacaa agcgggacca aagccatgac aaaaacgcgt    1140
aacaaaagtg tctataatca cggcagaaaa gtccacattg attatttgca cggcgtcaca    1200
ctttgctatg ccatagcatt tttatccata agattagcgg atcctacctg acgctttta    1260
tcgcaactct ctactgtttc tccatacccg ttttttggg ctagcaggag gaattcacca    1320
tggaagttaa attagaagaa agcggcggcg gtttggtgca acctggcggt tcgatgaagt    1380
tgagctgcgt cgcaagcggt ttcattttt ccaaccactg gatgaactgg gtgcgccagt    1440
```

```
ctccggaaaa gggtctggaa tgggttgcgg agatccgtag caagagcatc aatagcgcga   1500
cgcattatgc cgagagcgtc aaaggccgct tcaccatttc tcgtgacgac agcaaaagcg   1560
ctgtgtatct gcaaatgacc gacttgcgta ccgaggacac gggcgtgtat tactgctccc   1620
gcaactatta cggttccacc tacgactact ggggccaggg tacgaccctg accgttagct   1680
cggcgagcac caagggtccg agcgtctttc cgctggcacc gagcagcaaa agcaccagcg   1740
gtggtaccgc cgcactgggt tgcctggtga agattactt cccggaaccg gttactgtga   1800
gctggaacag cggcgcgctg acctctggcg tgcacacgtt cccggcagtt ctgcaaagca   1860
gcggcctgta ctccctgtcc agcgtcgtca ccgtgccgag cagcagcctg ggtacgcaaa   1920
cctatatttg taacgtcaat cacaagccga gcaacaccaa agtggacaaa aaagtcgaac   1980
cgaaaagctg cgataaaacc catacttgtc cgccgtgccc ggccccggag cttctgggtg   2040
gtccaagcgt ttttctgttc ccgccgaagc cgaaagacac cctgatgatc agcccgcaccc  2100 ctgaggtgac ctgtgtggta gttgacgttt cccacgaaga tccagaggtc aagtttaact   2160
ggtatgtgga tggcgtcgaa gttcacaatg caaagaccaa gccgcgtgaa gaacagtata   2220
actctacgta ccgtgtcgtg agcgttctga ctgttctgca ccaggattgg ctgaacggca   2280
aagagtacaa gtgcaaggtt agcaataaag cgctgccggc tccgatcgag aaaaccattt   2340
ctaaggctaa aggtcagccg cgtgagccgc aagtttacac cctgccaccg agccgtgatg   2400
agctgacgaa aaatcaagta tctctgacct gtctggtcaa aggtttttac ccaagcgata   2460
tcgcggttga atgggagagc aacggccagc cggagaataa ttacaagacg acgcctccgg   2520
tgctggatag cgatggttcg ttttcctgt acagcaagtt gacggttgat aaaagccgtt    2580
ggcaacaggg taacgtgttc tcctgttccg tcatgcatga agcgctgcac aaccattata   2640
ctcagaaaag cctcagcctg tccccgggta ataagtcga cctgcaggca tgcaagcttg    2700
gctgttttgg cggatgagag aagattttca gcctgataca gattaaatca gaacgcagaa   2760
gcggtctgat aaaacagaat ttgcctggcg gcagtagcgc ggtggtccca cctgacccca   2820
tgccgaactc agaagtgaaa cgccgtagcg ccgatggtag tgtggggtct ccccatgcga   2880
gagtagggaa ctgccaggca tcaaataaaa cgaaaggctc agtcgaaaga ctgggccttt   2940
cgttttatct gttgtttgtc ggtgaacgct ctcctgagta ggacaaatcc gccgggagcg   3000
gatttgaacg ttgcgaagca acggcccgga gggtggcggg caggacgccc gccataaact   3060
gccaggcatc aaattaagca gaaggccatc ctgacggatg cctttttgc gtttctacaa    3120 actcttttgt ttattttct aaatacattc aaatatgtat ccgctcatga gacaataacc     3180
ctgataaatg cttcaataat attgaaaaag gaagagtatg agtattcaac atttccgtgt   3240
cgcccttatt ccctttttg cggcattttg ccttcctgtt tttgctcacc cagaaacgct    3300
ggtgaaagta aaagatgctg aagatcagtt gggtgcacga gtgggttaca tcgaactgga   3360
tctcaacagc ggtaagatcc ttgagagttt tcgccccgaa gaacgttttc caatgatgag   3420 cactttaaa gttctgctat gtggcgcggt attatcccgt gttgacgccg ggcaagagca    3480
actcggtcgc cgcatacact attctcagaa tgacttggtt gagtactcac cagtcacaga   3540
aaagcatctt acgyatggca tgacagtaag agaattatgc agtgctgcca taaccatgag   3600
tgataacact gcggccaact tacttctgac aacgatcgga ggaccgaagg agctaaccgc   3660
ttttttgcac aacatggggg atcatgtaac tcgccttgat cgttgggaac cggagctgaa   3720
tgaagccata ccaaacgacg agcgtgacac cacgatgcct gtagcaatgg caacaacgtt   3780
gcgcaaacta ttaactggcg aactacttac tctagcttcc cggcaacaat taatagactg   3840
```

```
gatggaggcg ataaagttg caggaccact tctgcgctcg gcccttccgg ctggctggtt      3900
tattgctgat aaatctggag ccggtgagcg tgggtctcgc ggtatcattg cagcactggg      3960
gccagatggt aagccctccc gtatcgtagt tatctacacg acggggagtc aggcaactat      4020
ggatgaacga aatagacaga tcgctgagat aggtgcctca ctgattaagc attggtaact      4080
gtcagaccaa gtttactcat atatacttta gattgattta cgcgccctgt agcggcgcat      4140
taagcgcggc gggtgtggtg gttacgcgca gcgtgaccgc tacacttgcc agcgccctag      4200
cgcccgctcc tttcgctttc ttcccttcct ttctcgccac gttcgccggc tttccccgtc      4260
aagctctaaa tcgggggctc cctttagggt tccgatttag tgctttacgg cacctcgacc      4320
ccaaaaaact tgatttgggt gatggttcac gtagtgggcc atcgccctga tagacggttt      4380
ttcgcccttt gacgttggag tccacgttct ttaatagtgg actcttgttc caaacttgaa      4440
caacactcaa ccctatctcg gctattctt ttgatttata agggattttg ccgatttcgg      4500
cctattggtt aaaaaatgag ctgatttaac aaaaatttaa cgcgaatttt aacaaaatat      4560
taacgtttac aatttaaaag gatctaggtg aagatccttt ttgataatct catgaccaaa      4620
atcccttaac gtgagttttc gttccactga gcgtcagacc ccgtagaaaa gatcaaagga      4680
tcttcttgag atccttttt tctgcgcgta atctgctgct tgcaaacaaa aaaaccaccg      4740
ctaccagcgg tggtttgttt gccggatcaa gagctaccaa ctcttttcc gaaggtaact      4800
ggcttcagca gagcgcagat accaaatact gtccttctag tgtagccgta gttaggccac      4860
cacttcaaga actctgtagc accgcctaca tacctcgctc tgctaatcct gttaccagtg      4920
gctgctgcca gtggcgataa gtcgtgtctt accgggttgg actcaagacg atagttaccg      4980
gataaggcgc agcggtcggg ctgaacgggg gttcgtgca cacagcccag cttggagcga      5040
acgacctaca ccgaactgag atacctacag cgtgagctat gagaaagcgc cacgcttccc      5100
gaagggagaa aggcggacag gtatccggta agcggcaggg tcggaacagg agagcgcacg      5160
agggagcttc caggggggaaa cgcctggtat ctttatagtc ctgtcgggtt tcgccacctc      5220
tgacttgagc gtcgattttt gtgatgctcg tcaggggggc ggagcctatg gaaaaacgcc      5280
agcaacgcgg cctttttacg gttcctggcc ttttgctggc cttttgctca catgttcttt      5340
cctgcgttat cccctgattc tgtggataac cgtattaccg cctttgagtg agctgatacc      5400
gctcgccgca gccgaacgac cgagcgcagc gagtcagtga gcgaggaagc ggaagagcgc      5460
ctgatgcggt attttctcct tacgcatctg tgcggtattt cacaccgcat agggtcatgg      5520
ctgcgccccg acaccgcca acaccgctg acgcgccctg acgggcttgt ctgctcccgg      5580
catccgctta cagacaagct gtgaccgtct ccgggagctg catgtgtcag aggttttcac      5640
cgtcatcacc gaaacgcgcg aggcagcaag gagatgcgc caacagtcc ccggccacg      5700
gggcctgcca ccatacccac gccgaaacaa gcgctcatga gcccgaagtg gcgagcccga      5760
tcttccccat cggtgatgtc ggcgatatag gcgccagcaa ccgcacctgt ggcgccggtg      5820
atgccggcca cgatgcgtcc ggcgtagagg atctgctcat gtttgacagc ttatc          5875
```

<210> SEQ ID NO 33
<211> LENGTH: 6503
<212> TYPE: DNA
<213> ORGANISM: Artificial Sequence
<220> FEATURE:
<223> OTHER INFORMATION: pPRO33-Infliximab_LC expression construct

<400> SEQUENCE: 33

-continued

```
atcgattcag cttttcagcc gccgccagaa cgtcgtccgg ctgatgccta ataattcgc    60 cgctgctgtt ttatcgccat taaatttctc cagtgcctgt tgtggtgtca gtaagcgtgg   120
agcgggagtt ttcgccgact cgcgcgccag ttccggcagt agcagttgca taaactgcgg   180
cgttaaatcc ggcgtcggtt ccacacttaa aaacagcgcc agtcgttcca tcatattgcg   240
cagttcacga atattgcctg gccagtcgta gtgcagcagc acagtttcac ttgcctgtaa   300
cccctggcgt aatgcagcag aaaatggggc ggagagcgcc gccagagaca ctttcaaaaa   360
gctttccgcc agcggaagaa tatccgccac ccgctcgcgc agtggtggca attgcagacg   420
caaaatactc agccgataaa acagatcacg gcgaaaacgt ccttgctgca tatcttcttc   480
cagattgcag tgagtggcgc taatgacccg tacatctacc ggaacaggct gatgcccgcc   540
gacgcgggtg acctcttttt cttccagcac ccgcagcagc cgggtctgca aggtagcgg    600 catttcgcca atctcatcca gaaacagcgt accgccgtgg gcaatttcga acagcccggc   660
gcgacctccg cgtcgcgagc cggtaaacgc cccttcctca tagccaaaca gttctgcttc   720
cagcagcgat tcggcaatcg ccccgcagtt gacggcaaca aacggatgcg acttttttgcc  780 ctgtcgcgca tcgtggcggg caaaatattc ccgatgaatc gcctgggccg ccagctcttt   840
gcccgtcccc gtttcccccct caatcaacac cgccgcactg gagcgggcat acagcaaaat   900
agtctgccgt acttgttcca tctgtggtga ttgaccgagc atatcgccca gcacgtaacg   960
agtacgcagg gcgttgcggg tggcatcgtg agtgttatgg cgtaacgaca tgcgcgtcat  1020
atccagcgca tcgctgaacg cctggcgcac ggtggcggcg aatagataa aaattccggt   1080 cattccggct tcttctgcca aatcggtaat cagcccctgcg ccgaccaccg cttcggtgcc  1140
gttagctttt agctcgttaa tctgcccgcg tgcgtcttcc tcggtaatgt agctacgttg   1200
gtcgaggcgc aaattaaagg ttttttgaaa cgccaccagc gctggaatgg tttcctgata   1260
ggtgacaacg ccgatagaag aggtgagttt tccggctttt gccagtgcct gtaacacatc   1320
gtagccgctc ggtttaatca aaataactgg cactgacagg cggcttttca ggtacgcgcc   1380
gttagagcca gccgcgatga tggcgtcaca gcgttcgttt gccagtttct gcggatgta    1440 ggtcactgct ttttcaaagc caagctgaat aggggtaatg ttcgccaggt gatcaaactc   1500
gaggctgata tcgcgaaaca gctcgaacag gcgcgttaca gataccgtcc agataaccgg   1560
tttgtcgtca ttaagccgtg gtggatgtgc catagcgcac cgcaaagtta agaaaccgaa   1620
tattgggttt agtcttgttt cataattgtt gcaatgaaac gcggtgaaac attgcctgaa   1680
acgttaactg aaacgcatat ttgcggatta gttcatgact ttatctctaa caaattgaaa   1740
ttaaacattt aattttatta aggcaattgt ggcacacccc ttgctttgtc tttatcaacg   1800
caaataacaa gttgataaca agctagcagg aggaattcac catggatatt ttattgaccc   1860
aaagcccagc cattctgtct gtttccccgg gcgagcgtgt ttcttttagc tgccgtgcaa   1920
gccagttcgt tggttcatcg atccactggt accaacagcg tacgaacggt agcccgcgtc   1980
tgctgattaa gtacgcgagc gaaagcatga gcggtatccc gagccgcttc agcggtagcg   2040
gcagcggcac ggacttcacg ctgagcatca atacggttga aagcgaggac atcgcggact   2100
attactgcca gcagagccat tcttggccgt ttacctttgg cagcggtacc aatctggaag   2160
ttaaacgcac cgtggcagcg ccgtccgttt tcatttttcc tccgtccgat gagcaactga   2220
aatcgggcac ggccagcgtc gtgtgtctgt tgaacaactt ctacccgcgt gaggcgaagg   2280
tgcagtggaa agtggacaac gcgctgcaat ccggtaatag ccaggaaagc gtcaccgaac   2340
aagatagcaa ggacagcacc tacagcctga gctctactct gaccctgagc aaggctgatt   2400
```

```
atgagaaaca caaggtctat gcatgtgagg tgacccatca gggtctgtcc agcccggtca    2460
ccaaaagctt caatcgcggt gagtgctaag tcgacctgca ggcatgcaag cttggctgtt    2520
ttggcggatg agagaagatt ttcagcctga tacagattaa atcagaacgc agaagcggtc    2580
tgataaaaca gaatttgcct ggcggcagta gcgcggtggt cccacctgac ccatgccga    2640 actcagaagt gaaacgccgt agcgccgatg gtagtgtggg gtctccccat gcgagagtag    2700
ggaactgcca ggcatcaaat aaaacgaaag gctcagtcga aagactgggc ctttcgtttt    2760
atctgttgtt tgtcggtgaa cgctctcctg agtaggacaa atccgccggg agcggatttg    2820
aacgttgcga agcaacggcc cggagggtgg cgggcaggac gcccgccata aactgccagg    2880
catcaaatta agcagaaggc catcctgacg gatggccttt ttgcgtttct acaaactctt    2940
ttgtttattt ttctaaatac attcaaatat gtatccgctc atgagacaat aaccctgata    3000
aatgcttcaa taatattgaa aaaggaagag tatgagtatt caacatttcc gtgtcgccct    3060
tattcccttt tttgcggcat tttgccttcc tgttttgct cacccagaaa cgctggtgaa    3120
agtaaaagat gctgaagatc agttggggca aactattaac tggcgaacta cttactctag    3180
cttcccggca acaattaata gactggatgg aggcggataa agttgcagga ccacttctgc    3240
gctcggccct tccggctggc tggtttattg ctgataaatc tggagccggt gagcgtgggt    3300
ctcgcggtat cattgcagca ctggggccag atggtaagcc ctcccgtatc gtagttatct    3360
acacgacggg gagtcaggca actatggatg aacgaaatag acagatcgct gagataggtg    3420
cctcactgat taagcattgg taactgtcag accaagttta ctcatatata ctttagattg    3480
atttacgcgc cctgtagcgg cgcattaagc gcggcgggtg tggtggttac gcgcagcgtg    3540
accgctacac ttgccagcgc cctagcgccc gctcctttcg ctttcttccc ttcctttctc    3600
gccacgttcg ccggctttcc ccgtcaagct ctaaatcggg ggctcccttt agggttccga    3660
tttagtgctt tacggcacct cgaccccaaa aaacttgatt tgggtgatgg ttcacgtagt    3720
gggccatcgc cctgatagac ggtttttcgc cctttgacgt tggagtccac gttctttaat    3780
agtggactct tgttccaaac ttgaacaaca ctcaaccta tctcgggcta ttcttttgat    3840
ttataaggga ttttgccgat ttcggcctat tggttaaaaa atgagctgat ttaacaaaaa    3900
tttaacgcga attttaacaa atattaacg tttacaattt aaaaggatct aggtgaagat    3960 ccttttttgat aatctcatga ccaaaatccc ttaacgtgag ttttcgttcc actgagcgtc    4020
agaccccgta gaaaagatca aaggatcttc ttgagatcct ttttttctgc gcgtaatctg    4080
ctgcttgcaa acaaaaaaac caccgctacc agcggtggtt tgtttgccgg atcaagagct    4140
accaactctt tttccgaagg taactggctt cagcagagcg cagataccaa atactgtcct    4200
tctagtgtag ccgtagttag gccaccactt caagaactct gtagcaccgc ctacatacct    4260
cgctctgcta atcctgttac cagtcaggca tttgagaagc acacggtcac actgcttccg    4320
gtagtcaata aaccggtaaa ccagcaatag acataagcgg ctatttaacg accctgccct    4380
gaaccgacga ccgggtcgaa tttgctttcg aatttctgcc attcatccgc ttattatcac    4440
ttattcaggc gtagcaccag gcgtttaagg gcaccaataa ctgccttaaa aaaattacgc    4500
cccgccctgc cactcatcgc agtactgttg taattcatta agcattctgc cgacatggaa    4560
gccatcacag acggcatgat gaacctgaat cgccagcggc atcagcacct tgtcgccttg    4620 cgtataaat ttgcccatgg tgaaaacggg ggcgaagaag ttgtccatat tggccacgtt    4680
taaatcaaaa ctggtgaaac tcacccaggg attggctgag acgaaaaaca tattctcaat    4740
```

```
aaacccttta gggaaatagg ccaggttttc accgtaacac gccacatctt gcgaatatat    4800
gtgtagaaac tgccggaaat cgtcgtggta ttcactccag agcgatgaaa acgtttcagt    4860
ttgctcatgg aaaacggtgt aacaagggtg aacactatcc catatcacca gctcaccgtc    4920
tttcattgcc atacggaatt ccggatgagc attcatcagg cgggcaagaa tgtgaataaa    4980
ggccggataa aacttgtgct tattttttctt tacggtcttt aaaaaggccg taatatccag    5040
ctgaacggtc tggttatagg tacattgagc aactgactga aatgcctcaa aatgttcttt    5100
acgatgccat tgggatatat caacggtggt atatccagtg attttttttct ccatttttagc    5160 ttccttagct cctgaaaatc tcgataactc aaaaaatacg cccggtagtg atcttatttc    5220
attatggtga agttggaac ctcttacgtg ccgatcaacg tctcattttc gccaaaagtt    5280
ggcccagggc ttcccggtat caacagggac accaggattt atttattctg cgaagtgatc    5340
ttccgtcaca ggtatttatt cggcgcaaag tgcgtcgggt gatgctgcca acttactgat    5400
ttagtgtatg atggtgtttt tgaggtgctc cagtggcttc tgtttctatc agctgtccct    5460
cctgttcagc tactgacggg gtggtgcgta acggcaaaag caccgccgga catcagcggt    5520
agcggagtgt atactggctt actatgttgg cactgatgag ggtgtcagtg aagtgcttca    5580
tgtggcagga gaaaaaaggc tgcaccggtg cgtcagcaga atatgtgata caggatatat    5640
tccgcttcct cgctcactga ctcgctacgc tcggtcgttc gactgcggcg agcggaaatg    5700
gcttacgaac ggggcggaga tttcctggaa gatgccagga agatacttaa cagggaagtg    5760
agagggccgc ggcaaagccg ttttttccata ggctccgccc ccctgacaag catcacgaaa    5820
tctgacgctc aaatcagtgg tggcgaaacc cgacaggact ataaagatac caggcgtttc    5880
cccctggcgg ctccctcgtg cgctctcctg ttcctgcctt tcggtttacc ggtgtcattc    5940
cgctgttatg gccgcgtttg tctcattcca gcctgacac tcagttccgg gtaggcagtt    6000
cgctccaagc tggactgtat gcacgaaccc cccgttcagt ccgaccgctg cgccttatcc    6060
ggtaactatc gtcttgagtc aacccggaa agacatgcaa aagcaccact ggcagcagcc    6120
actggtaatt gatttagagg agttagtctt gaagtcatgc gccggttaag gctaaactga    6180
aaggacaagt tttggtgact gcgctcctcc aagccagtta cctcggttca aagagttggt    6240
agctcagaga accttcgaaa aaccgccctg caaggcggtt ttttcgtttt cagagcaaga    6300
gattacgcgc agaccaaaac gatctcaaga agatcatctt attaatcaga taaaatattt    6360
gctcatgagc ccgaagtggc gagcccgatc ttccccatcg gtgatgtcgg cgatataggc    6420
gccagcaacc gcacctgtgg cgccggtgat gccggccacg atgcgtccgg cgtagaggat    6480
ctgctcatgt ttgacagctt atc                                            6503
```

<210> SEQ ID NO 34
<211> LENGTH: 6545
<212> TYPE: DNA
<213> ORGANISM: Artificial Sequence
<220> FEATURE:
<223> OTHER INFORMATION: pJ1231-03C plasmid

<400> SEQUENCE: 34

```
tcagaattgg ttaattggtt gtaacactga cccctatttg tttatttttc taaatacatt      60
caaatatgta tccgctcatg agacaataac cctgataaat gcttcaataa tattgaaaaa     120
ggaagaatat gagccatatt caacgggaaa cgtcgaggcc gcgattaaat tccaacatgg     180
atgctgattt atatgggtat aaatgggctc gcgataatgt cgggcaatca ggtgcgacaa     240
tctatcgctt gtatgggaag cccgatgcgc cagagttgtt tctgaaacat ggcaaaggta     300
```

```
gcgttgccaa tgatgttaca gatgagatgg tcagactaaa ctggctgacg gaatttatgc    360
cacttccgac catcaagcat tttatccgta ctcctgatga tgcatggtta ctcaccactg    420
cgatccccgg aaaaacagcg ttccaggtat tagaagaata tcctgattca ggtgaaaata    480
ttgttgatgc gctggcagtg ttcctgcgcc ggttgcactc gattcctgtt tgtaattgtc    540
cttttaacag cgatcgcgta tttcgcctcg ctcaggcgca atcacgaatg aataacggtt    600
tggttgatgc gagtgatttt gatgacgagc gtaatgctg gcctgttgaa caagtctgga    660
aagaaatgca taaacttttg ccattctcac cggattcagt cgtcactcat ggtgatttct    720
cacttgataa ccttattttt gacgagggga aattaatagg ttgtattgat gttggacgag    780
tcggaatcgc agaccgatac caggatcttg ccatcctatg gaactgcctc ggtgagtttt    840
ctccttcatt acagaaacgg cttttcaaa aatatggtat tgataatcct gatatgaata    900
aattgcaatt tcatttgatg ctcgatgagt ttttctaact catgaccaaa atcccttaac    960
gtgagttacg cgcgcgtcgt tccactgagc gtcagacccc gtagaaaaga tcaaaggatc   1020
ttcttgagat cctttttttc tgcgcgtaat ctgctgcttg caaacaaaaa aaccaccgct   1080
accagcggtg gtttgtttgc cggatcaaga gctaccaact cttttccga aggtaactgg   1140 cttcagcaga gcgcagatac caaatactgt tcttctagtg tagccgtagt tagcccacca   1200
cttcaagaac tctgtagcac cgcctacata cctcgctctg ctaatcctgt taccagtggc   1260
tgctgccagt ggcgataagt cgtgtcttac cgggttggac tcaagacgat agttaccgga   1320
taaggcgcag cggtcgggct gaacgggggg ttcgtgcaca cagcccagct tggagcgaac   1380
gacctacacc gaactgagat acctacagcg tgagctatga gaaagcgcca cgcttcccga   1440
agggagaaag gcggacaggt atccggtaag cggcagggtc ggaacaggag agcgcacgag   1500
ggagcttcca gggggaaacg cctggtatct ttatagtcct gtcgggtttc gccacctctg   1560
acttgagcgt cgatttttgt gatgctcgtc agggggggcgg agcctatgga aaaacgccag   1620
caacgcggcc ttttttacggt tcctggcctt ttgctggcct tttgctcaca tgttctttcc   1680
tgcgttatcc cctgattctg tggataaccg tattaccgcc tttgagtgag ctgataccgc   1740
tcggggtcgt gcaggtagtt tatcattatc aatactcgcc atttcaaaga atacgtaaat   1800
aattaatagt agtgattttc ctaactttat ttagtcaaaa aattagcctt ttaattctgc   1860
tgtaacccgt acatgcccaa aataggggcc gggttacaca gaatatataa catcgtaggt   1920
gtctgggtga acagtttatt cctggcatcc actaaatata atggagcccg ctttttaagc   1980
tggcatccag aaaaaaaaag aatcccagca ccaaaatatt gttttcttca ccaaccatca   2040
gttcataggt ccattctctt agcgcaacta cagagaacag gggcacaaac aggcaaaaaa   2100
cgggcacaac ctcaatggag tgatgcaacc agcctggagt aaatgatgac acaaggcaat   2160
tgacccacgc atgtatctat ctcattttct tacaccttct attccttct gctctctctg   2220 atttggaaaa agctgaaaaa aaaggttgaa accagttccc tgaaattatt ccctacttg    2280 actaataagt atataaagac ggtaggtatt gattgtaatt ctgtaaatct atttcttaaa   2340
cttcttaaat tctactttta tagttagtct ttttttttagt tttaaaacac cagaacttag   2400
tttcgacgga taaaatgaca gctttaactg aaggggccaa gcttttcgaa aaagagatcc   2460
catatatcac cgaacttgaa ggtgacgttg agggtatgaa gtttatcata aaaggagaag   2520
gcacaggtga tgcgacaacg ggtacaatca aggcaaagta catttgtaca actgggacc    2580 tgcctgtccc atgggccact ttggtgtcta ctttgtctta cggcgtacaa tgttttgcta   2640
```

```
agtacccttc acacatcaaa gatttcttta agtctgcaat gcctgaagga tacacacagg    2700
aacgtacaat ttcatttgag ggcgacggtg tctataaaac aagagctatg gttacttatg    2760
aaagaggttc catctacaac agagtgacac taacgggcga aaatttcaaa aaggatggac    2820
atattttgcg taaaaacgta gctttccaat gcccaccatc aatactatac attctgccag    2880
atactgtaaa caatggtatt agagtcgagt ttaatcaagc ttatgatata gaaggtgtca    2940
ctgaaaaatt ggttacaaaa tgcagccaaa tgaatagacc attggcagga tctgccgctg    3000
tgcatatccc tagataccat cacattacct accacaccaa attaagtaaa gacagggatg    3060
aacgaagaga tcatatgtgt ttagttgagg ttgttaaggc agttgatctc gacacttacc    3120
aataaatcat gtaattagtt atgtcacgct tacattcacg ccctccccc acatccgctc     3180 taaccgaaaa ggaaggagtt agacaacctg aagtctaggt ccctatttat ttttttatag    3240
ttatgttagt attaagaacg ttatttatat ttcaaatttt tcttttttt ctgtacagac     3300 gcgtgtacgc atgtaacatt atactgaaaa ccttgcttga aaggttttg ggacgctcga     3360 aggctttaat ttgcggcccc tcacctgcac gcaaaatagg ataattatac tctatttctc    3420
aacaagtaat tggttgtttg gccgagcggt ctaaggcgcc tgattcaaga aatatcttga    3480
ccgcagttaa ctgtgggaat actcaggtat cgtaagatgc aagagttcga atctcttagc    3540
aaccattatt ttttcctca acataacgag aacacacagg ggcgctatcg cacagaatca     3600
aattcgatga ctggaaattt tttgttaatt tcagaggtcg cctgacgcat ataccttttt    3660
caactgaaaa attgggagaa aaggaaagg tgagagcgcc ggaaccggct tttcatatag     3720
aatagagaag cgttcatgac taaatgcttg catcacaata cttgaagttg acaatattat    3780
ttaaggacct attgtttttt ccaataggtg gttagcaatc gtcttacttt ctaacttttc    3840
ttacctttta catttcagca atatatatat atatatttca aggatatacc attctaatgt    3900
ctgcccctaa gaagatcgtc gttttgccag gtgaccacgt tggtcaagaa atcacagccg    3960
aagccattaa ggttcttaaa gctatttctg atgttcgttc caatgtcaag ttcgatttcg    4020
aaaatcattt aattggtggt gctgctatcg atgctacagg tgttccactt ccagatgagg    4080
cgctggaagc ctccaagaag gctgatgccg ttttgttagg tgctgtgggt ggtcctaaat    4140
ggggtaccgg tagtgttaga cctgaacaag gtttactaaa aatccgtaaa gaacttcaat    4200
tgtacgccaa cttaagacca tgtaactttg catccgactc tcttttagac ttatctccaa    4260
tcaagccaca atttgctaaa ggtactgact cgttgttgt cagagaatta gtgggaggta     4320
tttactttgg taagagaaag gaagatgatg gtgatggtgt cgcttgggat agtgaacaat    4380
acaccgttcc agaagtgcaa agaatcacaa gaatggccgc tttcatggcc ctacaacatg    4440
agccaccatt gcctatttgg tccttggata aagctaatgt tttggcctct tcaagattat    4500
ggagaaaaac tgtggaggaa accatcaaga acgaattccc tacattgaag gttcaacatc    4560
aattgattga ttctgccgcc atgatcctag ttaagaaccc aacccaccta aatggtatta    4620
taatcaccag caacatgttt ggtgatatca tctccgatga agcctccgtt atcccaggtt    4680
ccttgggttt gttgccatct gcgtccttgg cctcttttgcc agacaagaac accgcatttg    4740
gtttgtacga accatgccac ggttctgctc cagatttgcc aaagaataag gtcaacccta    4800
tcgccactat cttgtctgct gcaatgatgt tgaaattgtc attgaacttg cctgaagaag    4860
gtaaggccat tgaagatgca gttaaaaagg ttttggatgc aggcatcaga actggtgatt    4920
taggtggttc caacagtacc accgaagtcg gtgatgctgt cgccgaagaa gttaagaaaa    4980
tccttgctta aaaagattct cttttttttat gatatttgta cataaacttt ataaatgaaa    5040
```

```
ttcataatag aaacgacacg aaattacaaa atggaatatg ttcatagggt aacgctatga   5100
tccaatatca aaggaaatga tagcattgaa ggatgagact aatccaattg aggagtggca   5160
gcatatagaa cagctaaagg gtagtgctga aggaagcata cgataccccg catggaatgg   5220
gataatatca caggaggtac tagactacct ttcatcctac ataaatagac gcatataagt   5280
acgcatttaa gcataaacac gcactatgcc gttcttctca tgtatatata tatacaggca   5340
acacgcagat ataggtgcga cgtgaacagt gagctgtatg tgcgcagctc gcgttgcatt   5400
ttcggaagcg ctcgttttcg gaaacgcttt gaagttccta ttccgaagtt cctattctct   5460
agaaagtata ggaacttcag agcgcttttg aaaaccaaaa gcgctctgaa gtcgcacttt   5520
caaaaaacca aaaacgcacc ggactgtaac gagctactaa aatattgcga ataccgcttc   5580
cacaaacatt gctcaaaagt atctctttgc tatatatctc tgtgctatat ccctatataa   5640
cctacccatc caccctttcgc tccttgaact tgcatctaaa ctcgacctct acattttttta   5700
tgtttatctc tagtattact ctttagacaa aaaaattgta gtaagaacta ttcatagagt   5760
gaatcgaaaa caatacgaaa atgtaaacat ttcctatacg tagtatatag agacaaaata   5820
gaagaaaccg ttcataattt tctgaccaat gaagaatcat caacgctatc actttctgtt   5880
cacaaagtat gcgcaatcca catcggtata gaatataatc ggggatgcct ttatcttgaa   5940
aaaatgcacc cgcagcttcg ctagtaatca gtaaacgcgg gaagtggagt caggcttttt   6000
ttatggaaga gaaaatagac accaaagtag ccttcttcta accttaacgg acctacagtg   6060
caaaagtta tcaagagact gcattataga gcgcacaaag gagaaaaaaa gtaatctaag   6120
atgctttgtt agaaaaatag cgctctcggg atgcatttttt gtagaacaaa aagaagtat   6180
agattctttg ttggtaaaat agcgctctcg cgttgcattt ctgttctgta aaaatgcagc   6240
tcagattctt tgtttgaaaa attagcgctc tcgcgttgca ttttttgtttt acaaaaatga   6300
agcacagatt cttcgttggt aaaatagcgc tttcgcgttg catttctgtt ctgtaaaaat   6360
gcagctcaga ttctttgttt gaaaaattag cgctctcgcg ttgcattttt gttctacaaa   6420
atgaagcaca gatgcttcgt tcaggtggca cttttcgggg aaatgtgcgc ggaaccccta   6480
tttgtttatt tttctaaata cattcaaata tgtatccgct catgagacaa taaccctgat   6540
attgg                                                               6545
```

<210> SEQ ID NO 35
<211> LENGTH: 6009
<212> TYPE: DNA
<213> ORGANISM: Artificial Sequence
<220> FEATURE:
<223> OTHER INFORMATION: pJ1234-03C plasmid

<400> SEQUENCE: 35

```
tcagaattgg ttaattggtt gtaacactga cccctatttg tttatttttc taaatacatt    60
caaatatgta tccgctcatg agacaataac cctgataaat gcttcaataa tattgaaaaa   120
ggaagaatat gagtattcaa catttccgtg tcgcccttat tcccttttttt gcggcatttt   180
gccttcctgt ttttgctcac ccagaaacgc tggtgaaagt aaaagatgct gaagatcagt   240
tgggtgcacg agtgggttac atcgaactgg atctcaacag cggtaagatc cttgagagtt   300
ttcgccccga agaacgtttt ccaatgatga gcacttttaa agttctgcta tgtggcgcgg   360
tattatcccg tattgacgcc gggcaagagc aactcggtcg ccgcatacac tattctcaga   420
atgacttggt tgagtactca ccagtcacag aaaagcatct tacggatggc atgacagtaa   480
```

-continued

```
gagaattatg cagtgctgcc ataaccatga gtgataacac tgcggccaac ttacttctga    540
caacgatcgg aggaccgaag gagctaaccg cttttttgca caacatgggg gatcatgtaa    600
ctcgccttga tcgttgggaa ccggagctga atgaagccat accaaacgac gagcgtgaca    660
ccacgatgcc tgtagcgatg caacaacgt tgcgcaaact attaactggc gaactactta    720
ctctagcttc ccggcaacaa ttaatagact ggatggaggc ggataaagtt gcaggaccac    780
ttctgcgctc ggcccttccg gctggctggt ttattgctga taaatccgga gccggtgagc    840
gtggttctcg cggtatcatc gcagcgctgg ggccagatgg taagccctcc cgtatcgtag    900
ttatctacac gacggggagt caggcaacta tggatgaacg aaatagacag atcgctgaga    960
taggtgcctc actgattaag cattggtaac tcatgaccaa aatcccttaa cgtgagttac   1020
gcgcgcgtcg ttccactgag cgtcagaccc cgtagaaaag atcaaaggat cttcttgaga   1080 tcctttttt ctgcgcgtaa tctgctgctt gcaaacaaaa aaccaccgc taccagcggt   1140 ggtttgtttg ccggatcaag agctaccaac tctttttccg aaggtaactg gcttcagcag   1200
agcgcagata ccaaatactg ttcttctagt gtagccgtag ttagcccacc acttcaagaa   1260
ctctgtagca ccgcctacat acctcgctct gctaatcctg ttaccagtgg ctgctgccag   1320
tggcgataag tcgtgtctta ccgggttgga ctcaagacga tagttaccgg ataaggcgca   1380
gcggtcgggc tgaacggggg gttcgtgcac acagcccagc ttggagcgaa cgacctacac   1440
cgaactgaga tacctacagc gtgagctatg agaaagcgcc acgcttcccg aagggagaaa   1500
ggcggacagg tatccggtaa gcggcagggt cggaacagga gagcgcacga gggagcttcc   1560
agggggaaac gcctggtatc tttatagtcc tgtcgggttt cgccacctct gacttgagcg   1620
tcgatttttg tgatgctcgt cagggggcg gagcctatgg aaaaacgcca gcaacgcggc   1680 cttttttacgg ttcctggcct tttgctggcc ttttgctcac atgttctttc ctgcgttatc   1740
ccctgattct gtggataacc gtattaccgc cttttgagtga gctgataccg ctcggggtcg   1800
tgcaggtagt ttatcattat caatactcgc catttcaaag aatacgtaaa taattaatag   1860
tagtgatttt cctaacttta tttagtcaaa aaattagcct tttaattctg ctgtaacccg   1920
tacatgccca aaatagggg cgggttacac agaatatata acatcgtagg tgtctgggtg   1980
aacagtttat tcctggcatc cactaaatat aatggagccc gcttttttaag ctggcatcca   2040 gaaaaaaaaa gaatcccagc accaaaatat tgttttcttc accaaccatc agttcatagg   2100
tccattctct tagcgcaact acagagaaca ggggcacaaa caggcaaaaa acgggcacaa   2160
cctcaatgga gtgatgcaac cagcctggag taaatgatga cacaaggcaa ttgacccacg   2220
catgtatcta tctcatttc ttacaccttc tattaccttc tgctctctct gattttggaaa   2280 aagctgaaaa aaaaggttga aaccagttcc ctgaaattat tccccctactt gactaataag   2340 tatataaaga cggtaggtat tgattgtaat tctgtaaatc tatttcttaa acttcttaaa   2400
ttctactttt atagttagtc ttttttttag ttttaaaaca ccagaactta gtttcgacgg   2460
ataaaatgac agctttaact gaaggggcca agcttttcga aaaagagatc ccatatatca   2520
ccgaacttga aggtgacgtt gagggtatga agttttatcat aaaaggagaa ggcacaggtg   2580
atgcgacaac gggtacaatc aaggcaaagt acatttgtac aactggggac ctgcctgtcc   2640
catgggccac tttggtgtct actttgtctt acggcgtaca atgttttgct aagtacccctt   2700 cacacatcaa agatttcttt aagtctgcaa tgcctgaagg atacacacag gaacgtacaa   2760
tttcatttga gggcgacggt gtctataaaa caagagctat ggttacttat gaaagaggtt   2820
ccatctacaa cagagtgaca ctaacgggcg aaaatttcaa aaaggatgga catattttgc   2880
```

```
gtaaaaacgt agctttccaa tgcccaccat caatactata cattctgcca gatactgtaa    2940
acaatggtat tagagtcgag tttaatcaag cttatgatat agaaggtgtc actgaaaaat    3000
tggttacaaa atgcagccaa atgaatagac cattggcagg atctgccgct gtgcatatcc    3060
ctagatacca tcacattacc taccacacca aattaagtaa agacagggat gaacgaagag    3120
atcatatgtg tttagttgag gttgttaagg cagttgatct cgacacttac caataaatca    3180
tgtaattagt tatgtcacgc ttacattcac gccctccccc cacatccgct ctaaccgaaa    3240
aggaaggagt tagacaacct gaagtctagg tccctattta tttttttata gttatgttag    3300
tattaagaac gttatttata tttcaaattt ttcttttttt tctgtacaga cgcgtgtacg    3360
catgtaacat tatactgaaa accttgcttg agaaggtttt gggacgctcg aaggctttaa    3420
tttgcggccc ctcacctgca cgcaaaaagc ttttcaattc aattcatcat ttttttttta    3480
ttcttttttt tgatttcggt ttctttgaaa ttttttttgat tcggtaatct ccgaacagaa    3540
ggaagaacga aggaaggagc acagacttag attggtatat atacgcatat gtagtgttga    3600
agaaacatga aattgcccag tattcttaac ccaactgcac agaacaaaaa ccagcaggaa    3660
acgaagataa atcatgtcga aagctacata taaggaacgt gctgctactc atcctagtcc    3720
tgttgctgcc aagctattta atatcatgca cgaaaagcaa acaaacttgt gtgcttcatt    3780
ggatgttcgt accaccaagg aattactgga gttagttgaa gcattaggtc ccaaaatttg    3840
tttactaaaa acacatgtgg atatcttgac tgatttttcc atggagggca cagttaagcc    3900
gctaaaggca ttatccgcca agtacaattt tttactcttc gaagatagaa aatttgctga    3960
cattggtaat acagtcaaat tgcagtactc tgcgggtgta tacagaatag cagaatgggc    4020
agacattacg aatgcacacg gtgtggtggg cccaggtatt gttagcggtt tgaagcaggc    4080
ggcagaagaa gtaacaaagg aacctagagg ccttttgatg ttagcagaat tgtcatgcaa    4140
gggctcccta tctactggag aatatactaa gggtactgtt gacattgcga aaagcgacaa    4200
agattttgtt atcggcttta ttgctcaaag agacatgggt ggaagagatg aaggttacga    4260
ttggttgatt atgacacccg gtgtgggttt agatgacaag ggagatgcat tgggtcaaca    4320
gtatagaacc gtggatgatg ttgtctctac aggatctgac attattattg ttggaagagg    4380
actatttgca aagggaaggg atgctaaggt agagggtgaa cgttacagaa aagcaggctg    4440
ggaagcatat ttgagaagat gcggccagca aaactaaaaa actgtattat aagtaaatgc    4500
atgtatacta aactcacaaa ttagagcttc aatttaatta tatcagttat tacccacgct    4560
atgatccaat atcaaaggaa atgatagcat tgaaggatga gactaatcca attgaggagt    4620
ggcagcatat agaacagcta aagggtagtg ctgaaggaag catacgatac cccgcatgga    4680
atgggataat atcacaggag gtactagact acctttcatc ctacataaat agacgcatat    4740
aagtacgcat ttaagcataa acacgcacta tgccgttctt ctcatgtata tatatataca    4800
ggcaacacgc agatataggt gcgacgtgaa cagtgagctg tatgtgcgca gctcgcgttg    4860
cattttcgga agcgctcgtt ttcggaaacg ctttgaagtt cctattccga agttcctatt    4920
ctctagaaag tataggaact tcagagcgct tttgaaaacc aaaagcgctc tgaagtcgca    4980
ctttcaaaaa accaaaaacg caccggactg taacgagcta ctaaaatatt gcgaataccg    5040
cttccacaaa cattgctcaa aagtatctct ttgctatata tctctgtgct atatccctat    5100
ataacctacc catccaccct tcgctccttg aacttgcatc taaactcgac ctctacattt    5160
tttatgttta tctctagtat tactctttag acaaaaaaat tgtagtaaga actattcata    5220
```

```
gagtgaatcg aaaacaatac gaaaatgtaa acatttccta tacgtagtat atagagacaa    5280
aatagaagaa accgttcata attttctgac caatgaagaa tcatcaacgc tatcactttc    5340
tgttcacaaa gtatgcgcaa tccacatcgg tatagaatat aatcggggat gcctttatct    5400
tgaaaaaatg cacccgcagc ttcgctagta atcagtaaac gcgggaagtg gagtcaggct    5460
ttttttatgg aagagaaaat agacaccaaa gtagccttct tctaacctta acggacctac    5520
agtgcaaaaa gttatcaaga gactgcatta tagagcgcac aaaggagaaa aaagtaatc     5580 taagatgctt tgttagaaaa atagcgctct cgggatgcat ttttgtagaa caaaaaagaa    5640
gtatagattc tttgttggta aaatagcgct ctcgcgttgc atttctgttc tgtaaaaatg    5700
cagctcagat tctttgtttg aaaaattagc gctctcgcgt tgcatttttg ttttacaaaa    5760
atgaagcaca gattcttcgt tggtaaaata gcgcttcgc gttgcatttc tgttctgtaa     5820
aaatgcagct cagattcttt gtttgaaaaa ttagcgctct cgcgttgcat tttgttcta    5880 caaaatgaag cacagatgct tcgttcaggt ggcactttc ggggaaatgt gcgcggaacc     5940
cctatttgtt tattttccta aatacattca aatatgtatc cgctcatgag acaataaccc    6000
tgatattgg                                                            6009

<210> SEQ ID NO 36
<211> LENGTH: 42
<212> TYPE: DNA
<213> ORGANISM: Artificial Sequence
<220> FEATURE:
<223> OTHER INFORMATION: BsaI-AraC-MnP-H4_FT primer

<400> SEQUENCE: 36
taacttggtc tcagggggcc gtcaattgtc tgattcgtta cc                       42

<210> SEQ ID NO 37
<211> LENGTH: 63
<212> TYPE: DNA
<213> ORGANISM: Artificial Sequence
<220> FEATURE:
<223> OTHER INFORMATION: MnP-H4_FT-6xHis-reverse primer

<400> SEQUENCE: 37
tgatgcctgg ctctagtatt agtgatggtg atggtgatgc gccggaccgt cgaattgcac    60
acc                                                                  63

<210> SEQ ID NO 38
<211> LENGTH: 38
<212> TYPE: DNA
<213> ORGANISM: Artificial Sequence
<220> FEATURE:
<223> OTHER INFORMATION: MnP-H4_FT-6xHis-forward primer

<400> SEQUENCE: 38
catcaccatc accatcacta atactagagc caggcatc                            38

<210> SEQ ID NO 39
<211> LENGTH: 66
<212> TYPE: DNA
<213> ORGANISM: Artificial Sequence
<220> FEATURE:
<223> OTHER INFORMATION: ChuA-6xHis-BsaI primer

<400> SEQUENCE: 39
tctaactttt agagacctta gtggtgatgg tggtggtgcc attggtagga aacgaaaatc    60
ttgccg                                                               66
```

<210> SEQ ID NO 40
<211> LENGTH: 4569
<212> TYPE: DNA
<213> ORGANISM: Artificial Sequence
<220> FEATURE:
<223> OTHER INFORMATION: AraC-MnP-H4_FT-ChuA PCR product

<400> SEQUENCE: 40

| | | | | | | |
|---|---|---|---|---|---|---|
| gggggccgtc | aattgtctga | ttcgttacca | attatgacaa | cttgacggct | acatcattca | 60 |
| cttttcttc | acaaccggca | cggaactcgc | tcgggctggc | cccggtgcat | tttttaaata | 120 |
| cccgcgagaa | atagagttga | tcgtcaaaac | caacattgcg | accgacggtg | gcgataggca | 180 |
| tccgggtggt | gctcaaaagc | agcttcgcct | ggctgatacg | ttggtcctcg | cgccagctta | 240 |
| agacgctaat | ccctaactgc | tggcggaaaa | gatgtgacag | acgcgacggc | gacaagcaaa | 300 |
| catgctgtgc | gacgctggcg | atatcaaaat | tgctgtctgc | caggtgatcg | ctgatgtact | 360 |
| gacaagcctc | gcgtacccga | ttatccatcg | gtggatggag | cgactcgtta | atcgcttcca | 420 |
| tgcgccgcag | taacaattgc | tcaagcagat | ttatcgccag | cagctccgaa | tagcgccctt | 480 |
| ccccttgccc | ggcgttaatg | atttgcccaa | acaggtcgct | gaaatgcggc | tggtgcgctt | 540 |
| catccgggcg | aaagaacccc | gtattggcaa | atattgacgg | ccagttaagc | cattcatgcc | 600 |
| agtaggcgcg | cggacgaaag | taaacccact | ggtgatacca | ttcgcgagcc | tccgatgac | 660 |
| gaccgtagtg | atgaatctct | cctggcggga | acagcaaaat | atcacccggt | cggcaaacaa | 720 |
| attctcgtcc | ctgatttttc | accaccccct | gaccgcgaat | ggtgagattg | agaatataac | 780 |
| cttcattcc | cagcggtcgg | tcgataaaaa | aatcgagata | accgttggcc | tcaatcggcg | 840 |
| ttaaacccgc | caccagatgg | gcattaaacg | agtatcccgg | cagcagggga | tcattttgcg | 900 |
| cttcagccat | acttttcata | ctcccgccat | tcagagaaga | accaattgt | ccatattgca | 960 |
| tcagacattg | ccgtcactgc | gtctttact | ggctcttctc | gctaaccaaa | ccggtaaccc | 1020 |
| cgcttattaa | aagcattctg | taacaaagcg | ggaccaaagc | catgacaaaa | acgcgtaaca | 1080 |
| aaagtgtcta | taatcacggc | agaaaagtcc | acattgatta | tttgcacggc | gtcacacttt | 1140 |
| gctatgccat | agcattttta | tccataagat | tagcggatcc | tacctgacgc | tttttatcgc | 1200 |
| aactctctac | tgtttctcca | tacccgtttt | tttgggctag | caggaggaat | tcaccatggc | 1260 |
| agtatgtcca | gacggtacca | gagtgacgaa | tgcagcgtgt | tgcgcgttca | ttccgctggc | 1320 |
| gcaggatctg | caggaaaccc | tgttccaagg | cgattgcggc | gaggacgcgc | acgaggtcat | 1380 |
| tcgcctgacc | tttcacgatg | ccattgcaat | cagccagtct | ttgggtccgc | aagcgggtgg | 1440 |
| tggcgcggac | ggcagcatgt | tgcactttcc | gaccatcgag | ccgaatttct | cggccaatag | 1500 |
| cggtattgac | gatagcgtta | acaacctgtt | gccgtttatg | caaaagcatg | acaccatcag | 1560 |
| cgctgcggac | ctggttcagt | tcgcaggcgc | cgtggcgctg | agcaactgtc | ctggtgcgcc | 1620 |
| acgtctggag | ttcatggcgg | tcgcccgaa | taccacgatc | ccggcagttg | aaggtctgat | 1680 |
| tccggagccg | caggacagcg | tcaccaaaat | tctgcagcgt | ttcgaggatg | ccggtaactt | 1740 |
| tagcccgttc | gaggtcgtga | gcctgttggc | gagccatacg | gtggcgcgtg | ctgacaaagt | 1800 |
| tgatgaaacc | atcgacgccg | ctccgttcga | cagcaccccg | tttacgtttg | atacccaggt | 1860 |
| tttcctggaa | gttctgttga | aaggcaccgg | ctttccgggt | tccaataaca | acaccggtga | 1920 |
| agtcatgtct | ccgctgcctc | tgggctcggg | tagcgatact | ggtgagatgc | gcctgcaaag | 1980 |
| cgactttgct | ctggcccgtg | atgagcgtac | cgcgtgcttc | tggcagtcct | tcgtcaacga | 2040 |

```
acaagagttt atggcggcca gctttaaggc tgcgatggca aaactggcaa ttctgggcca    2100
tagccgttcc agcctgatcg attgcagcga cgtggttccg gtgccgaagc ctgcggtcaa    2160
taagccggcg accttcccgg cgaccaaagg cccgaaggac ctggatactc tgacgtgtaa    2220
agcgctgaag tttccgacgc tgacgtctga tccgggtgcc acggagactc tgatcccgca    2280
ctgcagcaat ggtggcatga gctgcccggg tgtgcaattc gacggtccgg cgcatcacca    2340
tcaccatcac taatactaga gccaggcatc aaataaaacg aaaggctcag tcgaaagact    2400
gggcctttcg ttttatctgt tgtttgtcgg tgaacgctct ctactagagt cacactggct    2460
caccttcggg tgggcctttc tgcgtttata gtcgacttga cagctagctc agtcctaggt    2520
attgtgctag ctactagaga aagaggagaa atactagatg tcccgccctc aattcacctc    2580
gctccgtttg tctttgctcg cactcgccgt atccgcaacg ctgccgacct ttgccttcgc    2640
taccgaaacc atgaccgtta ccgcgaccgg caacgcacgc agctcgttcg aggcgccgat    2700
gatggtgagc gtgatcgata cctctgctcc ggagaaccag acggcgacga gcgctaccga    2760
tctgctgcgc cacgtgccgg gtattacgct ggacggtacc ggtcgacgga acggtcaaga    2820
cgtgaacatg cgcggctacg accatcgcgg tgtgctggtc ctggtcgatg tgtgcgtca    2880
gggtacggat accggtcact tgaatggtac ctttctggat ccggcgctga ttaagcgtgt    2940
cgaaatcgtg cgtggcccgt cggcactgct gtatggtagc ggtgcgctgg gcggtgtgat    3000
cagctacgat accgtcgatg cgaaagacct gttgcaagag ggtcaaagct ccggtttccg    3060
cgttttggt actggtggta ccggtgacca tagcctgggc ctgggcgcga gcgcgtttgg    3120
tcgcacggaa aacctggatg gcatcgttgc gtggagcagc cgtgatcgtg gtgacttgcg    3180
ccagtctaat ggcgaaacgg ccctaacga tgaaagcatt aacaacatgc tggccaaggg    3240
tacgtggcag atcgatagcg cgcagagcct gagcggcctg tccgttact acaacaacga    3300
cgcgcgtgag ccgaaaaacc cgcagacggt cgaggcgagc gagagcagca cccgatggt    3360
ggaccgtagc accattcaac gtgatgccca actgagctat aagctggcac cgcaaggtaa    3420
tgactggctg aatgcggatg cgaaaatcta ctggagcgaa gttcgcatca atgcacagaa    3480
tacgggtagc tctggcgagt accgtgaaca gattaccaaa ggtgcacgtc tggagaatcg    3540
ttctacgctg tttgctgaca gcttcgcttc gcatctgctg acgtatggtg gcgagtatta    3600
tcgtcaggaa caacacccag gtggtgcgac cacgggtttc ccgcaggcga agatcgattt    3660
tagcagcggc tggctgcaag atgagatcac cttgcgtgac ttgccgatta ccctgctggg    3720
tggtacgcgt tatgacagct accgtggcag cagcgacggt tacaaagacg tcgatgcaga    3780
taaatggagc tcccgtgccg gcatgaccat taatccgacc aattggctga tgctgttcgg    3840
cagctatgcg caagcgttcc gtgccccaac catgggtgag atgtacaatg acagcaagca    3900
tttcagcatt ggtcgcttct acacgaatta ctgggtgccg aacccgaatc tgcgtccgga    3960
gactaatgaa acccaggagt atggttttgg cctgcgcttt gatgatctga tgctgagcaa    4020
cgacgccctg gaattcaagg cgagctactt tgacactaaa gccaaagact acattagcac    4080
tacggttgat tttgcggctg ctaccaccat gtcctataat gttccaaacg caaagatttg    4140
gggctgggac gtcatgacca agtacaccac cgacctgttt agcttggatg ttgcatacaa    4200
tcgcacccgt ggcaaagaca ccgatacccgg cgaatacatc agcagcatca atccggacac    4260
cgttacgtcc accctgaaca tcccgattgc gcacagcgt ttcagcgttg gttgggttgg    4320
tacgtttgcg gatcgctcca cccacatctc gtcgtcttat agcaagcaac cgggctacgg    4380
cgtgaatgat ttctatgtga gctatcaggg ccagcaagcc ctgaaaggta tgacgactac    4440
```

```
cctggttctg ggcaacgcat tcgacaaaga gtattggagc ccgcagggca ttccgcagga    4500
cggtcgtaac ggcaagattt tcgtttccta ccaatggcac caccaccatc accactaagg    4560
tctctaaaa                                                            4569

<210> SEQ ID NO 41
<211> LENGTH: 42
<212> TYPE: DNA
<213> ORGANISM: Artificial Sequence
<220> FEATURE:
<223> OTHER INFORMATION: BsaI-PrpR-PDI primer

<400> SEQUENCE: 41
taacttggtc tcaggggtca gcttttcagc cgccgccaga ac                         42

<210> SEQ ID NO 42
<211> LENGTH: 55
<212> TYPE: DNA
<213> ORGANISM: Artificial Sequence
<220> FEATURE:
<223> OTHER INFORMATION: PDI-5xHis-BsaI primer

<400> SEQUENCE: 42
tctaactttt agagacctta gtggtggtgg tggtgcagct catcgtgctc cgtcg           55

<210> SEQ ID NO 43
<211> LENGTH: 3326
<212> TYPE: DNA
<213> ORGANISM: Artificial Sequence
<220> FEATURE:
<223> OTHER INFORMATION: PrpR-PDI PCR product

<400> SEQUENCE: 43
ggggtcagct tttcagccgc cgccagaacg tcgtccggct gatgcctaaa taattcgccg      60
ctgctgtttt atcgccatta aatttctcca gtgcctgttg tggtgtcagt aagcgtggag     120
cgggagtttt cgccgactcg cgcgccagtt ccggcagtag cagttgcata aactgcggcg     180
ttaaatccgg cgtcggttcc acacttaaaa acagcgccag tcgttccatc atattgcgca     240
gttcacgaat attgcctggc cagtcgtagt gcagcagcac agtttcactt gcctgtaacc     300
cctggcgtaa tgcagcagaa atggggcgg agagcgccgc cagagacact ttcaaaaagc     360
tttccgccag cggaagaata tccgccaccc gctcgcgcag tggtggcaat tgcagacgca     420
aaatactcag ccgataaaac agatcacggc gaaaacgtcc ttgctgcata tcttcttcca     480
gattgcagtg agtggcgcta atgacccgta catctaccgg aacaggctga tgcccgccga     540
cgcgggtgac ctcttttttct tccagcaccc gcagcagccg ggtctgcaaa ggtagcggca     600
tttcgccaat ctcatccaga aacagcgtac cgccgtgggc aatttcgaac agcccggcgc     660
gacctccgcg tcgcgagccg gtaaacgccc cttcctcata gccaaacagt tctgcttcca     720
gcagcgattc ggcaatcgcc ccgcagttga cggcaacaaa cggatgcgac ttttgcccct     780
gtcgcgcatc gtggcgggca aaatattccc gatgaatcgc ctgggccgcc agctctttgc     840
ccgtccccgt ttccccctca atcaacaccg ccgcactgga gcgggcatac agcaaaatag     900
tctgccgtac ttgttccatc tgtggtgatt gaccgagcat atcgcccagc acgtaacgag     960
tacgcagggc gttgcgggtg gcatcgtgag tgttatggcg taacgacatg cgcgtcatat    1020
ccagcgcatc gctgaacgcc tggcgcacgg tggcggcgga atagataaaa attccggtca    1080
ttccggcttc ttctgccaaa tcggtaatca gccctgcgcc gaccaccgct tcggtgccgt    1140
```

```
tagcttttag ctcgttaatc tgcccgcgtg cgtcttcctc ggtaatgtag ctacgttggt    1200
cgaggcgcaa attaaaggtt ttttgaaacg ccaccagcgc tggaatggtt tcctgatagg    1260
tgacaacgcc gatagaagag gtgagttttc cggcttttgc cagtgcctgt aacacatcgt    1320
agccgctcgg tttaatcaaa ataactggca ctgacaggcg gcttttcagg tacgcgccgt    1380
tagagccagc cgcgatgatg gcgtcacagc gttcgtttgc cagtttcttg cggatgtagg    1440
tcactgcttt ttcaaagcca agctgaatag gggtaatgtt cgccaggtga tcaaactcga    1500
ggctgatatc gcgaaacagc tcgaacaggc gcgttacaga taccgtccag ataaccggtt    1560
tgtcgtcatt aagccgtggt ggatgtgcca tagcgcaccg caaagttaag aaaccgaata    1620
ttgggtttag tcttgtttca taattgttgc aatgaaacgc ggtgaaacat tgcctgaaac    1680
gttaactgaa acgcatattt gcggattagt tcatgacttt atctctaaca aattgaaatt    1740
aaacatttaa ttttattaag gcaattgtgg cacacccctt gctttgtctt tatcaacgca    1800
aataacaagt tgataacaag ctagcaggag gaattcacca tgtctgatgt tgtacaactg    1860
aagaaagata cgttcgatga ctttatcaaa actaatgact tggtgctggc agagtttttc    1920
gccccgtggt gtggccactg caaagctctg gctccggagt acgaagaggc cgcgaccacc    1980
ctgaaagaaa agaacatcaa actggcgaaa gtggactgta cggaagaaac cgacctgtgt    2040
cagcagcacg gcgtggaagg ttacccgacc ctgaaggtgt tcgtggcct ggacaatgtt    2100
agcccgtaca aaggtcaacg taaggccgca gcgatcacca gctacatgat caagcagtcg    2160
ctgcctgcag tctctgaggt gaccaaagat aatctggaag agttcaaaaa ggcagataag    2220
gcggtgctgg ttgcctatgt tgatgcaagc gacaaggcga gcagcgaggt ctttacccag    2280
gtcgcggaga aattgcgcga taactacccg ttcggcagca gctccgatgc agctttggcc    2340
gaggcggaag gtgtcaaggc tccggcgatc gttctgtaca aagatttcga cgagggtaaa    2400
gcggtgttca gcgaaaagtt tgaggtggaa gcaattgaaa agttcgcaaa accggtgcc    2460
acgcctttga ttggcgaaat cggtccggaa acctattctg actatatgag cgccggtatc    2520
ccgctggcct acattttcgc agaaacggca gaagagcgca agaactgag cgacaagttg    2580
aagccaattg cagaggcaca gcgtggcgtc atcaactttg gtaccattga cgcgaaagca    2640
tttggtgcgc atgccggtaa cctgaatctg aaaacggaca aatttccggc gtttgcgatt    2700
caagaggtgg cgaagaacca aaagtttccg ttcgatcaag aaaaagagat taccttcgag    2760
gcgatcaaag cgttcgttga cgactttgtt gccggtaaaa tcgagccgag cattaagagc    2820
gagccgatcc ggagaagca ggaaggcccg gtgaccgtcg tcgtcgcgaa gaattacaac    2880
gagattgttc tggatgacac gaaagacgtc ctgattgagt tctatgcgcc gtggtgcggt    2940
cattgcaaag cgctggcccc gaaatatgaa gagctgggtg cgctgtacgc gaagagcgag    3000
tttaaggacc gtgtggttat cgcgaaagta gatgcgaccg ccaatgacgt tcctgacgag    3060
atccaaggct tcccgaccat taaactgtat ccggctggtg ctaaaggcca gccagttacc    3120
tatagcggta gccgcacggt tgaggatctg attaagttca ttgccgagaa cggcaagtac    3180
aaggcggcaa tcagcgagga tgcagaagaa acgagctccg caaccgaaac cacgacggaa    3240
accgctacta agtccgaaga ggcggcgaaa gaaccgcgca cggagcacga tgagctgcac    3300
caccaccacc actaaggtct ctaaaa                                         3326
```

<210> SEQ ID NO 44
<211> LENGTH: 44
<212> TYPE: DNA
<213> ORGANISM: Artificial Sequence

```
<220> FEATURE:
<223> OTHER INFORMATION: BsaI-AraC-HC-forward primer

<400> SEQUENCE: 44
taacttggtc tcaggggaag ccgtcaattg tctgattcgt tacc            44

<210> SEQ ID NO 45
<211> LENGTH: 46
<212> TYPE: DNA
<213> ORGANISM: Artificial Sequence
<220> FEATURE:
<223> OTHER INFORMATION: HC-reverse primer

<400> SEQUENCE: 45
gctttgttgc agttgaactt ccatggtgaa ttcctcctgc tagccc          46

<210> SEQ ID NO 46
<211> LENGTH: 46
<212> TYPE: DNA
<213> ORGANISM: Artificial Sequence
<220> FEATURE:
<223> OTHER INFORMATION: HC-forward primer

<400> SEQUENCE: 46
gggctagcag gaggaattca ccatggaagt tcaactgcaa caaagc          46

<210> SEQ ID NO 47
<211> LENGTH: 45
<212> TYPE: DNA
<213> ORGANISM: Artificial Sequence
<220> FEATURE:
<223> OTHER INFORMATION: HC-BsaI-reverse primer

<400> SEQUENCE: 47
tctaactttt agagaccaag cttttatttacccggcgagt gggac            45

<210> SEQ ID NO 48
<211> LENGTH: 43
<212> TYPE: DNA
<213> ORGANISM: Artificial Sequence
<220> FEATURE:
<223> OTHER INFORMATION: BsaI-PrpR-LC-forward primer

<400> SEQUENCE: 48
taacttggtc tcaggggcg tagaggatct gctcatgttt gac               43

<210> SEQ ID NO 49
<211> LENGTH: 50
<212> TYPE: DNA
<213> ORGANISM: Artificial Sequence
<220> FEATURE:
<223> OTHER INFORMATION: LC-reverse primer

<400> SEQUENCE: 49
cgcttgcgtc ataacaatat cagccatggt gaattcctcc tgctagcttg       50

<210> SEQ ID NO 50
<211> LENGTH: 50
<212> TYPE: DNA
<213> ORGANISM: Artificial Sequence
<220> FEATURE:
<223> OTHER INFORMATION: LC-forward primer

<400> SEQUENCE: 50
caagctagca ggaggaattc accatggctg atattgttat gacgcaagcg       50
```

<210> SEQ ID NO 51
<211> LENGTH: 43
<212> TYPE: DNA
<213> ORGANISM: Artificial Sequence
<220> FEATURE:
<223> OTHER INFORMATION: LC-BsaI-reverse primer

<400> SEQUENCE: 51
tctaactttt agagacctct ctcatccgcc aaaacagcca agc                43

<210> SEQ ID NO 52
<211> LENGTH: 2615
<212> TYPE: DNA
<213> ORGANISM: Artificial Sequence
<220> FEATURE:
<223> OTHER INFORMATION: AraC-HC_NS PCR product

<400> SEQUENCE: 52
ggggaagccg tcaattgtct gattcgttac caattatgac aacttgacgg ctacatcatt    60 cacttttct tcacaaccgg cacggaactc gctcgggctg gccccggtgc attttttaaa    120
tacccgcgag aaatagagtt gatcgtcaaa accaacattg cgaccgacgg tggcgatagg    180
catccgggtg gtgctcaaaa gcagcttcgc ctggctgata cgttggtcct cgcgccagct    240
taagacgcta atccctaact gctggcggaa aagatgtgac agacgcgacg gcgacaagca    300
aacatgctgt gcgacgctgg cgatatcaaa attgctgtct gccaggtgat cgctgatgta    360
ctgacaagcc tcgcgtaccc gattatccat cggtggatgg agcgactcgt taatcgcttc    420
catgcgccgc agtaacaatt gctcaagcag atttatcgcc agcagctccg aatagcgccc    480
ttccccttgc ccggcgttaa tgatttgccc aaacaggtcg ctgaaatgcg gctggtgcgc    540
ttcatccggg cgaaagaacc ccgtattggc aaatattgac ggccagttaa gccattcatg    600
ccagtaggcg cgcggacgaa agtaaaccca ctggtgatac cattcgcgag cctccggatg    660
acgaccgtag tgatgaatct ctcctggcgg gaacagcaaa atatcacccg gtcggcaaac    720
aaattctcgt ccctgatttt tcaccacccc ctgaccgcga atggtgagat tgagaatata    780
acctttcatt cccagcggtc ggtcgataaa aaaatcgaga taaccgttgg cctcaatcgg    840
cgttaaaccc gccaccagat gggcattaaa cgagtatccc ggcagcaggg gatcattttg    900
cgcttcagcc atacttttca tactcccgcc attcagagaa gaaaccaatt gtccatattg    960
catcagacat tgccgtcact gcgtctttta ctggctcttc tcgctaacca aaccggtaac   1020
cccgcttatt aaaagcattc tgtaacaaag cgggaccaaa gccatgacaa aaacgcgtaa   1080
caaaagtgtc tataatcacg gcagaaaagt ccacattgat tatttgcacg gcgtcacact   1140
ttgctatgcc atagcatttt tatccataag attagcggat cctacctgac gctttttatc   1200
gcaactctct actgtttctc catacccgtt tttttgggct agcaggagga attcaccatg   1260
gaagttcaac tgcaacaaag cggtccggaa ctgattaaac cgggcgcgag cgtgaagatg   1320
tcttgcaaag ccagtggtta cacctttacg tcttatgtga tgcattgggt taaacagaag   1380
ccgggccaag gtctggaatg gattggctac atcaacccgt acaacgatgg taccaagtac   1440
aacgaaaagt tcaagggcaa agcaaccctg acgagtgaca aaagctctag tacggcttat   1500
atggaactgt cctcactgac ctcagaagat tcggcagtgt attactgcgc tcgtggcacg   1560
tattactatg gttcccgcgt ttttgattac tggggccagg gtaccacgct gaccgtttcg   1620
agcgcgaaaa ccacgccgcc gagcgtctat ccgctggcac cggttcggc agcacagacg   1680 aatagcatgg tgaccctggg ctgtctggtt aaaggttact ttccggaacc ggtgaccgtt   1740

| | |
|---|---|
| acgtggaaca gcggctctct gtctagtggt gtccatacgt tcccggcggt gctgcagtct | 1800 |
| gatctgtata ccctgtcctc atcggtcacg gtgccgagct ctacctggcc gagtgaaacc | 1860 |
| gtcacgtgca acgtggcaca cccggcaagt tccaccaaag ttgataaaaa gattgtcccg | 1920 |
| cgtgactgcg gctgtaaacc gtgcatctgt accgtgccgg aagtttcatc ggtctttatt | 1980 |
| ttcccgccga agccgaaaga tgtcctgacc atcacgctga ccccgaaggt gacctgtgtg | 2040 |
| gttgtcgaca tttctaaaga tgacccggaa gttcagttta gttggttcgt cgatgacgtt | 2100 |
| gaagtccata cggcgcagac ccaaccgcgt gaagaacagt ttaatagcac cttccgcagt | 2160 |
| gtgtccgaac tgccgatcat gcaccaagac tggctgaatg caaggaatt taaatgccgt | 2220 |
| gttaactcgg cagcttttcc ggccccgatt gaaaagacga tcagcaagac caaggtcgc | 2280 |
| ccgaaagcac cgcaggtgta taccattccg ccgccgaaag aacaaatggc taaggataaa | 2340 |
| gttagcctga cgtgtatgat taccgatttc tttccggaag acatcaccgt ggaatggcag | 2400 |
| tggaacggcc aaccggccga aaactataaa aatacgcagc cgatcatgga taccgacggt | 2460 |
| tcctactttg tgtattcaaa gctgaacgtt caaaaatcca attgggaagc cggtaacacg | 2520 |
| ttcacctgtt cagttctgca cgaaggtctg cacaatcacc atacggaaaa gtcgctgtcc | 2580 |
| cactcgccgg gtaaataaaa gcttggtctc taaaa | 2615 |

<210> SEQ ID NO 53
<211> LENGTH: 2584
<212> TYPE: DNA
<213> ORGANISM: Artificial Sequence
<220> FEATURE:
<223> OTHER INFORMATION: PrpR-LC_NS PCR product

<400> SEQUENCE: 53

| | |
|---|---|
| gggggcgtag aggatctgct catgtttgac agcttatcat cgattcagct tttcagccgc | 60 |
| cgccagaacg tcgtccggct gatgcctaaa taattcgccg ctgctgtttt atcgccatta | 120 |
| aatttctcca gtgcctgttg tggtgtcagt aagcgtggag cggagttttt cgccgactcg | 180 |
| cgcgccagtt ccggcagtag cagttgcata aactgcggcg ttaaatccgg cgtcggttcc | 240 |
| acacttaaaa acagcgccag tcgttccatc atattgcgca gttcacgaat attgcctggc | 300 |
| cagtcgtagt gcagcagcac agtttcactt gcctgtaacc cctggcgtaa tgcagcagaa | 360 |
| aatgggcgg agagcgccgc cagagacact ttcaaaaagc tttccgccag cggaagaata | 420 |
| tccgccaccc gctcgcgcag tggtggcaat tgcagacgca aaatactcag ccgataaaac | 480 |
| agatcacggc gaaaacgtcc ttgctgcata tcttcttcca gattgcagtg agtggcgcta | 540 |
| atgacccgta catctaccgg aacaggctga tgcccgccga cgcgggtgac ctcttttttct | 600 |
| tccagcaccc gcagcagccg ggtctgcaaa ggtagcggca tttcgccaat ctcatccaga | 660 |
| aacagcgtac cgccgtgggc aatttcgaac agcccggcgc gacctccgcg tcgcgagccg | 720 |
| gtaaacgccc cttcctcata gccaaacagt tctgcttcca gcagcgattc ggcaatcgcc | 780 |
| ccgcagttga cggcaacaaa cggatgcgac tttttgccct gtcgcgcatc gtggcgggca | 840 |
| aaatattccc gatgaatcgc ctgggccgcc agctctttgc ccgtcccgt ttcccccctca | 900 |
| atcaacaccg ccgcactgga gcgggcatac agcaaaatag tctgccgtac ttgttccatc | 960 |
| tgtggtgatt gaccgagcat atcgcccagc acgtaacgag tacgcagggc gttgcgggtg | 1020 |
| gcatcgtgag tgttatggcg taacgacatg cgcgtcatat ccagcgcatc gctgaacgcc | 1080 |
| tggcgcacgg tggcggcgga atagataaaa attccggtca ttccggcttc ttctgccaaa | 1140 |

-continued

```
tcggtaatca gccctgcgcc gaccaccgct tcggtgccgt tagcttttag ctcgttaatc    1200
tgcccgcgtg cgtcttcctc ggtaatgtag ctacgttggt cgaggcgcaa attaaaggtt    1260
ttttgaaacg ccaccagcgc tggaatggtt tcctgatagg tgacaacgcc gatagaagag    1320
gtgagttttc cggcttttgc cagtgcctgt aacacatcgt agccgctcgg tttaatcaaa    1380
ataactggca ctgacaggcg gcttttcagg tacgcgccgt tagagccagc cgcgatgatg    1440
gcgtcacagc gttcgtttgc cagtttcttg cggatgtagg tcactgcttt ttcaaagcca    1500
agctgaatag gggtaatgtt cgccaggtga tcaaactcga ggctgatatc gcgaaacagc    1560
tcgaacaggc gcgttacaga taccgtccag ataaccggtt tgtcgtcatt aagccgtggt    1620
ggatgtgcca tagcgcaccg caaagttaag aaaccgaata ttgggtttag tcttgtttca    1680
taattgttgc aatgaaacgc ggtgaaacat tgcctgaaac gttaactgaa acgcatattt    1740
gcggattagt tcatgacttt atctctaaca aattgaaatt aaacatttaa ttttattaag    1800
gcaattgtgg cacacccctt gctttgtctt tatcaacgca aataacaagt tgataacaag    1860
ctagcaggag gaattcacca tggctgatat tgttatgacg caagcggctc cgtctattcc    1920
ggttaccccg ggtgaaagcg tctctatcag ttgccgcagc tctaaatcgc tgctgaacag    1980
caatggtaac acctatctgt actggtttct gcagcgtccg ggtcagagcc cgcaactgct    2040
gatttatcgc atgtctaatc tggcaagtgg tgtcccggat cgttttttccg gttcaggttc    2100 gggtacggca ttcaccctgc gtatctcccg cgttgaagcc gaagacgtcg gcgtgtatta    2160
ctgcatgcag catctggaat acccgtttac gttcggtgca ggcaccaaac tggaactgaa    2220
acgcgctgat gcagcaccga ccgtgagcat ttttcccgccg agttccgaac aactgacctc    2280
cggcggtgca tcagtggttt gttttctgaa caacttctac ccgaaagata tcaacgtgaa    2340
atggaaaatc gacggttcgg aacgtcagaa tggcgttctg aacagctgga cggatcaaga    2400
cagtaaagat tccacctact caatgtcatc gaccctgacg ctgaccaaag acgaatatga    2460
acgccataac tcttacacgt gcgaagctac ccacaaaacg agcacctctc cgatcgttaa    2520 aagtttttaat cgtaacgaat gttaaaagct tggctgtttt ggcggatgag agaggtctct    2580
aaaa                                                                2584
```